(12) United States Patent
Chen et al.

(10) Patent No.: US 6,670,167 B1
(45) Date of Patent: Dec. 30, 2003

(54) CATALYTIC DOMAIN OF THE HUMAN EFFECTOR CELL CYCLE CHECKPOINT PROTEIN KINASE MATERIALS AND METHODS FOR IDENTIFICATION OF INHIBITORS THEREOF

(75) Inventors: Ping Chen, San Diego, CA (US); Mark Anderson, San Diego, CA (US); Ya-Li Deng, San Diego, CA (US); Smita Gaur, San Diego, CA (US); Chen Chen Kan, Arcadia, CA (US); Chun Luo, San Diego, CA (US); Karen Lundgren, San Diego, CA (US); Stephen Margosiak, Escondido, CA (US); Binh Nguyen, San Diego, CA (US); Patrick O'Connor, San Diego, CA (US); James Register, San Diego, CA (US); Anna Tempczyk Russell, San Diego, CA (US); Jay Sarup, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/460,421

(22) Filed: Dec. 14, 1999

Related U.S. Application Data

(60) Provisional application No. 60/162,887, filed on Nov. 1, 1999.

(51) Int. Cl.$^7$ .................. C07H 21/04; C12N 15/00; C12N 1/20
(52) U.S. Cl. ................ 435/252.33; 435/235.1; 435/348; 435/254.11; 435/252.3; 435/419; 435/325; 435/320.1; 536/23.2; 536/23.5
(58) Field of Search ............... 435/194, 15, 252.3, 435/320.1, 325, 419, 252.33, 254.11, 348, 235.1; 536/23.2, 23.5

(56) References Cited

U.S. PATENT DOCUMENTS 5,593,825 A   1/1997   Carman et al.
5,714,329 A   2/1998   Dracopoli et al.

FOREIGN PATENT DOCUMENTS

WO   WO97/18323   5/1997
WO   WO97/39143   10/1997
WO   WO99/11795   3/1999
WO   WO99/29894   6/1999
WO   WO00/03005   1/2000

OTHER PUBLICATIONS inNovations 1:1–3 (1994).*
GibcoBRL description of Catalog No. 10360–014 (1997).*
Johnson et al., *FEBS Letters*, 430, 1–11 (1998).
Imborgig, L. et al., *Proceedings of the American Association for Cancer Research*, 40, p. 406, abstract No. 2688 (1999).
Gilliland, G.L. et al., *Current Opinion in Structural Biology*, 6(5), 595–603 (1996).
Brondello, J.M., *Mol Cell Biol*, 19(6): 4264–4269 (1999).
Davidson, D., et al., *J Biol Chem*, 272(2): 1355–1362 (1997).
O'Connell, M.J., et al., *EMBOJ*, 16(3): 545–554 (Feb. 1997).
Rowley, R., et al., *EMBOJ*, 11(4): 1335–1342 (1992).
al–Khodairy, et al., *Mol Biol Cell*, 5(2): 1476–160 (1994).
Boddy, M.N., et al., *Science*, 280(5365): 909–912 (1998).
Bossemeyer, D., et al., *EMBOJ*, 12(3): 849–859 (1993).
Carr, et al., *Curr Biol*, 5(10): 1179–1190 (1995).
Cox, S., et al., *Curr Opin Struct Biol*, 4(6): 893–901 (1994).
De Bondt, H.L., et al., *Nature*, 363(6430): 595–602 (1993).
Fan, S., et a., *Cancer Res*, 55; 1649–1654 (1995).
Flaggs, et al., *Curr Biol*, 7(12): 977–986 (1997).
Furnari, et al., *Science*, 277: 1495–1497 (1997).
Gangal, M., et al., *Biochemistry*, 37(39): 13728–13735 (1998).
Hartwell, L.H., et al., *Science*, 246: 629–634 (1989).
Hartwell, L.H., et al., *Science*, 266, 1821–1828 (1994).
Hubbard, S.R., *EMBOJ*, 16(18): 5572–5581 (1997).
Knighton, D.R., et al., *J Mol Biol*, 220(2): 217–220 (1991).
Martinho, et al., *EMBOJ*, 17(24): 7239–7249 (1998).
Nakajo, et al., *Dev Biol*, 207(2): 432–444 (1999).
Nurse, P., *Cell*, 91: 865–867 (1997).
Nurse, P., *Nat Med*, 4(10): 1103–1106 (1998).
O'Connor, P.M., *Cancer Surveys*, 29: 151–182 (1997).
Owens, D.J., et al., *Structure*, 3(5): 467–482 (1995).
Peng, C.Y., et al., *Science*, 266: 1821–1828 (1994).
Powell, S.N., et al., *Cancer Res*, 55:1643–1648 (1995).
Russell, K.J., et al., *Cancer Res*, 55:1639–1642 (1995).
Sanchez, Y., et al., *Science*, 277: 1497–1501 (1997).
Schulze–Gahman, U., et al., *J Med Chem*, 39(23): 4540–4546 (1996).
Walworth, N., et al., *Nature*, 363(6427)L 3680371 (1993).
Wan, S., et al., *Yeast*, 15(10A): 821–828 (1999).
Wang, Q., et al., *PNAS*, 96: 3706–3711 (1999).
Wang, Q., et al., *J Natl Cancer Inst*, 88: 956–967 (1996).
Weinert, et al., *Genes and Dev*, 8: 652 (1994).
Weinert, T., *Science*, 277: 1450–1451 (1997).
Weinert, T.A., et al., *Genetics*, 134(1): 63–80 (May 1993).
Weinert, T.A., et al., *J Cell Sci Suppl*, 12: 145–148 (1989).
Zeng, et al., *Nature*, 395 (6701): 507–510 (1998).
Zheng, J., et al., *Protein Sci*, 2(10): 1559–1573 (1993).

* cited by examiner

Primary Examiner—Rebecca E. Prouty
Assistant Examiner—David Steadman
(74) Attorney, Agent, or Firm—Elsa Djuardi; Bryan C. Zielinski; Peter C. Richardson

(57) ABSTRACT

The present invention relates to the identification, isolation and purification of the catalytic domain of the human effector checkpoint protein kinase (hChk1). A 1.7Å crystal structure of the hChk1 kinase domain in the active conformation is reported herein. The kinase domain of hChk1 and its associated crystal structure is described for use in the discovery, identification and characterization of inhibitors of hChk1. This structure provides a three-dimensional description of the binding site of the hChk1 for structure-based design of small molecule inhibitors thereof as therapeutic agents. Inhibitors of hChk1 find utility in the treatment of hyperproliferative disorders such as HIV and cancer.

17 Claims, 126 Drawing Sheets

| ATOM | 1 | CB | ALA | 2 | 0.113 | 10.279 | -12.669 | 1.00 | 55.20 |
| --- | --- | --- | --- | --- | --- | --- | --- | --- | --- |
| ATOM | 2 | C | ALA | 2 | 0.954 | 8.071 | -13.488 | 1.00 | 54.08 |
| ATOM | 3 | O | ALA | 2 | 0.890 | 7.468 | -14.560 | 1.00 | 54.24 |
| ATOM | 4 | N | ALA | 2 | -0.778 | 8.182 | -11.709 | 1.00 | 57.23 |
| ATOM | 5 | CA | ALA | 2 | -0.258 | 8.824 | -12.949 | 1.00 | 55.69 |
| ATOM | 6 | N | VAL | 3 | 2.056 | 8.107 | -12.740 | 1.00 | 51.32 |
| ATOM | 7 | CA | VAL | 3 | 3.284 | 7.427 | -13.149 | 1.00 | 47.11 |
| ATOM | 8 | CB | VAL | 3 | 4.508 | 7.949 | -12.363 | 1.00 | 46.10 |
| ATOM | 9 | CG1 | VAL | 3 | 5.794 | 7.398 | -12.973 | 1.00 | 41.34 |
| ATOM | 10 | CG2 | VAL | 3 | 4.524 | 9.467 | -12.367 | 1.00 | 48.87 |
| ATOM | 11 | C | VAL | 3 | 3.143 | 5.920 | -12.922 | 1.00 | 44.85 |
| ATOM | 12 | O | VAL | 3 | 2.969 | 5.461 | -11.795 | 1.00 | 45.58 |
| ATOM | 13 | N | PRO | 4 | 3.231 | 5.132 | -14.003 | 1.00 | 41.89 |
| ATOM | 14 | CD | PRO | 4 | 3.546 | 5.613 | -15.363 | 1.00 | 37.40 |
| ATOM | 15 | CA | PRO | 4 | 3.112 | 3.672 | -13.991 | 1.00 | 41.11 |
| ATOM | 16 | CB | PRO | 4 | 3.743 | 3.276 | -15.323 | 1.00 | 34.82 |
| ATOM | 17 | CG | PRO | 4 | 3.281 | 4.388 | -16.215 | 1.00 | 31.95 |
| ATOM | 18 | C | PRO | 4 | 3.667 | 2.858 | -12.815 | 1.00 | 42.75 |
| ATOM | 19 | O | PRO | 4 | 2.936 | 2.534 | -11.875 | 1.00 | 47.35 |
| ATOM | 20 | N | PHE | 5 | 4.954 | 2.540 | -12.869 | 1.00 | 40.95 |
| ATOM | 21 | CA | PHE | 5 | 5.591 | 1.699 | -11.856 | 1.00 | 40.30 |
| ATOM | 22 | CB | PHE | 5 | 6.705 | 0.882 | -12.522 | 1.00 | 36.35 |
| ATOM | 23 | CG | PHE | 5 | 6.572 | 0.770 | -14.020 | 1.00 | 32.27 |
| ATOM | 24 | CD1 | PHE | 5 | 7.335 | 1.578 | -14.862 | 1.00 | 27.57 |
| ATOM | 25 | CD2 | PHE | 5 | 5.702 | -0.154 | -14.589 | 1.00 | 32.16 |
| ATOM | 26 | CE1 | PHE | 5 | 7.237 | 1.465 | -16.248 | 1.00 | 27.10 |
| ATOM | 27 | CE2 | PHE | 5 | 5.593 | -0.276 | -15.979 | 1.00 | 30.91 |
| ATOM | 28 | CZ | PHE | 5 | 6.363 | 0.535 | -16.809 | 1.00 | 28.05 |
| ATOM | 29 | C | PHE | 5 | 6.156 | 2.348 | -10.589 | 1.00 | 39.99 |
| ATOM | 30 | O | PHE | 5 | 7.191 | 1.908 | -10.088 | 1.00 | 38.49 |
| ATOM | 31 | N | VAL | 6 | 5.486 | 3.360 | -10.048 | 1.00 | 40.37 |
| ATOM | 32 | CA | VAL | 6 | 5.994 | 4.011 | -8.842 | 1.00 | 40.35 |
| ATOM | 33 | CB | VAL | 6 | 5.424 | 5.437 | -8.690 | 1.00 | 42.42 |
| ATOM | 34 | CG1 | VAL | 6 | 6.135 | 6.169 | -7.563 | 1.00 | 45.17 |
| ATOM | 35 | CG2 | VAL | 6 | 5.593 | 6.194 | -9.980 | 1.00 | 43.26 |
| ATOM | 36 | C | VAL | 6 | 5.676 | 3.219 | -7.573 | 1.00 | 39.11 |
| ATOM | 37 | O | VAL | 6 | 6.229 | 3.492 | -6.507 | 1.00 | 38.75 |
| ATOM | 38 | N | GLU | 7 | 4.796 | 2.232 | -7.693 | 1.00 | 36.63 |
| ATOM | 39 | CA | GLU | 7 | 4.408 | 1.411 | -6.550 | 1.00 | 34.52 |
| ATOM | 40 | CB | GLU | 7 | 2.931 | 1.035 | -6.659 | 1.00 | 41.81 |
| ATOM | 41 | CG | GLU | 7 | 1.981 | 2.219 | -6.618 | 1.00 | 51.32 |
| ATOM | 42 | CD | GLU | 7 | 1.963 | 2.906 | -5.267 | 1.00 | 60.70 |

FIG.11A-1

| | | | | | | | | |
|---|---|---|---|---|---|---|---|---|
| ATOM | 43 | OE1 | GLU | 7 | 3.021 | 3.416 | -4.840 | 1.00 63.96 |
| ATOM | 44 | OE2 | GLU | 7 | 0.888 | 2.935 | -4.631 | 1.00 70.24 |
| ATOM | 45 | C | GLU | 7 | 5.246 | 0.141 | -6.443 | 1.00 31.93 |
| ATOM | 46 | O | GLU | 7 | 5.036 | -0.675 | -5.544 | 1.00 32.27 |
| ATOM | 47 | N | ASP | 8 | 6.193 | -0.024 | -7.360 | 1.00 31.04 |
| ATOM | 48 | CA | ASP | 8 | 7.052 | -1.204 | -7.367 | 1.00 31.42 |
| ATOM | 49 | CB | ASP | 8 | 7.404 | -1.597 | -8.805 | 1.00 35.69 |
| ATOM | 50 | CG | ASP | 8 | 6.202 | -2.095 | -9.586 | 1.00 44.50 |
| ATOM | 51 | OD1 | ASP | 8 | 5.534 | -3.039 | -9.115 | 1.00 46.19 |
| ATOM | 52 | OD2 | ASP | 8 | 5.929 | -1.544 | -10.673 | 1.00 49.49 |
| ATOM | 53 | C | ASP | 8 | 8.338 | -1.002 | -6.576 | 1.00 31.44 |
| ATOM | 54 | O | ASP | 8 | 9.039 | -0.003 | -6.749 | 1.00 32.04 |
| ATOM | 55 | N | TRP | 9 | 8.644 | -1.972 | -5.720 | 1.00 30.97 |
| ATOM | 56 | CA | TRP | 9 | 9.837 | -1.939 | -4.883 | 1.00 31.19 |
| ATOM | 57 | CB | TRP | 9 | 9.435 | -1.779 | -3.408 | 1.00 32.92 |
| ATOM | 58 | CG | TRP | 9 | 9.527 | -0.371 | -2.877 | 1.00 37.61 |
| ATOM | 59 | CD2 | TRP | 9 | 8.464 | 0.583 | -2.781 | 1.00 34.10 |
| ATOM | 60 | CE2 | TRP | 9 | 9.014 | 1.770 | -2.242 | 1.00 35.49 |
| ATOM | 61 | CE3 | TRP | 9 | 7.100 | 0.554 | -3.100 | 1.00 28.78 |
| ATOM | 62 | CD1 | TRP | 9 | 10.648 | 0.258 | -2.404 | 1.00 37.08 |
| ATOM | 63 | NE1 | TRP | 9 | 10.347 | 1.543 | -2.020 | 1.00 32.55 |
| ATOM | 64 | CZ2 | TRP | 9 | 8.247 | 2.916 | -2.015 | 1.00 34.87 |
| ATOM | 65 | CZ3 | TRP | 9 | 6.337 | 1.693 | -2.876 | 1.00 36.67 |
| ATOM | 66 | CH2 | TRP | 9 | 6.914 | 2.860 | -2.338 | 1.00 40.32 |
| ATOM | 67 | C | TRP | 9 | 10.666 | -3.213 | -5.044 | 1.00 31.47 |
| ATOM | 68 | O | TRP | 9 | 10.127 | -4.320 | -5.057 | 1.00 32.63 |
| ATOM | 69 | N | ASP | 10 | 11.977 | -3.046 | -5.173 | 1.00 30.81 |
| ATOM | 70 | CA | ASP | 10 | 12.893 | -4.173 | -5.304 | 1.00 30.35 |
| ATOM | 71 | CB | ASP | 10 | 13.994 | -3.849 | -6.316 | 1.00 31.71 |
| ATOM | 72 | CG | ASP | 10 | 13.474 | -3.745 | -7.736 | 1.00 35.37 |
| ATOM | 73 | OD1 | ASP | 10 | 14.061 | -2.971 | -8.524 | 1.00 41.94 |
| ATOM | 74 | OD2 | ASP | 10 | 12.495 | -4.445 | -8.069 | 1.00 34.42 |
| ATOM | 75 | C | ASP | 10 | 13.539 | -4.444 | -3.945 | 1.00 30.57 |
| ATOM | 76 | O | ASP | 10 | 14.029 | -3.521 | -3.290 | 1.00 27.52 |
| ATOM | 77 | N | LEU | 11 | 13.535 | -5.703 | -3.522 | 1.00 32.48 |
| ATOM | 78 | CA | LEU | 11 | 14.148 | -6.078 | -2.249 | 1.00 36.27 |
| ATOM | 79 | CB | LEU | 11 | 13.432 | -7.290 | -1.645 | 1.00 37.99 |
| ATOM | 80 | CG | LEU | 11 | 11.990 | -7.058 | -1.182 | 1.00 39.05 |
| ATOM | 81 | CD1 | LEU | 11 | 11.125 | -6.630 | -2.357 | 1.00 40.90 |
| ATOM | 82 | CD2 | LEU | 11 | 11.442 | -8.335 | -0.563 | 1.00 43.43 |
| ATOM | 83 | C | LEU | 11 | 15.609 | -6.405 | -2.537 | 1.00 38.60 |
| ATOM | 84 | O | LEU | 11 | 15.934 | -7.508 | -2.975 | 1.00 38.62 |

FIG.11A-2

| | | | | | | | | | |
|---|---|---|---|---|---|---|---|---|---|
| ATOM | 85  | N   | VAL | 12 | 16.480 | -5.432  | -2.287 | 1.00 | 41.77 |
| ATOM | 86  | CA  | VAL | 12 | 17.909 | -5.563  | -2.557 | 1.00 | 44.63 |
| ATOM | 87  | CB  | VAL | 12 | 18.555 | -4.169  | -2.720 | 1.00 | 45.32 |
| ATOM | 88  | CG1 | VAL | 12 | 20.017 | -4.310  | -3.124 | 1.00 | 51.19 |
| ATOM | 89  | CG2 | VAL | 12 | 17.788 | -3.365  | -3.757 | 1.00 | 42.65 |
| ATOM | 90  | C   | VAL | 12 | 18.739 | -6.353  | -1.549 | 1.00 | 46.95 |
| ATOM | 91  | O   | VAL | 12 | 19.663 | -7.068  | -1.937 | 1.00 | 47.15 |
| ATOM | 92  | N   | GLN | 13 | 18.431 | -6.223  | -0.262 | 1.00 | 47.33 |
| ATOM | 93  | CA  | GLN | 13 | 19.195 | -6.940  |  0.752 | 1.00 | 47.97 |
| ATOM | 94  | CB  | GLN | 13 | 20.558 | -6.275  |  0.948 | 1.00 | 49.67 |
| ATOM | 95  | CG  | GLN | 13 | 20.482 | -4.801  |  1.303 | 1.00 | 53.58 |
| ATOM | 96  | CD  | GLN | 13 | 21.833 | -4.223  |  1.675 | 1.00 | 55.37 |
| ATOM | 97  | OE1 | GLN | 13 | 22.410 | -4.578  |  2.703 | 1.00 | 56.20 |
| ATOM | 98  | NE2 | GLN | 13 | 22.347 | -3.329  |  0.836 | 1.00 | 58.05 |
| ATOM | 99  | C   | GLN | 13 | 18.505 | -7.055  |  2.104 | 1.00 | 48.35 |
| ATOM | 100 | O   | GLN | 13 | 17.636 | -6.255  |  2.452 | 1.00 | 47.74 |
| ATOM | 101 | N   | THR | 14 | 18.916 | -8.063  |  2.866 | 1.00 | 48.79 |
| ATOM | 102 | CA  | THR | 14 | 18.365 | -8.310  |  4.192 | 1.00 | 49.84 |
| ATOM | 103 | CB  | THR | 14 | 18.497 | -9.795  |  4.575 | 1.00 | 51.16 |
| ATOM | 104 | OG1 | THR | 14 | 18.202 | -9.961  |  5.968 | 1.00 | 53.80 |
| ATOM | 105 | CG2 | THR | 14 | 19.907 | -10.293 |  4.293 | 1.00 | 55.63 |
| ATOM | 106 | C   | THR | 14 | 19.106 | -7.478  |  5.229 | 1.00 | 49.90 |
| ATOM | 107 | O   | THR | 14 | 20.334 | -7.512  |  5.293 | 1.00 | 51.70 |
| ATOM | 108 | N   | LEU | 15 | 18.363 | -6.726  |  6.034 | 1.00 | 48.90 |
| ATOM | 109 | CA  | LEU | 15 | 18.977 | -5.903  |  7.067 | 1.00 | 49.63 |
| ATOM | 110 | CB  | LEU | 15 | 18.139 | -4.650  |  7.344 | 1.00 | 44.87 |
| ATOM | 111 | CG  | LEU | 15 | 17.959 | -3.650  |  6.203 | 1.00 | 39.00 |
| ATOM | 112 | CD1 | LEU | 15 | 19.307 | -3.313  |  5.581 | 1.00 | 32.83 |
| ATOM | 113 | CD2 | LEU | 15 | 17.039 | -4.247  |  5.172 | 1.00 | 41.59 |
| ATOM | 114 | C   | LEU | 15 | 19.120 | -6.706  |  8.349 | 1.00 | 51.59 |
| ATOM | 115 | O   | LEU | 15 | 20.050 | -6.493  |  9.126 | 1.00 | 51.40 |
| ATOM | 116 | N   | GLY | 16 | 18.191 | -7.631  |  8.562 | 1.00 | 53.10 |
| ATOM | 117 | CA  | GLY | 16 | 18.227 | -8.458  |  9.752 | 1.00 | 55.79 |
| ATOM | 118 | C   | GLY | 16 | 17.043 | -9.401  |  9.824 | 1.00 | 58.51 |
| ATOM | 119 | O   | GLY | 16 | 15.909 | -9.008  |  9.550 | 1.00 | 58.89 |
| ATOM | 120 | N   | GLU | 17 | 17.307 | -10.651 | 10.191 | 1.00 | 60.68 |
| ATOM | 121 | CA  | GLU | 17 | 16.257 | -11.655 | 10.301 | 1.00 | 63.27 |
| ATOM | 122 | CB  | GLU | 17 | 16.703 | -12.961 |  9.644 | 1.00 | 67.17 |
| ATOM | 123 | CG  | GLU | 17 | 16.978 | -12.845 |  8.156 | 1.00 | 69.72 |
| ATOM | 124 | CD  | GLU | 17 | 17.430 | -14.155 |  7.548 | 1.00 | 74.27 |
| ATOM | 125 | OE1 | GLU | 17 | 18.488 | -14.672 |  7.965 | 1.00 | 77.30 |
| ATOM | 126 | OE2 | GLU | 17 | 16.727 | -14.670 |  6.653 | 1.00 | 75.48 |

FIG.11A-3

| ATOM | 127 | C   | GLU | 17 | 15.914 | -11.911 | 11.762 | 1.00 | 64.57 |
| ATOM | 128 | O   | GLU | 17 | 16.591 | -12.682 | 12.441 | 1.00 | 63.90 |
| ATOM | 129 | N   | GLY | 18 | 14.859 | -11.258 | 12.238 | 1.00 | 66.47 |
| ATOM | 130 | CA  | GLY | 18 | 14.445 | -11.429 | 13.618 | 1.00 | 66.94 |
| ATOM | 131 | C   | GLY | 18 | 13.834 | -12.793 | 13.870 | 1.00 | 67.94 |
| ATOM | 132 | O   | GLY | 18 | 13.610 | -13.565 | 12.936 | 1.00 | 68.20 |
| ATOM | 133 | N   | ALA | 19 | 13.565 | -13.093 | 15.137 | 1.00 | 68.69 |
| ATOM | 134 | CA  | ALA | 19 | 12.973 | -14.370 | 15.512 | 1.00 | 67.96 |
| ATOM | 135 | CB  | ALA | 19 | 13.110 | -14.586 | 17.015 | 1.00 | 67.41 |
| ATOM | 136 | C   | ALA | 19 | 11.504 | -14.412 | 15.107 | 1.00 | 67.21 |
| ATOM | 137 | O   | ALA | 19 | 10.812 | -15.403 | 15.346 | 1.00 | 67.90 |
| ATOM | 138 | N   | TYR | 20 | 11.035 | -13.330 | 14.493 | 1.00 | 66.16 |
| ATOM | 139 | CA  | TYR | 20 |  9.648 | -13.236 | 14.052 | 1.00 | 65.86 |
| ATOM | 140 | CB  | TYR | 20 |  8.813 | -12.492 | 15.101 | 1.00 | 66.27 |
| ATOM | 141 | CG  | TYR | 20 |  9.495 | -11.278 | 15.697 | 1.00 | 68.01 |
| ATOM | 142 | CD1 | TYR | 20 |  9.896 | -10.210 | 14.894 | 1.00 | 72.07 |
| ATOM | 143 | CE1 | TYR | 20 | 10.528 |  -9.093 | 15.442 | 1.00 | 72.81 |
| ATOM | 144 | CD2 | TYR | 20 |  9.743 | -11.201 | 17.068 | 1.00 | 64.75 |
| ATOM | 145 | CE2 | TYR | 20 | 10.373 | -10.090 | 17.625 | 1.00 | 66.10 |
| ATOM | 146 | CZ  | TYR | 20 | 10.762 |  -9.041 | 16.806 | 1.00 | 71.06 |
| ATOM | 147 | OH  | TYR | 20 | 11.385 |  -7.942 | 17.352 | 1.00 | 74.54 |
| ATOM | 148 | C   | TYR | 20 |  9.522 | -12.549 | 12.693 | 1.00 | 64.83 |
| ATOM | 149 | O   | TYR | 20 |  8.770 | -11.586 | 12.536 | 1.00 | 63.94 |
| ATOM | 150 | N   | GLY | 21 | 10.261 | -13.058 | 11.712 | 1.00 | 63.95 |
| ATOM | 151 | CA  | GLY | 21 | 10.222 | -12.488 | 10.378 | 1.00 | 62.81 |
| ATOM | 152 | C   | GLY | 21 | 11.583 | -12.006 |  9.915 | 1.00 | 61.39 |
| ATOM | 153 | O   | GLY | 21 | 12.616 | -12.527 | 10.341 | 1.00 | 61.10 |
| ATOM | 154 | N   | GLU | 22 | 11.587 | -11.008 |  9.038 | 1.00 | 58.87 |
| ATOM | 155 | CA  | GLU | 22 | 12.831 | -10.455 |  8.518 | 1.00 | 55.14 |
| ATOM | 156 | CB  | GLU | 22 | 13.362 | -11.322 |  7.373 | 1.00 | 58.20 |
| ATOM | 157 | CG  | GLU | 22 | 12.435 | -11.395 |  6.170 | 1.00 | 64.23 |
| ATOM | 158 | CD  | GLU | 22 | 13.021 | -12.200 |  5.027 | 1.00 | 70.83 |
| ATOM | 159 | OE1 | GLU | 22 | 12.352 | -12.322 |  3.979 | 1.00 | 70.63 |
| ATOM | 160 | OE2 | GLU | 22 | 14.152 | -12.711 |  5.174 | 1.00 | 75.29 |
| ATOM | 161 | C   | GLU | 22 | 12.620 |  -9.032 |  8.018 | 1.00 | 49.83 |
| ATOM | 162 | O   | GLU | 22 | 11.492 |  -8.610 |  7.773 | 1.00 | 48.81 |
| ATOM | 163 | N   | VAL | 23 | 13.716 |  -8.296 |  7.875 | 1.00 | 47.61 |
| ATOM | 164 | CA  | VAL | 23 | 13.656 |  -6.925 |  7.393 | 1.00 | 44.26 |
| ATOM | 165 | CB  | VAL | 23 | 14.211 |  -5.937 |  8.441 | 1.00 | 43.86 |
| ATOM | 166 | CG1 | VAL | 23 | 14.076 |  -4.512 |  7.935 | 1.00 | 42.93 |
| ATOM | 167 | CG2 | VAL | 23 | 13.469 |  -6.107 |  9.756 | 1.00 | 40.58 |
| ATOM | 168 | C   | VAL | 23 | 14.479 |  -6.819 |  6.117 | 1.00 | 40.96 |

FIG.11A-4

| ATOM | 169 | O | VAL | 23 | 15.651 | -7.190 | 6.091 | 1.00 | 38.29 |
|---|---|---|---|---|---|---|---|---|---|
| ATOM | 170 | N | GLN | 24 | 13.853 | -6.322 | 5.057 | 1.00 | 40.99 |
| ATOM | 171 | CA | GLN | 24 | 14.518 | -6.172 | 3.770 | 1.00 | 40.30 |
| ATOM | 172 | CB | GLN | 24 | 13.749 | -6.938 | 2.689 | 1.00 | 41.52 |
| ATOM | 173 | CG | GLN | 24 | 13.812 | -8.450 | 2.813 | 1.00 | 47.92 |
| ATOM | 174 | CD | GLN | 24 | 15.194 | -8.999 | 2.527 | 1.00 | 55.67 |
| ATOM | 175 | OE1 | GLN | 24 | 15.789 | -8.701 | 1.490 | 1.00 | 59.08 |
| ATOM | 176 | NE2 | GLN | 24 | 15.712 | -9.810 | 3.442 | 1.00 | 59.81 |
| ATOM | 177 | C | GLN | 24 | 14.634 | -4.711 | 3.353 | 1.00 | 39.30 |
| ATOM | 178 | O | GLN | 24 | 13.757 | -3.896 | 3.643 | 1.00 | 37.62 |
| ATOM | 179 | N | LEU | 25 | 15.733 | -4.387 | 2.680 | 1.00 | 38.08 |
| ATOM | 180 | CA | LEU | 25 | 15.952 | -3.036 | 2.189 | 1.00 | 36.35 |
| ATOM | 181 | CB | LEU | 25 | 17.449 | -2.765 | 2.017 | 1.00 | 33.98 |
| ATOM | 182 | CG | LEU | 25 | 17.903 | -1.405 | 1.474 | 1.00 | 34.17 |
| ATOM | 183 | CD1 | LEU | 25 | 17.676 | -1.327 | -0.018 | 1.00 | 37.28 |
| ATOM | 184 | CD2 | LEU | 25 | 17.159 | -0.293 | 2.191 | 1.00 | 37.37 |
| ATOM | 185 | C | LEU | 25 | 15.245 | -2.983 | 0.843 | 1.00 | 34.98 |
| ATOM | 186 | O | LEU | 25 | 15.589 | -3.731 | -0.072 | 1.00 | 34.14 |
| ATOM | 187 | N | ALA | 26 | 14.249 | -2.111 | 0.733 | 1.00 | 33.58 |
| ATOM | 188 | CA | ALA | 26 | 13.485 | -1.976 | -0.501 | 1.00 | 32.06 |
| ATOM | 189 | CB | ALA | 26 | 11.996 | -2.034 | -0.195 | 1.00 | 31.61 |
| ATOM | 190 | C | ALA | 26 | 13.816 | -0.682 | -1.229 | 1.00 | 30.85 |
| ATOM | 191 | O | ALA | 26 | 13.860 | 0.386 | -0.624 | 1.00 | 30.61 |
| ATOM | 192 | N | VAL | 27 | 14.047 | -0.788 | -2.535 | 1.00 | 29.88 |
| ATOM | 193 | CA | VAL | 27 | 14.366 | 0.373 | -3.353 | 1.00 | 28.11 |
| ATOM | 194 | CB | VAL | 27 | 15.735 | 0.207 | -4.046 | 1.00 | 25.40 |
| ATOM | 195 | CG1 | VAL | 27 | 16.053 | 1.442 | -4.877 | 1.00 | 23.89 |
| ATOM | 196 | CG2 | VAL | 27 | 16.818 | -0.016 | -2.997 | 1.00 | 24.52 |
| ATOM | 197 | C | VAL | 27 | 13.277 | 0.540 | -4.404 | 1.00 | 25.70 |
| ATOM | 198 | O | VAL | 27 | 12.933 | -0.409 | -5.112 | 1.00 | 26.38 |
| ATOM | 199 | N | ASN | 28 | 12.724 | 1.745 | -4.493 | 1.00 | 23.90 |
| ATOM | 200 | CA | ASN | 28 | 11.657 | 2.014 | -5.444 | 1.00 | 23.36 |
| ATOM | 201 | CB | ASN | 28 | 11.047 | 3.391 | -5.185 | 1.00 | 22.07 |
| ATOM | 202 | CG | ASN | 28 | 9.822 | 3.652 | -6.030 | 1.00 | 23.58 |
| ATOM | 203 | OD1 | ASN | 28 | 9.925 | 4.068 | -7.187 | 1.00 | 23.59 |
| ATOM | 204 | ND2 | ASN | 28 | 8.648 | 3.396 | -5.462 | 1.00 | 27.10 |
| ATOM | 205 | C | ASN | 28 | 12.169 | 1.926 | -6.872 | 1.00 | 23.17 |
| ATOM | 206 | O | ASN | 28 | 13.204 | 2.493 | -7.212 | 1.00 | 21.97 |
| ATOM | 207 | N | ARG | 29 | 11.427 | 1.197 | -7.693 | 1.00 | 25.26 |
| ATOM | 208 | CA | ARG | 29 | 11.771 | 0.981 | -9.094 | 1.00 | 25.06 |
| ATOM | 209 | CB | ARG | 29 | 10.695 | 0.099 | -9.728 | 1.00 | 24.87 |
| ATOM | 210 | CG | ARG | 29 | 10.782 | -0.044 | -11.235 | 1.00 | 22.45 |

FIG.11A-5

| | | | | | | | | |
|---|---|---|---|---|---|---|---|---|
| ATOM | 211 | CD | ARG | 29 | 9.652 | -0.930 | -11.737 | 1.00 20.20 |
| ATOM | 212 | NE | ARG | 29 | 9.593 | -0.954 | -13.198 | 1.00 19.85 |
| ATOM | 213 | CZ | ARG | 29 | 8.731 | -1.680 | -13.901 | 1.00 21.65 |
| ATOM | 214 | NH1 | ARG | 29 | 7.847 | -2.449 | -13.281 | 1.00 26.57 |
| ATOM | 215 | NH2 | ARG | 29 | 8.756 | -1.642 | -15.227 | 1.00 23.50 |
| ATOM | 216 | C | ARG | 29 | 11.938 | 2.269 | -9.901 | 1.00 25.06 |
| ATOM | 217 | O | ARG | 29 | 12.784 | 2.347 | -10.799 | 1.00 25.77 |
| ATOM | 218 | N | VAL | 30 | 11.136 | 3.277 | -9.576 | 1.00 23.54 |
| ATOM | 219 | CA | VAL | 30 | 11.178 | 4.548 | -10.291 | 1.00 22.97 |
| ATOM | 220 | CB | VAL | 30 | 9.753 | 5.109 | -10.499 | 1.00 22.15 |
| ATOM | 221 | CG1 | VAL | 30 | 9.824 | 6.517 | -11.081 | 1.00 23.25 |
| ATOM | 222 | CG2 | VAL | 30 | 8.956 | 4.190 | -11.413 | 1.00 20.64 |
| ATOM | 223 | C | VAL | 30 | 12.014 | 5.635 | -9.623 | 1.00 24.22 |
| ATOM | 224 | O | VAL | 30 | 12.907 | 6.210 | -10.244 | 1.00 24.96 |
| ATOM | 225 | N | THR | 31 | 11.724 | 5.915 | -8.355 | 1.00 25.29 |
| ATOM | 226 | CA | THR | 31 | 12.427 | 6.970 | -7.633 | 1.00 25.85 |
| ATOM | 227 | CB | THR | 31 | 11.537 | 7.554 | -6.528 | 1.00 29.34 |
| ATOM | 228 | OG1 | THR | 31 | 11.357 | 6.574 | -5.498 | 1.00 30.34 |
| ATOM | 229 | CG2 | THR | 31 | 10.177 | 7.945 | -7.093 | 1.00 32.37 |
| ATOM | 230 | C | THR | 31 | 13.742 | 6.557 | -6.989 | 1.00 25.05 |
| ATOM | 231 | O | THR | 31 | 14.588 | 7.405 | -6.695 | 1.00 24.93 |
| ATOM | 232 | N | GLU | 32 | 13.901 | 5.256 | -6.771 | 1.00 23.56 |
| ATOM | 233 | CA | GLU | 32 | 15.088 | 4.702 | -6.136 | 1.00 25.89 |
| ATOM | 234 | CB | GLU | 32 | 16.360 | 5.169 | -6.855 | 1.00 31.18 |
| ATOM | 235 | CG | GLU | 32 | 16.441 | 4.626 | -8.275 | 1.00 36.10 |
| ATOM | 236 | CD | GLU | 32 | 17.781 | 4.857 | -8.928 | 1.00 40.49 |
| ATOM | 237 | OE1 | GLU | 32 | 18.800 | 4.385 | -8.381 | 1.00 47.18 |
| ATOM | 238 | OE2 | GLU | 32 | 17.812 | 5.505 | -9.992 | 1.00 34.21 |
| ATOM | 239 | C | GLU | 32 | 15.125 | 5.060 | -4.653 | 1.00 28.39 |
| ATOM | 240 | O | GLU | 32 | 16.155 | 4.935 | -3.992 | 1.00 28.96 |
| ATOM | 241 | N | GLU | 33 | 13.985 | 5.506 | -4.140 | 1.00 29.00 |
| ATOM | 242 | CA | GLU | 33 | 13.876 | 5.833 | -2.722 | 1.00 30.79 |
| ATOM | 243 | CB | GLU | 33 | 12.483 | 6.375 | -2.395 | 1.00 31.20 |
| ATOM | 244 | CG | GLU | 33 | 12.198 | 6.452 | -0.897 | 1.00 47.15 |
| ATOM | 245 | CD | GLU | 33 | 10.798 | 6.945 | -0.577 | 1.00 57.42 |
| ATOM | 246 | OE1 | GLU | 33 | 9.828 | 6.400 | -1.144 | 1.00 63.55 |
| ATOM | 247 | OE2 | GLU | 33 | 10.666 | 7.871 | 0.252 | 1.00 63.48 |
| ATOM | 248 | C | GLU | 33 | 14.101 | 4.527 | -1.971 | 1.00 28.96 |
| ATOM | 249 | O | GLU | 33 | 13.613 | 3.476 | -2.391 | 1.00 28.97 |
| ATOM | 250 | N | ALA | 34 | 14.835 | 4.592 | -0.864 | 1.00 28.98 |
| ATOM | 251 | CA | ALA | 34 | 15.115 | 3.403 | -0.069 | 1.00 29.99 |
| ATOM | 252 | CB | ALA | 34 | 16.607 | 3.314 | 0.234 | 1.00 26.15 |

FIG.11A-6

| ATOM | 253 | C   | ALA | 34 | 14.319 | 3.410   | 1.230  | 1.00 | 32.79 |
| ---- | --- | --- | --- | -- | ------ | ------- | ------ | ---- | ----- |
| ATOM | 254 | O   | ALA | 34 | 14.272 | 4.418   | 1.933  | 1.00 | 34.60 |
| ATOM | 255 | N   | VAL | 35 | 13.685 | 2.281   | 1.530  | 1.00 | 31.99 |
| ATOM | 256 | CA  | VAL | 35 | 12.901 | 2.132   | 2.750  | 1.00 | 32.37 |
| ATOM | 257 | CB  | VAL | 35 | 11.388 | 2.327   | 2.497  | 1.00 | 32.24 |
| ATOM | 258 | CG1 | VAL | 35 | 11.132 | 3.701   | 1.902  | 1.00 | 31.97 |
| ATOM | 259 | CG2 | VAL | 35 | 10.866 | 1.230   | 1.579  | 1.00 | 32.80 |
| ATOM | 260 | C   | VAL | 35 | 13.117 | 0.726   | 3.282  | 1.00 | 33.29 |
| ATOM | 261 | O   | VAL | 35 | 13.609 | -0.149  | 2.564  | 1.00 | 31.06 |
| ATOM | 262 | N   | ALA | 36 | 12.759 | 0.513   | 4.543  | 1.00 | 32.66 |
| ATOM | 263 | CA  | ALA | 36 | 12.902 | -0.797  | 5.152  | 1.00 | 32.39 |
| ATOM | 264 | CB  | ALA | 36 | 13.444 | -0.669  | 6.577  | 1.00 | 30.92 |
| ATOM | 265 | C   | ALA | 36 | 11.535 | -1.462  | 5.166  | 1.00 | 32.53 |
| ATOM | 266 | O   | ALA | 36 | 10.533 | -0.845  | 5.532  | 1.00 | 29.98 |
| ATOM | 267 | N   | VAL | 37 | 11.492 | -2.720  | 4.749  | 1.00 | 34.45 |
| ATOM | 268 | CA  | VAL | 37 | 10.240 | -3.456  | 4.729  | 1.00 | 37.01 |
| ATOM | 269 | CB  | VAL | 37 | 9.919  | -3.981  | 3.316  | 1.00 | 39.07 |
| ATOM | 270 | CG1 | VAL | 37 | 8.660  | -4.841  | 3.352  | 1.00 | 41.91 |
| ATOM | 271 | CG2 | VAL | 37 | 9.729  | -2.810  | 2.366  | 1.00 | 40.40 |
| ATOM | 272 | C   | VAL | 37 | 10.322 | -4.629  | 5.690  | 1.00 | 37.16 |
| ATOM | 273 | O   | VAL | 37 | 11.134 | -5.534  | 5.514  | 1.00 | 36.61 |
| ATOM | 274 | N   | LYS | 38 | 9.485  | -4.592  | 6.720  | 1.00 | 37.96 |
| ATOM | 275 | CA  | LYS | 38 | 9.451  | -5.655  | 7.713  | 1.00 | 39.49 |
| ATOM | 276 | CB  | LYS | 38 | 9.048  | -5.086  | 9.077  | 1.00 | 38.70 |
| ATOM | 277 | CG  | LYS | 38 | 9.168  | -6.066  | 10.236 | 1.00 | 38.05 |
| ATOM | 278 | CD  | LYS | 38 | 8.840  | -5.378  | 11.554 | 1.00 | 40.91 |
| ATOM | 279 | CE  | LYS | 38 | 9.022  | -6.309  | 12.737 | 1.00 | 46.69 |
| ATOM | 280 | NZ  | LYS | 38 | 8.790  | -5.598  | 14.026 | 1.00 | 49.50 |
| ATOM | 281 | C   | LYS | 38 | 8.434  | -6.688  | 7.246  | 1.00 | 40.71 |
| ATOM | 282 | O   | LYS | 38 | 7.253  | -6.379  | 7.084  | 1.00 | 40.05 |
| ATOM | 283 | N   | ILE | 39 | 8.901  | -7.910  | 7.016  | 1.00 | 42.81 |
| ATOM | 284 | CA  | ILE | 39 | 8.030  | -8.983  | 6.553  | 1.00 | 45.99 |
| ATOM | 285 | CB  | ILE | 39 | 8.666  | -9.730  | 5.364  | 1.00 | 45.59 |
| ATOM | 286 | CG2 | ILE | 39 | 7.693  | -10.765 | 4.818  | 1.00 | 46.73 |
| ATOM | 287 | CG1 | ILE | 39 | 9.046  | -8.728  | 4.270  | 1.00 | 44.50 |
| ATOM | 288 | CD1 | ILE | 39 | 9.742  | -9.349  | 3.075  | 1.00 | 49.55 |
| ATOM | 289 | C   | ILE | 39 | 7.753  | -9.977  | 7.675  | 1.00 | 48.22 |
| ATOM | 290 | O   | ILE | 39 | 8.673  | -10.593 | 8.210  | 1.00 | 48.95 |
| ATOM | 291 | N   | VAL | 40 | 6.480  | -10.129 | 8.025  | 1.00 | 50.79 |
| ATOM | 292 | CA  | VAL | 40 | 6.090  | -11.046 | 9.089  | 1.00 | 53.10 |
| ATOM | 293 | CB  | VAL | 40 | 5.604  | -10.275 | 10.336 | 1.00 | 54.79 |
| ATOM | 294 | CG1 | VAL | 40 | 6.752  | -9.471  | 10.927 | 1.00 | 55.17 |

FIG.11A-7

| ATOM | 295 | CG2 | VAL | 40 | 4.453 | -9.352 | 9.963 | 1.00 | 49.52 |
| ATOM | 296 | C | VAL | 40 | 4.995 | -12.016 | 8.656 | 1.00 | 55.18 |
| ATOM | 297 | O | VAL | 40 | 3.925 | -11.608 | 8.206 | 1.00 | 54.97 |
| ATOM | 298 | N | ASP | 41 | 5.277 | -13.307 | 8.801 | 1.00 | 57.61 |
| ATOM | 299 | CA | ASP | 41 | 4.327 | -14.352 | 8.437 | 1.00 | 59.72 |
| ATOM | 300 | CB | ASP | 41 | 5.077 | -15.653 | 8.142 | 1.00 | 63.63 |
| ATOM | 301 | CG | ASP | 41 | 4.183 | -16.719 | 7.545 | 1.00 | 70.52 |
| ATOM | 302 | OD1 | ASP | 41 | 3.141 | -17.036 | 8.157 | 1.00 | 69.83 |
| ATOM | 303 | OD2 | ASP | 41 | 4.525 | -17.244 | 6.465 | 1.00 | 74.90 |
| ATOM | 304 | C | ASP | 41 | 3.352 | -14.561 | 9.595 | 1.00 | 58.84 |
| ATOM | 305 | O | ASP | 41 | 3.675 | -15.233 | 10.575 | 1.00 | 57.65 |
| ATOM | 306 | N | MET | 42 | 2.159 | -13.984 | 9.477 | 1.00 | 59.02 |
| ATOM | 307 | CA | MET | 42 | 1.142 | -14.092 | 10.520 | 1.00 | 60.04 |
| ATOM | 308 | CB | MET | 42 | -0.155 | -13.415 | 10.064 | 1.00 | 59.22 |
| ATOM | 309 | CG | MET | 42 | -0.036 | -11.910 | 9.863 | 1.00 | 60.26 |
| ATOM | 310 | SD | MET | 42 | -1.552 | -11.157 | 9.227 | 1.00 | 69.49 |
| ATOM | 311 | CE | MET | 42 | -2.295 | -10.547 | 10.725 | 1.00 | 66.84 |
| ATOM | 312 | C | MET | 42 | 0.847 | -15.532 | 10.931 | 1.00 | 60.57 |
| ATOM | 313 | O | MET | 42 | 0.297 | -15.774 | 12.006 | 1.00 | 60.43 |
| ATOM | 314 | N | ALA | 43 | 1.216 | -16.483 | 10.078 | 1.00 | 61.75 |
| ATOM | 315 | CA | ALA | 43 | 0.983 | -17.898 | 10.358 | 1.00 | 63.27 |
| ATOM | 316 | CB | ALA | 43 | 0.675 | -18.642 | 9.061 | 1.00 | 64.51 |
| ATOM | 317 | C | ALA | 43 | 2.180 | -18.538 | 11.054 | 1.00 | 63.20 |
| ATOM | 318 | O | ALA | 43 | 2.055 | -19.596 | 11.672 | 1.00 | 64.09 |
| ATOM | 319 | N | ALA | 44 | 3.337 | -17.894 | 10.950 | 1.00 | 62.86 |
| ATOM | 320 | CA | ALA | 44 | 4.555 | -18.404 | 11.568 | 1.00 | 65.57 |
| ATOM | 321 | CB | ALA | 44 | 5.777 | -17.767 | 10.910 | 1.00 | 67.13 |
| ATOM | 322 | C | ALA | 44 | 4.566 | -18.135 | 13.071 | 1.00 | 69.55 |
| ATOM | 323 | O | ALA | 44 | 5.527 | -17.497 | 13.550 | 1.00 | 69.48 |
| ATOM | 324 | OT | ALA | 44 | 3.614 | -18.571 | 13.752 | 1.00 | 73.84 |
| ATOM | 325 | CB | CYS | 48 | 1.032 | -12.998 | 16.789 | 1.00 | 61.49 |
| ATOM | 326 | SG | CYS | 48 | -0.413 | -12.709 | 17.840 | 1.00 | 66.53 |
| ATOM | 327 | C | CYS | 48 | -0.172 | -12.208 | 14.752 | 1.00 | 58.42 |
| ATOM | 328 | O | CYS | 48 | 0.282 | -11.074 | 14.587 | 1.00 | 58.49 |
| ATOM | 329 | N | CYS | 48 | 1.950 | -13.489 | 14.540 | 1.00 | 59.82 |
| ATOM | 330 | CA | CYS | 48 | 0.697 | -13.320 | 15.332 | 1.00 | 59.76 |
| ATOM | 331 | N | PRO | 49 | -1.437 | -12.524 | 14.431 | 1.00 | 57.61 |
| ATOM | 332 | CD | PRO | 49 | -2.015 | -13.880 | 14.439 | 1.00 | 59.35 |
| ATOM | 333 | CA | PRO | 49 | -2.389 | -11.562 | 13.865 | 1.00 | 57.53 |
| ATOM | 334 | CB | PRO | 49 | -3.655 | -12.397 | 13.690 | 1.00 | 58.94 |
| ATOM | 335 | CG | PRO | 49 | -3.112 | -13.762 | 13.407 | 1.00 | 60.96 |
| ATOM | 336 | C | PRO | 49 | -2.625 | -10.340 | 14.749 | 1.00 | 56.62 |

FIG.11A-8

| | | | | | | | | |
|---|---|---|---|---|---|---|---|---|
| ATOM | 337 | O | PRO | 49 | -2.602 | -9.205 | 14.273 | 1.00 56.98 |
| ATOM | 338 | N | GLU | 50 | -2.856 | -10.580 | 16.036 | 1.00 55.89 |
| ATOM | 339 | CA | GLU | 50 | -3.104 | -9.502 | 16.985 | 1.00 54.74 |
| ATOM | 340 | CB | GLU | 50 | -3.627 | -10.072 | 18.306 | 1.00 57.44 |
| ATOM | 341 | CG | GLU | 50 | -3.950 | -9.012 | 19.348 | 1.00 66.02 |
| ATOM | 342 | CD | GLU | 50 | -4.288 | -9.606 | 20.701 | 1.00 72.56 |
| ATOM | 343 | OE1 | GLU | 50 | -3.412 | -10.271 | 21.295 | 1.00 71.89 |
| ATOM | 344 | OE2 | GLU | 50 | -5.428 | -9.410 | 21.171 | 1.00 78.20 |
| ATOM | 345 | C | GLU | 50 | -1.846 | -8.680 | 17.256 | 1.00 51.37 |
| ATOM | 346 | O | GLU | 50 | -1.846 | -7.458 | 17.100 | 1.00 51.31 |
| ATOM | 347 | N | ALA | 51 | -0.779 | -9.359 | 17.666 | 1.00 48.02 |
| ATOM | 348 | CA | ALA | 51 | 0.487 | -8.701 | 17.969 | 1.00 45.05 |
| ATOM | 349 | CB | ALA | 51 | 1.577 | -9.747 | 18.180 | 1.00 42.33 |
| ATOM | 350 | C | ALA | 51 | 0.895 | -7.734 | 16.862 | 1.00 44.76 |
| ATOM | 351 | O | ALA | 51 | 1.156 | -6.558 | 17.116 | 1.00 43.03 |
| ATOM | 352 | N | ILE | 52 | 0.940 | -8.234 | 15.633 | 1.00 44.08 |
| ATOM | 353 | CA | ILE | 52 | 1.318 | -7.409 | 14.494 | 1.00 42.87 |
| ATOM | 354 | CB | ILE | 52 | 1.402 | -8.275 | 13.199 | 1.00 43.74 |
| ATOM | 355 | CG2 | ILE | 52 | 0.009 | -8.542 | 12.651 | 1.00 45.02 |
| ATOM | 356 | CG1 | ILE | 52 | 2.287 | -7.588 | 12.154 | 1.00 46.00 |
| ATOM | 357 | CD1 | ILE | 52 | 1.728 | -6.309 | 11.590 | 1.00 46.21 |
| ATOM | 358 | C | ILE | 52 | 0.309 | -6.267 | 14.321 | 1.00 39.96 |
| ATOM | 359 | O | ILE | 52 | 0.686 | -5.137 | 14.006 | 1.00 38.32 |
| ATOM | 360 | N | LYS | 53 | -0.968 | -6.560 | 14.544 | 1.00 38.61 |
| ATOM | 361 | CA | LYS | 53 | -2.012 | -5.548 | 14.412 | 1.00 38.67 |
| ATOM | 362 | CB | LYS | 53 | -3.394 | -6.176 | 14.612 | 1.00 40.27 |
| ATOM | 363 | CG | LYS | 53 | -4.205 | -6.289 | 13.327 | 1.00 50.21 |
| ATOM | 364 | CD | LYS | 53 | -3.501 | -7.151 | 12.289 | 1.00 54.17 |
| ATOM | 365 | CE | LYS | 53 | -4.213 | -7.088 | 10.948 | 1.00 59.51 |
| ATOM | 366 | NZ | LYS | 53 | -4.230 | -5.702 | 10.405 | 1.00 57.13 |
| ATOM | 367 | C | LYS | 53 | -1.829 | -4.396 | 15.396 | 1.00 37.31 |
| ATOM | 368 | O | LYS | 53 | -2.105 | -3.240 | 15.072 | 1.00 37.14 |
| ATOM | 369 | N | LYS | 54 | -1.370 | -4.712 | 16.602 | 1.00 35.35 |
| ATOM | 370 | CA | LYS | 54 | -1.155 | -3.685 | 17.612 | 1.00 32.72 |
| ATOM | 371 | CB | LYS | 54 | -0.959 | -4.332 | 18.984 | 1.00 32.05 |
| ATOM | 372 | CG | LYS | 54 | -0.850 | -3.344 | 20.138 | 1.00 29.96 |
| ATOM | 373 | CD | LYS | 54 | -0.733 | -4.081 | 21.465 | 1.00 31.32 |
| ATOM | 374 | CE | LYS | 54 | -0.720 | -3.119 | 22.644 | 1.00 32.19 |
| ATOM | 375 | NZ | LYS | 54 | -0.527 | -3.833 | 23.939 | 1.00 32.80 |
| ATOM | 376 | C | LYS | 54 | 0.070 | -2.852 | 17.240 | 1.00 30.86 |
| ATOM | 377 | O | LYS | 54 | 0.086 | -1.636 | 17.432 | 1.00 29.26 |
| ATOM | 378 | N | GLU | 55 | 1.092 | -3.514 | 16.703 | 1.00 30.10 |

FIG.11A-9

| | | | | | | | | | |
|---|---|---|---|---|---|---|---|---|---|
| ATOM | 379 | CA | GLU | 55 | 2.315 | -2.832 | 16.299 | 1.00 | 30.95 |
| ATOM | 380 | CB | GLU | 55 | 3.356 | -3.838 | 15.791 | 1.00 | 28.04 |
| ATOM | 381 | CG | GLU | 55 | 4.719 | -3.209 | 15.511 | 1.00 | 29.66 |
| ATOM | 382 | CD | GLU | 55 | 5.780 | -4.224 | 15.120 | 1.00 | 30.54 |
| ATOM | 383 | OE1 | GLU | 55 | 5.708 | -5.375 | 15.595 | 1.00 | 32.37 |
| ATOM | 384 | OE2 | GLU | 55 | 6.699 | -3.865 | 14.350 | 1.00 | 30.60 |
| ATOM | 385 | C | GLU | 55 | 2.004 | -1.818 | 15.203 | 1.00 | 31.62 |
| ATOM | 386 | O | GLU | 55 | 2.552 | -0.717 | 15.186 | 1.00 | 29.23 |
| ATOM | 387 | N | ILE | 56 | 1.121 | -2.197 | 14.285 | 1.00 | 32.35 |
| ATOM | 388 | CA | ILE | 56 | 0.741 | -1.300 | 13.203 | 1.00 | 31.04 |
| ATOM | 389 | CB | ILE | 56 | -0.135 | -2.018 | 12.151 | 1.00 | 30.54 |
| ATOM | 390 | CG2 | ILE | 56 | -0.659 | -1.014 | 11.138 | 1.00 | 28.78 |
| ATOM | 391 | CG1 | ILE | 56 | 0.678 | -3.108 | 11.454 | 1.00 | 27.54 |
| ATOM | 392 | CD1 | ILE | 56 | -0.104 | -3.863 | 10.397 | 1.00 | 28.92 |
| ATOM | 393 | C | ILE | 56 | -0.047 | -0.134 | 13.785 | 1.00 | 29.35 |
| ATOM | 394 | O | ILE | 56 | 0.185 | 1.022 | 13.432 | 1.00 | 26.97 |
| ATOM | 395 | N | CYS | 57 | -0.974 | -0.443 | 14.686 | 1.00 | 28.75 |
| ATOM | 396 | CA | CYS | 57 | -1.794 | 0.587 | 15.314 | 1.00 | 30.06 |
| ATOM | 397 | CB | CYS | 57 | -2.728 | -0.030 | 16.359 | 1.00 | 32.53 |
| ATOM | 398 | SG | CYS | 57 | -3.764 | 1.186 | 17.224 | 1.00 | 42.92 |
| ATOM | 399 | C | CYS | 57 | -0.907 | 1.630 | 15.986 | 1.00 | 27.01 |
| ATOM | 400 | O | CYS | 57 | -1.043 | 2.825 | 15.742 | 1.00 | 27.89 |
| ATOM | 401 | N | ILE | 58 | -0.001 | 1.166 | 16.838 | 1.00 | 23.73 |
| ATOM | 402 | CA | ILE | 58 | 0.896 | 2.076 | 17.538 | 1.00 | 24.79 |
| ATOM | 403 | CB | ILE | 58 | 1.810 | 1.305 | 18.522 | 1.00 | 29.75 |
| ATOM | 404 | CG2 | ILE | 58 | 2.934 | 2.212 | 19.039 | 1.00 | 23.87 |
| ATOM | 405 | CG1 | ILE | 58 | 0.968 | 0.787 | 19.691 | 1.00 | 28.05 |
| ATOM | 406 | CD1 | ILE | 58 | 1.773 | 0.086 | 20.780 | 1.00 | 29.21 |
| ATOM | 407 | C | ILE | 58 | 1.735 | 2.871 | 16.545 | 1.00 | 23.36 |
| ATOM | 408 | O | ILE | 58 | 1.910 | 4.077 | 16.703 | 1.00 | 23.90 |
| ATOM | 409 | N | ASN | 59 | 2.237 | 2.204 | 15.509 | 1.00 | 23.80 |
| ATOM | 410 | CA | ASN | 59 | 3.046 | 2.882 | 14.498 | 1.00 | 25.17 |
| ATOM | 411 | CB | ASN | 59 | 3.547 | 1.873 | 13.461 | 1.00 | 28.55 |
| ATOM | 412 | CG | ASN | 59 | 4.951 | 1.372 | 13.764 | 1.00 | 31.94 |
| ATOM | 413 | OD1 | ASN | 59 | 5.929 | 2.102 | 13.598 | 1.00 | 32.03 |
| ATOM | 414 | ND2 | ASN | 59 | 5.055 | 0.129 | 14.218 | 1.00 | 27.23 |
| ATOM | 415 | C | ASN | 59 | 2.302 | 4.023 | 13.801 | 1.00 | 26.97 |
| ATOM | 416 | O | ASN | 59 | 2.900 | 5.045 | 13.457 | 1.00 | 24.75 |
| ATOM | 417 | N | LYS | 60 | 0.999 | 3.856 | 13.595 | 1.00 | 28.98 |
| ATOM | 418 | CA | LYS | 60 | 0.207 | 4.892 | 12.936 | 1.00 | 30.49 |
| ATOM | 419 | CB | LYS | 60 | -1.205 | 4.376 | 12.635 | 1.00 | 33.22 |
| ATOM | 420 | CG | LYS | 60 | -1.254 | 3.289 | 11.574 | 1.00 | 39.31 |

FIG.11A-10

| | | | | | | | | |
|---|---|---|---|---|---|---|---|---|
| ATOM | 421 | CD | LYS | 60 | -2.689 | 2.881 | 11.275 | 1.00 50.07 |
| ATOM | 422 | CE | LYS | 60 | -2.751 | 1.811 | 10.199 | 1.00 63.36 |
| ATOM | 423 | NZ | LYS | 60 | -4.156 | 1.431 | 9.879 | 1.00 70.80 |
| ATOM | 424 | C | LYS | 60 | 0.112 | 6.167 | 13.769 | 1.00 30.79 |
| ATOM | 425 | O | LYS | 60 | -0.255 | 7.225 | 13.261 | 1.00 32.02 |
| ATOM | 426 | N | MET | 61 | 0.453 | 6.067 | 15.049 | 1.00 29.22 |
| ATOM | 427 | CA | MET | 61 | 0.402 | 7.214 | 15.948 | 1.00 28.15 |
| ATOM | 428 | CB | MET | 61 | 0.133 | 6.752 | 17.383 | 1.00 26.84 |
| ATOM | 429 | CG | MET | 61 | -1.123 | 5.934 | 17.601 | 1.00 33.92 |
| ATOM | 430 | SD | MET | 61 | -1.086 | 5.213 | 19.267 | 1.00 36.19 |
| ATOM | 431 | CE | MET | 61 | -1.338 | 6.689 | 20.282 | 1.00 35.78 |
| ATOM | 432 | C | MET | 61 | 1.719 | 7.982 | 15.969 | 1.00 27.73 |
| ATOM | 433 | O | MET | 61 | 1.773 | 9.126 | 16.419 | 1.00 30.14 |
| ATOM | 434 | N | LEU | 62 | 2.772 | 7.346 | 15.474 | 1.00 26.12 |
| ATOM | 435 | CA | LEU | 62 | 4.112 | 7.921 | 15.516 | 1.00 25.23 |
| ATOM | 436 | CB | LEU | 62 | 5.129 | 6.786 | 15.574 | 1.00 24.11 |
| ATOM | 437 | CG | LEU | 62 | 4.747 | 5.617 | 16.481 | 1.00 22.84 |
| ATOM | 438 | CD1 | LEU | 62 | 5.836 | 4.560 | 16.419 | 1.00 23.66 |
| ATOM | 439 | CD2 | LEU | 62 | 4.531 | 6.119 | 17.905 | 1.00 26.09 |
| ATOM | 440 | C | LEU | 62 | 4.546 | 8.901 | 14.438 | 1.00 26.40 |
| ATOM | 441 | O | LEU | 62 | 4.434 | 8.629 | 13.244 | 1.00 27.81 |
| ATOM | 442 | N | ASN | 63 | 5.060 | 10.044 | 14.883 | 1.00 25.22 |
| ATOM | 443 | CA | ASN | 63 | 5.576 | 11.064 | 13.981 | 1.00 24.06 |
| ATOM | 444 | CB | ASN | 63 | 4.438 | 11.900 | 13.388 | 1.00 28.33 |
| ATOM | 445 | CG | ASN | 63 | 4.938 | 12.925 | 12.399 | 1.00 31.22 |
| ATOM | 446 | OD1 | ASN | 63 | 5.933 | 12.696 | 11.711 | 1.00 34.87 |
| ATOM | 447 | ND2 | ASN | 63 | 4.249 | 14.058 | 12.310 | 1.00 31.84 |
| ATOM | 448 | C | ASN | 63 | 6.564 | 11.961 | 14.716 | 1.00 21.00 |
| ATOM | 449 | O | ASN | 63 | 6.202 | 13.010 | 15.240 | 1.00 20.80 |
| ATOM | 450 | N | HIS | 64 | 7.818 | 11.525 | 14.759 | 1.00 20.38 |
| ATOM | 451 | CA | HIS | 64 | 8.869 | 12.279 | 15.433 | 1.00 20.84 |
| ATOM | 452 | CB | HIS | 64 | 8.896 | 11.911 | 16.923 | 1.00 20.13 |
| ATOM | 453 | CG | HIS | 64 | 9.818 | 12.764 | 17.733 | 1.00 18.13 |
| ATOM | 454 | CD2 | HIS | 64 | 9.601 | 13.929 | 18.387 | 1.00 15.83 |
| ATOM | 455 | ND1 | HIS | 64 | 11.158 | 12.479 | 17.888 | 1.00 15.42 |
| ATOM | 456 | CE1 | HIS | 64 | 11.726 | 13.433 | 18.602 | 1.00 16.82 |
| ATOM | 457 | NE2 | HIS | 64 | 10.804 | 14.324 | 18.917 | 1.00 17.85 |
| ATOM | 458 | C | HIS | 64 | 10.221 | 11.983 | 14.786 | 1.00 19.49 |
| ATOM | 459 | O | HIS | 64 | 10.475 | 10.863 | 14.351 | 1.00 19.75 |
| ATOM | 460 | N | GLU | 65 | 11.094 | 12.985 | 14.733 | 1.00 21.02 |
| ATOM | 461 | CA | GLU | 65 | 12.397 | 12.816 | 14.100 | 1.00 21.68 |
| ATOM | 462 | CB | GLU | 65 | 13.124 | 14.163 | 14.000 | 1.00 24.01 |

FIG.11A-11

| | | | | | | | | | |
|---|---|---|---|---|---|---|---|---|---|
| ATOM | 463 | CG | GLU | 65 | 13.445 | 14.843 | 15.322 | 1.00 | 33.53 |
| ATOM | 464 | CD | GLU | 65 | 12.284 | 15.643 | 15.885 | 1.00 | 41.84 |
| ATOM | 465 | OE1 | GLU | 65 | 12.503 | 16.371 | 16.878 | 1.00 | 47.89 |
| ATOM | 466 | OE2 | GLU | 65 | 11.158 | 15.548 | 15.346 | 1.00 | 41.02 |
| ATOM | 467 | C | GLU | 65 | 13.323 | 11.781 | 14.733 | 1.00 | 22.44 |
| ATOM | 468 | O | GLU | 65 | 14.288 | 11.347 | 14.100 | 1.00 | 21.52 |
| ATOM | 469 | N | ASN | 66 | 13.038 | 11.380 | 15.972 | 1.00 | 21.25 |
| ATOM | 470 | CA | ASN | 66 | 13.873 | 10.383 | 16.636 | 1.00 | 20.43 |
| ATOM | 471 | CB | ASN | 66 | 14.389 | 10.926 | 17.970 | 1.00 | 18.34 |
| ATOM | 472 | CG | ASN | 66 | 15.360 | 12.089 | 17.790 | 1.00 | 18.97 |
| ATOM | 473 | OD1 | ASN | 66 | 15.096 | 13.205 | 18.234 | 1.00 | 19.31 |
| ATOM | 474 | ND2 | ASN | 66 | 16.487 | 11.827 | 17.137 | 1.00 | 19.95 |
| ATOM | 475 | C | ASN | 66 | 13.136 | 9.055 | 16.841 | 1.00 | 20.35 |
| ATOM | 476 | O | ASN | 66 | 13.463 | 8.278 | 17.739 | 1.00 | 18.70 |
| ATOM | 477 | N | VAL | 67 | 12.146 | 8.807 | 15.983 | 1.00 | 19.53 |
| ATOM | 478 | CA | VAL | 67 | 11.356 | 7.582 | 16.010 | 1.00 | 20.23 |
| ATOM | 479 | CB | VAL | 67 | 9.935 | 7.840 | 16.586 | 1.00 | 19.48 |
| ATOM | 480 | CG1 | VAL | 67 | 9.074 | 6.589 | 16.470 | 1.00 | 17.62 |
| ATOM | 481 | CG2 | VAL | 67 | 10.037 | 8.274 | 18.046 | 1.00 | 19.56 |
| ATOM | 482 | C | VAL | 67 | 11.231 | 7.090 | 14.566 | 1.00 | 20.28 |
| ATOM | 483 | O | VAL | 67 | 10.872 | 7.862 | 13.680 | 1.00 | 18.26 |
| ATOM | 484 | N | VAL | 68 | 11.541 | 5.818 | 14.333 | 1.00 | 19.74 |
| ATOM | 485 | CA | VAL | 68 | 11.449 | 5.247 | 12.991 | 1.00 | 20.39 |
| ATOM | 486 | CB | VAL | 68 | 11.694 | 3.710 | 13.015 | 1.00 | 18.90 |
| ATOM | 487 | CG1 | VAL | 68 | 11.334 | 3.093 | 11.665 | 1.00 | 18.65 |
| ATOM | 488 | CG2 | VAL | 68 | 13.155 | 3.420 | 13.327 | 1.00 | 16.32 |
| ATOM | 489 | C | VAL | 68 | 10.074 | 5.542 | 12.393 | 1.00 | 22.68 |
| ATOM | 490 | O | VAL | 68 | 9.046 | 5.217 | 12.986 | 1.00 | 22.91 |
| ATOM | 491 | N | LYS | 69 | 10.068 | 6.172 | 11.221 | 1.00 | 24.55 |
| ATOM | 492 | CA | LYS | 69 | 8.833 | 6.528 | 10.530 | 1.00 | 26.28 |
| ATOM | 493 | CB | LYS | 69 | 9.129 | 7.465 | 9.353 | 1.00 | 31.62 |
| ATOM | 494 | CG | LYS | 69 | 8.623 | 8.889 | 9.512 | 1.00 | 44.19 |
| ATOM | 495 | CD | LYS | 69 | 9.589 | 9.741 | 10.314 | 1.00 | 51.62 |
| ATOM | 496 | CE | LYS | 69 | 9.187 | 11.207 | 10.281 | 1.00 | 51.35 |
| ATOM | 497 | NZ | LYS | 69 | 10.241 | 12.081 | 10.865 | 1.00 | 48.96 |
| ATOM | 498 | C | LYS | 69 | 8.103 | 5.310 | 9.990 | 1.00 | 24.58 |
| ATOM | 499 | O | LYS | 69 | 8.729 | 4.348 | 9.539 | 1.00 | 25.04 |
| ATOM | 500 | N | PHE | 70 | 6.776 | 5.368 | 10.040 | 1.00 | 25.47 |
| ATOM | 501 | CA | PHE | 70 | 5.915 | 4.307 | 9.527 | 1.00 | 26.89 |
| ATOM | 502 | CB | PHE | 70 | 4.824 | 3.961 | 10.545 | 1.00 | 29.09 |
| ATOM | 503 | CG | PHE | 70 | 3.841 | 2.928 | 10.060 | 1.00 | 27.43 |
| ATOM | 504 | CD1 | PHE | 70 | 4.248 | 1.621 | 9.808 | 1.00 | 28.02 |

FIG.11A-12

| | | | | | | | | |
|---|---|---|---|---|---|---|---|---|
| ATOM | 505 | CD2 | PHE | 70 | 2.504 | 3.263 | 9.865 | 1.00 30.32 |
| ATOM | 506 | CE1 | PHE | 70 | 3.337 | 0.659 | 9.372 | 1.00 31.52 |
| ATOM | 507 | CE2 | PHE | 70 | 1.583 | 2.310 | 9.429 | 1.00 29.79 |
| ATOM | 508 | CZ | PHE | 70 | 1.999 | 1.006 | 9.182 | 1.00 30.08 |
| ATOM | 509 | C | PHE | 70 | 5.271 | 4.874 | 8.263 | 1.00 28.21 |
| ATOM | 510 | O | PHE | 70 | 4.564 | 5.880 | 8.318 | 1.00 28.68 |
| ATOM | 511 | N | TYR | 71 | 5.522 | 4.240 | 7.124 | 1.00 29.81 |
| ATOM | 512 | CA | TYR | 71 | 4.959 | 4.718 | 5.870 | 1.00 31.13 |
| ATOM | 513 | CB | TYR | 71 | 5.954 | 4.500 | 4.732 | 1.00 24.91 |
| ATOM | 514 | CG | TYR | 71 | 7.285 | 5.182 | 4.927 | 1.00 25.81 |
| ATOM | 515 | CD1 | TYR | 71 | 7.369 | 6.566 | 5.078 | 1.00 28.78 |
| ATOM | 516 | CE1 | TYR | 71 | 8.604 | 7.199 | 5.220 | 1.00 27.30 |
| ATOM | 517 | CD2 | TYR | 71 | 8.465 | 4.449 | 4.926 | 1.00 26.54 |
| ATOM | 518 | CE2 | TYR | 71 | 9.699 | 5.069 | 5.065 | 1.00 24.23 |
| ATOM | 519 | CZ | TYR | 71 | 9.763 | 6.442 | 5.209 | 1.00 23.46 |
| ATOM | 520 | OH | TYR | 71 | 10.991 | 7.056 | 5.330 | 1.00 29.32 |
| ATOM | 521 | C | TYR | 71 | 3.634 | 4.049 | 5.520 | 1.00 34.42 |
| ATOM | 522 | O | TYR | 71 | 2.842 | 4.596 | 4.753 | 1.00 36.42 |
| ATOM | 523 | N | GLY | 72 | 3.397 | 2.865 | 6.076 | 1.00 34.34 |
| ATOM | 524 | CA | GLY | 72 | 2.163 | 2.149 | 5.801 | 1.00 33.61 |
| ATOM | 525 | C | GLY | 72 | 2.392 | 0.653 | 5.757 | 1.00 34.42 |
| ATOM | 526 | O | GLY | 72 | 3.511 | 0.191 | 5.972 | 1.00 34.69 |
| ATOM | 527 | N | HIS | 73 | 1.341 | -0.111 | 5.475 | 1.00 37.74 |
| ATOM | 528 | CA | HIS | 73 | 1.463 | -1.564 | 5.413 | 1.00 40.55 |
| ATOM | 529 | CB | HIS | 73 | 1.102 | -2.174 | 6.769 | 1.00 39.94 |
| ATOM | 530 | CG | HIS | 73 | -0.340 | -2.012 | 7.141 | 1.00 41.03 |
| ATOM | 531 | CD2 | HIS | 73 | -1.017 | -0.953 | 7.642 | 1.00 38.25 |
| ATOM | 532 | ND1 | HIS | 73 | -1.265 | -3.021 | 6.986 | 1.00 42.56 |
| ATOM | 533 | CE1 | HIS | 73 | -2.452 | -2.591 | 7.377 | 1.00 39.22 |
| ATOM | 534 | NE2 | HIS | 73 | -2.329 | -1.338 | 7.779 | 1.00 37.48 |
| ATOM | 535 | C | HIS | 73 | 0.576 | -2.164 | 4.325 | 1.00 42.07 |
| ATOM | 536 | O | HIS | 73 | -0.407 | -1.553 | 3.907 | 1.00 40.35 |
| ATOM | 537 | N | ARG | 74 | 0.933 | -3.363 | 3.875 | 1.00 45.26 |
| ATOM | 538 | CA | ARG | 74 | 0.176 | -4.056 | 2.837 | 1.00 50.38 |
| ATOM | 539 | CB | ARG | 74 | 1.022 | -4.169 | 1.567 | 1.00 55.88 |
| ATOM | 540 | CG | ARG | 74 | 1.382 | -2.819 | 0.963 | 1.00 63.87 |
| ATOM | 541 | CD | ARG | 74 | 2.373 | -2.946 | -0.184 | 1.00 70.66 |
| ATOM | 542 | NE | ARG | 74 | 1.861 | -3.752 | -1.288 | 1.00 72.42 |
| ATOM | 543 | CZ | ARG | 74 | 2.485 | -3.897 | -2.453 | 1.00 73.76 |
| ATOM | 544 | NH1 | ARG | 74 | 3.645 | -3.289 | -2.667 | 1.00 64.85 |
| ATOM | 545 | NH2 | ARG | 74 | 1.951 | -4.650 | -3.406 | 1.00 78.24 |
| ATOM | 546 | C | ARG | 74 | -0.262 | -5.444 | 3.302 | 1.00 52.53 |

FIG.11A-13

| | | | | | | | | |
|---|---|---|---|---|---|---|---|---|
| ATOM | 547 | O | ARG | 74 | 0.550 | -6.237 | 3.785 | 1.00 50.95 |
| ATOM | 548 | N | ARG | 75 | -1.554 | -5.725 | 3.148 | 1.00 56.77 |
| ATOM | 549 | CA | ARG | 75 | -2.138 | -7.002 | 3.550 | 1.00 61.66 |
| ATOM | 550 | CB | ARG | 75 | -3.617 | -7.046 | 3.150 | 1.00 66.26 |
| ATOM | 551 | CG | ARG | 75 | -4.406 | -5.800 | 3.536 | 1.00 70.07 |
| ATOM | 552 | CD | ARG | 75 | -4.471 | -5.610 | 5.043 | 1.00 75.18 |
| ATOM | 553 | NE | ARG | 75 | -5.229 | -6.674 | 5.697 | 1.00 79.27 |
| ATOM | 554 | CZ | ARG | 75 | -5.442 | -6.742 | 7.007 | 1.00 81.70 |
| ATOM | 555 | NH1 | ARG | 75 | -4.953 | -5.806 | 7.810 | 1.00 80.67 |
| ATOM | 556 | NH2 | ARG | 75 | -6.147 | -7.744 | 7.514 | 1.00 80.01 |
| ATOM | 557 | C | ARG | 75 | -1.404 | -8.183 | 2.917 | 1.00 62.81 |
| ATOM | 558 | O | ARG | 75 | -0.570 | -8.821 | 3.557 | 1.00 62.78 |
| ATOM | 559 | N | GLU | 76 | -1.730 | -8.470 | 1.661 | 1.00 62.55 |
| ATOM | 560 | CA | GLU | 76 | -1.109 | -9.565 | 0.920 | 1.00 62.56 |
| ATOM | 561 | CB | GLU | 76 | 0.399 | -9.332 | 0.799 | 1.00 62.91 |
| ATOM | 562 | CG | GLU | 76 | 1.081 | -10.208 | -0.240 | 1.00 67.69 |
| ATOM | 563 | CD | GLU | 76 | 0.711 | -9.820 | -1.659 | 1.00 71.31 |
| ATOM | 564 | OE1 | GLU | 76 | 1.016 | -8.676 | -2.058 | 1.00 70.71 |
| ATOM | 565 | OE2 | GLU | 76 | 0.116 | -10.653 | -2.374 | 1.00 73.78 |
| ATOM | 566 | C | GLU | 76 | -1.361 | -10.931 | 1.561 | 1.00 62.35 |
| ATOM | 567 | O | GLU | 76 | -0.420 | -11.663 | 1.874 | 1.00 62.16 |
| ATOM | 568 | N | GLY | 77 | -2.632 | -11.270 | 1.751 | 1.00 61.81 |
| ATOM | 569 | CA | GLY | 77 | -2.978 | -12.551 | 2.343 | 1.00 60.86 |
| ATOM | 570 | C | GLY | 77 | -2.625 | -12.690 | 3.814 | 1.00 60.50 |
| ATOM | 571 | O | GLY | 77 | -3.260 | -12.078 | 4.673 | 1.00 60.41 |
| ATOM | 572 | N | ASN | 78 | -1.612 | -13.501 | 4.103 | 1.00 59.52 |
| ATOM | 573 | CA | ASN | 78 | -1.174 | -13.732 | 5.477 | 1.00 59.24 |
| ATOM | 574 | CB | ASN | 78 | -1.096 | -15.236 | 5.756 | 1.00 62.54 |
| ATOM | 575 | CG | ASN | 78 | -2.448 | -15.914 | 5.672 | 1.00 69.02 |
| ATOM | 576 | OD1 | ASN | 78 | -3.145 | -15.815 | 4.661 | 1.00 71.32 |
| ATOM | 577 | ND2 | ASN | 78 | -2.826 | -16.613 | 6.736 | 1.00 72.20 |
| ATOM | 578 | C | ASN | 78 | 0.182 | -13.096 | 5.770 | 1.00 57.34 |
| ATOM | 579 | O | ASN | 78 | 0.632 | -13.079 | 6.916 | 1.00 56.95 |
| ATOM | 580 | N | ILE | 79 | 0.831 | -12.579 | 4.732 | 1.00 55.93 |
| ATOM | 581 | CA | ILE | 79 | 2.136 | -11.947 | 4.889 | 1.00 54.66 |
| ATOM | 582 | CB | ILE | 79 | 3.065 | -12.281 | 3.700 | 1.00 54.22 |
| ATOM | 583 | CG2 | ILE | 79 | 4.399 | -11.570 | 3.864 | 1.00 53.56 |
| ATOM | 584 | CG1 | ILE | 79 | 3.273 | -13.795 | 3.607 | 1.00 52.83 |
| ATOM | 585 | CD1 | ILE | 79 | 3.890 | -14.415 | 4.846 | 1.00 50.48 |
| ATOM | 586 | C | ILE | 79 | 2.005 | -10.433 | 4.991 | 1.00 52.67 |
| ATOM | 587 | O | ILE | 79 | 1.668 | -9.767 | 4.012 | 1.00 50.87 |
| ATOM | 588 | N | GLN | 80 | 2.272 | -9.895 | 6.180 | 1.00 50.66 |

FIG.11A-14

| | | | | | | | | |
|---|---|---|---|---|---|---|---|---|
| ATOM | 589 | CA | GLN | 80 | 2.191 | -8.455 | 6.408 | 1.00 48.22 |
| ATOM | 590 | CB | GLN | 80 | 1.944 | -8.158 | 7.891 | 1.00 50.12 |
| ATOM | 591 | CG | GLN | 80 | 0.521 | -8.399 | 8.362 | 1.00 48.27 |
| ATOM | 592 | CD | GLN | 80 | -0.494 | -7.572 | 7.594 | 1.00 49.09 |
| ATOM | 593 | OE1 | GLN | 80 | -0.372 | -6.351 | 7.493 | 1.00 45.08 |
| ATOM | 594 | NE2 | GLN | 80 | -1.506 | -8.237 | 7.049 | 1.00 58.25 |
| ATOM | 595 | C | GLN | 80 | 3.469 | -7.750 | 5.966 | 1.00 46.07 |
| ATOM | 596 | O | GLN | 80 | 4.572 | -8.222 | 6.238 | 1.00 45.36 |
| ATOM | 597 | N | TYR | 81 | 3.307 | -6.618 | 5.288 | 1.00 45.11 |
| ATOM | 598 | CA | TYR | 81 | 4.436 | -5.829 | 4.805 | 1.00 43.61 |
| ATOM | 599 | CB | TYR | 81 | 4.385 | -5.706 | 3.280 | 1.00 42.41 |
| ATOM | 600 | CG | TYR | 81 | 4.641 | -7.001 | 2.545 | 1.00 43.09 |
| ATOM | 601 | CD1 | TYR | 81 | 5.918 | -7.559 | 2.504 | 1.00 40.63 |
| ATOM | 602 | CE1 | TYR | 81 | 6.157 | -8.756 | 1.834 | 1.00 45.03 |
| ATOM | 603 | CD2 | TYR | 81 | 3.606 | -7.672 | 1.896 | 1.00 41.43 |
| ATOM | 604 | CE2 | TYR | 81 | 3.835 | -8.870 | 1.225 | 1.00 44.97 |
| ATOM | 605 | CZ | TYR | 81 | 5.111 | -9.405 | 1.197 | 1.00 46.87 |
| ATOM | 606 | OH | TYR | 81 | 5.339 | -10.589 | 0.534 | 1.00 49.59 |
| ATOM | 607 | C | TYR | 81 | 4.409 | -4.433 | 5.419 | 1.00 42.40 |
| ATOM | 608 | O | TYR | 81 | 3.585 | -3.602 | 5.042 | 1.00 43.43 |
| ATOM | 609 | N | LEU | 82 | 5.309 | -4.178 | 6.365 | 1.00 39.70 |
| ATOM | 610 | CA | LEU | 82 | 5.372 | -2.874 | 7.010 | 1.00 37.19 |
| ATOM | 611 | CB | LEU | 82 | 5.616 | -3.028 | 8.517 | 1.00 39.36 |
| ATOM | 612 | CG | LEU | 82 | 4.579 | -3.785 | 9.358 | 1.00 38.76 |
| ATOM | 613 | CD1 | LEU | 82 | 4.968 | -3.697 | 10.827 | 1.00 32.68 |
| ATOM | 614 | CD2 | LEU | 82 | 3.199 | -3.191 | 9.155 | 1.00 39.92 |
| ATOM | 615 | C | LEU | 82 | 6.485 | -2.030 | 6.397 | 1.00 34.17 |
| ATOM | 616 | O | LEU | 82 | 7.659 | -2.406 | 6.445 | 1.00 32.38 |
| ATOM | 617 | N | PHE | 83 | 6.112 | -0.892 | 5.820 | 1.00 33.55 |
| ATOM | 618 | CA | PHE | 83 | 7.083 | 0.008 | 5.209 | 1.00 31.38 |
| ATOM | 619 | CB | PHE | 83 | 6.464 | 0.728 | 4.011 | 1.00 36.90 |
| ATOM | 620 | CG | PHE | 83 | 6.209 | -0.173 | 2.833 | 1.00 40.96 |
| ATOM | 621 | CD1 | PHE | 83 | 5.310 | -1.231 | 2.930 | 1.00 42.10 |
| ATOM | 622 | CD2 | PHE | 83 | 6.885 | 0.024 | 1.633 | 1.00 41.38 |
| ATOM | 623 | CE1 | PHE | 83 | 5.088 | -2.084 | 1.848 | 1.00 41.93 |
| ATOM | 624 | CE2 | PHE | 83 | 6.671 | -0.823 | 0.543 | 1.00 40.00 |
| ATOM | 625 | CZ | PHE | 83 | 5.770 | -1.879 | 0.652 | 1.00 39.51 |
| ATOM | 626 | C | PHE | 83 | 7.552 | 1.012 | 6.251 | 1.00 28.18 |
| ATOM | 627 | O | PHE | 83 | 6.797 | 1.892 | 6.676 | 1.00 24.97 |
| ATOM | 628 | N | LEU | 84 | 8.810 | 0.869 | 6.647 | 1.00 27.73 |
| ATOM | 629 | CA | LEU | 84 | 9.408 | 1.715 | 7.670 | 1.00 27.95 |
| ATOM | 630 | CB | LEU | 84 | 9.837 | 0.837 | 8.846 | 1.00 28.57 |

FIG.11-A15

| ATOM | 631 | CG | LEU | 84 | 8.720 | -0.038 | 9.430 | 1.00 | 24.56 |
| --- | --- | --- | --- | --- | --- | --- | --- | --- | --- |
| ATOM | 632 | CD1 | LEU | 84 | 9.313 | -1.254 | 10.122 | 1.00 | 21.64 |
| ATOM | 633 | CD2 | LEU | 84 | 7.874 | 0.787 | 10.386 | 1.00 | 24.46 |
| ATOM | 634 | C | LEU | 84 | 10.604 | 2.508 | 7.164 | 1.00 | 28.88 |
| ATOM | 635 | O | LEU | 84 | 11.204 | 2.184 | 6.138 | 1.00 | 28.67 |
| ATOM | 636 | N | GLU | 85 | 10.949 | 3.551 | 7.908 | 1.00 | 28.76 |
| ATOM | 637 | CA | GLU | 85 | 12.072 | 4.404 | 7.564 | 1.00 | 28.20 |
| ATOM | 638 | CB | GLU | 85 | 12.170 | 5.544 | 8.579 | 1.00 | 29.51 |
| ATOM | 639 | CG | GLU | 85 | 13.371 | 6.450 | 8.406 | 1.00 | 34.24 |
| ATOM | 640 | CD | GLU | 85 | 13.405 | 7.556 | 9.443 | 1.00 | 36.83 |
| ATOM | 641 | OE1 | GLU | 85 | 14.354 | 8.367 | 9.418 | 1.00 | 36.87 |
| ATOM | 642 | OE2 | GLU | 85 | 12.478 | 7.613 | 10.280 | 1.00 | 30.28 |
| ATOM | 643 | C | GLU | 85 | 13.367 | 3.599 | 7.551 | 1.00 | 27.67 |
| ATOM | 644 | O | GLU | 85 | 13.645 | 2.832 | 8.475 | 1.00 | 28.74 |
| ATOM | 645 | N | TYR | 86 | 14.150 | 3.760 | 6.492 | 1.00 | 24.64 |
| ATOM | 646 | CA | TYR | 86 | 15.421 | 3.059 | 6.378 | 1.00 | 23.98 |
| ATOM | 647 | CB | TYR | 86 | 15.793 | 2.870 | 4.901 | 1.00 | 24.65 |
| ATOM | 648 | CG | TYR | 86 | 17.208 | 2.376 | 4.671 | 1.00 | 25.72 |
| ATOM | 649 | CD1 | TYR | 86 | 17.652 | 1.177 | 5.229 | 1.00 | 22.83 |
| ATOM | 650 | CE1 | TYR | 86 | 18.954 | 0.719 | 5.014 | 1.00 | 20.99 |
| ATOM | 651 | CD2 | TYR | 86 | 18.103 | 3.108 | 3.888 | 1.00 | 24.91 |
| ATOM | 652 | CE2 | TYR | 86 | 19.404 | 2.659 | 3.668 | 1.00 | 25.43 |
| ATOM | 653 | CZ | TYR | 86 | 19.822 | 1.466 | 4.234 | 1.00 | 24.00 |
| ATOM | 654 | OH | TYR | 86 | 21.110 | 1.021 | 4.030 | 1.00 | 31.37 |
| ATOM | 655 | C | TYR | 86 | 16.499 | 3.879 | 7.081 | 1.00 | 24.51 |
| ATOM | 656 | O | TYR | 86 | 16.644 | 5.075 | 6.828 | 1.00 | 25.53 |
| ATOM | 657 | N | CYS | 87 | 17.241 | 3.236 | 7.974 | 1.00 | 23.81 |
| ATOM | 658 | CA | CYS | 87 | 18.303 | 3.914 | 8.714 | 1.00 | 24.33 |
| ATOM | 659 | CB | CYS | 87 | 18.059 | 3.747 | 10.218 | 1.00 | 21.77 |
| ATOM | 660 | SG | CYS | 87 | 16.439 | 4.374 | 10.742 | 1.00 | 22.54 |
| ATOM | 661 | C | CYS | 87 | 19.637 | 3.310 | 8.287 | 1.00 | 22.59 |
| ATOM | 662 | O | CYS | 87 | 20.090 | 2.310 | 8.840 | 1.00 | 22.98 |
| ATOM | 663 | N | SER | 88 | 20.263 | 3.935 | 7.291 | 1.00 | 22.63 |
| ATOM | 664 | CA | SER | 88 | 21.519 | 3.452 | 6.729 | 1.00 | 23.13 |
| ATOM | 665 | CB | SER | 88 | 21.869 | 4.258 | 5.470 | 1.00 | 23.11 |
| ATOM | 666 | OG | SER | 88 | 22.008 | 5.641 | 5.750 | 1.00 | 27.21 |
| ATOM | 667 | C | SER | 88 | 22.727 | 3.412 | 7.656 | 1.00 | 24.35 |
| ATOM | 668 | O | SER | 88 | 23.746 | 2.808 | 7.318 | 1.00 | 26.40 |
| ATOM | 669 | N | GLY | 89 | 22.618 | 4.049 | 8.818 | 1.00 | 23.40 |
| ATOM | 670 | CA | GLY | 89 | 23.720 | 4.053 | 9.764 | 1.00 | 21.46 |
| ATOM | 671 | C | GLY | 89 | 23.777 | 2.793 | 10.613 | 1.00 | 21.62 |
| ATOM | 672 | O | GLY | 89 | 24.747 | 2.566 | 11.336 | 1.00 | 23.85 |

FIG.11A-16

| ATOM | 673 | N | GLY | 90 | 22.736 | 1.974 | 10.523 | 1.00 | 19.99 |
| ATOM | 674 | CA | GLY | 90 | 22.700 | 0.733 | 11.275 | 1.00 | 19.98 |
| ATOM | 675 | C | GLY | 90 | 22.263 | 0.895 | 12.723 | 1.00 | 19.03 |
| ATOM | 676 | O | GLY | 90 | 21.563 | 1.845 | 13.066 | 1.00 | 19.39 |
| ATOM | 677 | N | GLU | 91 | 22.689 | -0.036 | 13.569 | 1.00 | 20.36 |
| ATOM | 678 | CA | GLU | 91 | 22.325 | -0.017 | 14.983 | 1.00 | 20.23 |
| ATOM | 679 | CB | GLU | 91 | 22.202 | -1.439 | 15.522 | 1.00 | 21.22 |
| ATOM | 680 | CG | GLU | 91 | 21.218 | -2.329 | 14.792 | 1.00 | 23.61 |
| ATOM | 681 | CD | GLU | 91 | 21.215 | -3.743 | 15.342 | 1.00 | 23.88 |
| ATOM | 682 | OE1 | GLU | 91 | 20.492 | -4.594 | 14.784 | 1.00 | 29.99 |
| ATOM | 683 | OE2 | GLU | 91 | 21.934 | -4.000 | 16.334 | 1.00 | 22.19 |
| ATOM | 684 | C | GLU | 91 | 23.334 | 0.721 | 15.846 | 1.00 | 20.72 |
| ATOM | 685 | O | GLU | 91 | 24.526 | 0.739 | 15.556 | 1.00 | 20.19 |
| ATOM | 686 | N | LEU | 92 | 22.847 | 1.311 | 16.932 | 1.00 | 19.98 |
| ATOM | 687 | CA | LEU | 92 | 23.712 | 2.020 | 17.864 | 1.00 | 19.39 |
| ATOM | 688 | CB | LEU | 92 | 22.868 | 2.671 | 18.963 | 1.00 | 18.03 |
| ATOM | 689 | CG | LEU | 92 | 23.616 | 3.333 | 20.122 | 1.00 | 19.18 |
| ATOM | 690 | CD1 | LEU | 92 | 24.427 | 4.513 | 19.612 | 1.00 | 22.62 |
| ATOM | 691 | CD2 | LEU | 92 | 22.596 | 3.783 | 21.176 | 1.00 | 16.79 |
| ATOM | 692 | C | LEU | 92 | 24.641 | 0.989 | 18.480 | 1.00 | 19.97 |
| ATOM | 693 | O | LEU | 92 | 25.781 | 1.284 | 18.834 | 1.00 | 19.58 |
| ATOM | 694 | N | PHE | 93 | 24.134 | -0.232 | 18.599 | 1.00 | 20.27 |
| ATOM | 695 | CA | PHE | 93 | 24.895 | -1.322 | 19.178 | 1.00 | 21.88 |
| ATOM | 696 | CB | PHE | 93 | 24.099 | -2.628 | 19.058 | 1.00 | 26.11 |
| ATOM | 697 | CG | PHE | 93 | 24.813 | -3.834 | 19.611 | 1.00 | 28.84 |
| ATOM | 698 | CD1 | PHE | 93 | 25.734 | -4.533 | 18.836 | 1.00 | 29.47 |
| ATOM | 699 | CD2 | PHE | 93 | 24.561 | -4.274 | 20.907 | 1.00 | 31.53 |
| ATOM | 700 | CE1 | PHE | 93 | 26.393 | -5.656 | 19.344 | 1.00 | 30.19 |
| ATOM | 701 | CE2 | PHE | 93 | 25.216 | -5.397 | 21.425 | 1.00 | 36.41 |
| ATOM | 702 | CZ | PHE | 93 | 26.132 | -6.088 | 20.641 | 1.00 | 30.51 |
| ATOM | 703 | C | PHE | 93 | 26.245 | -1.458 | 18.481 | 1.00 | 21.58 |
| ATOM | 704 | O | PHE | 93 | 27.270 | -1.675 | 19.130 | 1.00 | 20.32 |
| ATOM | 705 | N | ASP | 94 | 26.245 | -1.300 | 17.161 | 1.00 | 23.68 |
| ATOM | 706 | CA | ASP | 94 | 27.474 | -1.429 | 16.379 | 1.00 | 25.61 |
| ATOM | 707 | CB | ASP | 94 | 27.118 | -1.757 | 14.925 | 1.00 | 30.05 |
| ATOM | 708 | CG | ASP | 94 | 26.495 | -3.138 | 14.782 | 1.00 | 31.43 |
| ATOM | 709 | OD1 | ASP | 94 | 25.725 | -3.361 | 13.827 | 1.00 | 33.18 |
| ATOM | 710 | OD2 | ASP | 94 | 26.783 | -4.011 | 15.628 | 1.00 | 34.06 |
| ATOM | 711 | C | ASP | 94 | 28.423 | -0.232 | 16.451 | 1.00 | 24.95 |
| ATOM | 712 | O | ASP | 94 | 29.501 | -0.257 | 15.860 | 1.00 | 27.73 |
| ATOM | 713 | N | ARG | 95 | 28.035 | 0.801 | 17.194 | 1.00 | 23.99 |
| ATOM | 714 | CA | ARG | 95 | 28.870 | 1.991 | 17.363 | 1.00 | 23.16 |

FIG.11A-17

| ATOM | 715 | CB | ARG | 95 | 28.008 | 3.255 | 17.263 | 1.00 | 24.65 |
| ATOM | 716 | CG | ARG | 95 | 27.399 | 3.479 | 15.888 | 1.00 | 29.91 |
| ATOM | 717 | CD | ARG | 95 | 28.488 | 3.806 | 14.875 | 1.00 | 39.68 |
| ATOM | 718 | NE | ARG | 95 | 29.148 | 5.055 | 15.241 | 1.00 | 47.46 |
| ATOM | 719 | CZ | ARG | 95 | 28.687 | 6.262 | 14.929 | 1.00 | 46.44 |
| ATOM | 720 | NH1 | ARG | 95 | 27.568 | 6.386 | 14.227 | 1.00 | 39.38 |
| ATOM | 721 | NH2 | ARG | 95 | 29.325 | 7.346 | 15.353 | 1.00 | 42.03 |
| ATOM | 722 | C | ARG | 95 | 29.557 | 1.935 | 18.727 | 1.00 | 22.01 |
| ATOM | 723 | O | ARG | 95 | 30.340 | 2.819 | 19.090 | 1.00 | 21.05 |
| ATOM | 724 | N | ILE | 96 | 29.246 | 0.885 | 19.482 | 1.00 | 22.78 |
| ATOM | 725 | CA | ILE | 96 | 29.811 | 0.680 | 20.806 | 1.00 | 22.43 |
| ATOM | 726 | CB | ILE | 96 | 28.735 | 0.146 | 21.776 | 1.00 | 20.79 |
| ATOM | 727 | CG2 | ILE | 96 | 29.332 | -0.066 | 23.160 | 1.00 | 20.67 |
| ATOM | 728 | CG1 | ILE | 96 | 27.578 | 1.146 | 21.845 | 1.00 | 18.29 |
| ATOM | 729 | CD1 | ILE | 96 | 26.357 | 0.640 | 22.590 | 1.00 | 18.91 |
| ATOM | 730 | C | ILE | 96 | 30.963 | -0.315 | 20.732 | 1.00 | 24.50 |
| ATOM | 731 | O | ILE | 96 | 30.769 | -1.469 | 20.360 | 1.00 | 25.11 |
| ATOM | 732 | N | GLU | 97 | 32.162 | 0.136 | 21.076 | 1.00 | 24.39 |
| ATOM | 733 | CA | GLU | 97 | 33.318 | -0.751 | 21.038 | 1.00 | 26.52 |
| ATOM | 734 | CB | GLU | 97 | 34.605 | 0.055 | 20.849 | 1.00 | 30.76 |
| ATOM | 735 | CG | GLU | 97 | 34.830 | 0.623 | 19.444 | 1.00 | 46.58 |
| ATOM | 736 | CD | GLU | 97 | 33.846 | 1.719 | 19.056 | 1.00 | 53.97 |
| ATOM | 737 | OE1 | GLU | 97 | 33.759 | 2.740 | 19.776 | 1.00 | 50.74 |
| ATOM | 738 | OE2 | GLU | 97 | 33.165 | 1.561 | 18.019 | 1.00 | 58.08 |
| ATOM | 739 | C | GLU | 97 | 33.383 | -1.570 | 22.325 | 1.00 | 24.68 |
| ATOM | 740 | O | GLU | 97 | 33.415 | -1.020 | 23.424 | 1.00 | 23.06 |
| ATOM | 741 | N | PRO | 98 | 33.395 | -2.906 | 22.207 | 1.00 | 24.21 |
| ATOM | 742 | CD | PRO | 98 | 33.233 | -3.720 | 20.987 | 1.00 | 24.02 |
| ATOM | 743 | CA | PRO | 98 | 33.454 | -3.764 | 23.392 | 1.00 | 23.90 |
| ATOM | 744 | CB | PRO | 98 | 33.695 | -5.147 | 22.792 | 1.00 | 23.15 |
| ATOM | 745 | CG | PRO | 98 | 32.877 | -5.090 | 21.560 | 1.00 | 21.24 |
| ATOM | 746 | C | PRO | 98 | 34.510 | -3.366 | 24.421 | 1.00 | 24.35 |
| ATOM | 747 | O | PRO | 98 | 35.675 | -3.130 | 24.089 | 1.00 | 25.72 |
| ATOM | 748 | N | ASP | 99 | 34.071 | -3.280 | 25.673 | 1.00 | 23.80 |
| ATOM | 749 | CA | ASP | 99 | 34.919 | -2.918 | 26.797 | 1.00 | 25.53 |
| ATOM | 750 | CB | ASP | 99 | 36.119 | -3.870 | 26.892 | 1.00 | 36.73 |
| ATOM | 751 | CG | ASP | 99 | 35.726 | -5.255 | 27.365 | 1.00 | 47.74 |
| ATOM | 752 | OD1 | ASP | 99 | 35.109 | -6.005 | 26.579 | 1.00 | 56.16 |
| ATOM | 753 | OD2 | ASP | 99 | 36.030 | -5.590 | 28.531 | 1.00 | 54.00 |
| ATOM | 754 | C | ASP | 99 | 35.430 | -1.482 | 26.826 | 1.00 | 24.62 |
| ATOM | 755 | O | ASP | 99 | 36.168 | -1.119 | 27.741 | 1.00 | 26.81 |
| ATOM | 756 | N | ILE | 100 | 35.066 | -0.662 | 25.841 | 1.00 | 23.29 |

FIG.11-A18

| | | | | | | | | |
|---|---|---|---|---|---|---|---|---|
| ATOM | 757 | CA  | ILE | 100 | 35.532 | 0.721  | 25.862 | 1.00 23.28 |
| ATOM | 758 | CB  | ILE | 100 | 36.625 | 1.000  | 24.786 | 1.00 28.85 |
| ATOM | 759 | CG2 | ILE | 100 | 37.699 | -0.076 | 24.842 | 1.00 30.41 |
| ATOM | 760 | CG1 | ILE | 100 | 36.017 | 1.042  | 23.393 | 1.00 37.12 |
| ATOM | 761 | CD1 | ILE | 100 | 37.017 | 1.438  | 22.311 | 1.00 50.18 |
| ATOM | 762 | C   | ILE | 100 | 34.403 | 1.737  | 25.699 | 1.00 20.45 |
| ATOM | 763 | O   | ILE | 100 | 34.413 | 2.771  | 26.354 | 1.00 20.39 |
| ATOM | 764 | N   | GLY | 101 | 33.447 | 1.445  | 24.823 | 1.00 19.63 |
| ATOM | 765 | CA  | GLY | 101 | 32.334 | 2.355  | 24.610 | 1.00 19.62 |
| ATOM | 766 | C   | GLY | 101 | 32.521 | 3.227  | 23.384 | 1.00 18.97 |
| ATOM | 767 | O   | GLY | 101 | 32.745 | 2.721  | 22.285 | 1.00 19.10 |
| ATOM | 768 | N   | MET | 102 | 32.410 | 4.539  | 23.570 | 1.00 18.46 |
| ATOM | 769 | CA  | MET | 102 | 32.583 | 5.506  | 22.486 | 1.00 17.81 |
| ATOM | 770 | CB  | MET | 102 | 31.291 | 5.655  | 21.676 | 1.00 19.03 |
| ATOM | 771 | CG  | MET | 102 | 30.170 | 6.358  | 22.449 | 1.00 19.18 |
| ATOM | 772 | SD  | MET | 102 | 28.677 | 6.592  | 21.435 | 1.00 16.18 |
| ATOM | 773 | CE  | MET | 102 | 28.107 | 4.874  | 21.273 | 1.00 15.36 |
| ATOM | 774 | C   | MET | 102 | 32.931 | 6.853  | 23.120 | 1.00 18.77 |
| ATOM | 775 | O   | MET | 102 | 32.784 | 7.028  | 24.331 | 1.00 19.16 |
| ATOM | 776 | N   | PRO | 103 | 33.403 | 7.821  | 22.317 | 1.00 18.19 |
| ATOM | 777 | CD  | PRO | 103 | 33.736 | 7.749  | 20.882 | 1.00 16.39 |
| ATOM | 778 | CA  | PRO | 103 | 33.749 | 9.138  | 22.863 | 1.00 18.51 |
| ATOM | 779 | CB  | PRO | 103 | 34.109 | 9.940  | 21.619 | 1.00 17.03 |
| ATOM | 780 | CG  | PRO | 103 | 34.696 | 8.903  | 20.725 | 1.00 15.88 |
| ATOM | 781 | C   | PRO | 103 | 32.562 | 9.741  | 23.614 | 1.00 19.83 |
| ATOM | 782 | O   | PRO | 103 | 31.437 | 9.710  | 23.126 | 1.00 19.36 |
| ATOM | 783 | N   | GLU | 104 | 32.823 | 10.290 | 24.794 | 1.00 18.81 |
| ATOM | 784 | CA  | GLU | 104 | 31.771 | 10.873 | 25.617 | 1.00 19.36 |
| ATOM | 785 | CB  | GLU | 104 | 32.386 | 11.511 | 26.864 | 1.00 17.66 |
| ATOM | 786 | CG  | GLU | 104 | 31.406 | 11.735 | 27.996 | 1.00 16.18 |
| ATOM | 787 | CD  | GLU | 104 | 32.058 | 12.320 | 29.231 | 1.00 21.03 |
| ATOM | 788 | OE1 | GLU | 104 | 31.679 | 13.448 | 29.619 | 1.00 21.27 |
| ATOM | 789 | OE2 | GLU | 104 | 32.946 | 11.657 | 29.819 | 1.00 19.74 |
| ATOM | 790 | C   | GLU | 104 | 30.871 | 11.880 | 24.898 | 1.00 19.92 |
| ATOM | 791 | O   | GLU | 104 | 29.653 | 11.886 | 25.105 | 1.00 19.71 |
| ATOM | 792 | N   | PRO | 105 | 31.448 | 12.748 | 24.049 | 1.00 20.08 |
| ATOM | 793 | CD  | PRO | 105 | 32.877 | 13.000 | 23.789 | 1.00 20.80 |
| ATOM | 794 | CA  | PRO | 105 | 30.607 | 13.723 | 23.342 | 1.00 16.33 |
| ATOM | 795 | CB  | PRO | 105 | 31.621 | 14.529 | 22.530 | 1.00 16.90 |
| ATOM | 796 | CG  | PRO | 105 | 32.875 | 14.459 | 23.403 | 1.00 16.88 |
| ATOM | 797 | C   | PRO | 105 | 29.572 | 13.017 | 22.452 | 1.00 16.27 |
| ATOM | 798 | O   | PRO | 105 | 28.424 | 13.452 | 22.344 | 1.00 17.44 |

FIG.11A-19

| ATOM | 799 | N   | ASP | 106 | 29.995 | 11.934 | 21.809 | 1.00 | 15.51 |
| ATOM | 800 | CA  | ASP | 106 | 29.119 | 11.153 | 20.938 | 1.00 | 17.98 |
| ATOM | 801 | CB  | ASP | 106 | 29.906 | 10.029 | 20.264 | 1.00 | 20.63 |
| ATOM | 802 | CG  | ASP | 106 | 30.890 | 10.530 | 19.224 | 1.00 | 26.04 |
| ATOM | 803 | OD1 | ASP | 106 | 31.277 | 11.712 | 19.273 | 1.00 | 27.36 |
| ATOM | 804 | OD2 | ASP | 106 | 31.290 | 9.721  | 18.364 | 1.00 | 31.22 |
| ATOM | 805 | C   | ASP | 106 | 28.001 | 10.522 | 21.771 | 1.00 | 15.08 |
| ATOM | 806 | O   | ASP | 106 | 26.829 | 10.515 | 21.375 | 1.00 | 16.13 |
| ATOM | 807 | N   | ALA | 107 | 28.371 | 9.980  | 22.925 | 1.00 | 14.46 |
| ATOM | 808 | CA  | ALA | 107 | 27.392 | 9.348  | 23.802 | 1.00 | 16.06 |
| ATOM | 809 | CB  | ALA | 107 | 28.095 | 8.697  | 24.989 | 1.00 | 14.46 |
| ATOM | 810 | C   | ALA | 107 | 26.363 | 10.373 | 24.288 | 1.00 | 15.73 |
| ATOM | 811 | O   | ALA | 107 | 25.163 | 10.077 | 24.372 | 1.00 | 15.16 |
| ATOM | 812 | N   | GLN | 108 | 26.828 | 11.577 | 24.603 | 1.00 | 14.18 |
| ATOM | 813 | CA  | GLN | 108 | 25.932 | 12.630 | 25.075 | 1.00 | 14.33 |
| ATOM | 814 | CB  | GLN | 108 | 26.722 | 13.874 | 25.492 | 1.00 | 17.52 |
| ATOM | 815 | CG  | GLN | 108 | 25.868 | 14.876 | 26.277 | 1.00 | 16.31 |
| ATOM | 816 | CD  | GLN | 108 | 26.454 | 16.283 | 26.303 | 1.00 | 18.32 |
| ATOM | 817 | OE1 | GLN | 108 | 26.514 | 16.924 | 27.358 | 1.00 | 20.27 |
| ATOM | 818 | NE2 | GLN | 108 | 26.859 | 16.777 | 25.145 | 1.00 | 12.37 |
| ATOM | 819 | C   | GLN | 108 | 24.927 | 13.029 | 23.997 | 1.00 | 15.75 |
| ATOM | 820 | O   | GLN | 108 | 23.745 | 13.212 | 24.286 | 1.00 | 14.23 |
| ATOM | 821 | N   | ARG | 109 | 25.402 | 13.185 | 22.761 | 1.00 | 15.23 |
| ATOM | 822 | CA  | ARG | 109 | 24.526 | 13.555 | 21.649 | 1.00 | 13.42 |
| ATOM | 823 | CB  | ARG | 109 | 25.356 | 13.754 | 20.373 | 1.00 | 13.79 |
| ATOM | 824 | CG  | ARG | 109 | 24.552 | 14.236 | 19.160 | 1.00 | 17.49 |
| ATOM | 825 | CD  | ARG | 109 | 25.408 | 14.272 | 17.902 | 1.00 | 23.46 |
| ATOM | 826 | NE  | ARG | 109 | 25.536 | 12.928 | 17.355 | 1.00 | 31.04 |
| ATOM | 827 | CZ  | ARG | 109 | 24.873 | 12.482 | 16.294 | 1.00 | 23.24 |
| ATOM | 828 | NH1 | ARG | 109 | 24.035 | 13.274 | 15.636 | 1.00 | 27.75 |
| ATOM | 829 | NH2 | ARG | 109 | 25.034 | 11.227 | 15.910 | 1.00 | 29.28 |
| ATOM | 830 | C   | ARG | 109 | 23.473 | 12.458 | 21.422 | 1.00 | 12.94 |
| ATOM | 831 | O   | ARG | 109 | 22.285 | 12.746 | 21.243 | 1.00 | 14.78 |
| ATOM | 832 | N   | PHE | 110 | 23.904 | 11.199 | 21.424 | 1.00 | 11.75 |
| ATOM | 833 | CA  | PHE | 110 | 22.963 | 10.099 | 21.218 | 1.00 | 11.64 |
| ATOM | 834 | CB  | PHE | 110 | 23.681 | 8.752  | 21.151 | 1.00 | 11.80 |
| ATOM | 835 | CG  | PHE | 110 | 24.421 | 8.513  | 19.868 | 1.00 | 16.38 |
| ATOM | 836 | CD1 | PHE | 110 | 23.818 | 8.763  | 18.633 | 1.00 | 18.08 |
| ATOM | 837 | CD2 | PHE | 110 | 25.714 | 8.003  | 19.894 | 1.00 | 15.97 |
| ATOM | 838 | CE1 | PHE | 110 | 24.502 | 8.505  | 17.436 | 1.00 | 18.38 |
| ATOM | 839 | CE2 | PHE | 110 | 26.401 | 7.741  | 18.713 | 1.00 | 16.67 |
| ATOM | 840 | CZ  | PHE | 110 | 25.798 | 7.991  | 17.481 | 1.00 | 14.35 |

FIG.11A-20

| | | | | | | | | |
|---|---|---|---|---|---|---|---|---|
| ATOM | 841 | C | PHE | 110 | 21.962 | 10.059 | 22.366 | 1.00 12.75 |
| ATOM | 842 | O | PHE | 110 | 20.777 | 9.777 | 22.155 | 1.00 13.13 |
| ATOM | 843 | N | PHE | 111 | 22.435 | 10.339 | 23.579 | 1.00 12.26 |
| ATOM | 844 | CA | PHE | 111 | 21.554 | 10.325 | 24.743 | 1.00 14.38 |
| ATOM | 845 | CB | PHE | 111 | 22.367 | 10.450 | 26.039 | 1.00 15.94 |
| ATOM | 846 | CG | PHE | 111 | 21.565 | 10.174 | 27.273 | 1.00 13.02 |
| ATOM | 847 | CD1 | PHE | 111 | 21.146 | 8.877 | 27.566 | 1.00 12.96 |
| ATOM | 848 | CD2 | PHE | 111 | 21.183 | 11.212 | 28.119 | 1.00 9.52 |
| ATOM | 849 | CE1 | PHE | 111 | 20.354 | 8.617 | 28.683 | 1.00 10.93 |
| ATOM | 850 | CE2 | PHE | 111 | 20.391 | 10.969 | 29.239 | 1.00 9.75 |
| ATOM | 851 | CZ | PHE | 111 | 19.971 | 9.662 | 29.523 | 1.00 9.91 |
| ATOM | 852 | C | PHE | 111 | 20.519 | 11.454 | 24.655 | 1.00 12.76 |
| ATOM | 853 | O | PHE | 111 | 19.366 | 11.278 | 25.035 | 1.00 13.45 |
| ATOM | 854 | N | HIS | 112 | 20.938 | 12.608 | 24.144 | 1.00 13.86 |
| ATOM | 855 | CA | HIS | 112 | 20.027 | 13.742 | 23.970 | 1.00 14.60 |
| ATOM | 856 | CB | HIS | 112 | 20.760 | 14.924 | 23.331 | 1.00 15.24 |
| ATOM | 857 | CG | HIS | 112 | 21.699 | 15.642 | 24.249 | 1.00 15.45 |
| ATOM | 858 | CD2 | HIS | 112 | 21.734 | 15.739 | 25.599 | 1.00 17.90 |
| ATOM | 859 | ND1 | HIS | 112 | 22.718 | 16.444 | 23.779 | 1.00 17.44 |
| ATOM | 860 | CE1 | HIS | 112 | 23.336 | 17.009 | 24.802 | 1.00 15.77 |
| ATOM | 861 | NE2 | HIS | 112 | 22.757 | 16.598 | 25.918 | 1.00 22.23 |
| ATOM | 862 | C | HIS | 112 | 18.903 | 13.339 | 23.019 | 1.00 15.61 |
| ATOM | 863 | O | HIS | 112 | 17.726 | 13.619 | 23.263 | 1.00 16.06 |
| ATOM | 864 | N | GLN | 113 | 19.276 | 12.699 | 21.915 | 1.00 14.44 |
| ATOM | 865 | CA | GLN | 113 | 18.294 | 12.283 | 20.925 | 1.00 14.83 |
| ATOM | 866 | CB | GLN | 113 | 18.998 | 11.869 | 19.635 | 1.00 12.67 |
| ATOM | 867 | CG | GLN | 113 | 19.743 | 13.047 | 19.012 | 1.00 12.96 |
| ATOM | 868 | CD | GLN | 113 | 20.508 | 12.662 | 17.764 | 1.00 22.01 |
| ATOM | 869 | OE1 | GLN | 113 | 20.468 | 11.514 | 17.327 | 1.00 25.13 |
| ATOM | 870 | NE2 | GLN | 113 | 21.218 | 13.625 | 17.186 | 1.00 21.52 |
| ATOM | 871 | C | GLN | 113 | 17.406 | 11.170 | 21.450 | 1.00 14.34 |
| ATOM | 872 | O | GLN | 113 | 16.218 | 11.124 | 21.140 | 1.00 13.52 |
| ATOM | 873 | N | LEU | 114 | 17.970 | 10.294 | 22.273 | 1.00 14.36 |
| ATOM | 874 | CA | LEU | 114 | 17.177 | 9.217 | 22.863 | 1.00 13.96 |
| ATOM | 875 | CB | LEU | 114 | 18.075 | 8.287 | 23.683 | 1.00 13.60 |
| ATOM | 876 | CG | LEU | 114 | 17.404 | 7.167 | 24.485 | 1.00 14.47 |
| ATOM | 877 | CD1 | LEU | 114 | 16.559 | 6.292 | 23.575 | 1.00 12.86 |
| ATOM | 878 | CD2 | LEU | 114 | 18.491 | 6.320 | 25.175 | 1.00 11.34 |
| ATOM | 879 | C | LEU | 114 | 16.109 | 9.848 | 23.775 | 1.00 13.12 |
| ATOM | 880 | O | LEU | 114 | 14.925 | 9.483 | 23.730 | 1.00 12.42 |
| ATOM | 881 | N | MET | 115 | 16.521 | 10.806 | 24.597 | 1.00 13.13 |
| ATOM | 882 | CA | MET | 115 | 15.568 | 11.476 | 25.486 | 1.00 14.41 |

FIG.11A-21

| ATOM | 883 | CB  | MET | 115 | 16.274 | 12.516 | 26.367 | 1.00 | 13.67 |
| ATOM | 884 | CG  | MET | 115 | 17.130 | 11.938 | 27.481 | 1.00 | 16.47 |
| ATOM | 885 | SD  | MET | 115 | 16.170 | 10.931 | 28.639 | 1.00 | 16.82 |
| ATOM | 886 | CE  | MET | 115 | 16.565 | 9.273  | 27.955 | 1.00 | 11.48 |
| ATOM | 887 | C   | MET | 115 | 14.467 | 12.175 | 24.685 | 1.00 | 14.97 |
| ATOM | 888 | O   | MET | 115 | 13.297 | 12.136 | 25.059 | 1.00 | 15.73 |
| ATOM | 889 | N   | ALA | 116 | 14.842 | 12.819 | 23.585 | 1.00 | 16.10 |
| ATOM | 890 | CA  | ALA | 116 | 13.859 | 13.509 | 22.752 | 1.00 | 15.36 |
| ATOM | 891 | CB  | ALA | 116 | 14.551 | 14.203 | 21.581 | 1.00 | 14.43 |
| ATOM | 892 | C   | ALA | 116 | 12.818 | 12.508 | 22.244 | 1.00 | 15.44 |
| ATOM | 893 | O   | ALA | 116 | 11.617 | 12.785 | 22.269 | 1.00 | 17.74 |
| ATOM | 894 | N   | GLY | 117 | 13.286 | 11.342 | 21.815 | 1.00 | 13.85 |
| ATOM | 895 | CA  | GLY | 117 | 12.379 | 10.322 | 21.312 | 1.00 | 13.18 |
| ATOM | 896 | C   | GLY | 117 | 11.490 | 9.760  | 22.406 | 1.00 | 13.23 |
| ATOM | 897 | O   | GLY | 117 | 10.294 | 9.563  | 22.204 | 1.00 | 15.51 |
| ATOM | 898 | N   | VAL | 118 | 12.068 | 9.484  | 23.571 | 1.00 | 13.22 |
| ATOM | 899 | CA  | VAL | 118 | 11.275 | 8.944  | 24.669 | 1.00 | 13.42 |
| ATOM | 900 | CB  | VAL | 118 | 12.184 | 8.412  | 25.790 | 1.00 | 12.92 |
| ATOM | 901 | CG1 | VAL | 118 | 11.343 | 7.955  | 26.981 | 1.00 | 12.41 |
| ATOM | 902 | CG2 | VAL | 118 | 12.999 | 7.250  | 25.256 | 1.00 | 11.09 |
| ATOM | 903 | C   | VAL | 118 | 10.277 | 9.964  | 25.228 | 1.00 | 14.91 |
| ATOM | 904 | O   | VAL | 118 | 9.150  | 9.598  | 25.581 | 1.00 | 15.74 |
| ATOM | 905 | N   | VAL | 119 | 10.677 | 11.230 | 25.320 | 1.00 | 15.14 |
| ATOM | 906 | CA  | VAL | 119 | 9.764  | 12.274 | 25.809 | 1.00 | 15.80 |
| ATOM | 907 | CB  | VAL | 119 | 10.428 | 13.682 | 25.807 | 1.00 | 15.22 |
| ATOM | 908 | CG1 | VAL | 119 | 9.360  | 14.777 | 25.915 | 1.00 | 16.36 |
| ATOM | 909 | CG2 | VAL | 119 | 11.383 | 13.805 | 26.988 | 1.00 | 10.99 |
| ATOM | 910 | C   | VAL | 119 | 8.549  | 12.318 | 24.889 | 1.00 | 15.40 |
| ATOM | 911 | O   | VAL | 119 | 7.401  | 12.462 | 25.341 | 1.00 | 16.23 |
| ATOM | 912 | N   | TYR | 120 | 8.809  | 12.196 | 23.596 | 1.00 | 13.60 |
| ATOM | 913 | CA  | TYR | 120 | 7.737  | 12.226 | 22.610 | 1.00 | 15.80 |
| ATOM | 914 | CB  | TYR | 120 | 8.321  | 12.168 | 21.201 | 1.00 | 14.64 |
| ATOM | 915 | CG  | TYR | 120 | 7.266  | 11.942 | 20.151 | 1.00 | 16.47 |
| ATOM | 916 | CD1 | TYR | 120 | 6.407  | 12.969 | 19.774 | 1.00 | 17.46 |
| ATOM | 917 | CE1 | TYR | 120 | 5.373  | 12.742 | 18.861 | 1.00 | 16.07 |
| ATOM | 918 | CD2 | TYR | 120 | 7.080  | 10.685 | 19.593 | 1.00 | 14.78 |
| ATOM | 919 | CE2 | TYR | 120 | 6.055  | 10.448 | 18.679 | 1.00 | 21.86 |
| ATOM | 920 | CZ  | TYR | 120 | 5.205  | 11.482 | 18.321 | 1.00 | 23.00 |
| ATOM | 921 | OH  | TYR | 120 | 4.176  | 11.243 | 17.433 | 1.00 | 24.99 |
| ATOM | 922 | C   | TYR | 120 | 6.774  | 11.059 | 22.818 | 1.00 | 17.10 |
| ATOM | 923 | O   | TYR | 120 | 5.553  | 11.247 | 22.910 | 1.00 | 15.76 |
| ATOM | 924 | N   | LEU | 121 | 7.320  | 9.847  | 22.880 | 1.00 | 14.94 |

FIG.11A-22

| ATOM | 925 | CA | LEU | 121 | 6.491 | 8.670 | 23.074 | 1.00 | 14.73 |
|------|-----|-----|-----|-----|-------|-------|--------|------|-------|
| ATOM | 926 | CB | LEU | 121 | 7.351 | 7.407 | 23.136 | 1.00 | 14.27 |
| ATOM | 927 | CG | LEU | 121 | 8.129 | 7.046 | 21.867 | 1.00 | 15.46 |
| ATOM | 928 | CD1 | LEU | 121 | 8.970 | 5.796 | 22.125 | 1.00 | 15.26 |
| ATOM | 929 | CD2 | LEU | 121 | 7.165 | 6.825 | 20.711 | 1.00 | 11.93 |
| ATOM | 930 | C | LEU | 121 | 5.661 | 8.782 | 24.346 | 1.00 | 16.08 |
| ATOM | 931 | O | LEU | 121 | 4.453 | 8.565 | 24.328 | 1.00 | 14.61 |
| ATOM | 932 | N | HIS | 122 | 6.309 | 9.126 | 25.452 | 1.00 | 14.83 |
| ATOM | 933 | CA | HIS | 122 | 5.594 | 9.234 | 26.710 | 1.00 | 15.63 |
| ATOM | 934 | CB | HIS | 122 | 6.585 | 9.508 | 27.842 | 1.00 | 15.63 |
| ATOM | 935 | CG | HIS | 122 | 7.434 | 8.321 | 28.179 | 1.00 | 12.77 |
| ATOM | 936 | CD2 | HIS | 122 | 7.432 | 7.061 | 27.686 | 1.00 | 12.46 |
| ATOM | 937 | ND1 | HIS | 122 | 8.402 | 8.349 | 29.160 | 1.00 | 12.14 |
| ATOM | 938 | CE1 | HIS | 122 | 8.957 | 7.153 | 29.260 | 1.00 | 11.43 |
| ATOM | 939 | NE2 | HIS | 122 | 8.385 | 6.352 | 28.377 | 1.00 | 12.08 |
| ATOM | 940 | C | HIS | 122 | 4.515 | 10.307 | 26.646 | 1.00 | 17.17 |
| ATOM | 941 | O | HIS | 122 | 3.452 | 10.163 | 27.246 | 1.00 | 17.14 |
| ATOM | 942 | N | GLY | 123 | 4.783 | 11.362 | 25.886 | 1.00 | 17.18 |
| ATOM | 943 | CA | GLY | 123 | 3.818 | 12.439 | 25.755 | 1.00 | 19.68 |
| ATOM | 944 | C | GLY | 123 | 2.536 | 12.000 | 25.071 | 1.00 | 19.70 |
| ATOM | 945 | O | GLY | 123 | 1.468 | 12.559 | 25.333 | 1.00 | 22.02 |
| ATOM | 946 | N | ILE | 124 | 2.636 | 11.006 | 24.195 | 1.00 | 18.52 |
| ATOM | 947 | CA | ILE | 124 | 1.468 | 10.489 | 23.485 | 1.00 | 20.43 |
| ATOM | 948 | CB | ILE | 124 | 1.807 | 10.171 | 21.992 | 1.00 | 26.21 |
| ATOM | 949 | CG2 | ILE | 124 | 2.795 | 9.024 | 21.896 | 1.00 | 22.32 |
| ATOM | 950 | CG1 | ILE | 124 | 0.531 | 9.825 | 21.219 | 1.00 | 43.02 |
| ATOM | 951 | CD1 | ILE | 124 | -0.447 | 10.975 | 21.093 | 1.00 | 56.77 |
| ATOM | 952 | C | ILE | 124 | 0.922 | 9.246 | 24.200 | 1.00 | 19.54 |
| ATOM | 953 | O | ILE | 124 | 0.023 | 8.569 | 23.705 | 1.00 | 20.58 |
| ATOM | 954 | N | GLY | 125 | 1.468 | 8.953 | 25.379 | 1.00 | 19.44 |
| ATOM | 955 | CA | GLY | 125 | 0.989 | 7.816 | 26.148 | 1.00 | 17.08 |
| ATOM | 956 | C | GLY | 125 | 1.490 | 6.438 | 25.753 | 1.00 | 15.22 |
| ATOM | 957 | O | GLY | 125 | 0.872 | 5.425 | 26.100 | 1.00 | 15.72 |
| ATOM | 958 | N | ILE | 126 | 2.593 | 6.368 | 25.022 | 1.00 | 14.59 |
| ATOM | 959 | CA | ILE | 126 | 3.098 | 5.054 | 24.669 | 1.00 | 15.92 |
| ATOM | 960 | CB | ILE | 126 | 3.197 | 4.831 | 23.121 | 1.00 | 23.85 |
| ATOM | 961 | CG2 | ILE | 126 | 1.985 | 5.439 | 22.415 | 1.00 | 21.96 |
| ATOM | 962 | CG1 | ILE | 126 | 4.478 | 5.425 | 22.565 | 1.00 | 25.44 |
| ATOM | 963 | CD1 | ILE | 126 | 4.761 | 4.944 | 21.151 | 1.00 | 32.08 |
| ATOM | 964 | C | ILE | 126 | 4.452 | 4.759 | 25.304 | 1.00 | 14.58 |
| ATOM | 965 | O | ILE | 126 | 5.301 | 5.645 | 25.466 | 1.00 | 13.21 |
| ATOM | 966 | N | THR | 127 | 4.619 | 3.513 | 25.725 | 1.00 | 15.33 |

FIG.11A-23

```
ATOM    967  CA  THR  127    5.884   3.077  26.301  1.00 16.98
ATOM    968  CB  THR  127    5.710   2.492  27.730  1.00 21.08
ATOM    969  OG1 THR  127    6.963   1.951  28.171  1.00 42.01
ATOM    970  CG2 THR  127    4.657   1.398  27.753  1.00  8.51
ATOM    971  C   THR  127    6.458   2.024  25.350  1.00 15.46
ATOM    972  O   THR  127    5.738   1.154  24.862  1.00 13.84
ATOM    973  N   HIS  128    7.757   2.113  25.084  1.00 16.45
ATOM    974  CA  HIS  128    8.415   1.189  24.152  1.00 14.14
ATOM    975  CB  HIS  128    9.736   1.813  23.696  1.00 16.06
ATOM    976  CG  HIS  128   10.479   0.991  22.693  1.00 19.22
ATOM    977  CD2 HIS  128   10.596   1.113  21.349  1.00 20.26
ATOM    978  ND1 HIS  128   11.214  -0.121  23.043  1.00 17.03
ATOM    979  CE1 HIS  128   11.754  -0.647  21.958  1.00 19.24
ATOM    980  NE2 HIS  128   11.394   0.082  20.916  1.00 19.76
ATOM    981  C   HIS  128    8.635  -0.199  24.755  1.00 13.34
ATOM    982  O   HIS  128    8.422  -1.219  24.087  1.00 13.46
ATOM    983  N   ARG  129    9.044  -0.215  26.025  1.00 12.33
ATOM    984  CA  ARG  129    9.283  -1.427  26.820  1.00 13.03
ATOM    985  CB  ARG  129    7.998  -2.267  26.897  1.00 11.47
ATOM    986  CG  ARG  129    6.825  -1.460  27.467  1.00 16.16
ATOM    987  CD  ARG  129    5.740  -2.334  28.093  1.00 15.62
ATOM    988  NE  ARG  129    5.028  -3.116  27.086  1.00 17.92
ATOM    989  CZ  ARG  129    3.963  -3.861  27.354  1.00 19.53
ATOM    990  NH1 ARG  129    3.494  -3.919  28.599  1.00 15.95
ATOM    991  NH2 ARG  129    3.368  -4.544  26.382  1.00 20.39
ATOM    992  C   ARG  129   10.464  -2.327  26.468  1.00 14.38
ATOM    993  O   ARG  129   10.659  -3.371  27.097  1.00 14.82
ATOM    994  N   ASP  130   11.257  -1.939  25.478  1.00 13.77
ATOM    995  CA  ASP  130   12.427  -2.743  25.126  1.00 14.20
ATOM    996  CB  ASP  130   12.055  -3.833  24.111  1.00 14.89
ATOM    997  CG  ASP  130   13.050  -4.990  24.105  1.00 13.64
ATOM    998  OD1 ASP  130   13.026  -5.793  23.144  1.00 16.40
ATOM    999  OD2 ASP  130   13.850  -5.111  25.058  1.00 14.09
ATOM   1000  C   ASP  130   13.548  -1.877  24.561  1.00 12.69
ATOM   1001  O   ASP  130   14.166  -2.222  23.554  1.00 13.46
ATOM   1002  N   ILE  131   13.820  -0.751  25.214  1.00 13.80
ATOM   1003  CA  ILE  131   14.874   0.146  24.748  1.00 14.84
ATOM   1004  CB  ILE  131   14.779   1.517  25.449  1.00 15.30
ATOM   1005  CG2 ILE  131   15.976   2.412  25.055  1.00 13.40
ATOM   1006  CG1 ILE  131   13.458   2.185  25.057  1.00 14.31
ATOM   1007  CD1 ILE  131   13.093   3.399  25.917  1.00 15.14
ATOM   1008  C   ILE  131   16.244  -0.469  25.008  1.00 14.20
```

FIG.11A-24

| ATOM | 1009 | O   | ILE | 131 | 16.543 | -0.878 | 26.115 | 1.00 | 14.42 |
|------|------|-----|-----|-----|--------|--------|--------|------|-------|
| ATOM | 1010 | N   | LYS | 132 | 17.054 | -0.544 | 23.959 | 1.00 | 13.66 |
| ATOM | 1011 | CA  | LYS | 132 | 18.405 | -1.096 | 24.020 | 1.00 | 12.59 |
| ATOM | 1012 | CB  | LYS | 132 | 18.376 | -2.623 | 24.187 | 1.00 | 13.39 |
| ATOM | 1013 | CG  | LYS | 132 | 17.494 | -3.375 | 23.194 | 1.00 | 16.12 |
| ATOM | 1014 | CD  | LYS | 132 | 17.518 | -4.865 | 23.500 | 1.00 | 15.73 |
| ATOM | 1015 | CE  | LYS | 132 | 16.670 | -5.666 | 22.520 | 1.00 | 18.36 |
| ATOM | 1016 | NZ  | LYS | 132 | 16.639 | -7.121 | 22.872 | 1.00 | 16.42 |
| ATOM | 1017 | C   | LYS | 132 | 19.084 | -0.703 | 22.715 | 1.00 | 13.57 |
| ATOM | 1018 | O   | LYS | 132 | 18.413 | -0.351 | 21.749 | 1.00 | 15.48 |
| ATOM | 1019 | N   | PRO | 133 | 20.424 | -0.769 | 22.665 | 1.00 | 14.76 |
| ATOM | 1020 | CD  | PRO | 133 | 21.328 | -1.231 | 23.731 | 1.00 | 16.68 |
| ATOM | 1021 | CA  | PRO | 133 | 21.188 | -0.397 | 21.467 | 1.00 | 15.75 |
| ATOM | 1022 | CB  | PRO | 133 | 22.622 | -0.746 | 21.858 | 1.00 | 14.35 |
| ATOM | 1023 | CG  | PRO | 133 | 22.612 | -0.538 | 23.363 | 1.00 | 16.22 |
| ATOM | 1024 | C   | PRO | 133 | 20.758 | -1.055 | 20.162 | 1.00 | 16.05 |
| ATOM | 1025 | O   | PRO | 133 | 20.868 | -0.441 | 19.096 | 1.00 | 18.14 |
| ATOM | 1026 | N   | GLU | 134 | 20.265 | -2.289 | 20.246 | 1.00 | 15.05 |
| ATOM | 1027 | CA  | GLU | 134 | 19.820 | -3.010 | 19.061 | 1.00 | 17.14 |
| ATOM | 1028 | CB  | GLU | 134 | 19.562 | -4.488 | 19.404 | 1.00 | 15.98 |
| ATOM | 1029 | CG  | GLU | 134 | 20.792 | -5.246 | 19.898 | 1.00 | 21.80 |
| ATOM | 1030 | CD  | GLU | 134 | 20.945 | -5.241 | 21.415 | 1.00 | 24.82 |
| ATOM | 1031 | OE1 | GLU | 134 | 20.669 | -4.207 | 22.067 | 1.00 | 18.91 |
| ATOM | 1032 | OE2 | GLU | 134 | 21.363 | -6.287 | 21.957 | 1.00 | 27.97 |
| ATOM | 1033 | C   | GLU | 134 | 18.554 | -2.389 | 18.470 | 1.00 | 18.34 |
| ATOM | 1034 | O   | GLU | 134 | 18.276 | -2.539 | 17.280 | 1.00 | 21.57 |
| ATOM | 1035 | N   | ASN | 135 | 17.785 | -1.698 | 19.307 | 1.00 | 18.40 |
| ATOM | 1036 | CA  | ASN | 135 | 16.545 | -1.063 | 18.867 | 1.00 | 17.42 |
| ATOM | 1037 | CB  | ASN | 135 | 15.407 | -1.373 | 19.851 | 1.00 | 16.38 |
| ATOM | 1038 | CG  | ASN | 135 | 14.881 | -2.788 | 19.697 | 1.00 | 21.05 |
| ATOM | 1039 | OD1 | ASN | 135 | 14.895 | -3.344 | 18.596 | 1.00 | 25.80 |
| ATOM | 1040 | ND2 | ASN | 135 | 14.397 | -3.372 | 20.791 | 1.00 | 18.14 |
| ATOM | 1041 | C   | ASN | 135 | 16.663 |  0.448 | 18.687 | 1.00 | 17.18 |
| ATOM | 1042 | O   | ASN | 135 | 15.656 |  1.157 | 18.628 | 1.00 | 18.63 |
| ATOM | 1043 | N   | LEU | 136 | 17.895 |  0.935 | 18.609 | 1.00 | 15.45 |
| ATOM | 1044 | CA  | LEU | 136 | 18.149 |  2.356 | 18.399 | 1.00 | 13.88 |
| ATOM | 1045 | CB  | LEU | 136 | 18.902 |  2.944 | 19.597 | 1.00 | 14.66 |
| ATOM | 1046 | CG  | LEU | 136 | 18.121 |  2.860 | 20.919 | 1.00 | 13.43 |
| ATOM | 1047 | CD1 | LEU | 136 | 18.987 |  3.330 | 22.082 | 1.00 |  9.48 |
| ATOM | 1048 | CD2 | LEU | 136 | 16.856 |  3.724 | 20.826 | 1.00 | 16.23 |
| ATOM | 1049 | C   | LEU | 136 | 18.984 |  2.416 | 17.122 | 1.00 | 15.09 |
| ATOM | 1050 | O   | LEU | 136 | 20.162 |  2.068 | 17.120 | 1.00 | 15.49 |

FIG.11A-25

| | | | | | | | | |
|---|---|---|---|---|---|---|---|---|
| ATOM | 1051 | N | LEU | 137 | 18.346 | 2.824 | 16.031 | 1.00 16.71 |
| ATOM | 1052 | CA | LEU | 137 | 19.002 | 2.884 | 14.729 | 1.00 18.73 |
| ATOM | 1053 | CB | LEU | 137 | 18.025 | 2.408 | 13.650 | 1.00 18.99 |
| ATOM | 1054 | CG | LEU | 137 | 17.362 | 1.067 | 13.998 | 1.00 20.11 |
| ATOM | 1055 | CD1 | LEU | 137 | 16.443 | 0.625 | 12.863 | 1.00 21.15 |
| ATOM | 1056 | CD2 | LEU | 137 | 18.438 | 0.019 | 14.257 | 1.00 17.16 |
| ATOM | 1057 | C | LEU | 137 | 19.532 | 4.274 | 14.400 | 1.00 19.64 |
| ATOM | 1058 | O | LEU | 137 | 19.152 | 5.259 | 15.029 | 1.00 18.56 |
| ATOM | 1059 | N | LEU | 138 | 20.416 | 4.345 | 13.406 | 1.00 20.11 |
| ATOM | 1060 | CA | LEU | 138 | 21.030 | 5.605 | 13.012 | 1.00 21.10 |
| ATOM | 1061 | CB | LEU | 138 | 22.538 | 5.569 | 13.294 | 1.00 23.33 |
| ATOM | 1062 | CG | LEU | 138 | 23.028 | 5.317 | 14.724 | 1.00 24.15 |
| ATOM | 1063 | CD1 | LEU | 138 | 22.444 | 6.368 | 15.650 | 1.00 21.36 |
| ATOM | 1064 | CD2 | LEU | 138 | 22.620 | 3.921 | 15.169 | 1.00 27.70 |
| ATOM | 1065 | C | LEU | 138 | 20.825 | 5.872 | 11.526 | 1.00 23.67 |
| ATOM | 1066 | O | LEU | 138 | 20.963 | 4.959 | 10.707 | 1.00 23.81 |
| ATOM | 1067 | N | ASP | 139 | 20.498 | 7.116 | 11.184 | 1.00 24.02 |
| ATOM | 1068 | CA | ASP | 139 | 20.298 | 7.481 | 9.784 | 1.00 24.89 |
| ATOM | 1069 | CB | ASP | 139 | 19.295 | 8.642 | 9.657 | 1.00 23.61 |
| ATOM | 1070 | CG | ASP | 139 | 19.861 | 9.974 | 10.120 | 1.00 24.18 |
| ATOM | 1071 | OD1 | ASP | 139 | 19.136 | 10.986 | 10.021 | 1.00 27.10 |
| ATOM | 1072 | OD2 | ASP | 139 | 21.019 | 10.020 | 10.576 | 1.00 24.71 |
| ATOM | 1073 | C | ASP | 139 | 21.642 | 7.857 | 9.173 | 1.00 24.93 |
| ATOM | 1074 | O | ASP | 139 | 22.687 | 7.630 | 9.781 | 1.00 26.58 |
| ATOM | 1075 | N | GLU | 140 | 21.622 | 8.426 | 7.971 | 1.00 25.87 |
| ATOM | 1076 | CA | GLU | 140 | 22.857 | 8.808 | 7.296 | 1.00 28.66 |
| ATOM | 1077 | CB | GLU | 140 | 22.556 | 9.284 | 5.866 | 1.00 30.20 |
| ATOM | 1078 | CG | GLU | 140 | 21.489 | 10.364 | 5.756 | 1.00 39.13 |
| ATOM | 1079 | CD | GLU | 140 | 20.119 | 9.881 | 6.200 | 1.00 47.21 |
| ATOM | 1080 | OE1 | GLU | 140 | 19.686 | 8.808 | 5.732 | 1.00 50.57 |
| ATOM | 1081 | OE2 | GLU | 140 | 19.474 | 10.576 | 7.013 | 1.00 52.55 |
| ATOM | 1082 | C | GLU | 140 | 23.682 | 9.866 | 8.032 | 1.00 28.46 |
| ATOM | 1083 | O | GLU | 140 | 24.905 | 9.914 | 7.882 | 1.00 29.94 |
| ATOM | 1084 | N | ARG | 141 | 23.022 | 10.710 | 8.821 | 1.00 27.37 |
| ATOM | 1085 | CA | ARG | 141 | 23.715 | 11.756 | 9.576 | 1.00 27.01 |
| ATOM | 1086 | CB | ARG | 141 | 22.942 | 13.076 | 9.479 | 1.00 30.09 |
| ATOM | 1087 | CG | ARG | 141 | 22.830 | 13.619 | 8.059 | 1.00 37.24 |
| ATOM | 1088 | CD | ARG | 141 | 22.072 | 14.941 | 7.994 | 1.00 44.03 |
| ATOM | 1089 | NE | ARG | 141 | 22.712 | 15.992 | 8.783 | 1.00 54.80 |
| ATOM | 1090 | CZ | ARG | 141 | 22.445 | 16.242 | 10.062 | 1.00 62.47 |
| ATOM | 1091 | NH1 | ARG | 141 | 21.542 | 15.519 | 10.711 | 1.00 60.81 |
| ATOM | 1092 | NH2 | ARG | 141 | 23.084 | 17.218 | 10.695 | 1.00 64.44 |

FIG.11A-26

| | | | | | | | | |
|---|---|---|---|---|---|---|---|---|
| ATOM | 1093 | C | ARG | 141 | 23.891 | 11.362 | 11.045 | 1.00 25.81 |
| ATOM | 1094 | O | ARG | 141 | 24.141 | 12.206 | 11.909 | 1.00 26.51 |
| ATOM | 1095 | N | ASP | 142 | 23.779 | 10.066 | 11.312 | 1.00 24.59 |
| ATOM | 1096 | CA | ASP | 142 | 23.909 | 9.532 | 12.664 | 1.00 25.48 |
| ATOM | 1097 | CB | ASP | 142 | 25.296 | 9.822 | 13.251 | 1.00 25.98 |
| ATOM | 1098 | CG | ASP | 142 | 26.350 | 8.865 | 12.743 | 1.00 30.74 |
| ATOM | 1099 | OD1 | ASP | 142 | 26.006 | 7.694 | 12.494 | 1.00 30.35 |
| ATOM | 1100 | OD2 | ASP | 142 | 27.521 | 9.272 | 12.608 | 1.00 40.27 |
| ATOM | 1101 | C | ASP | 142 | 22.845 | 10.022 | 13.634 | 1.00 22.57 |
| ATOM | 1102 | O | ASP | 142 | 23.102 | 10.139 | 14.834 | 1.00 22.18 |
| ATOM | 1103 | N | ASN | 143 | 21.655 | 10.314 | 13.125 | 1.00 22.09 |
| ATOM | 1104 | CA | ASN | 143 | 20.563 | 10.733 | 13.999 | 1.00 23.36 |
| ATOM | 1105 | CB | ASN | 143 | 19.531 | 11.547 | 13.225 | 1.00 22.79 |
| ATOM | 1106 | CG | ASN | 143 | 20.055 | 12.906 | 12.826 | 1.00 26.55 |
| ATOM | 1107 | OD1 | ASN | 143 | 20.119 | 13.240 | 11.644 | 1.00 29.98 |
| ATOM | 1108 | ND2 | ASN | 143 | 20.442 | 13.697 | 13.815 | 1.00 24.11 |
| ATOM | 1109 | C | ASN | 143 | 19.928 | 9.461 | 14.543 | 1.00 22.26 |
| ATOM | 1110 | O | ASN | 143 | 19.689 | 8.519 | 13.798 | 1.00 22.91 |
| ATOM | 1111 | N | LEU | 144 | 19.667 | 9.438 | 15.846 | 1.00 20.92 |
| ATOM | 1112 | CA | LEU | 144 | 19.084 | 8.268 | 16.494 | 1.00 21.74 |
| ATOM | 1113 | CB | LEU | 144 | 19.402 | 8.318 | 17.992 | 1.00 18.53 |
| ATOM | 1114 | CG | LEU | 144 | 18.845 | 7.262 | 18.946 | 1.00 20.54 |
| ATOM | 1115 | CD1 | LEU | 144 | 19.807 | 7.095 | 20.113 | 1.00 19.77 |
| ATOM | 1116 | CD2 | LEU | 144 | 17.463 | 7.673 | 19.440 | 1.00 21.20 |
| ATOM | 1117 | C | LEU | 144 | 17.580 | 8.140 | 16.258 | 1.00 20.47 |
| ATOM | 1118 | O | LEU | 144 | 16.844 | 9.126 | 16.319 | 1.00 19.22 |
| ATOM | 1119 | N | LYS | 145 | 17.140 | 6.909 | 16.000 | 1.00 19.53 |
| ATOM | 1120 | CA | LYS | 145 | 15.737 | 6.605 | 15.730 | 1.00 18.88 |
| ATOM | 1121 | CB | LYS | 145 | 15.549 | 6.245 | 14.251 | 1.00 24.21 |
| ATOM | 1122 | CG | LYS | 145 | 16.214 | 7.188 | 13.260 | 1.00 23.93 |
| ATOM | 1123 | CD | LYS | 145 | 15.328 | 8.369 | 12.951 | 1.00 22.67 |
| ATOM | 1124 | CE | LYS | 145 | 15.970 | 9.275 | 11.913 | 1.00 27.57 |
| ATOM | 1125 | NZ | LYS | 145 | 15.022 | 10.333 | 11.462 | 1.00 27.78 |
| ATOM | 1126 | C | LYS | 145 | 15.302 | 5.398 | 16.556 | 1.00 15.99 |
| ATOM | 1127 | O | LYS | 145 | 15.869 | 4.314 | 16.414 | 1.00 16.13 |
| ATOM | 1128 | N | ILE | 146 | 14.300 | 5.579 | 17.410 | 1.00 16.28 |
| ATOM | 1129 | CA | ILE | 146 | 13.801 | 4.478 | 18.226 | 1.00 15.84 |
| ATOM | 1130 | CB | ILE | 146 | 12.849 | 4.993 | 19.319 | 1.00 15.02 |
| ATOM | 1131 | CG2 | ILE | 146 | 12.230 | 3.819 | 20.080 | 1.00 13.88 |
| ATOM | 1132 | CG1 | ILE | 146 | 13.635 | 5.884 | 20.284 | 1.00 17.67 |
| ATOM | 1133 | CD1 | ILE | 146 | 12.781 | 6.595 | 21.324 | 1.00 12.64 |
| ATOM | 1134 | C | ILE | 146 | 13.068 | 3.523 | 17.284 | 1.00 16.96 |

FIG.11A-27

| | | | | | | | | |
|---|---|---|---|---|---|---|---|---|
| ATOM | 1135 | O | ILE | 146 | 12.200 | 3.942 | 16.512 | 1.00 17.32 |
| ATOM | 1136 | N | SER | 147 | 13.417 | 2.245 | 17.375 | 1.00 16.60 |
| ATOM | 1137 | CA | SER | 147 | 12.876 | 1.212 | 16.495 | 1.00 17.35 |
| ATOM | 1138 | CB | SER | 147 | 14.016 | 0.692 | 15.618 | 1.00 16.68 |
| ATOM | 1139 | OG | SER | 147 | 13.617 | -0.411 | 14.821 | 1.00 20.69 |
| ATOM | 1140 | C | SER | 147 | 12.200 | 0.017 | 17.162 | 1.00 16.72 |
| ATOM | 1141 | O | SER | 147 | 12.504 | -0.329 | 18.306 | 1.00 15.17 |
| ATOM | 1142 | N | ASP | 148 | 11.286 | -0.602 | 16.414 | 1.00 16.05 |
| ATOM | 1143 | CA | ASP | 148 | 10.549 | -1.801 | 16.828 | 1.00 18.00 |
| ATOM | 1144 | CB | ASP | 148 | 11.536 | -2.919 | 17.200 | 1.00 20.31 |
| ATOM | 1145 | CG | ASP | 148 | 10.874 | -4.287 | 17.287 | 1.00 25.87 |
| ATOM | 1146 | OD1 | ASP | 148 | 11.601 | -5.305 | 17.231 | 1.00 29.19 |
| ATOM | 1147 | OD2 | ASP | 148 | 9.635 | -4.349 | 17.419 | 1.00 24.90 |
| ATOM | 1148 | C | ASP | 148 | 9.539 | -1.618 | 17.951 | 1.00 18.24 |
| ATOM | 1149 | O | ASP | 148 | 9.887 | -1.668 | 19.130 | 1.00 20.08 |
| ATOM | 1150 | N | PHE | 149 | 8.276 | -1.446 | 17.576 | 1.00 18.32 |
| ATOM | 1151 | CA | PHE | 149 | 7.218 | -1.265 | 18.554 | 1.00 19.50 |
| ATOM | 1152 | CB | PHE | 149 | 6.346 | -0.077 | 18.152 | 1.00 17.84 |
| ATOM | 1153 | CG | PHE | 149 | 7.065 | 1.232 | 18.263 | 1.00 19.16 |
| ATOM | 1154 | CD1 | PHE | 149 | 7.955 | 1.637 | 17.271 | 1.00 19.71 |
| ATOM | 1155 | CD2 | PHE | 149 | 6.932 | 2.014 | 19.407 | 1.00 15.99 |
| ATOM | 1156 | CE1 | PHE | 149 | 8.712 | 2.805 | 17.418 | 1.00 19.45 |
| ATOM | 1157 | CE2 | PHE | 149 | 7.687 | 3.184 | 19.564 | 1.00 20.50 |
| ATOM | 1158 | CZ | PHE | 149 | 8.576 | 3.576 | 18.568 | 1.00 19.86 |
| ATOM | 1159 | C | PHE | 149 | 6.391 | -2.516 | 18.780 | 1.00 20.77 |
| ATOM | 1160 | O | PHE | 149 | 5.235 | -2.445 | 19.187 | 1.00 21.42 |
| ATOM | 1161 | N | GLY | 150 | 7.020 | -3.663 | 18.539 | 1.00 20.98 |
| ATOM | 1162 | CA | GLY | 150 | 6.361 | -4.942 | 18.725 | 1.00 21.69 |
| ATOM | 1163 | C | GLY | 150 | 6.002 | -5.220 | 20.176 | 1.00 21.45 |
| ATOM | 1164 | O | GLY | 150 | 5.111 | -6.018 | 20.449 | 1.00 24.57 |
| ATOM | 1165 | N | LEU | 151 | 6.687 | -4.568 | 21.111 | 1.00 19.98 |
| ATOM | 1166 | CA | LEU | 151 | 6.396 | -4.763 | 22.535 | 1.00 21.36 |
| ATOM | 1167 | CB | LEU | 151 | 7.659 | -5.180 | 23.289 | 1.00 18.98 |
| ATOM | 1168 | CG | LEU | 151 | 8.189 | -6.589 | 23.004 | 1.00 24.33 |
| ATOM | 1169 | CD1 | LEU | 151 | 9.497 | -6.797 | 23.744 | 1.00 25.19 |
| ATOM | 1170 | CD2 | LEU | 151 | 7.153 | -7.628 | 23.440 | 1.00 27.70 |
| ATOM | 1171 | C | LEU | 151 | 5.811 | -3.520 | 23.195 | 1.00 19.87 |
| ATOM | 1172 | O | LEU | 151 | 5.517 | -3.530 | 24.389 | 1.00 20.65 |
| ATOM | 1173 | N | ALA | 152 | 5.640 | -2.458 | 22.413 | 1.00 18.07 |
| ATOM | 1174 | CA | ALA | 152 | 5.102 | -1.199 | 22.915 | 1.00 18.82 |
| ATOM | 1175 | CB | ALA | 152 | 5.296 | -0.103 | 21.867 | 1.00 16.88 |
| ATOM | 1176 | C | ALA | 152 | 3.627 | -1.290 | 23.285 | 1.00 19.46 |

FIG.11A-28

| ATOM | 1177 | O   | ALA | 152 |  2.895 | -2.129 | 22.758 | 1.00 | 21.66 |
|------|------|-----|-----|-----|--------|--------|--------|------|-------|
| ATOM | 1178 | N   | THR | 153 |  3.192 | -0.418 | 24.189 | 1.00 | 19.05 |
| ATOM | 1179 | CA  | THR | 153 |  1.796 | -0.397 | 24.593 | 1.00 | 18.72 |
| ATOM | 1180 | CB  | THR | 153 |  1.509 | -1.442 | 25.712 | 1.00 | 18.18 |
| ATOM | 1181 | OG1 | THR | 153 |  0.090 | -1.652 | 25.809 | 1.00 | 16.70 |
| ATOM | 1182 | CG2 | THR | 153 |  2.038 | -0.970 | 27.071 | 1.00 | 16.94 |
| ATOM | 1183 | C   | THR | 153 |  1.396 |  1.000 | 25.056 | 1.00 | 19.47 |
| ATOM | 1184 | O   | THR | 153 |  2.244 |  1.853 | 25.325 | 1.00 | 17.58 |
| ATOM | 1185 | N   | VAL | 154 |  0.096 |  1.249 | 25.112 | 1.00 | 21.41 |
| ATOM | 1186 | CA  | VAL | 154 | -0.401 |  2.543 | 25.547 | 1.00 | 22.13 |
| ATOM | 1187 | CB  | VAL | 154 | -1.765 |  2.863 | 24.877 | 1.00 | 26.46 |
| ATOM | 1188 | CG1 | VAL | 154 | -2.295 |  4.213 | 25.354 | 1.00 | 28.65 |
| ATOM | 1189 | CG2 | VAL | 154 | -1.600 |  2.873 | 23.367 | 1.00 | 24.98 |
| ATOM | 1190 | C   | VAL | 154 | -0.559 |  2.472 | 27.056 | 1.00 | 21.16 |
| ATOM | 1191 | O   | VAL | 154 | -1.195 |  1.553 | 27.577 | 1.00 | 21.97 |
| ATOM | 1192 | N   | PHE | 155 |  0.047 |  3.416 | 27.770 | 1.00 | 19.24 |
| ATOM | 1193 | CA  | PHE | 155 | -0.061 |  3.414 | 29.220 | 1.00 | 18.72 |
| ATOM | 1194 | CB  | PHE | 155 |  1.322 |  3.426 | 29.889 | 1.00 | 19.67 |
| ATOM | 1195 | CG  | PHE | 155 |  2.055 |  4.721 | 29.748 | 1.00 | 17.34 |
| ATOM | 1196 | CD1 | PHE | 155 |  2.843 |  4.972 | 28.628 | 1.00 | 13.52 |
| ATOM | 1197 | CD2 | PHE | 155 |  1.924 |  5.711 | 30.716 | 1.00 | 16.84 |
| ATOM | 1198 | CE1 | PHE | 155 |  3.488 |  6.191 | 28.470 | 1.00 | 13.59 |
| ATOM | 1199 | CE2 | PHE | 155 |  2.565 |  6.944 | 30.570 | 1.00 | 16.30 |
| ATOM | 1200 | CZ  | PHE | 155 |  3.350 |  7.187 | 29.445 | 1.00 | 15.78 |
| ATOM | 1201 | C   | PHE | 155 | -0.889 |  4.590 | 29.717 | 1.00 | 20.17 |
| ATOM | 1202 | O   | PHE | 155 | -1.170 |  4.696 | 30.907 | 1.00 | 20.34 |
| ATOM | 1203 | N   | ARG | 156 | -1.259 |  5.489 | 28.812 | 1.00 | 19.17 |
| ATOM | 1204 | CA  | ARG | 156 | -2.096 |  6.622 | 29.204 | 1.00 | 18.98 |
| ATOM | 1205 | CB  | ARG | 156 | -1.282 |  7.904 | 29.388 | 1.00 | 17.96 |
| ATOM | 1206 | CG  | ARG | 156 | -2.081 |  9.008 | 30.101 | 1.00 | 20.91 |
| ATOM | 1207 | CD  | ARG | 156 | -1.432 | 10.382 | 29.971 | 1.00 | 26.19 |
| ATOM | 1208 | NE  | ARG | 156 | -0.049 | 10.410 | 30.438 | 1.00 | 25.61 |
| ATOM | 1209 | CZ  | ARG | 156 |  1.002 | 10.600 | 29.642 | 1.00 | 20.60 |
| ATOM | 1210 | NH1 | ARG | 156 |  0.830 | 10.774 | 28.340 | 1.00 | 19.60 |
| ATOM | 1211 | NH2 | ARG | 156 |  2.226 | 10.628 | 30.150 | 1.00 | 18.11 |
| ATOM | 1212 | C   | ARG | 156 | -3.134 |  6.847 | 28.122 | 1.00 | 21.82 |
| ATOM | 1213 | O   | ARG | 156 | -2.802 |  7.039 | 26.954 | 1.00 | 21.83 |
| ATOM | 1214 | N   | TYR | 157 | -4.398 |  6.824 | 28.521 | 1.00 | 21.32 |
| ATOM | 1215 | CA  | TYR | 157 | -5.493 |  7.016 | 27.584 | 1.00 | 19.71 |
| ATOM | 1216 | CB  | TYR | 157 | -6.101 |  5.663 | 27.218 | 1.00 | 18.64 |
| ATOM | 1217 | CG  | TYR | 157 | -6.960 |  5.702 | 25.983 | 1.00 | 23.71 |
| ATOM | 1218 | CD1 | TYR | 157 | -6.384 |  5.726 | 24.712 | 1.00 | 21.76 |

FIG.11A-29

| | | | | | | | | |
|---|---|---|---|---|---|---|---|---|
| ATOM | 1219 | CE1 | TYR | 157 | -7.174 | 5.767 | 23.566 | 1.00 25.10 |
| ATOM | 1220 | CD2 | TYR | 157 | -8.350 | 5.719 | 26.081 | 1.00 19.65 |
| ATOM | 1221 | CE2 | TYR | 157 | -9.147 | 5.756 | 24.946 | 1.00 19.21 |
| ATOM | 1222 | CZ | TYR | 157 | -8.559 | 5.780 | 23.693 | 1.00 22.17 |
| ATOM | 1223 | OH | TYR | 157 | -9.347 | 5.818 | 22.566 | 1.00 25.91 |
| ATOM | 1224 | C | TYR | 157 | -6.533 | 7.882 | 28.282 | 1.00 18.10 |
| ATOM | 1225 | O | TYR | 157 | -6.851 | 7.651 | 29.449 | 1.00 18.79 |
| ATOM | 1226 | N | ASN | 158 | -7.045 | 8.881 | 27.571 | 1.00 19.43 |
| ATOM | 1227 | CA | ASN | 158 | -8.041 | 9.797 | 28.130 | 1.00 22.45 |
| ATOM | 1228 | CB | ASN | 158 | -9.375 | 9.068 | 28.342 | 1.00 17.95 |
| ATOM | 1229 | CG | ASN | 158 | -10.134 | 8.861 | 27.046 | 1.00 15.00 |
| ATOM | 1230 | OD1 | ASN | 158 | -11.036 | 8.025 | 26.968 | 1.00 21.50 |
| ATOM | 1231 | ND2 | ASN | 158 | -9.777 | 9.620 | 26.018 | 1.00 14.33 |
| ATOM | 1232 | C | ASN | 158 | -7.565 | 10.417 | 29.442 | 1.00 24.59 |
| ATOM | 1233 | O | ASN | 158 | -8.339 | 10.591 | 30.383 | 1.00 25.26 |
| ATOM | 1234 | N | ASN | 159 | -6.272 | 10.731 | 29.482 | 1.00 27.27 |
| ATOM | 1235 | CA | ASN | 159 | -5.624 | 11.353 | 30.630 | 1.00 28.47 |
| ATOM | 1236 | CB | ASN | 159 | -6.285 | 12.702 | 30.934 | 1.00 34.81 |
| ATOM | 1237 | CG | ASN | 159 | -5.380 | 13.624 | 31.730 | 1.00 46.84 |
| ATOM | 1238 | OD1 | ASN | 159 | -4.243 | 13.884 | 31.332 | 1.00 48.82 |
| ATOM | 1239 | ND2 | ASN | 159 | -5.880 | 14.126 | 32.856 | 1.00 48.82 |
| ATOM | 1240 | C | ASN | 159 | -5.597 | 10.489 | 31.889 | 1.00 27.91 |
| ATOM | 1241 | O | ASN | 159 | -5.381 | 10.991 | 32.993 | 1.00 30.07 |
| ATOM | 1242 | N | ARG | 160 | -5.818 | 9.189 | 31.725 | 1.00 24.35 |
| ATOM | 1243 | CA | ARG | 160 | -5.788 | 8.265 | 32.854 | 1.00 23.07 |
| ATOM | 1244 | CB | ARG | 160 | -7.104 | 7.485 | 32.961 | 1.00 24.32 |
| ATOM | 1245 | CG | ARG | 160 | -8.050 | 7.997 | 34.040 | 1.00 31.06 |
| ATOM | 1246 | CD | ARG | 160 | -7.472 | 7.775 | 35.429 | 1.00 36.21 |
| ATOM | 1247 | NE | ARG | 160 | -8.462 | 7.992 | 36.479 | 1.00 49.83 |
| ATOM | 1248 | CZ | ARG | 160 | -8.983 | 9.174 | 36.791 | 1.00 58.03 |
| ATOM | 1249 | NH1 | ARG | 160 | -8.608 | 10.264 | 36.135 | 1.00 61.87 |
| ATOM | 1250 | NH2 | ARG | 160 | -9.887 | 9.265 | 37.758 | 1.00 59.82 |
| ATOM | 1251 | C | ARG | 160 | -4.639 | 7.289 | 32.648 | 1.00 22.67 |
| ATOM | 1252 | O | ARG | 160 | -4.562 | 6.628 | 31.618 | 1.00 20.87 |
| ATOM | 1253 | N | GLU | 161 | -3.750 | 7.204 | 33.630 | 1.00 22.22 |
| ATOM | 1254 | CA | GLU | 161 | -2.613 | 6.298 | 33.527 | 1.00 22.53 |
| ATOM | 1255 | CB | GLU | 161 | -1.459 | 6.768 | 34.429 | 1.00 22.92 |
| ATOM | 1256 | CG | GLU | 161 | -0.214 | 5.877 | 34.340 | 1.00 21.95 |
| ATOM | 1257 | CD | GLU | 161 | 0.902 | 6.279 | 35.305 | 1.00 24.35 |
| ATOM | 1258 | OE1 | GLU | 161 | 1.976 | 5.637 | 35.272 | 1.00 20.96 |
| ATOM | 1259 | OE2 | GLU | 161 | 0.706 | 7.226 | 36.095 | 1.00 25.52 |
| ATOM | 1260 | C | GLU | 161 | -3.007 | 4.885 | 33.926 | 1.00 21.71 |

FIG.11A-30

| ATOM | 1261 | O   | GLU | 161 | -3.755 | 4.683  | 34.885 | 1.00 | 23.04 |
| ATOM | 1262 | N   | ARG | 162 | -2.503 | 3.909  | 33.182 | 1.00 | 21.16 |
| ATOM | 1263 | CA  | ARG | 162 | -2.754 | 2.505  | 33.465 | 1.00 | 21.51 |
| ATOM | 1264 | CB  | ARG | 162 | -3.207 | 1.781  | 32.191 | 1.00 | 26.46 |
| ATOM | 1265 | CG  | ARG | 162 | -3.326 | 0.274  | 32.326 | 1.00 | 33.90 |
| ATOM | 1266 | CD  | ARG | 162 | -3.916 | -0.347 | 31.061 | 1.00 | 44.41 |
| ATOM | 1267 | NE  | ARG | 162 | -3.035 | -0.230 | 29.898 | 1.00 | 54.96 |
| ATOM | 1268 | CZ  | ARG | 162 | -2.050 | -1.077 | 29.612 | 1.00 | 52.17 |
| ATOM | 1269 | NH1 | ARG | 162 | -1.303 | -0.884 | 28.534 | 1.00 | 48.31 |
| ATOM | 1270 | NH2 | ARG | 162 | -1.816 | -2.123 | 30.392 | 1.00 | 49.02 |
| ATOM | 1271 | C   | ARG | 162 | -1.442 | 1.892  | 33.957 | 1.00 | 21.44 |
| ATOM | 1272 | O   | ARG | 162 | -0.405 | 2.058  | 33.319 | 1.00 | 20.36 |
| ATOM | 1273 | N   | LEU | 163 | -1.481 | 1.215  | 35.098 | 1.00 | 20.22 |
| ATOM | 1274 | CA  | LEU | 163 | -0.279 | 0.573  | 35.623 | 1.00 | 21.99 |
| ATOM | 1275 | CB  | LEU | 163 | -0.448 | 0.226  | 37.100 | 1.00 | 22.03 |
| ATOM | 1276 | CG  | LEU | 163 | -0.661 | 1.398  | 38.057 | 1.00 | 23.54 |
| ATOM | 1277 | CD1 | LEU | 163 | -1.002 | 0.862  | 39.439 | 1.00 | 21.82 |
| ATOM | 1278 | CD2 | LEU | 163 | 0.598  | 2.269  | 38.100 | 1.00 | 23.24 |
| ATOM | 1279 | C   | LEU | 163 | -0.051 | -0.699 | 34.823 | 1.00 | 22.61 |
| ATOM | 1280 | O   | LEU | 163 | -1.000 | -1.362 | 34.411 | 1.00 | 23.66 |
| ATOM | 1281 | N   | LEU | 164 | 1.211  | -1.045 | 34.604 | 1.00 | 21.45 |
| ATOM | 1282 | CA  | LEU | 164 | 1.526  | -2.245 | 33.839 | 1.00 | 19.50 |
| ATOM | 1283 | CB  | LEU | 164 | 2.699  | -1.966 | 32.898 | 1.00 | 19.82 |
| ATOM | 1284 | CG  | LEU | 164 | 2.524  | -0.748 | 31.991 | 1.00 | 21.21 |
| ATOM | 1285 | CD1 | LEU | 164 | 3.741  | -0.606 | 31.096 | 1.00 | 23.59 |
| ATOM | 1286 | CD2 | LEU | 164 | 1.260  | -0.897 | 31.166 | 1.00 | 21.35 |
| ATOM | 1287 | C   | LEU | 164 | 1.887  | -3.402 | 34.752 | 1.00 | 17.33 |
| ATOM | 1288 | O   | LEU | 164 | 2.254  | -3.194 | 35.909 | 1.00 | 16.78 |
| ATOM | 1289 | N   | ASN | 165 | 1.784  | -4.621 | 34.222 | 1.00 | 17.32 |
| ATOM | 1290 | CA  | ASN | 165 | 2.139  | -5.818 | 34.978 | 1.00 | 19.46 |
| ATOM | 1291 | CB  | ASN | 165 | 0.898  | -6.443 | 35.622 | 1.00 | 22.03 |
| ATOM | 1292 | CG  | ASN | 165 | -0.189 | -6.740 | 34.611 | 1.00 | 24.96 |
| ATOM | 1293 | OD1 | ASN | 165 | -1.219 | -6.065 | 34.574 | 1.00 | 31.70 |
| ATOM | 1294 | ND2 | ASN | 165 | 0.037  | -7.748 | 33.776 | 1.00 | 22.31 |
| ATOM | 1295 | C   | ASN | 165 | 2.816  | -6.855 | 34.084 | 1.00 | 19.59 |
| ATOM | 1296 | O   | ASN | 165 | 3.349  | -7.849 | 34.569 | 1.00 | 21.55 |
| ATOM | 1297 | N   | LYS | 166 | 2.804  | -6.625 | 32.778 | 1.00 | 20.65 |
| ATOM | 1298 | CA  | LYS | 166 | 3.425  | -7.570 | 31.854 | 1.00 | 23.25 |
| ATOM | 1299 | CB  | LYS | 166 | 3.029  | -7.232 | 30.414 | 1.00 | 25.58 |
| ATOM | 1300 | CG  | LYS | 166 | 3.605  | -8.164 | 29.356 | 1.00 | 28.68 |
| ATOM | 1301 | CD  | LYS | 166 | 3.109  | -7.776 | 27.968 | 1.00 | 34.56 |
| ATOM | 1302 | CE  | LYS | 166 | 3.602  | -8.742 | 26.904 | 1.00 | 40.12 |

FIG.11A-31

| ATOM | 1303 | NZ | LYS | 166 | 5.089 | -8.750 | 26.811 | 1.00 | 47.83 |
| ATOM | 1304 | C | LYS | 166 | 4.949 | -7.569 | 31.982 | 1.00 | 22.75 |
| ATOM | 1305 | O | LYS | 166 | 5.594 | -6.523 | 31.884 | 1.00 | 20.68 |
| ATOM | 1306 | N | MET | 167 | 5.523 | -8.741 | 32.230 | 1.00 | 22.74 |
| ATOM | 1307 | CA | MET | 167 | 6.973 | -8.835 | 32.320 | 1.00 | 23.09 |
| ATOM | 1308 | CB | MET | 167 | 7.404 | -10.040 | 33.163 | 1.00 | 24.13 |
| ATOM | 1309 | CG | MET | 167 | 7.362 | -9.790 | 34.665 | 1.00 | 24.94 |
| ATOM | 1310 | SD | MET | 167 | 8.034 | -11.177 | 35.618 | 1.00 | 44.99 |
| ATOM | 1311 | CE | MET | 167 | 6.628 | -12.283 | 35.657 | 1.00 | 40.11 |
| ATOM | 1312 | C | MET | 167 | 7.472 | -8.985 | 30.891 | 1.00 | 23.61 |
| ATOM | 1313 | O | MET | 167 | 7.164 | -9.962 | 30.213 | 1.00 | 24.88 |
| ATOM | 1314 | N | CYS | 168 | 8.214 | -7.989 | 30.424 | 1.00 | 19.83 |
| ATOM | 1315 | CA | CYS | 168 | 8.744 | -8.018 | 29.071 | 1.00 | 19.64 |
| ATOM | 1316 | CB | CYS | 168 | 7.687 | -7.578 | 28.061 | 1.00 | 19.32 |
| ATOM | 1317 | SG | CYS | 168 | 6.981 | -5.932 | 28.333 | 1.00 | 25.33 |
| ATOM | 1318 | C | CYS | 168 | 9.959 | -7.112 | 28.979 | 1.00 | 19.48 |
| ATOM | 1319 | O | CYS | 168 | 10.243 | -6.341 | 29.899 | 1.00 | 19.57 |
| ATOM | 1320 | N | GLY | 169 | 10.668 | -7.212 | 27.860 | 1.00 | 18.34 |
| ATOM | 1321 | CA | GLY | 169 | 11.867 | -6.422 | 27.671 | 1.00 | 16.84 |
| ATOM | 1322 | C | GLY | 169 | 13.056 | -7.347 | 27.473 | 1.00 | 17.86 |
| ATOM | 1323 | O | GLY | 169 | 12.910 | -8.446 | 26.932 | 1.00 | 17.29 |
| ATOM | 1324 | N | THR | 170 | 14.225 | -6.898 | 27.922 | 1.00 | 16.83 |
| ATOM | 1325 | CA | THR | 170 | 15.473 | -7.649 | 27.811 | 1.00 | 17.19 |
| ATOM | 1326 | CB | THR | 170 | 16.343 | -7.057 | 26.678 | 1.00 | 16.59 |
| ATOM | 1327 | OG1 | THR | 170 | 15.593 | -7.087 | 25.453 | 1.00 | 16.29 |
| ATOM | 1328 | CG2 | THR | 170 | 17.606 | -7.871 | 26.483 | 1.00 | 17.54 |
| ATOM | 1329 | C | THR | 170 | 16.160 | -7.520 | 29.176 | 1.00 | 15.39 |
| ATOM | 1330 | O | THR | 170 | 16.494 | -6.416 | 29.608 | 1.00 | 13.60 |
| ATOM | 1331 | N | LEU | 171 | 16.374 | -8.658 | 29.838 | 1.00 | 15.78 |
| ATOM | 1332 | CA | LEU | 171 | 16.938 | -8.697 | 31.190 | 1.00 | 15.62 |
| ATOM | 1333 | CB | LEU | 171 | 17.420 | -10.126 | 31.494 | 1.00 | 17.62 |
| ATOM | 1334 | CG | LEU | 171 | 16.781 | -10.963 | 32.621 | 1.00 | 24.25 |
| ATOM | 1335 | CD1 | LEU | 171 | 15.469 | -10.373 | 33.131 | 1.00 | 20.87 |
| ATOM | 1336 | CD2 | LEU | 171 | 16.577 | -12.390 | 32.116 | 1.00 | 14.78 |
| ATOM | 1337 | C | LEU | 171 | 18.007 | -7.675 | 31.615 | 1.00 | 15.63 |
| ATOM | 1338 | O | LEU | 171 | 17.835 | -6.989 | 32.625 | 1.00 | 14.39 |
| ATOM | 1339 | N | PRO | 172 | 19.123 | -7.559 | 30.872 | 1.00 | 15.88 |
| ATOM | 1340 | CD | PRO | 172 | 19.564 | -8.355 | 29.713 | 1.00 | 18.04 |
| ATOM | 1341 | CA | PRO | 172 | 20.156 | -6.589 | 31.270 | 1.00 | 16.57 |
| ATOM | 1342 | CB | PRO | 172 | 21.268 | -6.815 | 30.244 | 1.00 | 16.20 |
| ATOM | 1343 | CG | PRO | 172 | 21.060 | -8.248 | 29.811 | 1.00 | 17.53 |
| ATOM | 1344 | C | PRO | 172 | 19.689 | -5.133 | 31.284 | 1.00 | 16.25 |

FIG.11A-32

| ATOM | 1345 | O | PRO | 172 | 20.268 | -4.291 | 31.972 | 1.00 | 18.87 |
|------|------|-----|-----|-----|--------|--------|--------|------|-------|
| ATOM | 1346 | N | TYR | 173 | 18.630 | -4.852 | 30.532 | 1.00 | 15.37 |
| ATOM | 1347 | CA | TYR | 173 | 18.073 | -3.506 | 30.421 | 1.00 | 14.75 |
| ATOM | 1348 | CB | TYR | 173 | 17.757 | -3.218 | 28.950 | 1.00 | 13.39 |
| ATOM | 1349 | CG | TYR | 173 | 18.954 | -3.298 | 28.046 | 1.00 | 14.82 |
| ATOM | 1350 | CD1 | TYR | 173 | 19.745 | -2.182 | 27.811 | 1.00 | 15.47 |
| ATOM | 1351 | CE1 | TYR | 173 | 20.872 | -2.255 | 26.993 | 1.00 | 20.45 |
| ATOM | 1352 | CD2 | TYR | 173 | 19.314 | -4.503 | 27.438 | 1.00 | 19.99 |
| ATOM | 1353 | CE2 | TYR | 173 | 20.435 | -4.585 | 26.617 | 1.00 | 23.28 |
| ATOM | 1354 | CZ | TYR | 173 | 21.208 | -3.455 | 26.401 | 1.00 | 20.15 |
| ATOM | 1355 | OH | TYR | 173 | 22.317 | -3.523 | 25.586 | 1.00 | 23.35 |
| ATOM | 1356 | C | TYR | 173 | 16.795 | -3.271 | 31.223 | 1.00 | 14.06 |
| ATOM | 1357 | O | TYR | 173 | 16.336 | -2.135 | 31.351 | 1.00 | 13.16 |
| ATOM | 1358 | N | VAL | 174 | 16.212 | -4.328 | 31.771 | 1.00 | 15.36 |
| ATOM | 1359 | CA | VAL | 174 | 14.950 | -4.171 | 32.485 | 1.00 | 15.69 |
| ATOM | 1360 | CB | VAL | 174 | 14.183 | -5.529 | 32.498 | 1.00 | 18.37 |
| ATOM | 1361 | CG1 | VAL | 174 | 14.686 | -6.421 | 33.634 | 1.00 | 16.95 |
| ATOM | 1362 | CG2 | VAL | 174 | 12.689 | -5.284 | 32.590 | 1.00 | 20.81 |
| ATOM | 1363 | C | VAL | 174 | 15.083 | -3.596 | 33.909 | 1.00 | 14.76 |
| ATOM | 1364 | O | VAL | 174 | 16.048 | -3.875 | 34.616 | 1.00 | 14.52 |
| ATOM | 1365 | N | ALA | 175 | 14.109 | -2.778 | 34.302 | 1.00 | 14.40 |
| ATOM | 1366 | CA | ALA | 175 | 14.099 | -2.152 | 35.628 | 1.00 | 14.61 |
| ATOM | 1367 | CB | ALA | 175 | 13.044 | -1.055 | 35.669 | 1.00 | 15.96 |
| ATOM | 1368 | C | ALA | 175 | 13.830 | -3.185 | 36.729 | 1.00 | 14.55 |
| ATOM | 1369 | O | ALA | 175 | 13.079 | -4.130 | 36.529 | 1.00 | 14.73 |
| ATOM | 1370 | N | PRO | 176 | 14.435 | -3.001 | 37.912 | 1.00 | 14.46 |
| ATOM | 1371 | CD | PRO | 176 | 15.321 | -1.891 | 38.303 | 1.00 | 16.61 |
| ATOM | 1372 | CA | PRO | 176 | 14.247 | -3.941 | 39.022 | 1.00 | 15.95 |
| ATOM | 1373 | CB | PRO | 176 | 15.154 | -3.372 | 40.120 | 1.00 | 18.53 |
| ATOM | 1374 | CG | PRO | 176 | 15.200 | -1.896 | 39.812 | 1.00 | 17.80 |
| ATOM | 1375 | C | PRO | 176 | 12.805 | -4.157 | 39.487 | 1.00 | 17.01 |
| ATOM | 1376 | O | PRO | 176 | 12.456 | -5.257 | 39.923 | 1.00 | 18.04 |
| ATOM | 1377 | N | GLU | 177 | 11.958 | -3.134 | 39.381 | 1.00 | 17.70 |
| ATOM | 1378 | CA | GLU | 177 | 10.578 | -3.294 | 39.819 | 1.00 | 19.33 |
| ATOM | 1379 | CB | GLU | 177 | 9.831 | -1.954 | 39.825 | 1.00 | 19.43 |
| ATOM | 1380 | CG | GLU | 177 | 9.711 | -1.238 | 38.479 | 1.00 | 18.24 |
| ATOM | 1381 | CD | GLU | 177 | 10.866 | -0.291 | 38.199 | 1.00 | 18.08 |
| ATOM | 1382 | OE1 | GLU | 177 | 10.672 | 0.643 | 37.389 | 1.00 | 15.25 |
| ATOM | 1383 | OE2 | GLU | 177 | 11.962 | -0.481 | 38.775 | 1.00 | 19.51 |
| ATOM | 1384 | C | GLU | 177 | 9.815 | -4.314 | 38.977 | 1.00 | 19.97 |
| ATOM | 1385 | O | GLU | 177 | 8.877 | -4.941 | 39.455 | 1.00 | 18.86 |
| ATOM | 1386 | N | LEU | 178 | 10.214 | -4.485 | 37.721 | 1.00 | 18.60 |

FIG.11A-33

```
ATOM   1387  CA   LEU  178    9.540   -5.448  36.861  1.00  21.80
ATOM   1388  CB   LEU  178   10.037   -5.283  35.412  1.00  26.36
ATOM   1389  CG   LEU  178    9.551   -6.196  34.281  1.00  30.81
ATOM   1390  CD1  LEU  178   10.271   -7.531  34.349  1.00  32.00
ATOM   1391  CD2  LEU  178    8.053   -6.389  34.371  1.00  34.42
ATOM   1392  C    LEU  178    9.789   -6.866  37.379  1.00  21.49
ATOM   1393  O    LEU  178    8.987   -7.776  37.148  1.00  22.54
ATOM   1394  N    LEU  179   10.886   -7.051  38.107  1.00  22.22
ATOM   1395  CA   LEU  179   11.213   -8.365  38.648  1.00  23.39
ATOM   1396  CB   LEU  179   12.719   -8.621  38.558  1.00  23.03
ATOM   1397  CG   LEU  179   13.416   -8.495  37.200  1.00  26.29
ATOM   1398  CD1  LEU  179   14.903   -8.733  37.390  1.00  24.67
ATOM   1399  CD2  LEU  179   12.837   -9.491  36.204  1.00  26.57
ATOM   1400  C    LEU  179   10.770   -8.558  40.096  1.00  24.84
ATOM   1401  O    LEU  179   10.847   -9.667  40.627  1.00  26.92
ATOM   1402  N    LYS  180   10.295   -7.504  40.746  1.00  23.35
ATOM   1403  CA   LYS  180    9.908   -7.666  42.143  1.00  25.69
ATOM   1404  CB   LYS  180   10.916   -6.949  43.044  1.00  31.39
ATOM   1405  CG   LYS  180   11.002   -5.452  42.823  1.00  40.61
ATOM   1406  CD   LYS  180   12.048   -4.816  43.737  1.00  49.38
ATOM   1407  CE   LYS  180   13.441   -5.362  43.457  1.00  56.38
ATOM   1408  NZ   LYS  180   14.482   -4.726  44.313  1.00  63.75
ATOM   1409  C    LYS  180    8.508   -7.228  42.521  1.00  26.89
ATOM   1410  O    LYS  180    8.025   -7.586  43.596  1.00  27.55
ATOM   1411  N    ARG  181    7.849   -6.471  41.651  1.00  25.95
ATOM   1412  CA   ARG  181    6.507   -5.985  41.953  1.00  23.62
ATOM   1413  CB   ARG  181    6.515   -4.457  42.013  1.00  20.86
ATOM   1414  CG   ARG  181    7.886   -3.864  42.345  1.00  23.41
ATOM   1415  CD   ARG  181    7.952   -3.096  43.655  1.00  28.25
ATOM   1416  NE   ARG  181    7.769   -3.932  44.835  1.00  26.30
ATOM   1417  CZ   ARG  181    8.303   -3.678  46.032  1.00  25.03
ATOM   1418  NH1  ARG  181    8.059   -4.494  47.048  1.00  21.28
ATOM   1419  NH2  ARG  181    9.096   -2.632  46.221  1.00  26.39
ATOM   1420  C    ARG  181    5.489   -6.459  40.921  1.00  24.18
ATOM   1421  O    ARG  181    5.813   -6.625  39.743  1.00  23.59
ATOM   1422  N    ARG  182    4.257   -6.685  41.362  1.00  26.62
ATOM   1423  CA   ARG  182    3.214   -7.141  40.452  1.00  27.87
ATOM   1424  CB   ARG  182    1.958   -7.550  41.229  1.00  32.39
ATOM   1425  CG   ARG  182    0.955   -8.322  40.382  1.00  45.18
ATOM   1426  CD   ARG  182   -0.386   -8.462  41.083  1.00  54.85
ATOM   1427  NE   ARG  182   -1.032   -7.166  41.265  1.00  60.82
ATOM   1428  CZ   ARG  182   -2.245   -6.998  41.781  1.00  66.47
```

FIG.11A-34

| | | | | | | | | |
|---|---|---|---|---|---|---|---|---|
| ATOM | 1429 | NH1 | ARG | 182 | -2.954 | -8.049 | 42.170 | 1.00 73.47 |
| ATOM | 1430 | NH2 | ARG | 182 | -2.750 | -5.778 | 41.905 | 1.00 66.10 |
| ATOM | 1431 | C | ARG | 182 | 2.852 | -6.046 | 39.450 | 1.00 25.07 |
| ATOM | 1432 | O | ARG | 182 | 2.667 | -6.320 | 38.261 | 1.00 25.61 |
| ATOM | 1433 | N | GLU | 183 | 2.744 | -4.812 | 39.936 | 1.00 23.08 |
| ATOM | 1434 | CA | GLU | 183 | 2.406 | -3.673 | 39.085 | 1.00 23.45 |
| ATOM | 1435 | CB | GLU | 183 | 1.067 | -3.059 | 39.501 | 1.00 21.25 |
| ATOM | 1436 | CG | GLU | 183 | -0.147 | -3.899 | 39.187 | 1.00 24.48 |
| ATOM | 1437 | CD | GLU | 183 | -1.423 | -3.181 | 39.569 | 1.00 30.66 |
| ATOM | 1438 | OE1 | GLU | 183 | -1.611 | -2.902 | 40.771 | 1.00 34.79 |
| ATOM | 1439 | OE2 | GLU | 183 | -2.228 | -2.883 | 38.666 | 1.00 30.34 |
| ATOM | 1440 | C | GLU | 183 | 3.482 | -2.600 | 39.169 | 1.00 21.06 |
| ATOM | 1441 | O | GLU | 183 | 4.209 | -2.512 | 40.158 | 1.00 21.34 |
| ATOM | 1442 | N | PHE | 184 | 3.565 | -1.768 | 38.137 | 1.00 18.15 |
| ATOM | 1443 | CA | PHE | 184 | 4.567 | -0.717 | 38.105 | 1.00 15.58 |
| ATOM | 1444 | CB | PHE | 184 | 5.945 | -1.346 | 37.819 | 1.00 16.74 |
| ATOM | 1445 | CG | PHE | 184 | 5.926 | -2.381 | 36.726 | 1.00 14.62 |
| ATOM | 1446 | CD1 | PHE | 184 | 5.951 | -2.005 | 35.392 | 1.00 18.17 |
| ATOM | 1447 | CD2 | PHE | 184 | 5.815 | -3.739 | 37.036 | 1.00 17.28 |
| ATOM | 1448 | CE1 | PHE | 184 | 5.860 | -2.959 | 34.375 | 1.00 20.20 |
| ATOM | 1449 | CE2 | PHE | 184 | 5.721 | -4.698 | 36.029 | 1.00 16.96 |
| ATOM | 1450 | CZ | PHE | 184 | 5.741 | -4.306 | 34.696 | 1.00 17.04 |
| ATOM | 1451 | C | PHE | 184 | 4.222 | 0.353 | 37.067 | 1.00 16.19 |
| ATOM | 1452 | O | PHE | 184 | 3.506 | 0.084 | 36.096 | 1.00 15.45 |
| ATOM | 1453 | N | HIS | 185 | 4.707 | 1.569 | 37.298 | 1.00 16.14 |
| ATOM | 1454 | CA | HIS | 185 | 4.499 | 2.688 | 36.380 | 1.00 17.03 |
| ATOM | 1455 | CB | HIS | 185 | 4.911 | 3.998 | 37.057 | 1.00 15.20 |
| ATOM | 1456 | CG | HIS | 185 | 3.954 | 4.462 | 38.110 | 1.00 17.47 |
| ATOM | 1457 | CD2 | HIS | 185 | 4.016 | 4.403 | 39.463 | 1.00 16.97 |
| ATOM | 1458 | ND1 | HIS | 185 | 2.755 | 5.074 | 37.808 | 1.00 17.76 |
| ATOM | 1459 | CE1 | HIS | 185 | 2.122 | 5.373 | 38.930 | 1.00 15.00 |
| ATOM | 1460 | NE2 | HIS | 185 | 2.866 | 4.978 | 39.948 | 1.00 16.42 |
| ATOM | 1461 | C | HIS | 185 | 5.346 | 2.468 | 35.121 | 1.00 16.88 |
| ATOM | 1462 | O | HIS | 185 | 6.489 | 2.023 | 35.202 | 1.00 15.15 |
| ATOM | 1463 | N | ALA | 186 | 4.789 | 2.789 | 33.959 | 1.00 15.23 |
| ATOM | 1464 | CA | ALA | 186 | 5.500 | 2.584 | 32.696 | 1.00 14.49 |
| ATOM | 1465 | CB | ALA | 186 | 4.543 | 2.773 | 31.529 | 1.00 11.65 |
| ATOM | 1466 | C | ALA | 186 | 6.719 | 3.472 | 32.469 | 1.00 15.84 |
| ATOM | 1467 | O | ALA | 186 | 7.768 | 2.999 | 32.039 | 1.00 13.75 |
| ATOM | 1468 | N | GLU | 187 | 6.579 | 4.760 | 32.747 | 1.00 13.01 |
| ATOM | 1469 | CA | GLU | 187 | 7.665 | 5.694 | 32.475 | 1.00 14.78 |
| ATOM | 1470 | CB | GLU | 187 | 7.190 | 7.118 | 32.758 | 1.00 13.83 |

FIG.11A-35

| | | | | | | | |
|---|---|---|---|---|---|---|---|
| ATOM | 1471 | CG | GLU | 187 | 6.131 | 7.564 | 31.755 | 1.00 | 14.84 |
| ATOM | 1472 | CD | GLU | 187 | 5.476 | 8.860 | 32.155 | 1.00 | 17.06 |
| ATOM | 1473 | OE1 | GLU | 187 | 5.783 | 9.898 | 31.537 | 1.00 | 17.90 |
| ATOM | 1474 | OE2 | GLU | 187 | 4.669 | 8.836 | 33.101 | 1.00 | 25.47 |
| ATOM | 1475 | C | GLU | 187 | 9.023 | 5.420 | 33.119 | 1.00 | 13.36 |
| ATOM | 1476 | O | GLU | 187 | 10.044 | 5.468 | 32.435 | 1.00 | 14.03 |
| ATOM | 1477 | N | PRO | 188 | 9.064 | 5.134 | 34.427 | 1.00 | 12.65 |
| ATOM | 1478 | CD | PRO | 188 | 8.004 | 5.222 | 35.448 | 1.00 | 12.15 |
| ATOM | 1479 | CA | PRO | 188 | 10.369 | 4.868 | 35.042 | 1.00 | 11.62 |
| ATOM | 1480 | CB | PRO | 188 | 10.029 | 4.690 | 36.532 | 1.00 | 13.87 |
| ATOM | 1481 | CG | PRO | 188 | 8.799 | 5.543 | 36.707 | 1.00 | 12.10 |
| ATOM | 1482 | C | PRO | 188 | 11.079 | 3.639 | 34.471 | 1.00 | 11.69 |
| ATOM | 1483 | O | PRO | 188 | 12.302 | 3.525 | 34.575 | 1.00 | 13.08 |
| ATOM | 1484 | N | VAL | 189 | 10.324 | 2.709 | 33.878 | 1.00 | 12.14 |
| ATOM | 1485 | CA | VAL | 189 | 10.934 | 1.508 | 33.313 | 1.00 | 12.36 |
| ATOM | 1486 | CB | VAL | 189 | 9.845 | 0.440 | 32.946 | 1.00 | 11.17 |
| ATOM | 1487 | CG1 | VAL | 189 | 10.485 | -0.758 | 32.243 | 1.00 | 11.29 |
| ATOM | 1488 | CG2 | VAL | 189 | 9.135 | -0.030 | 34.207 | 1.00 | 12.20 |
| ATOM | 1489 | C | VAL | 189 | 11.746 | 1.907 | 32.069 | 1.00 | 14.29 |
| ATOM | 1490 | O | VAL | 189 | 12.877 | 1.442 | 31.873 | 1.00 | 13.97 |
| ATOM | 1491 | N | ASP | 190 | 11.180 | 2.781 | 31.237 | 1.00 | 13.89 |
| ATOM | 1492 | CA | ASP | 190 | 11.882 | 3.237 | 30.042 | 1.00 | 13.47 |
| ATOM | 1493 | CB | ASP | 190 | 10.952 | 4.039 | 29.115 | 1.00 | 15.20 |
| ATOM | 1494 | CG | ASP | 190 | 10.078 | 3.154 | 28.230 | 1.00 | 17.71 |
| ATOM | 1495 | OD1 | ASP | 190 | 10.434 | 1.981 | 27.987 | 1.00 | 16.91 |
| ATOM | 1496 | OD2 | ASP | 190 | 9.037 | 3.652 | 27.754 | 1.00 | 17.19 |
| ATOM | 1497 | C | ASP | 190 | 13.062 | 4.124 | 30.462 | 1.00 | 13.29 |
| ATOM | 1498 | O | ASP | 190 | 14.109 | 4.135 | 29.820 | 1.00 | 11.95 |
| ATOM | 1499 | N | VAL | 191 | 12.903 | 4.870 | 31.547 | 1.00 | 13.34 |
| ATOM | 1500 | CA | VAL | 191 | 14.009 | 5.716 | 31.988 | 1.00 | 14.45 |
| ATOM | 1501 | CB | VAL | 191 | 13.602 | 6.603 | 33.187 | 1.00 | 14.74 |
| ATOM | 1502 | CG1 | VAL | 191 | 14.842 | 7.202 | 33.852 | 1.00 | 12.70 |
| ATOM | 1503 | CG2 | VAL | 191 | 12.688 | 7.727 | 32.692 | 1.00 | 13.03 |
| ATOM | 1504 | C | VAL | 191 | 15.203 | 4.840 | 32.386 | 1.00 | 13.08 |
| ATOM | 1505 | O | VAL | 191 | 16.346 | 5.146 | 32.053 | 1.00 | 11.25 |
| ATOM | 1506 | N | TRP | 192 | 14.921 | 3.756 | 33.094 | 1.00 | 12.71 |
| ATOM | 1507 | CA | TRP | 192 | 15.958 | 2.833 | 33.546 | 1.00 | 12.03 |
| ATOM | 1508 | CB | TRP | 192 | 15.322 | 1.727 | 34.409 | 1.00 | 9.46 |
| ATOM | 1509 | CG | TRP | 192 | 16.294 | 0.677 | 34.852 | 1.00 | 12.75 |
| ATOM | 1510 | CD2 | TRP | 192 | 16.899 | 0.563 | 36.145 | 1.00 | 13.79 |
| ATOM | 1511 | CE2 | TRP | 192 | 17.767 | -0.550 | 36.104 | 1.00 | 11.39 |
| ATOM | 1512 | CE3 | TRP | 192 | 16.789 | 1.294 | 37.338 | 1.00 | 12.63 |

FIG.11A-36

| | | | | | | | | |
|---|---|---|---|---|---|---|---|---|
| ATOM | 1513 | CD1 | TRP | 192 | 16.804 | -0.342 | 34.098 | 1.00 12.01 |
| ATOM | 1514 | NE1 | TRP | 192 | 17.691 | -1.086 | 34.846 | 1.00 12.49 |
| ATOM | 1515 | CZ2 | TRP | 192 | 18.525 | -0.952 | 37.215 | 1.00 12.51 |
| ATOM | 1516 | CZ3 | TRP | 192 | 17.537 | 0.894 | 38.439 | 1.00 14.40 |
| ATOM | 1517 | CH2 | TRP | 192 | 18.396 | -0.221 | 38.368 | 1.00 12.56 |
| ATOM | 1518 | C | TRP | 192 | 16.713 | 2.226 | 32.364 | 1.00 12.79 |
| ATOM | 1519 | O | TRP | 192 | 17.947 | 2.240 | 32.345 | 1.00 12.82 |
| ATOM | 1520 | N | SER | 193 | 15.991 | 1.706 | 31.373 | 1.00 13.03 |
| ATOM | 1521 | CA | SER | 193 | 16.676 | 1.118 | 30.221 | 1.00 13.36 |
| ATOM | 1522 | CB | SER | 193 | 15.672 | 0.467 | 29.263 | 1.00 11.41 |
| ATOM | 1523 | OG | SER | 193 | 14.658 | 1.368 | 28.864 | 1.00 14.36 |
| ATOM | 1524 | C | SER | 193 | 17.523 | 2.175 | 29.506 | 1.00 13.32 |
| ATOM | 1525 | O | SER | 193 | 18.582 | 1.866 | 28.973 | 1.00 12.69 |
| ATOM | 1526 | N | CYS | 194 | 17.064 | 3.420 | 29.471 | 1.00 12.77 |
| ATOM | 1527 | CA | CYS | 194 | 17.886 | 4.463 | 28.840 | 1.00 13.01 |
| ATOM | 1528 | CB | CYS | 194 | 17.136 | 5.799 | 28.793 | 1.00 11.84 |
| ATOM | 1529 | SG | CYS | 194 | 15.813 | 5.829 | 27.558 | 1.00 12.71 |
| ATOM | 1530 | C | CYS | 194 | 19.195 | 4.643 | 29.624 | 1.00 11.67 |
| ATOM | 1531 | O | CYS | 194 | 20.223 | 4.970 | 29.050 | 1.00 13.09 |
| ATOM | 1532 | N | GLY | 195 | 19.137 | 4.424 | 30.934 | 1.00 11.41 |
| ATOM | 1533 | CA | GLY | 195 | 20.324 | 4.541 | 31.776 | 1.00 12.03 |
| ATOM | 1534 | C | GLY | 195 | 21.311 | 3.421 | 31.480 | 1.00 12.90 |
| ATOM | 1535 | O | GLY | 195 | 22.529 | 3.624 | 31.491 | 1.00 12.32 |
| ATOM | 1536 | N | ILE | 196 | 20.792 | 2.225 | 31.223 | 1.00 13.85 |
| ATOM | 1537 | CA | ILE | 196 | 21.673 | 1.100 | 30.899 | 1.00 15.56 |
| ATOM | 1538 | CB | ILE | 196 | 20.896 | -0.240 | 30.942 | 1.00 21.20 |
| ATOM | 1539 | CG2 | ILE | 196 | 19.649 | -0.143 | 30.132 | 1.00 21.27 |
| ATOM | 1540 | CG1 | ILE | 196 | 21.763 | -1.380 | 30.415 | 1.00 20.74 |
| ATOM | 1541 | CD1 | ILE | 196 | 22.970 | -1.620 | 31.237 | 1.00 36.22 |
| ATOM | 1542 | C | ILE | 196 | 22.294 | 1.345 | 29.516 | 1.00 13.15 |
| ATOM | 1543 | O | ILE | 196 | 23.459 | 1.009 | 29.277 | 1.00 12.36 |
| ATOM | 1544 | N | VAL | 197 | 21.527 | 1.941 | 28.603 | 1.00 12.90 |
| ATOM | 1545 | CA | VAL | 197 | 22.054 | 2.257 | 27.278 | 1.00 13.36 |
| ATOM | 1546 | CB | VAL | 197 | 20.957 | 2.852 | 26.349 | 1.00 13.82 |
| ATOM | 1547 | CG1 | VAL | 197 | 21.593 | 3.495 | 25.106 | 1.00 12.22 |
| ATOM | 1548 | CG2 | VAL | 197 | 19.986 | 1.740 | 25.929 | 1.00 13.53 |
| ATOM | 1549 | C | VAL | 197 | 23.193 | 3.270 | 27.438 | 1.00 14.88 |
| ATOM | 1550 | O | VAL | 197 | 24.220 | 3.168 | 26.767 | 1.00 16.68 |
| ATOM | 1551 | N | LEU | 198 | 23.026 | 4.231 | 28.344 | 1.00 13.75 |
| ATOM | 1552 | CA | LEU | 198 | 24.060 | 5.244 | 28.561 | 1.00 13.15 |
| ATOM | 1553 | CB | LEU | 198 | 23.579 | 6.306 | 29.552 | 1.00 12.43 |
| ATOM | 1554 | CG | LEU | 198 | 23.930 | 7.793 | 29.353 | 1.00 21.66 |

FIG.11A-37

| | | | | | | | | |
|---|---|---|---|---|---|---|---|---|
| ATOM | 1555 | CD1 | LEU | 198 | 23.945 | 8.469 | 30.718 | 1.00 15.92 |
| ATOM | 1556 | CD2 | LEU | 198 | 25.243 | 8.000 | 28.625 | 1.00 14.52 |
| ATOM | 1557 | C | LEU | 198 | 25.313 | 4.560 | 29.110 | 1.00 14.88 |
| ATOM | 1558 | O | LEU | 198 | 26.436 | 4.864 | 28.702 | 1.00 14.46 |
| ATOM | 1559 | N | THR | 199 | 25.117 | 3.639 | 30.044 | 1.00 14.39 |
| ATOM | 1560 | CA | THR | 199 | 26.250 | 2.909 | 30.623 | 1.00 16.47 |
| ATOM | 1561 | CB | THR | 199 | 25.766 | 1.920 | 31.698 | 1.00 14.59 |
| ATOM | 1562 | OG1 | THR | 199 | 25.085 | 2.643 | 32.728 | 1.00 15.04 |
| ATOM | 1563 | CG2 | THR | 199 | 26.947 | 1.174 | 32.321 | 1.00 13.58 |
| ATOM | 1564 | C | THR | 199 | 27.005 | 2.156 | 29.523 | 1.00 17.44 |
| ATOM | 1565 | O | THR | 199 | 28.237 | 2.192 | 29.465 | 1.00 18.28 |
| ATOM | 1566 | N | ALA | 200 | 26.261 | 1.486 | 28.646 | 1.00 15.89 |
| ATOM | 1567 | CA | ALA | 200 | 26.866 | 0.736 | 27.546 | 1.00 16.21 |
| ATOM | 1568 | CB | ALA | 200 | 25.777 | 0.003 | 26.749 | 1.00 14.29 |
| ATOM | 1569 | C | ALA | 200 | 27.662 | 1.660 | 26.623 | 1.00 17.57 |
| ATOM | 1570 | O | ALA | 200 | 28.781 | 1.337 | 26.225 | 1.00 18.68 |
| ATOM | 1571 | N | MET | 201 | 27.090 | 2.808 | 26.271 | 1.00 16.39 |
| ATOM | 1572 | CA | MET | 201 | 27.792 | 3.742 | 25.389 | 1.00 14.62 |
| ATOM | 1573 | CB | MET | 201 | 26.904 | 4.941 | 25.025 | 1.00 11.19 |
| ATOM | 1574 | CG | MET | 201 | 25.656 | 4.594 | 24.221 | 1.00 13.75 |
| ATOM | 1575 | SD | MET | 201 | 24.917 | 6.071 | 23.450 | 1.00 18.10 |
| ATOM | 1576 | CE | MET | 201 | 24.144 | 6.895 | 24.918 | 1.00 13.57 |
| ATOM | 1577 | C | MET | 201 | 29.080 | 4.275 | 26.006 | 1.00 15.76 |
| ATOM | 1578 | O | MET | 201 | 30.055 | 4.523 | 25.296 | 1.00 15.99 |
| ATOM | 1579 | N | LEU | 202 | 29.086 | 4.444 | 27.325 | 1.00 15.81 |
| ATOM | 1580 | CA | LEU | 202 | 30.258 | 4.996 | 28.014 | 1.00 17.08 |
| ATOM | 1581 | CB | LEU | 202 | 29.805 | 5.866 | 29.195 | 1.00 15.75 |
| ATOM | 1582 | CG | LEU | 202 | 29.018 | 7.136 | 28.828 | 1.00 15.95 |
| ATOM | 1583 | CD1 | LEU | 202 | 28.622 | 7.901 | 30.095 | 1.00 12.72 |
| ATOM | 1584 | CD2 | LEU | 202 | 29.870 | 8.009 | 27.910 | 1.00 16.64 |
| ATOM | 1585 | C | LEU | 202 | 31.309 | 3.992 | 28.512 | 1.00 18.70 |
| ATOM | 1586 | O | LEU | 202 | 32.440 | 4.381 | 28.815 | 1.00 20.36 |
| ATOM | 1587 | N | ALA | 203 | 30.956 | 2.716 | 28.592 | 1.00 17.89 |
| ATOM | 1588 | CA | ALA | 203 | 31.906 | 1.721 | 29.088 | 1.00 19.09 |
| ATOM | 1589 | CB | ALA | 203 | 31.509 | 1.296 | 30.493 | 1.00 16.50 |
| ATOM | 1590 | C | ALA | 203 | 32.064 | 0.496 | 28.191 | 1.00 19.03 |
| ATOM | 1591 | O | ALA | 203 | 32.957 | -0.334 | 28.404 | 1.00 19.86 |
| ATOM | 1592 | N | GLY | 204 | 31.197 | 0.373 | 27.195 | 1.00 17.84 |
| ATOM | 1593 | CA | GLY | 204 | 31.279 | -0.756 | 26.283 | 1.00 19.26 |
| ATOM | 1594 | C | GLY | 204 | 30.967 | -2.097 | 26.920 | 1.00 21.43 |
| ATOM | 1595 | O | GLY | 204 | 31.435 | -3.137 | 26.453 | 1.00 23.21 |
| ATOM | 1596 | N | GLU | 205 | 30.199 | -2.074 | 28.002 | 1.00 20.75 |

FIG.11A-38

| | | | | | | | | | |
|---|---|---|---|---|---|---|---|---|---|
| ATOM | 1597 | CA | GLU | 205 | 29.806 | -3.302 | 28.688 | 1.00 | 20.39 |
| ATOM | 1598 | CB | GLU | 205 | 30.935 | -3.826 | 29.588 | 1.00 | 22.16 |
| ATOM | 1599 | CG | GLU | 205 | 31.143 | -3.074 | 30.887 | 1.00 | 27.49 |
| ATOM | 1600 | CD | GLU | 205 | 32.247 | -3.681 | 31.751 | 1.00 | 29.22 |
| ATOM | 1601 | OE1 | GLU | 205 | 32.138 | -4.860 | 32.146 | 1.00 | 35.45 |
| ATOM | 1602 | OE2 | GLU | 205 | 33.225 | -2.971 | 32.040 | 1.00 | 28.80 |
| ATOM | 1603 | C | GLU | 205 | 28.563 | -3.054 | 29.518 | 1.00 | 18.62 |
| ATOM | 1604 | O | GLU | 205 | 28.305 | -1.932 | 29.958 | 1.00 | 19.35 |
| ATOM | 1605 | N | LEU | 206 | 27.779 | -4.105 | 29.714 | 1.00 | 19.99 |
| ATOM | 1606 | CA | LEU | 206 | 26.562 | -4.013 | 30.505 | 1.00 | 20.37 |
| ATOM | 1607 | CB | LEU | 206 | 25.543 | -5.044 | 30.013 | 1.00 | 18.33 |
| ATOM | 1608 | CG | LEU | 206 | 24.899 | -4.783 | 28.643 | 1.00 | 20.09 |
| ATOM | 1609 | CD1 | LEU | 206 | 25.952 | -4.511 | 27.586 | 1.00 | 30.30 |
| ATOM | 1610 | CD2 | LEU | 206 | 24.075 | -5.987 | 28.246 | 1.00 | 18.48 |
| ATOM | 1611 | C | LEU | 206 | 26.976 | -4.290 | 31.944 | 1.00 | 21.02 |
| ATOM | 1612 | O | LEU | 206 | 27.769 | -5.195 | 32.205 | 1.00 | 21.65 |
| ATOM | 1613 | N | PRO | 207 | 26.449 | -3.510 | 32.898 | 1.00 | 21.06 |
| ATOM | 1614 | CD | PRO | 207 | 25.507 | -2.400 | 32.678 | 1.00 | 18.20 |
| ATOM | 1615 | CA | PRO | 207 | 26.760 | -3.646 | 34.323 | 1.00 | 21.75 |
| ATOM | 1616 | CB | PRO | 207 | 26.118 | -2.405 | 34.932 | 1.00 | 19.82 |
| ATOM | 1617 | CG | PRO | 207 | 24.920 | -2.200 | 34.055 | 1.00 | 17.27 |
| ATOM | 1618 | C | PRO | 207 | 26.330 | -4.929 | 35.027 | 1.00 | 23.19 |
| ATOM | 1619 | O | PRO | 207 | 27.002 | -5.363 | 35.958 | 1.00 | 25.40 |
| ATOM | 1620 | N | TRP | 208 | 25.222 | -5.533 | 34.600 | 1.00 | 20.85 |
| ATOM | 1621 | CA | TRP | 208 | 24.759 | -6.768 | 35.227 | 1.00 | 19.87 |
| ATOM | 1622 | CB | TRP | 208 | 24.037 | -6.449 | 36.542 | 1.00 | 17.82 |
| ATOM | 1623 | CG | TRP | 208 | 23.079 | -5.294 | 36.431 | 1.00 | 16.93 |
| ATOM | 1624 | CD2 | TRP | 208 | 23.259 | -3.986 | 36.978 | 1.00 | 15.33 |
| ATOM | 1625 | CE2 | TRP | 208 | 22.156 | -3.203 | 36.564 | 1.00 | 19.36 |
| ATOM | 1626 | CE3 | TRP | 208 | 24.245 | -3.394 | 37.777 | 1.00 | 16.72 |
| ATOM | 1627 | CD1 | TRP | 208 | 21.906 | -5.261 | 35.730 | 1.00 | 19.54 |
| ATOM | 1628 | NE1 | TRP | 208 | 21.344 | -4.005 | 35.805 | 1.00 | 19.05 |
| ATOM | 1629 | CZ2 | TRP | 208 | 22.017 | -1.861 | 36.923 | 1.00 | 17.14 |
| ATOM | 1630 | CZ3 | TRP | 208 | 24.102 | -2.057 | 38.137 | 1.00 | 17.80 |
| ATOM | 1631 | CH2 | TRP | 208 | 22.994 | -1.306 | 37.708 | 1.00 | 17.63 |
| ATOM | 1632 | C | TRP | 208 | 23.847 | -7.604 | 34.334 | 1.00 | 21.19 |
| ATOM | 1633 | O | TRP | 208 | 23.243 | -7.094 | 33.389 | 1.00 | 21.45 |
| ATOM | 1634 | N | ASP | 209 | 23.758 | -8.896 | 34.635 | 1.00 | 22.55 |
| ATOM | 1635 | CA | ASP | 209 | 22.901 | -9.800 | 33.865 | 1.00 | 23.07 |
| ATOM | 1636 | CB | ASP | 209 | 23.087 | -11.256 | 34.317 | 1.00 | 24.77 |
| ATOM | 1637 | CG | ASP | 209 | 24.456 | -11.812 | 33.973 | 1.00 | 29.47 |
| ATOM | 1638 | OD1 | ASP | 209 | 24.996 | -11.464 | 32.901 | 1.00 | 32.08 |

FIG.11A-39

| | | | | | | | | |
|---|---|---|---|---|---|---|---|---|
| ATOM | 1639 | OD2 | ASP | 209 | 24.981 | -12.619 | 34.770 | 1.00 37.34 |
| ATOM | 1640 | C | ASP | 209 | 21.439 | -9.398 | 34.063 | 1.00 22.59 |
| ATOM | 1641 | O | ASP | 209 | 20.623 | -9.498 | 33.143 | 1.00 21.49 |
| ATOM | 1642 | N | GLN | 210 | 21.123 | -8.953 | 35.276 | 1.00 21.47 |
| ATOM | 1643 | CA | GLN | 210 | 19.775 | -8.522 | 35.635 | 1.00 21.65 |
| ATOM | 1644 | CB | GLN | 210 | 18.832 | -9.729 | 35.725 | 1.00 21.36 |
| ATOM | 1645 | CG | GLN | 210 | 19.346 | -10.845 | 36.622 | 1.00 22.91 |
| ATOM | 1646 | CD | GLN | 210 | 18.428 | -12.051 | 36.635 | 1.00 24.69 |
| ATOM | 1647 | OE1 | GLN | 210 | 18.188 | -12.676 | 35.600 | 1.00 28.77 |
| ATOM | 1648 | NE2 | GLN | 210 | 17.905 | -12.383 | 37.810 | 1.00 29.76 |
| ATOM | 1649 | C | GLN | 210 | 19.832 | -7.792 | 36.972 | 1.00 24.10 |
| ATOM | 1650 | O | GLN | 210 | 20.731 | -8.031 | 37.789 | 1.00 24.28 |
| ATOM | 1651 | N | PRO | 211 | 18.874 | -6.886 | 37.214 | 1.00 23.45 |
| ATOM | 1652 | CD | PRO | 211 | 17.887 | -6.387 | 36.234 | 1.00 19.42 |
| ATOM | 1653 | CA | PRO | 211 | 18.815 | -6.108 | 38.451 | 1.00 23.88 |
| ATOM | 1654 | CB | PRO | 211 | 18.038 | -4.869 | 38.024 | 1.00 23.48 |
| ATOM | 1655 | CG | PRO | 211 | 17.044 | -5.443 | 37.072 | 1.00 18.80 |
| ATOM | 1656 | C | PRO | 211 | 18.169 | -6.826 | 39.634 | 1.00 25.58 |
| ATOM | 1657 | O | PRO | 211 | 17.121 | -6.407 | 40.127 | 1.00 25.13 |
| ATOM | 1658 | N | SER | 212 | 18.811 | -7.898 | 40.091 | 1.00 27.11 |
| ATOM | 1659 | CA | SER | 212 | 18.303 | -8.678 | 41.214 | 1.00 30.46 |
| ATOM | 1660 | CB | SER | 212 | 18.006 | -10.110 | 40.770 | 1.00 30.00 |
| ATOM | 1661 | OG | SER | 212 | 17.174 | -10.129 | 39.621 | 1.00 37.91 |
| ATOM | 1662 | C | SER | 212 | 19.324 | -8.707 | 42.349 | 1.00 32.05 |
| ATOM | 1663 | O | SER | 212 | 20.524 | -8.599 | 42.117 | 1.00 30.68 |
| ATOM | 1664 | N | ASP | 213 | 18.834 | -8.857 | 43.575 | 1.00 35.30 |
| ATOM | 1665 | CA | ASP | 213 | 19.706 | -8.912 | 44.741 | 1.00 39.23 |
| ATOM | 1666 | CB | ASP | 213 | 18.866 | -9.031 | 46.014 | 1.00 46.49 |
| ATOM | 1667 | CG | ASP | 213 | 18.025 | -7.795 | 46.273 | 1.00 52.63 |
| ATOM | 1668 | OD1 | ASP | 213 | 17.193 | -7.823 | 47.204 | 1.00 56.41 |
| ATOM | 1669 | OD2 | ASP | 213 | 18.199 | -6.793 | 45.547 | 1.00 59.76 |
| ATOM | 1670 | C | ASP | 213 | 20.663 | -10.098 | 44.632 | 1.00 38.86 |
| ATOM | 1671 | O | ASP | 213 | 21.765 | -10.070 | 45.180 | 1.00 41.19 |
| ATOM | 1672 | N | SER | 214 | 20.235 | -11.133 | 43.914 | 1.00 37.29 |
| ATOM | 1673 | CA | SER | 214 | 21.047 | -12.329 | 43.721 | 1.00 36.16 |
| ATOM | 1674 | CB | SER | 214 | 20.186 | -13.463 | 43.157 | 1.00 39.69 |
| ATOM | 1675 | OG | SER | 214 | 19.604 | -13.090 | 41.917 | 1.00 44.23 |
| ATOM | 1676 | C | SER | 214 | 22.214 | -12.063 | 42.774 | 1.00 35.29 |
| ATOM | 1677 | O | SER | 214 | 23.187 | -12.819 | 42.746 | 1.00 37.89 |
| ATOM | 1678 | N | CYS | 215 | 22.110 | -10.991 | 41.994 | 1.00 33.00 |
| ATOM | 1679 | CA | CYS | 215 | 23.159 | -10.632 | 41.045 | 1.00 31.71 |
| ATOM | 1680 | CB | CYS | 215 | 22.557 | -9.851 | 39.871 | 1.00 33.69 |

FIG.11A-40

| ATOM | 1681 | SG  | CYS | 215 | 23.706 | -9.553  | 38.523 | 1.00 | 33.80 |
| ---- | ---- | --- | --- | --- | ------ | ------- | ------ | ---- | ----- |
| ATOM | 1682 | C   | CYS | 215 | 24.223 | -9.792  | 41.749 | 1.00 | 30.56 |
| ATOM | 1683 | O   | CYS | 215 | 23.976 | -8.648  | 42.123 | 1.00 | 30.45 |
| ATOM | 1684 | N   | GLN | 216 | 25.410 | -10.369 | 41.918 | 1.00 | 30.39 |
| ATOM | 1685 | CA  | GLN | 216 | 26.497 | -9.687  | 42.602 | 1.00 | 27.76 |
| ATOM | 1686 | CB  | GLN | 216 | 27.753 | -10.569 | 42.621 | 1.00 | 28.61 |
| ATOM | 1687 | CG  | GLN | 216 | 28.854 | -10.012 | 43.510 | 1.00 | 32.96 |
| ATOM | 1688 | CD  | GLN | 216 | 28.421 | -9.895  | 44.963 | 1.00 | 42.47 |
| ATOM | 1689 | OE1 | GLN | 216 | 28.866 | -9.004  | 45.686 | 1.00 | 41.12 |
| ATOM | 1690 | NE2 | GLN | 216 | 27.554 | -10.803 | 45.398 | 1.00 | 48.90 |
| ATOM | 1691 | C   | GLN | 216 | 26.838 | -8.319  | 42.014 | 1.00 | 26.11 |
| ATOM | 1692 | O   | GLN | 216 | 27.078 | -7.375  | 42.759 | 1.00 | 23.93 |
| ATOM | 1693 | N   | GLU | 217 | 26.861 | -8.212  | 40.688 | 1.00 | 25.76 |
| ATOM | 1694 | CA  | GLU | 217 | 27.176 | -6.937  | 40.045 | 1.00 | 23.96 |
| ATOM | 1695 | CB  | GLU | 217 | 27.213 | -7.092  | 38.521 | 1.00 | 24.39 |
| ATOM | 1696 | CG  | GLU | 217 | 28.404 | -7.884  | 37.980 | 1.00 | 27.80 |
| ATOM | 1697 | CD  | GLU | 217 | 28.416 | -9.327  | 38.453 | 1.00 | 30.02 |
| ATOM | 1698 | OE1 | GLU | 217 | 27.330 | -9.944  | 38.514 | 1.00 | 26.98 |
| ATOM | 1699 | OE2 | GLU | 217 | 29.515 | -9.845  | 38.754 | 1.00 | 34.80 |
| ATOM | 1700 | C   | GLU | 217 | 26.154 | -5.868  | 40.432 | 1.00 | 22.37 |
| ATOM | 1701 | O   | GLU | 217 | 26.507 | -4.701  | 40.629 | 1.00 | 20.68 |
| ATOM | 1702 | N   | TYR | 218 | 24.888 | -6.261  | 40.547 | 1.00 | 22.07 |
| ATOM | 1703 | CA  | TYR | 218 | 23.858 | -5.303  | 40.927 | 1.00 | 22.82 |
| ATOM | 1704 | CB  | TYR | 218 | 22.454 | -5.858  | 40.664 | 1.00 | 24.84 |
| ATOM | 1705 | CG  | TYR | 218 | 21.371 | -4.831  | 40.920 | 1.00 | 26.40 |
| ATOM | 1706 | CD1 | TYR | 218 | 21.373 | -3.611  | 40.245 | 1.00 | 22.79 |
| ATOM | 1707 | CE1 | TYR | 218 | 20.402 | -2.644  | 40.496 | 1.00 | 21.41 |
| ATOM | 1708 | CD2 | TYR | 218 | 20.363 | -5.062  | 41.856 | 1.00 | 27.38 |
| ATOM | 1709 | CE2 | TYR | 218 | 19.385 | -4.101  | 42.114 | 1.00 | 24.51 |
| ATOM | 1710 | CZ  | TYR | 218 | 19.413 | -2.896  | 41.433 | 1.00 | 21.04 |
| ATOM | 1711 | OH  | TYR | 218 | 18.469 | -1.929  | 41.702 | 1.00 | 23.17 |
| ATOM | 1712 | C   | TYR | 218 | 23.991 | -4.917  | 42.397 | 1.00 | 22.65 |
| ATOM | 1713 | O   | TYR | 218 | 23.811 | -3.754  | 42.750 | 1.00 | 23.66 |
| ATOM | 1714 | N   | SER | 219 | 24.302 | -5.888  | 43.256 | 1.00 | 25.18 |
| ATOM | 1715 | CA  | SER | 219 | 24.470 | -5.600  | 44.681 | 1.00 | 24.31 |
| ATOM | 1716 | CB  | SER | 219 | 24.737 | -6.889  | 45.471 | 1.00 | 26.30 |
| ATOM | 1717 | OG  | SER | 219 | 23.648 | -7.782  | 45.364 | 1.00 | 36.64 |
| ATOM | 1718 | C   | SER | 219 | 25.629 | -4.628  | 44.888 | 1.00 | 22.69 |
| ATOM | 1719 | O   | SER | 219 | 25.527 | -3.697  | 45.688 | 1.00 | 22.21 |
| ATOM | 1720 | N   | ASP | 220 | 26.725 | -4.853  | 44.168 | 1.00 | 24.43 |
| ATOM | 1721 | CA  | ASP | 220 | 27.904 | -3.992  | 44.257 | 1.00 | 24.43 |
| ATOM | 1722 | CB  | ASP | 220 | 28.990 | -4.469  | 43.288 | 1.00 | 23.90 |

FIG.11A-41

| ATOM | 1723 | CG  | ASP | 220 | 29.662 | -5.759 | 43.742 | 1.00 | 29.00 |
|------|------|-----|-----|-----|--------|--------|--------|------|-------|
| ATOM | 1724 | OD1 | ASP | 220 | 30.451 | -6.320 | 42.954 | 1.00 | 35.56 |
| ATOM | 1725 | OD2 | ASP | 220 | 29.406 | -6.205 | 44.881 | 1.00 | 33.13 |
| ATOM | 1726 | C   | ASP | 220 | 27.532 | -2.545 | 43.935 | 1.00 | 24.18 |
| ATOM | 1727 | O   | ASP | 220 | 28.007 | -1.613 | 44.584 | 1.00 | 23.82 |
| ATOM | 1728 | N   | TRP | 221 | 26.679 | -2.360 | 42.930 | 1.00 | 22.56 |
| ATOM | 1729 | CA  | TRP | 221 | 26.247 | -1.016 | 42.545 | 1.00 | 20.51 |
| ATOM | 1730 | CB  | TRP | 221 | 25.414 | -1.090 | 41.256 | 1.00 | 19.85 |
| ATOM | 1731 | CG  | TRP | 221 | 24.672 | 0.179  | 40.909 | 1.00 | 20.17 |
| ATOM | 1732 | CD2 | TRP | 221 | 25.238 | 1.408  | 40.434 | 1.00 | 20.07 |
| ATOM | 1733 | CE2 | TRP | 221 | 24.163 | 2.309  | 40.226 | 1.00 | 17.90 |
| ATOM | 1734 | CE3 | TRP | 221 | 26.542 | 1.841  | 40.165 | 1.00 | 17.56 |
| ATOM | 1735 | CD1 | TRP | 221 | 23.322 | 0.378  | 40.972 | 1.00 | 18.44 |
| ATOM | 1736 | NE1 | TRP | 221 | 23.008 | 1.653  | 40.563 | 1.00 | 18.49 |
| ATOM | 1737 | CZ2 | TRP | 221 | 24.360 | 3.614  | 39.758 | 1.00 | 15.58 |
| ATOM | 1738 | CZ3 | TRP | 221 | 26.738 | 3.141  | 39.701 | 1.00 | 18.36 |
| ATOM | 1739 | CH2 | TRP | 221 | 25.650 | 4.012  | 39.501 | 1.00 | 17.00 |
| ATOM | 1740 | C   | TRP | 221 | 25.446 | -0.356 | 43.667 | 1.00 | 21.95 |
| ATOM | 1741 | O   | TRP | 221 | 25.662 | 0.810  | 43.995 | 1.00 | 21.87 |
| ATOM | 1742 | N   | LYS | 222 | 24.521 | -1.099 | 44.262 | 1.00 | 24.52 |
| ATOM | 1743 | CA  | LYS | 222 | 23.721 | -0.543 | 45.343 | 1.00 | 26.38 |
| ATOM | 1744 | CB  | LYS | 222 | 22.596 | -1.505 | 45.726 | 1.00 | 27.07 |
| ATOM | 1745 | CG  | LYS | 222 | 21.565 | -1.698 | 44.618 | 1.00 | 24.09 |
| ATOM | 1746 | CD  | LYS | 222 | 20.299 | -2.376 | 45.123 | 1.00 | 27.22 |
| ATOM | 1747 | CE  | LYS | 222 | 20.538 | -3.831 | 45.493 | 1.00 | 25.58 |
| ATOM | 1748 | NZ  | LYS | 222 | 19.279 | -4.473 | 45.958 | 1.00 | 28.43 |
| ATOM | 1749 | C   | LYS | 222 | 24.601 | -0.233 | 46.553 | 1.00 | 28.55 |
| ATOM | 1750 | O   | LYS | 222 | 24.251 | 0.601  | 47.385 | 1.00 | 29.05 |
| ATOM | 1751 | N   | GLU | 223 | 25.750 | -0.898 | 46.635 | 1.00 | 29.11 |
| ATOM | 1752 | CA  | GLU | 223 | 26.691 | -0.674 | 47.730 | 1.00 | 31.70 |
| ATOM | 1753 | CB  | GLU | 223 | 27.482 | -1.950 | 48.026 | 1.00 | 35.51 |
| ATOM | 1754 | CG  | GLU | 223 | 26.650 | -3.085 | 48.592 | 1.00 | 49.01 |
| ATOM | 1755 | CD  | GLU | 223 | 27.485 | -4.311 | 48.900 | 1.00 | 57.47 |
| ATOM | 1756 | OE1 | GLU | 223 | 28.415 | -4.205 | 49.726 | 1.00 | 62.72 |
| ATOM | 1757 | OE2 | GLU | 223 | 27.214 | -5.381 | 48.313 | 1.00 | 63.79 |
| ATOM | 1758 | C   | GLU | 223 | 27.658 | 0.455  | 47.381 | 1.00 | 32.76 |
| ATOM | 1759 | O   | GLU | 223 | 28.578 | 0.756  | 48.144 | 1.00 | 33.37 |
| ATOM | 1760 | N   | LYS | 224 | 27.446 | 1.068  | 46.219 | 1.00 | 32.14 |
| ATOM | 1761 | CA  | LYS | 224 | 28.272 | 2.178  | 45.745 | 1.00 | 33.92 |
| ATOM | 1762 | CB  | LYS | 224 | 28.229 | 3.338  | 46.750 | 1.00 | 38.46 |
| ATOM | 1763 | CG  | LYS | 224 | 26.913 | 4.109  | 46.777 | 1.00 | 46.23 |
| ATOM | 1764 | CD  | LYS | 224 | 25.775 | 3.286  | 47.359 | 1.00 | 56.20 |

FIG.11A-42

| ATOM | 1765 | CE  | LYS | 224 | 25.974 | 3.040  | 48.848 | 1.00 | 61.78 |
|------|------|-----|-----|-----|--------|--------|--------|------|-------|
| ATOM | 1766 | NZ  | LYS | 224 | 25.995 | 4.315  | 49.618 | 1.00 | 65.83 |
| ATOM | 1767 | C   | LYS | 224 | 29.729 | 1.830  | 45.440 | 1.00 | 34.18 |
| ATOM | 1768 | O   | LYS | 224 | 30.615 | 2.673  | 45.573 | 1.00 | 34.19 |
| ATOM | 1769 | N   | LYS | 225 | 29.978 | 0.597  | 45.016 | 1.00 | 33.64 |
| ATOM | 1770 | CA  | LYS | 225 | 31.336 | 0.172  | 44.688 | 1.00 | 35.23 |
| ATOM | 1771 | CB  | LYS | 225 | 31.453 | -1.347 | 44.837 | 1.00 | 36.69 |
| ATOM | 1772 | CG  | LYS | 225 | 31.093 | -1.853 | 46.230 | 1.00 | 40.35 |
| ATOM | 1773 | CD  | LYS | 225 | 31.044 | -3.377 | 46.290 | 1.00 | 46.38 |
| ATOM | 1774 | CE  | LYS | 225 | 32.383 | -4.004 | 45.943 | 1.00 | 52.69 |
| ATOM | 1775 | NZ  | LYS | 225 | 32.346 | -5.490 | 46.067 | 1.00 | 60.52 |
| ATOM | 1776 | C   | LYS | 225 | 31.670 | 0.588  | 43.254 | 1.00 | 36.02 |
| ATOM | 1777 | O   | LYS | 225 | 31.918 | -0.255 | 42.391 | 1.00 | 34.27 |
| ATOM | 1778 | N   | THR | 226 | 31.684 | 1.895  | 43.010 | 1.00 | 37.19 |
| ATOM | 1779 | CA  | THR | 226 | 31.957 | 2.424  | 41.678 | 1.00 | 38.34 |
| ATOM | 1780 | CB  | THR | 226 | 31.516 | 3.902  | 41.571 | 1.00 | 38.25 |
| ATOM | 1781 | OG1 | THR | 226 | 32.145 | 4.670  | 42.602 | 1.00 | 38.16 |
| ATOM | 1782 | CG2 | THR | 226 | 30.005 | 4.011  | 41.714 | 1.00 | 32.35 |
| ATOM | 1783 | C   | THR | 226 | 33.409 | 2.303  | 41.227 | 1.00 | 39.24 |
| ATOM | 1784 | O   | THR | 226 | 33.757 | 2.710  | 40.118 | 1.00 | 38.72 |
| ATOM | 1785 | N   | TYR | 227 | 34.257 | 1.745  | 42.084 | 1.00 | 40.18 |
| ATOM | 1786 | CA  | TYR | 227 | 35.658 | 1.560  | 41.733 | 1.00 | 39.40 |
| ATOM | 1787 | CB  | TYR | 227 | 36.521 | 1.474  | 42.998 | 1.00 | 40.25 |
| ATOM | 1788 | CG  | TYR | 227 | 36.050 | 0.445  | 43.999 | 1.00 | 41.05 |
| ATOM | 1789 | CD1 | TYR | 227 | 36.283 | -0.916 | 43.797 | 1.00 | 41.13 |
| ATOM | 1790 | CE1 | TYR | 227 | 35.832 | -1.867 | 44.709 | 1.00 | 37.13 |
| ATOM | 1791 | CD2 | TYR | 227 | 35.353 | 0.831  | 45.143 | 1.00 | 38.67 |
| ATOM | 1792 | CE2 | TYR | 227 | 34.897 | -0.111 | 46.060 | 1.00 | 39.51 |
| ATOM | 1793 | CZ  | TYR | 227 | 35.140 | -1.456 | 45.837 | 1.00 | 39.20 |
| ATOM | 1794 | OH  | TYR | 227 | 34.680 | -2.387 | 46.738 | 1.00 | 46.31 |
| ATOM | 1795 | C   | TYR | 227 | 35.776 | 0.280  | 40.914 | 1.00 | 39.74 |
| ATOM | 1796 | O   | TYR | 227 | 36.862 | -0.083 | 40.459 | 1.00 | 40.52 |
| ATOM | 1797 | N   | LEU | 228 | 34.643 | -0.395 | 40.728 | 1.00 | 39.05 |
| ATOM | 1798 | CA  | LEU | 228 | 34.590 | -1.634 | 39.962 | 1.00 | 39.33 |
| ATOM | 1799 | CB  | LEU | 228 | 33.447 | -2.523 | 40.456 | 1.00 | 40.20 |
| ATOM | 1800 | CG  | LEU | 228 | 33.661 | -3.195 | 41.817 | 1.00 | 45.84 |
| ATOM | 1801 | CD1 | LEU | 228 | 32.410 | -3.961 | 42.217 | 1.00 | 43.62 |
| ATOM | 1802 | CD2 | LEU | 228 | 34.859 | -4.135 | 41.740 | 1.00 | 44.55 |
| ATOM | 1803 | C   | LEU | 228 | 34.442 | -1.390 | 38.462 | 1.00 | 39.82 |
| ATOM | 1804 | O   | LEU | 228 | 33.843 | -0.403 | 38.033 | 1.00 | 37.15 |
| ATOM | 1805 | N   | ASN | 229 | 34.987 | -2.332 | 37.698 | 1.00 | 41.12 |
| ATOM | 1806 | CA  | ASN | 229 | 35.041 | -2.348 | 36.235 | 1.00 | 42.82 |

FIG.11A-43

| | | | | | | | | | |
|---|---|---|---|---|---|---|---|---|---|
| ATOM | 1807 | CB | ASN | 229 | 34.836 | -3.784 | 35.733 | 1.00 | 47.56 |
| ATOM | 1808 | CG | ASN | 229 | 35.542 | -4.046 | 34.413 | 1.00 | 53.15 |
| ATOM | 1809 | OD1 | ASN | 229 | 36.739 | -3.789 | 34.276 | 1.00 | 50.92 |
| ATOM | 1810 | ND2 | ASN | 229 | 34.806 | -4.567 | 33.438 | 1.00 | 57.87 |
| ATOM | 1811 | C | ASN | 229 | 34.192 | -1.399 | 35.389 | 1.00 | 41.75 |
| ATOM | 1812 | O | ASN | 229 | 34.726 | -0.466 | 34.785 | 1.00 | 44.90 |
| ATOM | 1813 | N | PRO | 230 | 32.866 | -1.608 | 35.328 | 1.00 | 37.73 |
| ATOM | 1814 | CD | PRO | 230 | 31.965 | -2.470 | 36.114 | 1.00 | 33.11 |
| ATOM | 1815 | CA | PRO | 230 | 32.103 | -0.675 | 34.490 | 1.00 | 30.88 |
| ATOM | 1816 | CB | PRO | 230 | 30.680 | -1.229 | 34.575 | 1.00 | 30.85 |
| ATOM | 1817 | CG | PRO | 230 | 30.624 | -1.763 | 35.958 | 1.00 | 30.64 |
| ATOM | 1818 | C | PRO | 230 | 32.193 | 0.798 | 34.890 | 1.00 | 25.71 |
| ATOM | 1819 | O | PRO | 230 | 32.654 | 1.638 | 34.112 | 1.00 | 24.73 |
| ATOM | 1820 | N | TRP | 231 | 31.782 | 1.097 | 36.116 | 1.00 | 23.16 |
| ATOM | 1821 | CA | TRP | 231 | 31.757 | 2.462 | 36.635 | 1.00 | 21.32 |
| ATOM | 1822 | CB | TRP | 231 | 31.099 | 2.450 | 38.020 | 1.00 | 19.67 |
| ATOM | 1823 | CG | TRP | 231 | 29.965 | 1.469 | 38.087 | 1.00 | 23.28 |
| ATOM | 1824 | CD2 | TRP | 231 | 28.741 | 1.522 | 37.344 | 1.00 | 21.23 |
| ATOM | 1825 | CE2 | TRP | 231 | 28.023 | 0.344 | 37.637 | 1.00 | 20.01 |
| ATOM | 1826 | CE3 | TRP | 231 | 28.188 | 2.451 | 36.450 | 1.00 | 20.09 |
| ATOM | 1827 | CD1 | TRP | 231 | 29.934 | 0.297 | 38.789 | 1.00 | 22.83 |
| ATOM | 1828 | NE1 | TRP | 231 | 28.773 | -0.386 | 38.523 | 1.00 | 21.22 |
| ATOM | 1829 | CZ2 | TRP | 231 | 26.774 | 0.067 | 37.071 | 1.00 | 19.20 |
| ATOM | 1830 | CZ3 | TRP | 231 | 26.945 | 2.176 | 35.886 | 1.00 | 24.61 |
| ATOM | 1831 | CH2 | TRP | 231 | 26.255 | 0.990 | 36.200 | 1.00 | 21.84 |
| ATOM | 1832 | C | TRP | 231 | 33.098 | 3.210 | 36.685 | 1.00 | 22.69 |
| ATOM | 1833 | O | TRP | 231 | 33.138 | 4.425 | 36.503 | 1.00 | 20.98 |
| ATOM | 1834 | N | LYS | 232 | 34.199 | 2.507 | 36.921 | 1.00 | 23.86 |
| ATOM | 1835 | CA | LYS | 232 | 35.487 | 3.199 | 36.992 | 1.00 | 25.79 |
| ATOM | 1836 | CB | LYS | 232 | 36.560 | 2.276 | 37.586 | 1.00 | 24.84 |
| ATOM | 1837 | CG | LYS | 232 | 36.812 | 0.989 | 36.824 | 1.00 | 33.96 |
| ATOM | 1838 | CD | LYS | 232 | 37.851 | 0.136 | 37.560 | 1.00 | 39.70 |
| ATOM | 1839 | CE | LYS | 232 | 38.112 | -1.185 | 36.856 | 1.00 | 44.39 |
| ATOM | 1840 | NZ | LYS | 232 | 39.067 | -2.042 | 37.620 | 1.00 | 48.06 |
| ATOM | 1841 | C | LYS | 232 | 35.962 | 3.760 | 35.649 | 1.00 | 25.77 |
| ATOM | 1842 | O | LYS | 232 | 36.920 | 4.530 | 35.596 | 1.00 | 26.85 |
| ATOM | 1843 | N | LYS | 233 | 35.277 | 3.393 | 34.570 | 1.00 | 24.28 |
| ATOM | 1844 | CA | LYS | 233 | 35.638 | 3.852 | 33.228 | 1.00 | 21.58 |
| ATOM | 1845 | CB | LYS | 233 | 35.460 | 2.714 | 32.220 | 1.00 | 21.63 |
| ATOM | 1846 | CG | LYS | 233 | 36.298 | 1.481 | 32.489 | 1.00 | 21.89 |
| ATOM | 1847 | CD | LYS | 233 | 36.181 | 0.466 | 31.357 | 1.00 | 21.02 |
| ATOM | 1848 | CE | LYS | 233 | 34.839 | -0.229 | 31.329 | 1.00 | 23.92 |

FIG.11A-44

| | | | | | | | | |
|---|---|---|---|---|---|---|---|---|
| ATOM | 1849 | NZ | LYS | 233 | 34.817 | -1.324 | 30.311 | 1.00 24.83 |
| ATOM | 1850 | C | LYS | 233 | 34.800 | 5.025 | 32.731 | 1.00 22.49 |
| ATOM | 1851 | O | LYS | 233 | 35.041 | 5.545 | 31.642 | 1.00 22.51 |
| ATOM | 1852 | N | ILE | 234 | 33.848 | 5.471 | 33.533 | 1.00 23.05 |
| ATOM | 1853 | CA | ILE | 234 | 32.933 | 6.504 | 33.062 | 1.00 23.85 |
| ATOM | 1854 | CB | ILE | 234 | 31.526 | 6.124 | 33.584 | 1.00 18.85 |
| ATOM | 1855 | CG2 | ILE | 234 | 30.523 | 7.242 | 33.345 | 1.00 16.49 |
| ATOM | 1856 | CG1 | ILE | 234 | 31.128 | 4.813 | 32.893 | 1.00 16.83 |
| ATOM | 1857 | CD1 | ILE | 234 | 29.773 | 4.256 | 33.265 | 1.00 15.87 |
| ATOM | 1858 | C | ILE | 234 | 33.206 | 8.015 | 33.175 | 1.00 26.97 |
| ATOM | 1859 | O | ILE | 234 | 33.655 | 8.629 | 32.202 | 1.00 34.42 |
| ATOM | 1860 | N | ASP | 235 | 32.953 | 8.592 | 34.339 | 1.00 25.59 |
| ATOM | 1861 | CA | ASP | 235 | 33.136 | 10.025 | 34.646 | 1.00 24.80 |
| ATOM | 1862 | CB | ASP | 235 | 32.528 | 10.995 | 33.623 | 1.00 22.82 |
| ATOM | 1863 | CG | ASP | 235 | 33.342 | 12.289 | 33.509 | 1.00 29.58 |
| ATOM | 1864 | OD1 | ASP | 235 | 33.015 | 13.294 | 34.187 | 1.00 28.74 |
| ATOM | 1865 | OD2 | ASP | 235 | 34.341 | 12.292 | 32.758 | 1.00 24.88 |
| ATOM | 1866 | C | ASP | 235 | 32.512 | 10.282 | 35.990 | 1.00 22.84 |
| ATOM | 1867 | O | ASP | 235 | 31.766 | 9.448 | 36.503 | 1.00 19.57 |
| ATOM | 1868 | N | SER | 236 | 32.824 | 11.450 | 36.540 | 1.00 22.97 |
| ATOM | 1869 | CA | SER | 236 | 32.144 | 11.667 | 37.793 | 1.00 23.58 |
| ATOM | 1870 | CB | SER | 236 | 32.929 | 12.818 | 38.441 | 1.00 22.04 |
| ATOM | 1871 | OG | SER | 236 | 32.992 | 13.941 | 37.583 | 1.00 27.67 |
| ATOM | 1872 | C | SER | 236 | 30.991 | 12.390 | 37.096 | 1.00 21.73 |
| ATOM | 1873 | O | SER | 236 | 29.952 | 12.112 | 37.692 | 1.00 19.53 |
| ATOM | 1874 | N | ALA | 237 | 31.031 | 13.258 | 36.083 | 1.00 20.61 |
| ATOM | 1875 | CA | ALA | 237 | 29.816 | 13.944 | 35.639 | 1.00 19.05 |
| ATOM | 1876 | CB | ALA | 237 | 30.137 | 14.988 | 34.566 | 1.00 14.22 |
| ATOM | 1877 | C | ALA | 237 | 28.746 | 12.973 | 35.134 | 1.00 17.61 |
| ATOM | 1878 | O | ALA | 237 | 27.639 | 12.950 | 35.664 | 1.00 17.49 |
| ATOM | 1879 | N | PRO | 238 | 29.049 | 12.175 | 34.097 | 1.00 15.48 |
| ATOM | 1880 | CD | PRO | 238 | 30.217 | 12.121 | 33.199 | 1.00 15.00 |
| ATOM | 1881 | CA | PRO | 238 | 27.999 | 11.252 | 33.646 | 1.00 16.82 |
| ATOM | 1882 | CB | PRO | 238 | 28.572 | 10.670 | 32.347 | 1.00 13.41 |
| ATOM | 1883 | CG | PRO | 238 | 30.067 | 10.766 | 32.552 | 1.00 10.20 |
| ATOM | 1884 | C | PRO | 238 | 27.670 | 10.183 | 34.694 | 1.00 14.91 |
| ATOM | 1885 | O | PRO | 238 | 26.539 | 9.701 | 34.770 | 1.00 14.08 |
| ATOM | 1886 | N | LEU | 239 | 28.657 | 9.815 | 35.508 | 1.00 16.50 |
| ATOM | 1887 | CA | LEU | 239 | 28.434 | 8.819 | 36.554 | 1.00 17.72 |
| ATOM | 1888 | CB | LEU | 239 | 29.744 | 8.522 | 37.296 | 1.00 18.57 |
| ATOM | 1889 | CG | LEU | 239 | 30.096 | 7.069 | 37.643 | 1.00 22.40 |
| ATOM | 1890 | CD1 | LEU | 239 | 31.090 | 7.086 | 38.795 | 1.00 23.81 |

FIG.11A-45

```
ATOM  1891  CD2 LEU  239    28.873   6.257  38.017  1.00  22.04
ATOM  1892  C   LEU  239    27.394   9.351  37.543  1.00  17.57
ATOM  1893  O   LEU  239    26.543   8.605  38.026  1.00  16.91
ATOM  1894  N   ALA  240    27.464  10.645  37.846  1.00  16.87
ATOM  1895  CA  ALA  240    26.508  11.254  38.766  1.00  17.94
ATOM  1896  CB  ALA  240    26.867  12.725  39.024  1.00  15.97
ATOM  1897  C   ALA  240    25.091  11.143  38.198  1.00  16.55
ATOM  1898  O   ALA  240    24.136  10.974  38.950  1.00  16.22
ATOM  1899  N   LEU  241    24.954  11.241  36.878  1.00  15.65
ATOM  1900  CA  LEU  241    23.627  11.111  36.264  1.00  15.31
ATOM  1901  CB  LEU  241    23.652  11.540  34.785  1.00  12.35
ATOM  1902  CG  LEU  241    22.354  11.270  33.991  1.00  13.16
ATOM  1903  CD1 LEU  241    21.170  11.991  34.606  1.00  14.35
ATOM  1904  CD2 LEU  241    22.535  11.720  32.557  1.00  12.21
ATOM  1905  C   LEU  241    23.175   9.655  36.384  1.00  16.01
ATOM  1906  O   LEU  241    22.025   9.377  36.739  1.00  15.78
ATOM  1907  N   LEU  242    24.076   8.719  36.095  1.00  15.89
ATOM  1908  CA  LEU  242    23.734   7.303  36.194  1.00  16.35
ATOM  1909  CB  LEU  242    24.942   6.430  35.808  1.00  17.35
ATOM  1910  CG  LEU  242    25.054   5.624  34.500  1.00  22.28
ATOM  1911  CD1 LEU  242    23.930   5.888  33.505  1.00  16.11
ATOM  1912  CD2 LEU  242    26.412   5.912  33.896  1.00  15.21
ATOM  1913  C   LEU  242    23.291   6.979  37.624  1.00  16.88
ATOM  1914  O   LEU  242    22.418   6.135  37.834  1.00  15.72
ATOM  1915  N   HIS  243    23.883   7.652  38.609  1.00  18.68
ATOM  1916  CA  HIS  243    23.507   7.417  40.004  1.00  17.89
ATOM  1917  CB  HIS  243    24.436   8.178  40.958  1.00  17.93
ATOM  1918  CG  HIS  243    25.587   7.362  41.458  1.00  27.59
ATOM  1919  CD2 HIS  243    25.622   6.251  42.232  1.00  27.35
ATOM  1920  ND1 HIS  243    26.900   7.673  41.176  1.00  30.65
ATOM  1921  CE1 HIS  243    27.695   6.790  41.755  1.00  31.26
ATOM  1922  NE2 HIS  243    26.944   5.917  42.402  1.00  27.77
ATOM  1923  C   HIS  243    22.069   7.855  40.265  1.00  17.20
ATOM  1924  O   HIS  243    21.425   7.366  41.189  1.00  17.65
ATOM  1925  N   LYS  244    21.577   8.792  39.460  1.00  17.08
ATOM  1926  CA  LYS  244    20.212   9.279  39.617  1.00  17.67
ATOM  1927  CB  LYS  244    20.137  10.751  39.212  1.00  15.78
ATOM  1928  CG  LYS  244    20.904  11.670  40.163  1.00  19.56
ATOM  1929  CD  LYS  244    20.750  13.143  39.815  1.00  19.62
ATOM  1930  CE  LYS  244    21.549  13.543  38.581  1.00  15.60
ATOM  1931  NZ  LYS  244    21.582  15.043  38.422  1.00  18.38
ATOM  1932  C   LYS  244    19.213   8.447  38.805  1.00  16.94
```

FIG.11A-46

| | | | | | | | | |
|---|---|---|---|---|---|---|---|---|
| ATOM | 1933 | O | LYS | 244 | 18.044 | 8.339 | 39.170 | 1.00 16.00 |
| ATOM | 1934 | N | ILE | 245 | 19.681 | 7.849 | 37.713 | 1.00 15.92 |
| ATOM | 1935 | CA | ILE | 245 | 18.812 | 7.023 | 36.871 | 1.00 14.11 |
| ATOM | 1936 | CB | ILE | 245 | 19.338 | 6.955 | 35.404 | 1.00 12.65 |
| ATOM | 1937 | CG2 | ILE | 245 | 18.465 | 5.982 | 34.573 | 1.00 14.27 |
| ATOM | 1938 | CG1 | ILE | 245 | 19.307 | 8.352 | 34.776 | 1.00 11.69 |
| ATOM | 1939 | CD1 | ILE | 245 | 19.923 | 8.441 | 33.379 | 1.00 17.04 |
| ATOM | 1940 | C | ILE | 245 | 18.684 | 5.586 | 37.387 | 1.00 13.68 |
| ATOM | 1941 | O | ILE | 245 | 17.583 | 5.041 | 37.481 | 1.00 15.46 |
| ATOM | 1942 | N | LEU | 246 | 19.809 | 4.963 | 37.724 | 1.00 14.19 |
| ATOM | 1943 | CA | LEU | 246 | 19.765 | 3.574 | 38.173 | 1.00 15.34 |
| ATOM | 1944 | CB | LEU | 246 | 21.062 | 2.865 | 37.776 | 1.00 13.75 |
| ATOM | 1945 | CG | LEU | 246 | 21.346 | 2.984 | 36.278 | 1.00 10.86 |
| ATOM | 1946 | CD1 | LEU | 246 | 22.703 | 2.364 | 35.923 | 1.00 12.91 |
| ATOM | 1947 | CD2 | LEU | 246 | 20.211 | 2.303 | 35.512 | 1.00 14.82 |
| ATOM | 1948 | C | LEU | 246 | 19.477 | 3.429 | 39.663 | 1.00 18.00 |
| ATOM | 1949 | O | LEU | 246 | 20.229 | 2.803 | 40.422 | 1.00 18.52 |
| ATOM | 1950 | N | VAL | 247 | 18.357 | 4.022 | 40.057 | 1.00 17.55 |
| ATOM | 1951 | CA | VAL | 247 | 17.881 | 4.000 | 41.433 | 1.00 16.51 |
| ATOM | 1952 | CB | VAL | 247 | 17.268 | 5.356 | 41.795 | 1.00 15.11 |
| ATOM | 1953 | CG1 | VAL | 247 | 16.553 | 5.278 | 43.136 | 1.00 19.34 |
| ATOM | 1954 | CG2 | VAL | 247 | 18.380 | 6.408 | 41.842 | 1.00 16.66 |
| ATOM | 1955 | C | VAL | 247 | 16.834 | 2.899 | 41.513 | 1.00 18.51 |
| ATOM | 1956 | O | VAL | 247 | 15.903 | 2.864 | 40.709 | 1.00 18.14 |
| ATOM | 1957 | N | GLU | 248 | 16.990 | 2.000 | 42.481 | 1.00 16.77 |
| ATOM | 1958 | CA | GLU | 248 | 16.078 | 0.864 | 42.613 | 1.00 17.92 |
| ATOM | 1959 | CB | GLU | 248 | 16.522 | -0.034 | 43.767 | 1.00 19.95 |
| ATOM | 1960 | CG | GLU | 248 | 15.805 | -1.376 | 43.799 | 1.00 28.58 |
| ATOM | 1961 | CD | GLU | 248 | 16.404 | -2.315 | 44.822 | 1.00 43.56 |
| ATOM | 1962 | OE1 | GLU | 248 | 16.396 | -1.965 | 46.021 | 1.00 48.24 |
| ATOM | 1963 | OE2 | GLU | 248 | 16.889 | -3.396 | 44.425 | 1.00 46.86 |
| ATOM | 1964 | C | GLU | 248 | 14.605 | 1.224 | 42.781 | 1.00 18.01 |
| ATOM | 1965 | O | GLU | 248 | 13.741 | 0.633 | 42.131 | 1.00 17.60 |
| ATOM | 1966 | N | ASN | 249 | 14.317 | 2.185 | 43.652 | 1.00 17.72 |
| ATOM | 1967 | CA | ASN | 249 | 12.940 | 2.611 | 43.886 | 1.00 16.89 |
| ATOM | 1968 | CB | ASN | 249 | 12.866 | 3.392 | 45.206 | 1.00 19.13 |
| ATOM | 1969 | CG | ASN | 249 | 11.480 | 3.970 | 45.480 | 1.00 21.33 |
| ATOM | 1970 | OD1 | ASN | 249 | 10.562 | 3.832 | 44.676 | 1.00 21.93 |
| ATOM | 1971 | ND2 | ASN | 249 | 11.331 | 4.624 | 46.631 | 1.00 17.12 |
| ATOM | 1972 | C | ASN | 249 | 12.480 | 3.483 | 42.716 | 1.00 15.11 |
| ATOM | 1973 | O | ASN | 249 | 12.954 | 4.607 | 42.553 | 1.00 16.33 |
| ATOM | 1974 | N | PRO | 250 | 11.550 | 2.978 | 41.880 | 1.00 15.15 |

FIG.11A-47

| | | | | | | | | |
|---|---|---|---|---|---|---|---|---|
| ATOM | 1975 | CD | PRO | 250 | 10.830 | 1.694 | 41.960 | 1.00 16.54 |
| ATOM | 1976 | CA | PRO | 250 | 11.080 | 3.774 | 40.737 | 1.00 15.50 |
| ATOM | 1977 | CB | PRO | 250 | 10.110 | 2.825 | 40.025 | 1.00 14.37 |
| ATOM | 1978 | CG | PRO | 250 | 9.569 | 1.973 | 41.153 | 1.00 13.99 |
| ATOM | 1979 | C | PRO | 250 | 10.437 | 5.111 | 41.105 | 1.00 16.72 |
| ATOM | 1980 | O | PRO | 250 | 10.409 | 6.039 | 40.298 | 1.00 16.34 |
| ATOM | 1981 | N | SER | 251 | 9.910 | 5.211 | 42.321 | 1.00 17.93 |
| ATOM | 1982 | CA | SER | 251 | 9.296 | 6.460 | 42.744 | 1.00 18.37 |
| ATOM | 1983 | CB | SER | 251 | 8.391 | 6.212 | 43.954 | 1.00 18.23 |
| ATOM | 1984 | OG | SER | 251 | 7.326 | 5.351 | 43.584 | 1.00 20.47 |
| ATOM | 1985 | C | SER | 251 | 10.347 | 7.524 | 43.060 | 1.00 18.31 |
| ATOM | 1986 | O | SER | 251 | 10.075 | 8.720 | 42.944 | 1.00 21.19 |
| ATOM | 1987 | N | ALA | 252 | 11.549 | 7.092 | 43.430 | 1.00 17.56 |
| ATOM | 1988 | CA | ALA | 252 | 12.638 | 8.020 | 43.749 | 1.00 16.14 |
| ATOM | 1989 | CB | ALA | 252 | 13.471 | 7.479 | 44.919 | 1.00 17.50 |
| ATOM | 1990 | C | ALA | 252 | 13.545 | 8.257 | 42.544 | 1.00 16.13 |
| ATOM | 1991 | O | ALA | 252 | 14.355 | 9.184 | 42.533 | 1.00 18.76 |
| ATOM | 1992 | N | ARG | 253 | 13.408 | 7.410 | 41.530 | 1.00 16.12 |
| ATOM | 1993 | CA | ARG | 253 | 14.227 | 7.520 | 40.322 | 1.00 16.16 |
| ATOM | 1994 | CB | ARG | 253 | 13.888 | 6.363 | 39.382 | 1.00 15.22 |
| ATOM | 1995 | CG | ARG | 253 | 14.795 | 6.205 | 38.149 | 1.00 14.94 |
| ATOM | 1996 | CD | ARG | 253 | 14.429 | 4.904 | 37.433 | 1.00 14.49 |
| ATOM | 1997 | NE | ARG | 253 | 14.393 | 3.796 | 38.391 | 1.00 15.13 |
| ATOM | 1998 | CZ | ARG | 253 | 13.637 | 2.709 | 38.264 | 1.00 12.50 |
| ATOM | 1999 | NH1 | ARG | 253 | 13.671 | 1.770 | 39.199 | 1.00 10.88 |
| ATOM | 2000 | NH2 | ARG | 253 | 12.849 | 2.560 | 37.203 | 1.00 13.34 |
| ATOM | 2001 | C | ARG | 253 | 13.998 | 8.859 | 39.625 | 1.00 17.48 |
| ATOM | 2002 | O | ARG | 253 | 12.889 | 9.389 | 39.624 | 1.00 16.77 |
| ATOM | 2003 | N | ILE | 254 | 15.054 | 9.405 | 39.033 | 1.00 15.92 |
| ATOM | 2004 | CA | ILE | 254 | 14.952 | 10.684 | 38.346 | 1.00 14.89 |
| ATOM | 2005 | CB | ILE | 254 | 16.359 | 11.151 | 37.864 | 1.00 16.24 |
| ATOM | 2006 | CG2 | ILE | 254 | 16.867 | 10.225 | 36.749 | 1.00 14.32 |
| ATOM | 2007 | CG1 | ILE | 254 | 16.305 | 12.604 | 37.390 | 1.00 16.57 |
| ATOM | 2008 | CD1 | ILE | 254 | 17.679 | 13.194 | 37.079 | 1.00 15.04 |
| ATOM | 2009 | C | ILE | 254 | 13.981 | 10.583 | 37.164 | 1.00 16.39 |
| ATOM | 2010 | O | ILE | 254 | 13.878 | 9.537 | 36.519 | 1.00 17.01 |
| ATOM | 2011 | N | THR | 255 | 13.242 | 11.660 | 36.908 | 1.00 17.02 |
| ATOM | 2012 | CA | THR | 255 | 12.292 | 11.692 | 35.800 | 1.00 16.23 |
| ATOM | 2013 | CB | THR | 255 | 11.037 | 12.517 | 36.147 | 1.00 16.45 |
| ATOM | 2014 | OG1 | THR | 255 | 11.433 | 13.837 | 36.542 | 1.00 19.30 |
| ATOM | 2015 | CG2 | THR | 255 | 10.263 | 11.864 | 37.276 | 1.00 16.34 |
| ATOM | 2016 | C | THR | 255 | 12.997 | 12.370 | 34.635 | 1.00 17.07 |

FIG.11A-48

| | | | | | | | | |
|---|---|---|---|---|---|---|---|---|
| ATOM | 2017 | O | THR | 255 | 14.058 | 12.959 | 34.808 | 1.00 16.74 |
| ATOM | 2018 | N | ILE | 256 | 12.410 | 12.321 | 33.450 | 1.00 18.82 |
| ATOM | 2019 | CA | ILE | 256 | 13.070 | 12.954 | 32.320 | 1.00 18.31 |
| ATOM | 2020 | CB | ILE | 256 | 12.393 | 12.576 | 30.995 | 1.00 16.73 |
| ATOM | 2021 | CG2 | ILE | 256 | 13.076 | 13.305 | 29.844 | 1.00 16.91 |
| ATOM | 2022 | CG1 | ILE | 256 | 12.482 | 11.058 | 30.805 | 1.00 15.14 |
| ATOM | 2023 | CD1 | ILE | 256 | 11.814 | 10.538 | 29.555 | 1.00 17.21 |
| ATOM | 2024 | C | ILE | 256 | 13.162 | 14.472 | 32.461 | 1.00 18.90 |
| ATOM | 2025 | O | ILE | 256 | 14.182 | 15.062 | 32.112 | 1.00 19.82 |
| ATOM | 2026 | N | PRO | 257 | 12.099 | 15.135 | 32.959 | 1.00 19.76 |
| ATOM | 2027 | CD | PRO | 257 | 10.697 | 14.733 | 33.185 | 1.00 18.99 |
| ATOM | 2028 | CA | PRO | 257 | 12.256 | 16.590 | 33.079 | 1.00 19.66 |
| ATOM | 2029 | CB | PRO | 257 | 10.948 | 17.019 | 33.739 | 1.00 19.59 |
| ATOM | 2030 | CG | PRO | 257 | 9.953 | 16.075 | 33.104 | 1.00 19.54 |
| ATOM | 2031 | C | PRO | 257 | 13.494 | 16.949 | 33.911 | 1.00 19.08 |
| ATOM | 2032 | O | PRO | 257 | 14.176 | 17.941 | 33.637 | 1.00 19.37 |
| ATOM | 2033 | N | ASP | 258 | 13.794 | 16.133 | 34.917 | 1.00 19.06 |
| ATOM | 2034 | CA | ASP | 258 | 14.958 | 16.373 | 35.760 | 1.00 18.81 |
| ATOM | 2035 | CB | ASP | 258 | 14.735 | 15.728 | 37.128 | 1.00 18.17 |
| ATOM | 2036 | CG | ASP | 258 | 13.772 | 16.542 | 37.978 | 1.00 23.21 |
| ATOM | 2037 | OD1 | ASP | 258 | 13.193 | 16.012 | 38.948 | 1.00 23.28 |
| ATOM | 2038 | OD2 | ASP | 258 | 13.611 | 17.738 | 37.652 | 1.00 23.96 |
| ATOM | 2039 | C | ASP | 258 | 16.266 | 15.922 | 35.101 | 1.00 18.56 |
| ATOM | 2040 | O | ASP | 258 | 17.327 | 16.504 | 35.349 | 1.00 20.13 |
| ATOM | 2041 | N | ILE | 259 | 16.197 | 14.906 | 34.246 | 1.00 18.38 |
| ATOM | 2042 | CA | ILE | 259 | 17.392 | 14.471 | 33.531 | 1.00 19.58 |
| ATOM | 2043 | CB | ILE | 259 | 17.114 | 13.239 | 32.618 | 1.00 16.93 |
| ATOM | 2044 | CG2 | ILE | 259 | 18.241 | 13.063 | 31.600 | 1.00 14.51 |
| ATOM | 2045 | CG1 | ILE | 259 | 16.994 | 11.966 | 33.464 | 1.00 16.72 |
| ATOM | 2046 | CD1 | ILE | 259 | 16.489 | 10.748 | 32.677 | 1.00 11.48 |
| ATOM | 2047 | C | ILE | 259 | 17.823 | 15.659 | 32.659 | 1.00 21.42 |
| ATOM | 2048 | O | ILE | 259 | 19.005 | 15.958 | 32.543 | 1.00 20.64 |
| ATOM | 2049 | N | LYS | 260 | 16.851 | 16.354 | 32.070 | 1.00 23.12 |
| ATOM | 2050 | CA | LYS | 260 | 17.152 | 17.499 | 31.208 | 1.00 23.95 |
| ATOM | 2051 | CB | LYS | 260 | 15.876 | 18.020 | 30.538 | 1.00 25.83 |
| ATOM | 2052 | CG | LYS | 260 | 15.150 | 19.064 | 31.356 | 1.00 38.93 |
| ATOM | 2053 | CD | LYS | 260 | 13.885 | 19.551 | 30.678 | 1.00 48.71 |
| ATOM | 2054 | CE | LYS | 260 | 13.278 | 20.709 | 31.455 | 1.00 44.94 |
| ATOM | 2055 | NZ | LYS | 260 | 14.210 | 21.872 | 31.510 | 1.00 42.57 |
| ATOM | 2056 | C | LYS | 260 | 17.827 | 18.646 | 31.961 | 1.00 22.24 |
| ATOM | 2057 | O | LYS | 260 | 18.369 | 19.558 | 31.340 | 1.00 22.70 |
| ATOM | 2058 | N | LYS | 261 | 17.787 | 18.598 | 33.290 | 1.00 20.88 |

FIG.11A-49

| | | | | | | | | |
|---|---|---|---|---|---|---|---|---|
| ATOM | 2059 | CA | LYS | 261 | 18.402 | 19.628 | 34.129 | 1.00 21.74 |
| ATOM | 2060 | CB | LYS | 261 | 17.474 | 19.984 | 35.298 | 1.00 24.31 |
| ATOM | 2061 | CG | LYS | 261 | 16.176 | 20.661 | 34.881 | 1.00 33.19 |
| ATOM | 2062 | CD | LYS | 261 | 15.245 | 20.857 | 36.071 | 1.00 47.75 |
| ATOM | 2063 | CE | LYS | 261 | 14.008 | 21.650 | 35.680 | 1.00 57.96 |
| ATOM | 2064 | NZ | LYS | 261 | 13.280 | 21.031 | 34.537 | 1.00 64.19 |
| ATOM | 2065 | C | LYS | 261 | 19.750 | 19.181 | 34.687 | 1.00 21.66 |
| ATOM | 2066 | O | LYS | 261 | 20.462 | 19.964 | 35.320 | 1.00 23.16 |
| ATOM | 2067 | N | ASP | 262 | 20.105 | 17.926 | 34.442 | 1.00 19.55 |
| ATOM | 2068 | CA | ASP | 262 | 21.352 | 17.371 | 34.950 | 1.00 19.62 |
| ATOM | 2069 | CB | ASP | 262 | 21.419 | 15.874 | 34.618 | 1.00 18.71 |
| ATOM | 2070 | CG | ASP | 262 | 22.781 | 15.266 | 34.903 | 1.00 15.55 |
| ATOM | 2071 | OD1 | ASP | 262 | 23.584 | 15.162 | 33.955 | 1.00 14.99 |
| ATOM | 2072 | OD2 | ASP | 262 | 23.049 | 14.889 | 36.064 | 1.00 15.43 |
| ATOM | 2073 | C | ASP | 262 | 22.588 | 18.102 | 34.437 | 1.00 19.73 |
| ATOM | 2074 | O | ASP | 262 | 22.628 | 18.557 | 33.294 | 1.00 20.79 |
| ATOM | 2075 | N | ARG | 263 | 23.600 | 18.209 | 35.290 | 1.00 18.70 |
| ATOM | 2076 | CA | ARG | 263 | 24.825 | 18.910 | 34.925 | 1.00 18.98 |
| ATOM | 2077 | CB | ARG | 263 | 25.798 | 18.937 | 36.109 | 1.00 20.52 |
| ATOM | 2078 | CG | ARG | 263 | 27.078 | 19.713 | 35.820 | 1.00 28.61 |
| ATOM | 2079 | CD | ARG | 263 | 27.963 | 19.850 | 37.068 | 1.00 38.40 |
| ATOM | 2080 | NE | ARG | 263 | 28.937 | 18.768 | 37.219 | 1.00 45.20 |
| ATOM | 2081 | CZ | ARG | 263 | 28.637 | 17.502 | 37.499 | 1.00 56.82 |
| ATOM | 2082 | NH1 | ARG | 263 | 27.375 | 17.129 | 37.665 | 1.00 58.45 |
| ATOM | 2083 | NH2 | ARG | 263 | 29.607 | 16.606 | 37.626 | 1.00 62.85 |
| ATOM | 2084 | C | ARG | 263 | 25.516 | 18.320 | 33.700 | 1.00 18.37 |
| ATOM | 2085 | O | ARG | 263 | 25.850 | 19.046 | 32.769 | 1.00 17.68 |
| ATOM | 2086 | N | TRP | 264 | 25.732 | 17.008 | 33.684 | 1.00 17.26 |
| ATOM | 2087 | CA | TRP | 264 | 26.390 | 16.400 | 32.531 | 1.00 15.96 |
| ATOM | 2088 | CB | TRP | 264 | 26.684 | 14.918 | 32.788 | 1.00 15.01 |
| ATOM | 2089 | CG | TRP | 264 | 27.354 | 14.260 | 31.610 | 1.00 14.46 |
| ATOM | 2090 | CD2 | TRP | 264 | 26.733 | 13.407 | 30.639 | 1.00 16.57 |
| ATOM | 2091 | CE2 | TRP | 264 | 27.715 | 13.090 | 29.672 | 1.00 14.53 |
| ATOM | 2092 | CE3 | TRP | 264 | 25.437 | 12.878 | 30.490 | 1.00 15.64 |
| ATOM | 2093 | CD1 | TRP | 264 | 28.652 | 14.419 | 31.205 | 1.00 12.93 |
| ATOM | 2094 | NE1 | TRP | 264 | 28.875 | 13.722 | 30.042 | 1.00 13.60 |
| ATOM | 2095 | CZ2 | TRP | 264 | 27.446 | 12.269 | 28.570 | 1.00 14.44 |
| ATOM | 2096 | CZ3 | TRP | 264 | 25.168 | 12.061 | 29.391 | 1.00 13.46 |
| ATOM | 2097 | CH2 | TRP | 264 | 26.166 | 11.764 | 28.447 | 1.00 13.11 |
| ATOM | 2098 | C | TRP | 264 | 25.545 | 16.540 | 31.260 | 1.00 15.93 |
| ATOM | 2099 | O | TRP | 264 | 26.064 | 16.818 | 30.179 | 1.00 13.92 |
| ATOM | 2100 | N | TYR | 265 | 24.240 | 16.339 | 31.393 | 1.00 15.00 |

FIG.11A-50

| | | | | | | | | |
|---|---|---|---|---|---|---|---|---|
| ATOM | 2101 | CA | TYR | 265 | 23.342 | 16.447 | 30.257 | 1.00 13.62 |
| ATOM | 2102 | CB | TYR | 265 | 21.895 | 16.265 | 30.738 | 1.00 11.92 |
| ATOM | 2103 | CG | TYR | 265 | 20.888 | 16.112 | 29.629 | 1.00 15.19 |
| ATOM | 2104 | CD1 | TYR | 265 | 20.259 | 17.220 | 29.060 | 1.00 16.33 |
| ATOM | 2105 | CE1 | TYR | 265 | 19.317 | 17.062 | 28.039 | 1.00 16.52 |
| ATOM | 2106 | CD2 | TYR | 265 | 20.555 | 14.843 | 29.150 | 1.00 13.45 |
| ATOM | 2107 | CE2 | TYR | 265 | 19.628 | 14.676 | 28.148 | 1.00 13.56 |
| ATOM | 2108 | CZ | TYR | 265 | 19.010 | 15.781 | 27.594 | 1.00 16.67 |
| ATOM | 2109 | OH | TYR | 265 | 18.084 | 15.582 | 26.608 | 1.00 19.16 |
| ATOM | 2110 | C | TYR | 265 | 23.508 | 17.798 | 29.551 | 1.00 14.32 |
| ATOM | 2111 | O | TYR | 265 | 23.459 | 17.882 | 28.322 | 1.00 15.01 |
| ATOM | 2112 | N | ASN | 266 | 23.751 | 18.847 | 30.335 | 1.00 15.47 |
| ATOM | 2113 | CA | ASN | 266 | 23.897 | 20.193 | 29.790 | 1.00 17.01 |
| ATOM | 2114 | CB | ASN | 266 | 23.166 | 21.184 | 30.704 | 1.00 17.43 |
| ATOM | 2115 | CG | ASN | 266 | 21.661 | 21.021 | 30.636 | 1.00 19.60 |
| ATOM | 2116 | OD1 | ASN | 266 | 21.030 | 21.428 | 29.659 | 1.00 21.30 |
| ATOM | 2117 | ND2 | ASN | 266 | 21.080 | 20.396 | 31.661 | 1.00 19.15 |
| ATOM | 2118 | C | ASN | 266 | 25.330 | 20.676 | 29.552 | 1.00 18.03 |
| ATOM | 2119 | O | ASN | 266 | 25.536 | 21.820 | 29.154 | 1.00 16.54 |
| ATOM | 2120 | N | LYS | 267 | 26.319 | 19.815 | 29.773 | 1.00 18.76 |
| ATOM | 2121 | CA | LYS | 267 | 27.716 | 20.221 | 29.574 | 1.00 18.99 |
| ATOM | 2122 | CB | LYS | 267 | 28.666 | 19.244 | 30.273 | 1.00 24.39 |
| ATOM | 2123 | CG | LYS | 267 | 28.804 | 19.442 | 31.769 | 1.00 35.68 |
| ATOM | 2124 | CD | LYS | 267 | 29.767 | 18.424 | 32.368 | 1.00 48.27 |
| ATOM | 2125 | CE | LYS | 267 | 31.138 | 18.481 | 31.702 | 1.00 51.14 |
| ATOM | 2126 | NZ | LYS | 267 | 31.800 | 19.802 | 31.888 | 1.00 56.24 |
| ATOM | 2127 | C | LYS | 267 | 28.123 | 20.307 | 28.110 | 1.00 19.25 |
| ATOM | 2128 | O | LYS | 267 | 27.919 | 19.365 | 27.350 | 1.00 18.64 |
| ATOM | 2129 | N | PRO | 268 | 28.708 | 21.444 | 27.694 | 1.00 21.76 |
| ATOM | 2130 | CD | PRO | 268 | 28.826 | 22.742 | 28.378 | 1.00 22.13 |
| ATOM | 2131 | CA | PRO | 268 | 29.119 | 21.547 | 26.289 | 1.00 23.47 |
| ATOM | 2132 | CB | PRO | 268 | 29.556 | 23.008 | 26.158 | 1.00 22.99 |
| ATOM | 2133 | CG | PRO | 268 | 28.746 | 23.713 | 27.219 | 1.00 24.42 |
| ATOM | 2134 | C | PRO | 268 | 30.276 | 20.570 | 26.084 | 1.00 22.96 |
| ATOM | 2135 | O | PRO | 268 | 31.280 | 20.627 | 26.800 | 1.00 22.64 |
| ATOM | 2136 | N | LEU | 269 | 30.132 | 19.670 | 25.120 | 1.00 21.85 |
| ATOM | 2137 | CA | LEU | 269 | 31.155 | 18.667 | 24.863 | 1.00 23.57 |
| ATOM | 2138 | CB | LEU | 269 | 30.751 | 17.324 | 25.473 | 1.00 23.55 |
| ATOM | 2139 | CG | LEU | 269 | 30.576 | 17.187 | 26.982 | 1.00 22.37 |
| ATOM | 2140 | CD1 | LEU | 269 | 29.980 | 15.818 | 27.298 | 1.00 23.62 |
| ATOM | 2141 | CD2 | LEU | 269 | 31.920 | 17.367 | 27.665 | 1.00 21.81 |
| ATOM | 2142 | C | LEU | 269 | 31.442 | 18.424 | 23.394 | 1.00 26.56 |

FIG.11A-51

| | | | | | | | | |
|---|---|---|---|---|---|---|---|---|
| ATOM | 2143 | O | LEU | 269 | 32.592 | 18.228 | 23.012 | 1.00 26.46 |
| ATOM | 2144 | N | LYS | 270 | 30.400 | 18.421 | 22.571 | 1.00 28.53 |
| ATOM | 2145 | CA | LYS | 270 | 30.595 | 18.128 | 21.158 | 1.00 31.73 |
| ATOM | 2146 | CB | LYS | 270 | 29.790 | 16.881 | 20.777 | 1.00 33.10 |
| ATOM | 2147 | CG | LYS | 270 | 30.179 | 16.292 | 19.431 | 1.00 37.08 |
| ATOM | 2148 | CD | LYS | 270 | 29.461 | 14.981 | 19.167 | 1.00 35.35 |
| ATOM | 2149 | CE | LYS | 270 | 29.881 | 14.383 | 17.833 | 1.00 33.40 |
| ATOM | 2150 | NZ | LYS | 270 | 29.137 | 13.123 | 17.546 | 1.00 40.91 |
| ATOM | 2151 | C | LYS | 270 | 30.290 | 19.241 | 20.171 | 1.00 34.07 |
| ATOM | 2152 | O | LYS | 270 | 29.304 | 19.968 | 20.301 | 1.00 34.39 |
| ATOM | 2153 | N | LYS | 271 | 31.162 | 19.358 | 19.177 | 1.00 36.37 |
| ATOM | 2154 | CA | LYS | 271 | 31.018 | 20.349 | 18.124 | 1.00 39.68 |
| ATOM | 2155 | CB | LYS | 271 | 32.345 | 20.528 | 17.381 | 1.00 40.41 |
| ATOM | 2156 | CG | LYS | 271 | 33.534 | 20.899 | 18.259 | 1.00 37.20 |
| ATOM | 2157 | CD | LYS | 271 | 33.431 | 22.328 | 18.752 | 1.00 32.85 |
| ATOM | 2158 | CE | LYS | 271 | 34.718 | 22.773 | 19.440 | 1.00 26.35 |
| ATOM | 2159 | NZ | LYS | 271 | 34.639 | 24.202 | 19.855 | 1.00 21.18 |
| ATOM | 2160 | C | LYS | 271 | 29.975 | 19.818 | 17.146 | 1.00 41.40 |
| ATOM | 2161 | O | LYS | 271 | 29.709 | 18.615 | 17.109 | 1.00 39.59 |
| ATOM | 2162 | N | GLY | 272 | 29.393 | 20.711 | 16.354 | 1.00 43.87 |
| ATOM | 2163 | CA | GLY | 272 | 28.407 | 20.287 | 15.377 | 1.00 46.49 |
| ATOM | 2164 | C | GLY | 272 | 29.090 | 19.497 | 14.275 | 1.00 49.32 |
| ATOM | 2165 | O | GLY | 272 | 30.317 | 19.377 | 14.269 | 1.00 49.55 |
| ATOM | 2166 | N | ALA | 273 | 28.306 | 18.958 | 13.346 | 1.00 50.80 |
| ATOM | 2167 | CA | ALA | 273 | 28.850 | 18.175 | 12.240 | 1.00 53.37 |
| ATOM | 2168 | CB | ALA | 273 | 27.749 | 17.859 | 11.234 | 1.00 52.51 |
| ATOM | 2169 | C | ALA | 273 | 29.998 | 18.905 | 11.547 | 1.00 55.13 |
| ATOM | 2170 | O | ALA | 273 | 30.024 | 20.134 | 11.501 | 1.00 55.65 |
| ATOM | 2171 | N | ALA | 274 | 30.945 | 18.140 | 11.012 | 1.00 56.46 |
| ATOM | 2172 | CA | ALA | 274 | 32.101 | 18.707 | 10.323 | 1.00 57.69 |
| ATOM | 2173 | CB | ALA | 274 | 33.043 | 17.591 | 9.883 | 1.00 55.97 |
| ATOM | 2174 | C | ALA | 274 | 31.681 | 19.539 | 9.116 | 1.00 58.75 |
| ATOM | 2175 | O | ALA | 274 | 31.092 | 19.018 | 8.169 | 1.00 58.34 |
| ATOM | 2176 | N | ALA | 275 | 31.991 | 20.833 | 9.157 | 1.00 60.19 |
| ATOM | 2177 | CA | ALA | 275 | 31.653 | 21.751 | 8.073 | 1.00 61.34 |
| ATOM | 2178 | CB | ALA | 275 | 32.417 | 21.370 | 6.808 | 1.00 63.01 |
| ATOM | 2179 | C | ALA | 275 | 30.155 | 21.764 | 7.794 | 1.00 62.70 |
| ATOM | 2180 | O | ALA | 275 | 29.687 | 21.161 | 6.827 | 1.00 64.42 |
| ATOM | 2181 | N | ALA | 276 | 29.406 | 22.459 | 8.644 | 1.00 63.05 |
| ATOM | 2182 | CA | ALA | 276 | 27.959 | 22.553 | 8.493 | 1.00 64.39 |
| ATOM | 2183 | CB | ALA | 276 | 27.300 | 21.252 | 8.938 | 1.00 65.25 |
| ATOM | 2184 | C | ALA | 276 | 27.409 | 23.722 | 9.302 | 1.00 66.43 |

FIG.11A-52

```
ATOM   2185 OCT1 ALA   276      26.726   24.582    8.707  1.00 66.01
ATOM   2186 OT   ALA   276      27.665   23.761   10.524  1.00 72.06
ATOM   2187 OH2  WAT   500       7.288    0.582   30.446  1.00 12.93
ATOM   2188 OH2  WAT   501       7.551   -2.385   30.926  1.00 14.51
ATOM   2189 OH2  WAT   502      15.648   -3.549   26.581  1.00 12.66
ATOM   2190 OH2  WAT   503      22.995   -4.531   32.505  1.00 14.00
ATOM   2191 OH2  WAT   504      12.370   -2.139   29.668  1.00 12.75
ATOM   2192 OH2  WAT   505       8.243    1.795   37.412  1.00 13.95
ATOM   2193 OH2  WAT   506      12.211   -1.687   42.460  1.00 18.17
ATOM   2194 OH2  WAT   507      12.547    0.038   27.856  1.00 14.35
ATOM   2195 OH2  WAT   508       9.787   10.899   33.147  1.00 15.08
ATOM   2196 OH2  WAT   510      11.744    7.842   36.365  1.00 15.19
ATOM   2197 OH2  WAT   511       9.925   -3.492   29.777  1.00 15.10
ATOM   2198 OH2  WAT   512       9.590    8.537   34.696  1.00 17.43
ATOM   2199 OH2  WAT   513       2.021    3.295   33.836  1.00 15.34
ATOM   2200 OH2  WAT   514       6.563   13.229   27.860  1.00 18.19
ATOM   2201 OH2  WAT   515      10.555    8.269   38.785  1.00 18.00
ATOM   2202 OH2  WAT   516      10.674   15.405   22.497  1.00 19.56
ATOM   2203 OH2  WAT   517      25.750   15.101   36.287  1.00 17.00
ATOM   2204 OH2  WAT   518       4.386    6.182   34.218  1.00 15.43
ATOM   2205 OH2  WAT   519      13.712   -1.171   31.851  1.00 19.69
ATOM   2206 OH2  WAT   520      27.652   18.967   23.808  1.00 20.13
ATOM   2207 OH2  WAT   521      14.113   -4.152   28.944  1.00 16.61
ATOM   2208 OH2  WAT   522       8.101    9.135   38.813  1.00 23.68
ATOM   2209 OH2  WAT   523       6.549    1.866   39.438  1.00 17.99
ATOM   2210 OH2  WAT   524       8.387   10.486   30.847  1.00 15.91
ATOM   2211 OH2  WAT   525      12.082    9.839   11.918  1.00 19.48
ATOM   2212 OH2  WAT   526      18.804   -3.707   34.246  1.00 13.10
ATOM   2213 OH2  WAT   527      13.250   13.468   39.304  1.00 19.10
ATOM   2214 OH2  WAT   528       7.275    8.982   36.188  1.00 19.69
ATOM   2215 OH2  WAT   529       5.361    7.284   36.859  1.00 17.02
ATOM   2216 OH2  WAT   530       8.547   12.919   29.494  1.00 20.63
ATOM   2217 OH2  WAT   531      33.657    6.673   29.562  1.00 19.62
ATOM   2218 OH2  WAT   532      23.095   17.810   38.035  1.00 20.16
ATOM   2219 OH2  WAT   533       7.044    4.516   40.668  1.00 18.41
ATOM   2220 OH2  WAT   534       8.572   -2.181   21.497  1.00 19.99
ATOM   2221 OH2  WAT   535       5.165   -3.897   30.946  1.00 16.72
ATOM   2222 OH2  WAT   536      35.064   12.912   30.402  1.00 24.78
ATOM   2223 OH2  WAT   537       7.785    2.872   44.403  1.00 19.77
ATOM   2224 OH2  WAT   538       2.503   10.234   33.144  1.00 23.38
ATOM   2225 OH2  WAT   539       2.763   -3.299   20.083  1.00 22.50
ATOM   2226 OH2  WAT   540       6.475    6.912   39.440  1.00 22.13
```

FIG.11A-53

```
ATOM   2227  OH2  WAT   541    -6.228    9.593   24.818  1.00  26.15
ATOM   2228  OH2  WAT   542    37.153    5.154   30.029  1.00  23.86
ATOM   2229  OH2  WAT   543     8.552    2.510   13.829  1.00  21.71
ATOM   2230  OH2  WAT   544    16.101    3.059   45.670  1.00  22.52
ATOM   2231  OH2  WAT   545    32.130   14.940   31.845  1.00  22.82
ATOM   2232  OH2  WAT   546    18.050   14.095   15.782  1.00  22.03
ATOM   2233  OH2  WAT   547    24.287   11.877   41.531  1.00  25.65
ATOM   2234  OH2  WAT   548     0.491   -4.750   31.613  1.00  21.18
ATOM   2235  OH2  WAT   549     7.787   12.606   34.142  1.00  23.30
ATOM   2236  OH2  WAT   550    12.435   -5.647   20.701  1.00  31.34
ATOM   2237  OH2  WAT   552    25.857  -10.012   36.222  1.00  28.63
ATOM   2238  OH2  WAT   553     3.334   15.175   20.677  1.00  36.96
ATOM   2239  OH2  WAT   554    -4.014    0.643   36.230  1.00  24.61
ATOM   2240  OH2  WAT   555    10.571   -0.361  -16.930  1.00  26.27
ATOM   2241  OH2  WAT   556    14.828   -2.773   15.913  1.00  23.41
ATOM   2242  OH2  WAT   557     5.825   15.674   24.158  1.00  27.12
ATOM   2243  OH2  WAT   558    10.922   19.080   30.780  1.00  31.85
ATOM   2244  OH2  WAT   559    28.720   -6.638   28.476  1.00  27.77
ATOM   2245  OH2  WAT   560     3.832   -6.269   44.319  1.00  30.04
ATOM   2246  OH2  WAT   561     4.426   13.762   22.733  1.00  17.65
ATOM   2247  OH2  WAT   563    28.205   -3.067   39.437  1.00  24.33
ATOM   2248  OH2  WAT   564     2.857    8.453   37.278  1.00  24.76
ATOM   2249  OH2  WAT   565    25.621   21.668   32.817  1.00  22.51
ATOM   2250  OH2  WAT   566    10.036   -1.136   43.949  1.00  22.61
ATOM   2251  OH2  WAT   567    19.146   16.682   37.504  1.00  23.78
ATOM   2252  OH2  WAT   568     8.258    8.945   13.451  1.00  26.53
ATOM   2253  OH2  WAT   569     5.792   10.982   34.708  1.00  27.31
ATOM   2254  OH2  WAT   570     4.400   12.602   29.260  1.00  24.68
ATOM   2255  OH2  WAT   571     8.030   15.813   22.347  1.00  24.44
ATOM   2256  OH2  WAT   572    30.240   10.872   40.240  1.00  30.85
ATOM   2257  OH2  WAT   573     3.021    5.306   42.778  1.00  33.27
ATOM   2258  OH2  WAT   574    12.290   16.620   24.591  1.00  34.06
ATOM   2259  OH2  WAT   575     2.437   -4.157   42.875  1.00  24.07
ATOM   2260  OH2  WAT   576    19.000    2.392   44.605  1.00  32.41
ATOM   2261  OH2  WAT   577    -3.658    4.410   15.376  1.00  31.82
ATOM   2262  OH2  WAT   578    17.547   12.393   41.174  1.00  28.94
ATOM   2263  OH2  WAT   579     9.859   -9.730   26.441  1.00  24.36
ATOM   2264  OH2  WAT   580     7.649   -1.350   14.768  1.00  29.54
ATOM   2265  OH2  WAT   581    12.303   -0.250   12.412  1.00  26.66
ATOM   2266  OH2  WAT   582     6.958   15.256   16.519  1.00  46.73
ATOM   2267  OH2  WAT   583     4.897   12.398   31.727  1.00  29.49
ATOM   2268  OH2  WAT   584    17.449  -10.259   23.231  1.00  43.02
```

FIG.11A-54

| | | | | | | | | |
|---|---|---|---|---|---|---|---|---|
| ATOM | 2269 | OH2 | WAT | 585 | -8.993 | 2.971 | 28.486 | 1.00 30.80 |
| ATOM | 2270 | OH2 | WAT | 586 | -0.139 | -3.655 | 43.071 | 1.00 37.06 |
| ATOM | 2271 | OH2 | WAT | 588 | 16.750 | 16.297 | 23.374 | 1.00 29.48 |
| ATOM | 2272 | OH2 | WAT | 589 | 5.136 | 6.789 | 43.328 | 1.00 32.09 |
| ATOM | 2273 | OH2 | WAT | 590 | 5.961 | 15.786 | 26.926 | 1.00 22.25 |
| ATOM | 2274 | OH2 | WAT | 591 | 11.771 | 0.434 | -14.604 | 1.00 25.03 |
| ATOM | 2275 | OH2 | WAT | 592 | 20.674 | -11.849 | 31.603 | 1.00 28.56 |
| ATOM | 2276 | OH2 | WAT | 593 | 16.561 | 0.669 | 8.704 | 1.00 30.46 |
| ATOM | 2277 | OH2 | WAT | 594 | 25.900 | 1.235 | 13.342 | 1.00 25.92 |
| ATOM | 2278 | OH2 | WAT | 595 | 14.762 | 0.666 | -11.939 | 1.00 27.07 |
| ATOM | 2279 | OH2 | WAT | 596 | 19.928 | 0.579 | 42.222 | 1.00 33.09 |
| ATOM | 2280 | OH2 | WAT | 597 | 2.749 | -4.838 | 23.485 | 1.00 28.02 |
| ATOM | 2281 | OH2 | WAT | 599 | 2.241 | 12.981 | 17.063 | 1.00 32.27 |
| ATOM | 2282 | OH2 | WAT | 600 | 17.311 | -11.858 | 43.919 | 1.00 46.62 |
| ATOM | 2283 | OH2 | WAT | 601 | 10.116 | 0.287 | 13.907 | 1.00 23.36 |
| ATOM | 2284 | OH2 | WAT | 602 | -5.766 | 4.131 | 31.307 | 1.00 37.38 |
| ATOM | 2285 | OH2 | WAT | 603 | 8.777 | -6.752 | 16.659 | 1.00 36.23 |
| ATOM | 2286 | OH2 | WAT | 604 | 2.780 | 13.085 | 33.578 | 1.00 56.17 |
| ATOM | 2287 | OH2 | WAT | 605 | 13.505 | -9.621 | 24.772 | 1.00 27.48 |
| ATOM | 2288 | OH2 | WAT | 606 | 19.499 | -8.171 | 22.784 | 1.00 35.47 |
| ATOM | 2289 | OH2 | WAT | 607 | 18.981 | 6.434 | 6.609 | 1.00 39.96 |
| ATOM | 2290 | OH2 | WAT | 609 | 19.617 | 1.498 | -10.274 | 1.00 46.75 |
| ATOM | 2291 | OH2 | WAT | 610 | 7.105 | 14.231 | 31.956 | 1.00 30.92 |
| ATOM | 2292 | OH2 | WAT | 611 | -2.597 | 7.596 | 24.441 | 1.00 52.94 |
| ATOM | 2293 | OH2 | WAT | 612 | 38.962 | 0.347 | 34.269 | 1.00 28.21 |
| ATOM | 2294 | OH2 | WAT | 613 | 34.567 | 6.357 | 38.002 | 1.00 53.59 |
| ATOM | 2295 | OH2 | WAT | 614 | 19.967 | 5.584 | -11.241 | 1.00 30.33 |
| ATOM | 2296 | OH2 | WAT | 615 | 0.984 | 14.444 | 27.279 | 1.00 41.31 |
| ATOM | 2297 | OH2 | WAT | 616 | 31.944 | 18.357 | 34.770 | 1.00 56.14 |
| ATOM | 2298 | OH2 | WAT | 617 | 23.842 | 3.527 | 43.838 | 1.00 39.09 |
| ATOM | 2299 | OH2 | WAT | 618 | 24.265 | -10.048 | 29.048 | 1.00 43.37 |
| ATOM | 2300 | OH2 | WAT | 619 | 13.920 | 0.583 | 10.143 | 1.00 28.77 |
| ATOM | 2301 | OH2 | WAT | 620 | 13.884 | 17.699 | 20.194 | 1.00 53.38 |
| ATOM | 2302 | OH2 | WAT | 621 | 15.456 | 13.880 | 40.976 | 1.00 38.26 |
| ATOM | 2303 | OH2 | WAT | 622 | -4.209 | 10.695 | 27.546 | 1.00 31.65 |
| ATOM | 2304 | OH2 | WAT | 623 | 9.422 | 15.446 | 37.303 | 1.00 35.02 |
| ATOM | 2305 | OH2 | WAT | 624 | 28.277 | 9.830 | 16.219 | 1.00 32.83 |
| ATOM | 2306 | OH2 | WAT | 625 | -2.164 | -0.376 | 23.957 | 1.00 32.44 |
| ATOM | 2307 | OH2 | WAT | 626 | 13.795 | -8.227 | 22.617 | 1.00 47.18 |
| ATOM | 2308 | OH2 | WAT | 627 | 12.663 | -2.391 | 45.836 | 1.00 32.05 |
| ATOM | 2309 | OH2 | WAT | 628 | 3.919 | -11.060 | 32.966 | 1.00 44.73 |
| ATOM | 2310 | OH2 | WAT | 629 | -2.517 | 11.533 | 34.098 | 1.00 54.44 |

FIG.11A-55

```
ATOM  2311  OH2  WAT  630   25.613  14.652  11.863  1.00 63.79
ATOM  2312  OH2  WAT  631   11.909  11.704  41.097  1.00 34.25
ATOM  2313  OH2  WAT  632   -1.360  10.995  26.456  1.00 38.16
ATOM  2314  OH2  WAT  633   31.933   5.045  17.791  1.00 39.91
ATOM  2315  OH2  WAT  634   22.722  -5.823  24.321  1.00 28.24
ATOM  2316  OH2  WAT  635   16.867  10.054  41.617  1.00 32.20
ATOM  2317  OH2  WAT  636   -0.030  10.808  17.607  1.00 37.23
ATOM  2318  OH2  WAT  637   -2.623  -2.811  32.773  1.00 41.25
ATOM  2319  OH2  WAT  638   31.929  21.354  29.330  1.00 38.21
ATOM  2320  OH2  WAT  639   17.980  15.951  20.755  1.00 60.27
ATOM  2321  OH2  WAT  640   29.018  -3.356  20.263  1.00 36.21
ATOM  2322  OH2  WAT  641   20.664  16.288  14.235  1.00 42.55
ATOM  2323  OH2  WAT  642    7.328  13.948  36.591  1.00 55.67
ATOM  2324  OH2  WAT  643   11.409  16.717  20.413  1.00 25.47
ATOM  2325  OH2  WAT  644   16.547  13.154  13.670  1.00 25.26
ATOM  2326  OH2  WAT  645   15.596  15.812  18.554  1.00 34.13
ATOM  2327  OH2  WAT  646   25.131   5.610   6.079  1.00 53.07
ATOM  2328  OH2  WAT  647   -3.556  15.275  34.402  1.00 61.62
ATOM  2329  OH2  WAT  648   10.229  -7.176  19.982  1.00 41.83
ATOM  2330  OH2  WAT  649   20.662   8.866  43.464  1.00 51.89
ATOM  2331  OH2  WAT  650   23.069  16.777  21.097  1.00 25.83
ATOM  2332  OH2  WAT  651   26.751  11.131  18.349  1.00 16.47
ATOM  2333  OH2  WAT  652    4.110  -8.428  37.000  1.00 23.09
ATOM  2334  OH2  WAT  654   16.700 -14.479  41.296  1.00 33.14
ATOM  2335  OH2  WAT  655   13.831  16.895  27.725  1.00 39.59
ATOM  2336  OH2  WAT  656   13.478   5.441   4.355  1.00 41.26
ATOM  2337  OH2  WAT  657   14.527  -6.733  41.081  1.00 39.50
ATOM  2338  OH2  WAT  658   12.344  -8.188  -4.840  1.00 31.36
ATOM  2339  OH2  WAT  659    2.335   0.119 -12.679  1.00 46.96
ATOM  2340  OH2  WAT  660   -4.072   8.903  35.840  1.00 33.73
ATOM  2341  OH2  WAT  661   11.199  -3.361  13.690  1.00 30.89
ATOM  2342  OH2  WAT  662   33.630  13.397  20.072  1.00 32.18
ATOM  2343  OH2  WAT  663   -8.225   5.595  20.237  1.00 42.51
ATOM  2344  OH2  WAT  664    4.851   8.191  41.111  1.00 38.06
ATOM  2345  OH2  WAT  665    9.375   6.937  -3.912  1.00 45.24
ATOM  2346  OH2  WAT  666   16.913  -0.045 -10.717  1.00 42.04
ATOM  2347  OH2  WAT  667   29.488  -4.757  36.815  1.00 47.43
ATOM  2348  OH2  WAT  668   23.202  16.279  14.705  1.00 36.53
ATOM  2349  OH2  WAT  669    1.557 -10.157  34.020  1.00 34.64
ATOM  2350  OH2  WAT  670   30.193   6.969  18.404  1.00 43.94
ATOM  2351  OH2  WAT  671    9.581  18.649  26.362  1.00 38.51
ATOM  2352  OH2  WAT  672    3.957  11.310  37.024  1.00 42.49
```

FIG.11A-56

```
ATOM  2353 OH2 WAT  673    23.314 -12.393  29.627 1.00 44.03
ATOM  2354 OH2 WAT  674    29.567  -4.326  22.984 1.00 38.54
ATOM  2355 OH2 WAT  675    20.341 -13.530  33.695 1.00 35.66
ATOM  2356 OH2 WAT  676    24.115  -2.262  12.332 1.00 24.55
ATOM  2357 OH2 WAT  677    21.496  16.243  18.532 1.00 38.18
ATOM  2358 OH2 WAT  678     1.474  14.677  18.946 1.00 34.15
ATOM  2359 OH2 WAT  679    22.623  10.998  43.542 1.00 34.98
ATOM  2360 OH2 WAT  680    22.204   4.868  42.384 1.00 35.66
ATOM  2361 OH2 WAT  681     4.974  18.238  22.943 1.00 43.25
ATOM  2362 OH2 WAT  682     7.600  17.266  28.095 1.00 47.36
ATOM  2363 OH2 WAT  683     9.887  -4.665  20.529 1.00 55.08
ATOM  2364 OH2 WAT  684    34.174  16.468  30.910 1.00 59.36
ATOM  2365 OH2 WAT  685    14.332  -9.413  41.717 1.00 44.97
ATOM  2366 OH2 WAT  686    -6.650  -2.511  31.135 1.00 56.20
ATOM  2367 OH2 WAT  687     3.069  14.962  28.974 1.00 53.45
ATOM  2368 S   SO4  901    -0.036  -4.899  27.988 1.00 27.31
ATOM  2369 O1  SO4  901     0.702  -5.486  26.855 1.00 27.32
ATOM  2370 O2  SO4  901     0.883  -4.694  29.123 1.00 30.06
ATOM  2371 O3  SO4  901    -1.115  -5.818  28.406 1.00 25.85
ATOM  2372 O4  SO4  901    -0.628  -3.611  27.579 1.00 30.90
END
```

FIG.11A-57

| ATOM | 1 | CB | ALA | 2 | -1.758 | 8.559 | -13.637 | 1.00 | 37.12 |
|------|---|----|----|---|--------|-------|---------|------|-------|
| ATOM | 2 | C | ALA | 2 | 0.707 | 8.098 | -13.520 | 1.00 | 36.78 |
| ATOM | 3 | O | ALA | 2 | 0.588 | 7.652 | -14.662 | 1.00 | 37.76 |
| ATOM | 4 | N | ALA | 2 | -0.253 | 10.204 | -12.575 | 1.00 | 37.69 |
| ATOM | 5 | CA | ALA | 2 | -0.489 | 8.748 | -12.807 | 1.00 | 37.30 |
| ATOM | 6 | N | VAL | 3 | 1.848 | 8.047 | -12.838 | 1.00 | 35.55 |
| ATOM | 7 | CA | VAL | 3 | 3.063 | 7.454 | -13.398 | 1.00 | 34.24 |
| ATOM | 8 | CB | VAL | 3 | 4.313 | 7.955 | -12.643 | 1.00 | 34.18 |
| ATOM | 9 | CG1 | VAL | 3 | 5.571 | 7.440 | -13.323 | 1.00 | 34.29 |
| ATOM | 10 | CG2 | VAL | 3 | 4.317 | 9.475 | -12.588 | 1.00 | 34.68 |
| ATOM | 11 | C | VAL | 3 | 2.978 | 5.903 | -13.310 | 1.00 | 33.32 |
| ATOM | 12 | O | VAL | 3 | 2.931 | 5.330 | -12.229 | 1.00 | 32.18 |
| ATOM | 13 | N | PRO | 4 | 2.991 | 5.224 | -14.464 | 1.00 | 31.94 |
| ATOM | 14 | CD | PRO | 4 | 3.225 | 5.848 | -15.781 | 1.00 | 31.07 |
| ATOM | 15 | CA | PRO | 4 | 2.907 | 3.767 | -14.603 | 1.00 | 32.30 |
| ATOM | 16 | CB | PRO | 4 | 3.523 | 3.536 | -15.977 | 1.00 | 31.18 |
| ATOM | 17 | CG | PRO | 4 | 2.992 | 4.691 | -16.737 | 1.00 | 30.95 |
| ATOM | 18 | C | PRO | 4 | 3.439 | 2.787 | -13.560 | 1.00 | 32.70 |
| ATOM | 19 | O | PRO | 4 | 2.692 | 1.913 | -13.099 | 1.00 | 34.83 |
| ATOM | 20 | N | PHE | 5 | 4.703 | 2.917 | -13.182 | 1.00 | 31.29 |
| ATOM | 21 | CA | PHE | 5 | 5.317 | 1.949 | -12.268 | 1.00 | 29.35 |
| ATOM | 22 | CB | PHE | 5 | 6.565 | 1.362 | -12.934 | 1.00 | 27.15 |
| ATOM | 23 | CG | PHE | 5 | 6.385 | 1.053 | -14.399 | 1.00 | 22.94 |
| ATOM | 24 | CD1 | PHE | 5 | 7.159 | 1.694 | -15.365 | 1.00 | 22.19 |
| ATOM | 25 | CD2 | PHE | 5 | 5.455 | 0.112 | -14.812 | 1.00 | 21.56 |
| ATOM | 26 | CE1 | PHE | 5 | 7.001 | 1.390 | -16.724 | 1.00 | 20.64 |
| ATOM | 27 | CE2 | PHE | 5 | 5.289 | -0.198 | -16.162 | 1.00 | 20.80 |
| ATOM | 28 | CZ | PHE | 5 | 6.067 | 0.444 | -17.119 | 1.00 | 20.05 |
| ATOM | 29 | C | PHE | 5 | 5.770 | 2.421 | -10.879 | 1.00 | 29.91 |
| ATOM | 30 | O | PHE | 5 | 6.569 | 1.742 | -10.226 | 1.00 | 29.38 |
| ATOM | 31 | N | VAL | 6 | 5.261 | 3.559 | -10.428 | 1.00 | 30.15 |
| ATOM | 32 | CA | VAL | 6 | 5.665 | 4.110 | -9.137 | 1.00 | 30.31 |
| ATOM | 33 | CB | VAL | 6 | 5.120 | 5.548 | -8.959 | 1.00 | 30.49 |
| ATOM | 34 | CG1 | VAL | 6 | 5.730 | 6.201 | -7.727 | 1.00 | 30.84 |
| ATOM | 35 | CG2 | VAL | 6 | 5.439 | 6.368 | -10.181 | 1.00 | 30.64 |
| ATOM | 36 | C | VAL | 6 | 5.270 | 3.291 | -7.898 | 1.00 | 30.97 |
| ATOM | 37 | O | VAL | 6 | 5.731 | 3.579 | -6.792 | 1.00 | 30.99 |
| ATOM | 38 | N | GLU | 7 | 4.441 | 2.268 | -8.074 | 1.00 | 30.81 |
| ATOM | 39 | CA | GLU | 7 | 4.023 | 1.465 | -6.929 | 1.00 | 30.96 |
| ATOM | 40 | CB | GLU | 7 | 2.536 | 1.131 | -7.032 | 1.00 | 33.16 |
| ATOM | 41 | CG | GLU | 7 | 1.797 | 2.481 | -6.822 | 1.00 | 35.64 |

FIG.11B-1

| | | | | | | | | |
|---|---|---|---|---|---|---|---|---|
| ATOM | 42 | CD | GLU | 7 | 2.340 | 3.275 | -5.622 | 1.00 37.65 |
| ATOM | 43 | OE1 | GLU | 7 | 3.400 | 3.921 | -5.755 | 1.00 38.88 |
| ATOM | 44 | OE2 | GLU | 7 | 1.728 | 3.259 | -4.532 | 1.00 37.93 |
| ATOM | 45 | C | GLU | 7 | 4.819 | 0.213 | -6.723 | 1.00 29.89 |
| ATOM | 46 | O | GLU | 7 | 4.546 | -0.563 | -5.806 | 1.00 28.91 |
| ATOM | 47 | N | ASP | 8 | 5.827 | 0.010 | -7.566 | 1.00 27.92 |
| ATOM | 48 | CA | ASP | 8 | 6.671 | -1.163 | -7.451 | 1.00 26.87 |
| ATOM | 49 | CB | ASP | 8 | 7.122 | -1.675 | -8.820 | 1.00 27.02 |
| ATOM | 50 | CG | ASP | 8 | 5.988 | -2.243 | -9.636 | 1.00 28.55 |
| ATOM | 51 | OD1 | ASP | 8 | 5.115 | -2.957 | -9.092 | 1.00 28.96 |
| ATOM | 52 | OD2 | ASP | 8 | 5.984 | -1.978 | -10.856 | 1.00 29.04 |
| ATOM | 53 | C | ASP | 8 | 7.902 | -0.881 | -6.651 | 1.00 26.17 |
| ATOM | 54 | O | ASP | 8 | 8.599 | 0.112 | -6.880 | 1.00 25.38 |
| ATOM | 55 | N | TRP | 9 | 8.165 | -1.767 | -5.698 | 1.00 25.50 |
| ATOM | 56 | CA | TRP | 9 | 9.316 | -1.674 | -4.814 | 1.00 25.48 |
| ATOM | 57 | CB | TRP | 9 | 8.856 | -1.476 | -3.360 | 1.00 26.35 |
| ATOM | 58 | CG | TRP | 9 | 8.975 | -0.060 | -2.872 | 1.00 27.81 |
| ATOM | 59 | CD2 | TRP | 9 | 7.939 | 0.920 | -2.829 | 1.00 27.99 |
| ATOM | 60 | CE2 | TRP | 9 | 8.511 | 2.110 | -2.324 | 1.00 28.08 |
| ATOM | 61 | CE3 | TRP | 9 | 6.580 | 0.910 | -3.169 | 1.00 27.50 |
| ATOM | 62 | CD1 | TRP | 9 | 10.108 | 0.557 | -2.404 | 1.00 28.28 |
| ATOM | 63 | NE1 | TRP | 9 | 9.837 | 1.860 | -2.074 | 1.00 27.98 |
| ATOM | 64 | CZ2 | TRP | 9 | 7.775 | 3.279 | -2.150 | 1.00 27.32 |
| ATOM | 65 | CZ3 | TRP | 9 | 5.848 | 2.070 | -2.996 | 1.00 29.26 |
| ATOM | 66 | CH2 | TRP | 9 | 6.447 | 3.243 | -2.488 | 1.00 29.79 |
| ATOM | 67 | C | TRP | 9 | 10.129 | -2.960 | -4.877 | 1.00 25.40 |
| ATOM | 68 | O | TRP | 9 | 9.634 | -4.028 | -4.523 | 1.00 25.51 |
| ATOM | 69 | N | ASP | 10 | 11.374 | -2.857 | -5.328 | 1.00 24.86 |
| ATOM | 70 | CA | ASP | 10 | 12.260 | -4.015 | -5.414 | 1.00 25.35 |
| ATOM | 71 | CB | ASP | 10 | 13.412 | -3.734 | -6.381 | 1.00 25.70 |
| ATOM | 72 | CG | ASP | 10 | 12.908 | -3.616 | -7.816 | 1.00 26.56 |
| ATOM | 73 | OD1 | ASP | 10 | 13.473 | -2.799 | -8.588 | 1.00 27.18 |
| ATOM | 74 | OD2 | ASP | 10 | 11.959 | -4.361 | -8.157 | 1.00 26.29 |
| ATOM | 75 | C | ASP | 10 | 12.875 | -4.328 | -4.035 | 1.00 26.53 |
| ATOM | 76 | O | ASP | 10 | 13.358 | -3.426 | -3.342 | 1.00 25.47 |
| ATOM | 77 | N | LEU | 11 | 12.836 | -5.602 | -3.645 | 1.00 27.39 |
| ATOM | 78 | CA | LEU | 11 | 13.415 | -6.041 | -2.373 | 1.00 29.13 |
| ATOM | 79 | CB | LEU | 11 | 12.585 | -7.191 | -1.780 | 1.00 29.22 |
| ATOM | 80 | CG | LEU | 11 | 11.165 | -6.817 | -1.329 | 1.00 29.89 |
| ATOM | 81 | CD1 | LEU | 11 | 10.370 | -6.260 | -2.494 | 1.00 31.00 |
| ATOM | 82 | CD2 | LEU | 11 | 10.463 | -8.052 | -0.768 | 1.00 29.99 |
| ATOM | 83 | C | LEU | 11 | 14.828 | -6.461 | -2.720 | 1.00 30.25 |

FIG.11B-2

| ATOM | 84  | O   | LEU | 11 | 15.058 | -7.557  | -3.235 | 1.00 | 30.42 |
|------|-----|-----|-----|----|--------|---------|--------|------|-------|
| ATOM | 85  | N   | VAL | 12 | 15.783 | -5.581  | -2.436 | 1.00 | 31.49 |
| ATOM | 86  | CA  | VAL | 12 | 17.176 | -5.813  | -2.797 | 1.00 | 32.51 |
| ATOM | 87  | CB  | VAL | 12 | 17.798 | -4.495  | -3.312 | 1.00 | 33.09 |
| ATOM | 88  | CG1 | VAL | 12 | 19.207 | -4.740  | -3.855 | 1.00 | 34.30 |
| ATOM | 89  | CG2 | VAL | 12 | 16.907 | -3.905  | -4.400 | 1.00 | 33.06 |
| ATOM | 90  | C   | VAL | 12 | 18.130 | -6.437  | -1.774 | 1.00 | 33.49 |
| ATOM | 91  | O   | VAL | 12 | 19.202 | -6.906  | -2.151 | 1.00 | 33.55 |
| ATOM | 92  | N   | GLN | 13 | 17.767 | -6.444  | -0.495 | 1.00 | 34.17 |
| ATOM | 93  | CA  | GLN | 13 | 18.646 | -7.043  | 0.511  | 1.00 | 35.23 |
| ATOM | 94  | CB  | GLN | 13 | 19.962 | -6.269  | 0.625  | 1.00 | 36.13 |
| ATOM | 95  | CG  | GLN | 13 | 19.957 | -4.746  | 0.685  | 1.00 | 37.34 |
| ATOM | 96  | CD  | GLN | 13 | 21.380 | -4.268  | 0.950  | 1.00 | 38.25 |
| ATOM | 97  | OE1 | GLN | 13 | 21.930 | -4.495  | 2.029  | 1.00 | 38.73 |
| ATOM | 98  | NE2 | GLN | 13 | 21.981 | -3.608  | -0.039 | 1.00 | 39.12 |
| ATOM | 99  | C   | GLN | 13 | 18.064 | -7.158  | 1.892  | 1.00 | 35.56 |
| ATOM | 100 | O   | GLN | 13 | 17.359 | -6.266  | 2.362  | 1.00 | 35.04 |
| ATOM | 101 | N   | THR | 14 | 18.359 | -8.275  | 2.549  | 1.00 | 36.12 |
| ATOM | 102 | CA  | THR | 14 | 17.871 | -8.516  | 3.901  | 1.00 | 37.26 |
| ATOM | 103 | CB  | THR | 14 | 18.035 | -9.992  | 4.309  | 1.00 | 37.85 |
| ATOM | 104 | OG1 | THR | 14 | 17.689 | -10.148 | 5.691  | 1.00 | 39.17 |
| ATOM | 105 | CG2 | THR | 14 | 19.471 | -10.442 | 4.102  | 1.00 | 38.49 |
| ATOM | 106 | C   | THR | 14 | 18.653 | -7.673  | 4.879  | 1.00 | 37.46 |
| ATOM | 107 | O   | THR | 14 | 19.864 | -7.503  | 4.737  | 1.00 | 37.37 |
| ATOM | 108 | N   | LEU | 15 | 17.961 | -7.130  | 5.872  | 1.00 | 37.76 |
| ATOM | 109 | CA  | LEU | 15 | 18.604 | -6.302  | 6.884  | 1.00 | 38.54 |
| ATOM | 110 | CB  | LEU | 15 | 17.827 | -5.003  | 7.100  | 1.00 | 38.69 |
| ATOM | 111 | CG  | LEU | 15 | 17.768 | -4.000  | 5.946  | 1.00 | 38.81 |
| ATOM | 112 | CD1 | LEU | 15 | 19.162 | -3.533  | 5.539  | 1.00 | 38.58 |
| ATOM | 113 | CD2 | LEU | 15 | 17.075 | -4.674  | 4.787  | 1.00 | 39.25 |
| ATOM | 114 | C   | LEU | 15 | 18.662 | -7.039  | 8.201  | 1.00 | 39.26 |
| ATOM | 115 | O   | LEU | 15 | 19.189 | -6.528  | 9.190  | 1.00 | 39.06 |
| ATOM | 116 | N   | GLY | 16 | 18.112 | -8.248  | 8.210  | 1.00 | 40.02 |
| ATOM | 117 | CA  | GLY | 16 | 18.101 | -9.054  | 9.416  | 1.00 | 41.67 |
| ATOM | 118 | C   | GLY | 16 | 16.767 | -9.752  | 9.569  | 1.00 | 42.84 |
| ATOM | 119 | O   | GLY | 16 | 15.726 | -9.165  | 9.280  | 1.00 | 43.09 |
| ATOM | 120 | N   | GLU | 17 | 16.791 | -11.003 | 10.024 | 1.00 | 43.99 |
| ATOM | 121 | CA  | GLU | 17 | 15.564 | -11.775 | 10.203 | 1.00 | 44.96 |
| ATOM | 122 | CB  | GLU | 17 | 15.744 | -13.210 | 9.707  | 1.00 | 45.76 |
| ATOM | 123 | CG  | GLU | 17 | 16.145 | -13.419 | 8.237  | 1.00 | 46.77 |
| ATOM | 124 | CD  | GLU | 17 | 16.308 | -14.915 | 8.042  | 1.00 | 47.36 |
| ATOM | 125 | OE1 | GLU | 17 | 17.089 | -15.524 | 8.805  | 1.00 | 47.74 |

FIG.11B-3

| | | | | | | | | |
|---|---|---|---|---|---|---|---|---|
| ATOM | 126 | OE2 | GLU | 17 | 15.667 | -15.486 | 7.134 | 1.00 48.12 |
| ATOM | 127 | C | GLU | 17 | 15.131 | -11.854 | 11.664 | 1.00 45.33 |
| ATOM | 128 | O | GLU | 17 | 15.952 | -11.725 | 12.576 | 1.00 45.16 |
| ATOM | 129 | N | GLY | 18 | 13.835 | -12.066 | 11.872 | 1.00 45.83 |
| ATOM | 130 | CA | GLY | 18 | 13.296 | -12.170 | 13.216 | 1.00 46.41 |
| ATOM | 131 | C | GLY | 18 | 12.627 | -13.515 | 13.409 | 1.00 46.60 |
| ATOM | 132 | O | GLY | 18 | 12.340 | -14.212 | 12.437 | 1.00 46.89 |
| ATOM | 133 | N | ALA | 19 | 12.376 | -13.880 | 14.663 | 1.00 46.88 |
| ATOM | 134 | CA | ALA | 19 | 11.745 | -15.155 | 14.977 | 1.00 46.85 |
| ATOM | 135 | CB | ALA | 19 | 11.695 | -15.350 | 16.492 | 1.00 46.77 |
| ATOM | 136 | C | ALA | 19 | 10.342 | -15.268 | 14.390 | 1.00 46.78 |
| ATOM | 137 | O | ALA | 19 | 9.701 | -16.310 | 14.505 | 1.00 47.08 |
| ATOM | 138 | N | TYR | 20 | 9.867 | -14.196 | 13.763 | 1.00 46.62 |
| ATOM | 139 | CA | TYR | 20 | 8.533 | -14.187 | 13.165 | 1.00 46.18 |
| ATOM | 140 | CB | TYR | 20 | 7.504 | -13.682 | 14.185 | 1.00 46.74 |
| ATOM | 141 | CG | TYR | 20 | 8.056 | -12.671 | 15.169 | 1.00 47.27 |
| ATOM | 142 | CD1 | TYR | 20 | 8.661 | -11.493 | 14.728 | 1.00 47.21 |
| ATOM | 143 | CE1 | TYR | 20 | 9.195 | -10.576 | 15.629 | 1.00 47.56 |
| ATOM | 144 | CD2 | TYR | 20 | 7.994 | -12.904 | 16.544 | 1.00 47.53 |
| ATOM | 145 | CE2 | TYR | 20 | 8.524 | -11.993 | 17.454 | 1.00 47.75 |
| ATOM | 146 | CZ | TYR | 20 | 9.125 | -10.833 | 16.990 | 1.00 47.80 |
| ATOM | 147 | OH | TYR | 20 | 9.673 | -9.940 | 17.884 | 1.00 48.14 |
| ATOM | 148 | C | TYR | 20 | 8.449 | -13.336 | 11.886 | 1.00 45.48 |
| ATOM | 149 | O | TYR | 20 | 7.509 | -12.557 | 11.708 | 1.00 45.95 |
| ATOM | 150 | N | GLY | 21 | 9.432 | -13.496 | 11.004 | 1.00 44.27 |
| ATOM | 151 | CA | GLY | 21 | 9.441 | -12.742 | 9.761 | 1.00 42.92 |
| ATOM | 152 | C | GLY | 21 | 10.817 | -12.250 | 9.349 | 1.00 41.50 |
| ATOM | 153 | O | GLY | 21 | 11.833 | -12.774 | 9.800 | 1.00 41.92 |
| ATOM | 154 | N | GLU | 22 | 10.850 | -11.236 | 8.489 | 1.00 40.28 |
| ATOM | 155 | CA | GLU | 22 | 12.111 | -10.671 | 8.012 | 1.00 38.41 |
| ATOM | 156 | CB | GLU | 22 | 12.571 | -11.389 | 6.736 | 1.00 39.39 |
| ATOM | 157 | CG | GLU | 22 | 11.451 | -11.244 | 5.667 | 1.00 40.60 |
| ATOM | 158 | CD | GLU | 22 | 11.755 | -11.845 | 4.292 | 1.00 41.48 |
| ATOM | 159 | OE1 | GLU | 22 | 10.825 | -11.842 | 3.459 | 1.00 42.22 |
| ATOM | 160 | OE2 | GLU | 22 | 12.882 | -12.309 | 4.019 | 1.00 42.38 |
| ATOM | 161 | C | GLU | 22 | 11.967 | -9.174 | 7.684 | 1.00 36.25 |
| ATOM | 162 | O | GLU | 22 | 10.858 | -8.655 | 7.577 | 1.00 36.15 |
| ATOM | 163 | N | VAL | 23 | 13.098 | -8.497 | 7.537 | 1.00 34.42 |
| ATOM | 164 | CA | VAL | 23 | 13.116 | -7.077 | 7.198 | 1.00 32.22 |
| ATOM | 165 | CB | VAL | 23 | 13.731 | -6.227 | 8.338 | 1.00 32.25 |
| ATOM | 166 | CG1 | VAL | 23 | 13.708 | -4.749 | 7.965 | 1.00 30.96 |
| ATOM | 167 | CG2 | VAL | 23 | 12.958 | -6.456 | 9.622 | 1.00 31.12 |

FIG. 11B-4

| | | | | | | | | |
|---|---|---|---|---|---|---|---|---|
| ATOM | 168 | C | VAL | 23 | 13.967 | -6.926 | 5.945 | 1.00 31.31 |
| ATOM | 169 | O | VAL | 23 | 15.121 | -7.343 | 5.915 | 1.00 30.82 |
| ATOM | 170 | N | GLN | 24 | 13.389 | -6.335 | 4.909 | 1.00 30.37 |
| ATOM | 171 | CA | GLN | 24 | 14.093 | -6.148 | 3.647 | 1.00 29.94 |
| ATOM | 172 | CB | GLN | 24 | 13.339 | -6.832 | 2.504 | 1.00 31.05 |
| ATOM | 173 | CG | GLN | 24 | 13.176 | -8.363 | 2.473 | 1.00 33.39 |
| ATOM | 174 | CD | GLN | 24 | 14.549 | -8.990 | 2.258 | 1.00 34.46 |
| ATOM | 175 | OE1 | GLN | 24 | 15.284 | -8.607 | 1.342 | 1.00 35.21 |
| ATOM | 176 | NE2 | GLN | 24 | 14.896 | -9.958 | 3.101 | 1.00 35.38 |
| ATOM | 177 | C | GLN | 24 | 14.224 | -4.699 | 3.268 | 1.00 28.82 |
| ATOM | 178 | O | GLN | 24 | 13.376 | -3.878 | 3.612 | 1.00 28.38 |
| ATOM | 179 | N | LEU | 25 | 15.301 | -4.374 | 2.559 | 1.00 27.94 |
| ATOM | 180 | CA | LEU | 25 | 15.515 | -3.015 | 2.086 | 1.00 27.18 |
| ATOM | 181 | CB | LEU | 25 | 17.008 | -2.729 | 1.878 | 1.00 28.17 |
| ATOM | 182 | CG | LEU | 25 | 17.457 | -1.432 | 1.183 | 1.00 29.19 |
| ATOM | 183 | CD1 | LEU | 25 | 17.192 | -1.511 | -0.302 | 1.00 31.15 |
| ATOM | 184 | CD2 | LEU | 25 | 16.728 | -0.244 | 1.790 | 1.00 29.21 |
| ATOM | 185 | C | LEU | 25 | 14.808 | -2.978 | 0.765 | 1.00 26.32 |
| ATOM | 186 | O | LEU | 25 | 15.078 | -3.808 | -0.103 | 1.00 26.83 |
| ATOM | 187 | N | ALA | 26 | 13.886 | -2.037 | 0.608 | 1.00 25.18 |
| ATOM | 188 | CA | ALA | 26 | 13.134 | -1.921 | -0.635 | 1.00 23.91 |
| ATOM | 189 | CB | ALA | 26 | 11.638 | -1.992 | -0.351 | 1.00 24.21 |
| ATOM | 190 | C | ALA | 26 | 13.464 | -0.641 | -1.335 | 1.00 23.39 |
| ATOM | 191 | O | ALA | 26 | 13.543 | 0.414 | -0.713 | 1.00 23.17 |
| ATOM | 192 | N | VAL | 27 | 13.646 | -0.719 | -2.648 | 1.00 22.24 |
| ATOM | 193 | CA | VAL | 27 | 13.979 | 0.460 | -3.433 | 1.00 21.16 |
| ATOM | 194 | CB | VAL | 27 | 15.397 | 0.311 | -4.031 | 1.00 21.43 |
| ATOM | 195 | CG1 | VAL | 27 | 15.735 | 1.514 | -4.896 | 1.00 21.22 |
| ATOM | 196 | CG2 | VAL | 27 | 16.422 | 0.177 | -2.900 | 1.00 20.94 |
| ATOM | 197 | C | VAL | 27 | 12.926 | 0.626 | -4.503 | 1.00 20.42 |
| ATOM | 198 | O | VAL | 27 | 12.603 | -0.320 | -5.223 | 1.00 20.31 |
| ATOM | 199 | N | ASN | 28 | 12.381 | 1.831 | -4.606 | 1.00 19.21 |
| ATOM | 200 | CA | ASN | 28 | 11.331 | 2.108 | -5.575 | 1.00 18.90 |
| ATOM | 201 | CB | ASN | 28 | 10.775 | 3.511 | -5.343 | 1.00 19.28 |
| ATOM | 202 | CG | ASN | 28 | 9.535 | 3.680 | -6.151 | 1.00 19.66 |
| ATOM | 203 | OD1 | ASN | 28 | 9.584 | 4.128 | -7.294 | 1.00 18.90 |
| ATOM | 204 | ND2 | ASN | 28 | 8.394 | 3.313 | -5.574 | 1.00 20.03 |
| ATOM | 205 | C | ASN | 28 | 11.834 | 1.962 | -6.985 | 1.00 18.62 |
| ATOM | 206 | O | ASN | 28 | 12.893 | 2.482 | -7.343 | 1.00 19.04 |
| ATOM | 207 | N | ARG | 29 | 11.062 | 1.253 | -7.797 | 1.00 17.64 |
| ATOM | 208 | CA | ARG | 29 | 11.440 | 1.009 | -9.185 | 1.00 17.42 |
| ATOM | 209 | CB | ARG | 29 | 10.344 | 0.191 | -9.860 | 1.00 17.14 |

FIG.11B-5

| | | | | | | | | |
|---|---|---|---|---|---|---|---|---|
| ATOM | 210 | CG | ARG | 29 | 10.521 | 0.026 | -11.359 | 1.00 16.26 |
| ATOM | 211 | CD | ARG | 29 | 9.318 | -0.788 | -11.804 | 1.00 15.93 |
| ATOM | 212 | NE | ARG | 29 | 9.278 | -0.897 | -13.267 | 1.00 14.41 |
| ATOM | 213 | CZ | ARG | 29 | 8.410 | -1.645 | -13.940 | 1.00 16.02 |
| ATOM | 214 | NH1 | ARG | 29 | 7.484 | -2.359 | -13.289 | 1.00 17.06 |
| ATOM | 215 | NH2 | ARG | 29 | 8.481 | -1.699 | -15.267 | 1.00 15.37 |
| ATOM | 216 | C | ARG | 29 | 11.684 | 2.279 | -9.978 | 1.00 18.14 |
| ATOM | 217 | O | ARG | 29 | 12.641 | 2.364 | -10.759 | 1.00 18.01 |
| ATOM | 218 | N | VAL | 30 | 10.821 | 3.266 | -9.769 | 1.00 18.31 |
| ATOM | 219 | CA | VAL | 30 | 10.901 | 4.540 | -10.477 | 1.00 18.70 |
| ATOM | 220 | CB | VAL | 30 | 9.492 | 5.153 | -10.639 | 1.00 18.65 |
| ATOM | 221 | CG1 | VAL | 30 | 9.587 | 6.584 | -11.138 | 1.00 18.77 |
| ATOM | 222 | CG2 | VAL | 30 | 8.653 | 4.297 | -11.581 | 1.00 17.98 |
| ATOM | 223 | C | VAL | 30 | 11.797 | 5.605 | -9.819 | 1.00 18.99 |
| ATOM | 224 | O | VAL | 30 | 12.723 | 6.110 | -10.444 | 1.00 19.65 |
| ATOM | 225 | N | THR | 31 | 11.527 | 5.930 | -8.555 | 1.00 19.32 |
| ATOM | 226 | CA | THR | 31 | 12.277 | 6.980 | -7.868 | 1.00 20.78 |
| ATOM | 227 | CB | THR | 31 | 11.406 | 7.701 | -6.820 | 1.00 21.46 |
| ATOM | 228 | OG1 | THR | 31 | 11.118 | 6.801 | -5.742 | 1.00 21.87 |
| ATOM | 229 | CG2 | THR | 31 | 10.110 | 8.198 | -7.448 | 1.00 21.89 |
| ATOM | 230 | C | THR | 31 | 13.559 | 6.616 | -7.144 | 1.00 20.65 |
| ATOM | 231 | O | THR | 31 | 14.339 | 7.507 | -6.784 | 1.00 20.94 |
| ATOM | 232 | N | GLU | 32 | 13.767 | 5.319 | -6.934 | 1.00 21.15 |
| ATOM | 233 | CA | GLU | 32 | 14.927 | 4.772 | -6.238 | 1.00 21.92 |
| ATOM | 234 | CB | GLU | 32 | 16.239 | 5.257 | -6.861 | 1.00 23.54 |
| ATOM | 235 | CG | GLU | 32 | 16.258 | 4.557 | -8.256 | 1.00 25.53 |
| ATOM | 236 | CD | GLU | 32 | 17.606 | 4.686 | -8.924 | 1.00 27.14 |
| ATOM | 237 | OE1 | GLU | 32 | 18.624 | 4.258 | -8.330 | 1.00 29.51 |
| ATOM | 238 | OE2 | GLU | 32 | 17.636 | 5.212 | -10.049 | 1.00 26.82 |
| ATOM | 239 | C | GLU | 32 | 14.912 | 5.113 | -4.755 | 1.00 22.53 |
| ATOM | 240 | O | GLU | 32 | 15.918 | 4.948 | -4.067 | 1.00 21.93 |
| ATOM | 241 | N | GLU | 33 | 13.770 | 5.584 | -4.271 | 1.00 23.56 |
| ATOM | 242 | CA | GLU | 33 | 13.632 | 5.907 | -2.851 | 1.00 25.27 |
| ATOM | 243 | CB | GLU | 33 | 12.281 | 6.581 | -2.581 | 1.00 27.64 |
| ATOM | 244 | CG | GLU | 33 | 11.945 | 6.632 | -1.055 | 1.00 30.98 |
| ATOM | 245 | CD | GLU | 33 | 10.594 | 7.270 | -0.711 | 1.00 32.85 |
| ATOM | 246 | OE1 | GLU | 33 | 9.689 | 7.294 | -1.571 | 1.00 34.30 |
| ATOM | 247 | OE2 | GLU | 33 | 10.425 | 7.742 | 0.437 | 1.00 35.48 |
| ATOM | 248 | C | GLU | 33 | 13.727 | 4.575 | -2.097 | 1.00 24.84 |
| ATOM | 249 | O | GLU | 33 | 13.229 | 3.546 | -2.575 | 1.00 23.78 |
| ATOM | 250 | N | ALA | 34 | 14.373 | 4.595 | -0.931 | 1.00 24.67 |
| ATOM | 251 | CA | ALA | 34 | 14.537 | 3.388 | -0.132 | 1.00 25.43 |

FIG.11B-6

| ATOM | 252 | CB | ALA | 34 | 16.006 | 3.207 | 0.244 | 1.00 | 25.80 |
| ATOM | 253 | C | ALA | 34 | 13.694 | 3.404 | 1.125 | 1.00 | 25.49 |
| ATOM | 254 | O | ALA | 34 | 13.559 | 4.435 | 1.785 | 1.00 | 25.71 |
| ATOM | 255 | N | VAL | 35 | 13.117 | 2.254 | 1.449 | 1.00 | 25.20 |
| ATOM | 256 | CA | VAL | 35 | 12.324 | 2.110 | 2.666 | 1.00 | 25.48 |
| ATOM | 257 | CB | VAL | 35 | 10.799 | 2.237 | 2.414 | 1.00 | 25.90 |
| ATOM | 258 | CG1 | VAL | 35 | 10.461 | 3.621 | 1.870 | 1.00 | 25.96 |
| ATOM | 259 | CG2 | VAL | 35 | 10.339 | 1.150 | 1.467 | 1.00 | 27.05 |
| ATOM | 260 | C | VAL | 35 | 12.585 | 0.738 | 3.180 | 1.00 | 25.10 |
| ATOM | 261 | O | VAL | 35 | 13.041 | -0.129 | 2.433 | 1.00 | 25.54 |
| ATOM | 262 | N | ALA | 36 | 12.324 | 0.521 | 4.465 | 1.00 | 24.18 |
| ATOM | 263 | CA | ALA | 36 | 12.503 | -0.793 | 5.058 | 1.00 | 23.82 |
| ATOM | 264 | CB | ALA | 36 | 13.081 | -0.671 | 6.479 | 1.00 | 23.63 |
| ATOM | 265 | C | ALA | 36 | 11.143 | -1.443 | 5.099 | 1.00 | 24.17 |
| ATOM | 266 | O | ALA | 36 | 10.147 | -0.807 | 5.451 | 1.00 | 23.23 |
| ATOM | 267 | N | VAL | 37 | 11.087 | -2.714 | 4.719 | 1.00 | 24.59 |
| ATOM | 268 | CA | VAL | 37 | 9.832 | -3.439 | 4.718 | 1.00 | 25.64 |
| ATOM | 269 | CB | VAL | 37 | 9.506 | -4.006 | 3.316 | 1.00 | 25.94 |
| ATOM | 270 | CG1 | VAL | 37 | 8.174 | -4.755 | 3.356 | 1.00 | 25.77 |
| ATOM | 271 | CG2 | VAL | 37 | 9.453 | -2.870 | 2.311 | 1.00 | 26.82 |
| ATOM | 272 | C | VAL | 37 | 9.915 | -4.556 | 5.683 | 1.00 | 26.26 |
| ATOM | 273 | O | VAL | 37 | 10.724 | -5.462 | 5.532 | 1.00 | 25.86 |
| ATOM | 274 | N | LYS | 38 | 9.091 | -4.489 | 6.716 | 1.00 | 27.45 |
| ATOM | 275 | CA | LYS | 38 | 9.066 | -5.534 | 7.725 | 1.00 | 29.32 |
| ATOM | 276 | CB | LYS | 38 | 8.729 | -4.923 | 9.091 | 1.00 | 29.33 |
| ATOM | 277 | CG | LYS | 38 | 8.764 | -5.913 | 10.243 | 1.00 | 30.35 |
| ATOM | 278 | CD | LYS | 38 | 8.546 | -5.119 | 11.550 | 1.00 | 30.39 |
| ATOM | 279 | CE | LYS | 38 | 8.715 | -5.997 | 12.796 | 1.00 | 30.62 |
| ATOM | 280 | NZ | LYS | 38 | 8.705 | -5.183 | 14.038 | 1.00 | 29.08 |
| ATOM | 281 | C | LYS | 38 | 8.007 | -6.537 | 7.295 | 1.00 | 30.44 |
| ATOM | 282 | O | LYS | 38 | 6.824 | -6.212 | 7.247 | 1.00 | 30.48 |
| ATOM | 283 | N | ILE | 39 | 8.443 | -7.748 | 6.964 | 1.00 | 32.39 |
| ATOM | 284 | CA | ILE | 39 | 7.539 | -8.805 | 6.528 | 1.00 | 34.05 |
| ATOM | 285 | CB | ILE | 39 | 8.130 | -9.560 | 5.322 | 1.00 | 34.69 |
| ATOM | 286 | CG2 | ILE | 39 | 7.073 | -10.462 | 4.702 | 1.00 | 34.87 |
| ATOM | 287 | CG1 | ILE | 39 | 8.603 | -8.553 | 4.271 | 1.00 | 34.64 |
| ATOM | 288 | CD1 | ILE | 39 | 9.193 | -9.188 | 3.005 | 1.00 | 35.49 |
| ATOM | 289 | C | ILE | 39 | 7.295 | -9.775 | 7.672 | 1.00 | 35.39 |
| ATOM | 290 | O | ILE | 39 | 8.238 | -10.291 | 8.273 | 1.00 | 35.78 |
| ATOM | 291 | N | VAL | 40 | 6.025 | -10.018 | 7.977 | 1.00 | 36.68 |
| ATOM | 292 | CA | VAL | 40 | 5.672 | -10.919 | 9.069 | 1.00 | 38.18 |
| ATOM | 293 | CB | VAL | 40 | 5.304 | -10.116 | 10.337 | 1.00 | 38.57 |

FIG.11B-7

| | | | | | | | | |
|---|---|---|---|---|---|---|---|---|
| ATOM | 294 | CG1 | VAL | 40 | 6.530 | -9.382 | 10.863 | 1.00 38.14 |
| ATOM | 295 | CG2 | VAL | 40 | 4.204 | -9.118 | 10.019 | 1.00 38.65 |
| ATOM | 296 | C | VAL | 40 | 4.514 | -11.850 | 8.710 | 1.00 39.27 |
| ATOM | 297 | O | VAL | 40 | 3.393 | -11.401 | 8.470 | 1.00 39.49 |
| ATOM | 298 | N | ASP | 41 | 4.794 | -13.150 | 8.678 | 1.00 40.75 |
| ATOM | 299 | CA | ASP | 41 | 3.772 | -14.145 | 8.355 | 1.00 42.21 |
| ATOM | 300 | CB | ASP | 41 | 4.412 | -15.507 | 8.078 | 1.00 42.73 |
| ATOM | 301 | CG | ASP | 41 | 3.334 | -16.461 | 7.562 | 1.00 43.32 |
| ATOM | 302 | OD1 | ASP | 41 | 2.325 | -16.676 | 8.268 | 1.00 44.00 |
| ATOM | 303 | OD2 | ASP | 41 | 3.499 | -16.997 | 6.445 | 1.00 43.83 |
| ATOM | 304 | C | ASP | 41 | 2.790 | -14.290 | 9.515 | 1.00 42.79 |
| ATOM | 305 | O | ASP | 41 | 3.155 | -14.759 | 10.596 | 1.00 43.26 |
| ATOM | 306 | N | MET | 42 | 1.542 | -13.895 | 9.278 | 1.00 43.17 |
| ATOM | 307 | CA | MET | 42 | 0.495 | -13.954 | 10.295 | 1.00 43.48 |
| ATOM | 308 | CB | MET | 42 | -0.859 | -13.567 | 9.690 | 1.00 44.53 |
| ATOM | 309 | CG | MET | 42 | -0.894 | -12.152 | 9.054 | 1.00 45.50 |
| ATOM | 310 | SD | MET | 42 | -2.480 | -11.758 | 8.271 | 1.00 47.53 |
| ATOM | 311 | CE | MET | 42 | -3.298 | -10.869 | 9.602 | 1.00 45.69 |
| ATOM | 312 | C | MET | 42 | 0.324 | -15.322 | 10.981 | 1.00 43.53 |
| ATOM | 313 | O | MET | 42 | -0.488 | -15.458 | 11.898 | 1.00 43.38 |
| ATOM | 314 | N | ALA | 43 | 1.087 | -16.320 | 10.543 | 1.00 43.07 |
| ATOM | 315 | CA | ALA | 43 | 0.991 | -17.656 | 11.125 | 1.00 43.42 |
| ATOM | 316 | CB | ALA | 43 | -0.040 | -18.484 | 10.359 | 1.00 43.10 |
| ATOM | 317 | C | ALA | 43 | 2.327 | -18.378 | 11.137 | 1.00 43.21 |
| ATOM | 318 | O | ALA | 43 | 2.386 | -19.594 | 10.955 | 1.00 43.78 |
| ATOM | 319 | N | ALA | 44 | 3.403 | -17.633 | 11.357 | 1.00 42.71 |
| ATOM | 320 | CA | ALA | 44 | 4.733 | -18.227 | 11.388 | 1.00 42.36 |
| ATOM | 321 | CB | ALA | 44 | 5.750 | -17.260 | 10.792 | 1.00 41.81 |
| ATOM | 322 | C | ALA | 44 | 5.117 | -18.581 | 12.817 | 1.00 42.44 |
| ATOM | 323 | O | ALA | 44 | 6.254 | -18.285 | 13.244 | 1.00 42.57 |
| ATOM | 324 | OT | ALA | 44 | 4.263 | -19.178 | 13.504 | 1.00 42.66 |
| ATOM | 325 | CB | CYS | 48 | 0.655 | -13.396 | 16.575 | 1.00 44.68 |
| ATOM | 326 | SG | CYS | 48 | -0.887 | -13.047 | 17.451 | 1.00 46.03 |
| ATOM | 327 | C | CYS | 48 | -0.464 | -12.204 | 14.719 | 1.00 43.08 |
| ATOM | 328 | O | CYS | 48 | 0.015 | -11.080 | 14.888 | 1.00 42.59 |
| ATOM | 329 | N | CYS | 48 | 1.582 | -13.589 | 14.278 | 1.00 42.75 |
| ATOM | 330 | CA | CYS | 48 | 0.332 | -13.460 | 15.083 | 1.00 43.49 |
| ATOM | 331 | N | PRO | 49 | -1.700 | -12.387 | 14.224 | 1.00 42.07 |
| ATOM | 332 | CD | PRO | 49 | -2.344 | -13.692 | 13.989 | 1.00 42.03 |
| ATOM | 333 | CA | PRO | 49 | -2.591 | -11.294 | 13.824 | 1.00 42.17 |
| ATOM | 334 | CB | PRO | 49 | -3.891 | -12.028 | 13.488 | 1.00 42.12 |
| ATOM | 335 | CG | PRO | 49 | -3.406 | -13.342 | 12.979 | 1.00 41.95 |

FIG.11B-8

| | | | | | | | | | |
|---|---|---|---|---|---|---|---|---|---|
| ATOM | 336 | C | PRO | 49 | -2.745 | -10.224 | 14.887 | 1.00 | 41.81 |
| ATOM | 337 | O | PRO | 49 | -2.664 | -9.031 | 14.592 | 1.00 | 42.45 |
| ATOM | 338 | N | GLU | 50 | -2.969 | -10.652 | 16.126 | 1.00 | 41.02 |
| ATOM | 339 | CA | GLU | 50 | -3.156 | -9.729 | 17.246 | 1.00 | 39.67 |
| ATOM | 340 | CB | GLU | 50 | -3.526 | -10.488 | 18.522 | 1.00 | 40.23 |
| ATOM | 341 | CG | GLU | 50 | -3.682 | -9.495 | 19.715 | 1.00 | 40.60 |
| ATOM | 342 | CD | GLU | 50 | -3.534 | -10.215 | 21.053 | 1.00 | 41.12 |
| ATOM | 343 | OE1 | GLU | 50 | -2.452 | -10.793 | 21.314 | 1.00 | 42.36 |
| ATOM | 344 | OE2 | GLU | 50 | -4.504 | -10.196 | 21.839 | 1.00 | 42.30 |
| ATOM | 345 | C | GLU | 50 | -1.926 | -8.886 | 17.586 | 1.00 | 38.68 |
| ATOM | 346 | O | GLU | 50 | -2.025 | -7.666 | 17.747 | 1.00 | 38.74 |
| ATOM | 347 | N | ALA | 51 | -0.775 | -9.542 | 17.714 | 1.00 | 37.63 |
| ATOM | 348 | CA | ALA | 51 | 0.468 | -8.856 | 18.055 | 1.00 | 36.16 |
| ATOM | 349 | CB | ALA | 51 | 1.591 | -9.872 | 18.236 | 1.00 | 36.72 |
| ATOM | 350 | C | ALA | 51 | 0.863 | -7.832 | 17.010 | 1.00 | 35.47 |
| ATOM | 351 | O | ALA | 51 | 1.150 | -6.675 | 17.330 | 1.00 | 34.50 |
| ATOM | 352 | N | ILE | 52 | 0.885 | -8.260 | 15.754 | 1.00 | 34.45 |
| ATOM | 353 | CA | ILE | 52 | 1.248 | -7.370 | 14.664 | 1.00 | 33.77 |
| ATOM | 354 | CB | ILE | 52 | 1.420 | -8.194 | 13.354 | 1.00 | 34.35 |
| ATOM | 355 | CG2 | ILE | 52 | 0.066 | -8.432 | 12.708 | 1.00 | 34.21 |
| ATOM | 356 | CG1 | ILE | 52 | 2.451 | -7.522 | 12.440 | 1.00 | 34.69 |
| ATOM | 357 | CD1 | ILE | 52 | 2.122 | -6.082 | 12.050 | 1.00 | 35.78 |
| ATOM | 358 | C | ILE | 52 | 0.158 | -6.248 | 14.543 | 1.00 | 33.00 |
| ATOM | 359 | O | ILE | 52 | 0.462 | -5.095 | 14.214 | 1.00 | 32.57 |
| ATOM | 360 | N | LYS | 53 | -1.092 | -6.600 | 14.826 | 1.00 | 32.29 |
| ATOM | 361 | CA | LYS | 53 | -2.177 | -5.627 | 14.744 | 1.00 | 31.31 |
| ATOM | 362 | CB | LYS | 53 | -3.520 | -6.275 | 15.097 | 1.00 | 32.79 |
| ATOM | 363 | CG | LYS | 53 | -4.591 | -5.745 | 14.135 | 1.00 | 35.30 |
| ATOM | 364 | CD | LYS | 53 | -4.333 | -6.330 | 12.710 | 1.00 | 36.83 |
| ATOM | 365 | CE | LYS | 53 | -5.147 | -5.687 | 11.568 | 1.00 | 37.66 |
| ATOM | 366 | NZ | LYS | 53 | -4.748 | -4.262 | 11.361 | 1.00 | 39.01 |
| ATOM | 367 | C | LYS | 53 | -1.922 | -4.469 | 15.733 | 1.00 | 29.81 |
| ATOM | 368 | O | LYS | 53 | -2.123 | -3.297 | 15.410 | 1.00 | 29.51 |
| ATOM | 369 | N | LYS | 54 | -1.471 | -4.810 | 16.933 | 1.00 | 28.14 |
| ATOM | 370 | CA | LYS | 54 | -1.202 | -3.801 | 17.942 | 1.00 | 26.62 |
| ATOM | 371 | CB | LYS | 54 | -0.984 | -4.475 | 19.292 | 1.00 | 26.85 |
| ATOM | 372 | CG | LYS | 54 | -0.815 | -3.468 | 20.426 | 1.00 | 26.40 |
| ATOM | 373 | CD | LYS | 54 | -0.807 | -4.242 | 21.744 | 1.00 | 27.28 |
| ATOM | 374 | CE | LYS | 54 | -0.732 | -3.338 | 22.970 | 1.00 | 27.15 |
| ATOM | 375 | NZ | LYS | 54 | -0.636 | -4.143 | 24.224 | 1.00 | 27.93 |
| ATOM | 376 | C | LYS | 54 | 0.008 | -2.953 | 17.542 | 1.00 | 25.67 |
| ATOM | 377 | O | LYS | 54 | 0.027 | -1.738 | 17.751 | 1.00 | 25.37 |

FIG.11B-9

| | | | | | | | | |
|---|---|---|---|---|---|---|---|---|
| ATOM | 378 | N | GLU | 55 | 1.010 | -3.599 | 16.950 | 1.00 24.57 |
| ATOM | 379 | CA | GLU | 55 | 2.210 | -2.892 | 16.517 | 1.00 22.90 |
| ATOM | 380 | CB | GLU | 55 | 3.246 | -3.892 | 15.987 | 1.00 22.70 |
| ATOM | 381 | CG | GLU | 55 | 4.551 | -3.198 | 15.516 | 1.00 22.01 |
| ATOM | 382 | CD | GLU | 55 | 5.645 | -4.208 | 15.112 | 1.00 22.15 |
| ATOM | 383 | OE1 | GLU | 55 | 5.523 | -5.412 | 15.423 | 1.00 23.29 |
| ATOM | 384 | OE2 | GLU | 55 | 6.643 | -3.798 | 14.487 | 1.00 22.01 |
| ATOM | 385 | C | GLU | 55 | 1.842 | -1.857 | 15.436 | 1.00 22.77 |
| ATOM | 386 | O | GLU | 55 | 2.387 | -0.756 | 15.399 | 1.00 21.95 |
| ATOM | 387 | N | ILE | 56 | 0.898 | -2.215 | 14.570 | 1.00 22.54 |
| ATOM | 388 | CA | ILE | 56 | 0.467 | -1.320 | 13.507 | 1.00 22.45 |
| ATOM | 389 | CB | ILE | 56 | -0.378 | -2.105 | 12.475 | 1.00 23.28 |
| ATOM | 390 | CG2 | ILE | 56 | -0.995 | -1.170 | 11.459 | 1.00 23.81 |
| ATOM | 391 | CG1 | ILE | 56 | 0.516 | -3.127 | 11.778 | 1.00 22.95 |
| ATOM | 392 | CD1 | ILE | 56 | -0.237 | -4.041 | 10.775 | 1.00 23.35 |
| ATOM | 393 | C | ILE | 56 | -0.299 | -0.174 | 14.087 | 1.00 22.53 |
| ATOM | 394 | O | ILE | 56 | -0.092 | 0.979 | 13.712 | 1.00 22.30 |
| ATOM | 395 | N | CYS | 57 | -1.179 | -0.493 | 15.030 | 1.00 22.44 |
| ATOM | 396 | CA | CYS | 57 | -2.008 | 0.497 | 15.709 | 1.00 23.00 |
| ATOM | 397 | CB | CYS | 57 | -2.832 | -0.188 | 16.804 | 1.00 23.58 |
| ATOM | 398 | SG | CYS | 57 | -3.925 | 0.986 | 17.618 | 1.00 26.04 |
| ATOM | 399 | C | CYS | 57 | -1.157 | 1.603 | 16.347 | 1.00 22.83 |
| ATOM | 400 | O | CYS | 57 | -1.441 | 2.795 | 16.203 | 1.00 23.71 |
| ATOM | 401 | N | ILE | 58 | -0.115 | 1.187 | 17.055 | 1.00 21.58 |
| ATOM | 402 | CA | ILE | 58 | 0.757 | 2.129 | 17.725 | 1.00 20.88 |
| ATOM | 403 | CB | ILE | 58 | 1.594 | 1.391 | 18.786 | 1.00 21.07 |
| ATOM | 404 | CG2 | ILE | 58 | 2.703 | 2.311 | 19.326 | 1.00 20.39 |
| ATOM | 405 | CG1 | ILE | 58 | 0.661 | 0.937 | 19.916 | 1.00 21.01 |
| ATOM | 406 | CD1 | ILE | 58 | 1.368 | 0.216 | 21.094 | 1.00 21.40 |
| ATOM | 407 | C | ILE | 58 | 1.583 | 2.907 | 16.737 | 1.00 19.99 |
| ATOM | 408 | O | ILE | 58 | 1.747 | 4.110 | 16.888 | 1.00 19.32 |
| ATOM | 409 | N | ASN | 59 | 2.092 | 2.244 | 15.706 | 1.00 19.84 |
| ATOM | 410 | CA | ASN | 59 | 2.883 | 2.955 | 14.705 | 1.00 20.70 |
| ATOM | 411 | CB | ASN | 59 | 3.358 | 1.996 | 13.612 | 1.00 19.66 |
| ATOM | 412 | CG | ASN | 59 | 4.803 | 1.554 | 13.836 | 1.00 19.76 |
| ATOM | 413 | OD1 | ASN | 59 | 5.736 | 2.319 | 13.609 | 1.00 21.26 |
| ATOM | 414 | ND2 | ASN | 59 | 4.985 | 0.321 | 14.287 | 1.00 19.87 |
| ATOM | 415 | C | ASN | 59 | 2.045 | 4.083 | 14.048 | 1.00 21.81 |
| ATOM | 416 | O | ASN | 59 | 2.567 | 5.147 | 13.720 | 1.00 21.63 |
| ATOM | 417 | N | LYS | 60 | 0.752 | 3.836 | 13.864 | 1.00 22.44 |
| ATOM | 418 | CA | LYS | 60 | -0.118 | 4.839 | 13.249 | 1.00 23.91 |
| ATOM | 419 | CB | LYS | 60 | -1.528 | 4.280 | 13.027 | 1.00 24.44 |

FIG.11B-10

| ATOM | 420 | CG | LYS | 60 | -1.552 | 3.237 | 11.885 | 1.00 | 27.44 |
|---|---|---|---|---|---|---|---|---|---|
| ATOM | 421 | CD | LYS | 60 | -2.997 | 2.663 | 11.665 | 1.00 | 29.48 |
| ATOM | 422 | CE | LYS | 60 | -4.024 | 3.744 | 11.233 | 1.00 | 30.95 |
| ATOM | 423 | NZ | LYS | 60 | -5.377 | 3.169 | 10.933 | 1.00 | 32.88 |
| ATOM | 424 | C | LYS | 60 | -0.251 | 6.101 | 14.078 | 1.00 | 24.30 |
| ATOM | 425 | O | LYS | 60 | -0.657 | 7.145 | 13.574 | 1.00 | 24.07 |
| ATOM | 426 | N | MET | 61 | 0.104 | 6.012 | 15.354 | 1.00 | 24.01 |
| ATOM | 427 | CA | MET | 61 | -0.002 | 7.157 | 16.244 | 1.00 | 25.12 |
| ATOM | 428 | CB | MET | 61 | -0.249 | 6.693 | 17.676 | 1.00 | 25.40 |
| ATOM | 429 | CG | MET | 61 | -1.470 | 5.835 | 17.988 | 1.00 | 26.45 |
| ATOM | 430 | SD | MET | 61 | -1.392 | 5.217 | 19.669 | 1.00 | 29.36 |
| ATOM | 431 | CE | MET | 61 | -1.535 | 6.797 | 20.599 | 1.00 | 28.93 |
| ATOM | 432 | C | MET | 61 | 1.255 | 8.008 | 16.297 | 1.00 | 24.94 |
| ATOM | 433 | O | MET | 61 | 1.218 | 9.153 | 16.749 | 1.00 | 26.47 |
| ATOM | 434 | N | LEU | 62 | 2.359 | 7.458 | 15.809 | 1.00 | 24.38 |
| ATOM | 435 | CA | LEU | 62 | 3.651 | 8.133 | 15.886 | 1.00 | 24.10 |
| ATOM | 436 | CB | LEU | 62 | 4.742 | 7.099 | 16.141 | 1.00 | 24.29 |
| ATOM | 437 | CG | LEU | 62 | 4.251 | 6.128 | 17.219 | 1.00 | 24.77 |
| ATOM | 438 | CD1 | LEU | 62 | 5.273 | 5.004 | 17.283 | 1.00 | 24.61 |
| ATOM | 439 | CD2 | LEU | 62 | 4.088 | 6.800 | 18.578 | 1.00 | 24.56 |
| ATOM | 440 | C | LEU | 62 | 4.141 | 8.977 | 14.723 | 1.00 | 23.68 |
| ATOM | 441 | O | LEU | 62 | 3.965 | 8.615 | 13.556 | 1.00 | 23.81 |
| ATOM | 442 | N | ASN | 63 | 4.783 | 10.095 | 15.062 | 1.00 | 22.77 |
| ATOM | 443 | CA | ASN | 63 | 5.365 | 11.007 | 14.084 | 1.00 | 22.30 |
| ATOM | 444 | CB | ASN | 63 | 4.255 | 11.825 | 13.407 | 1.00 | 24.66 |
| ATOM | 445 | CG | ASN | 63 | 4.808 | 12.770 | 12.364 | 1.00 | 26.67 |
| ATOM | 446 | OD1 | ASN | 63 | 5.808 | 12.479 | 11.719 | 1.00 | 28.66 |
| ATOM | 447 | ND2 | ASN | 63 | 4.140 | 13.905 | 12.177 | 1.00 | 28.45 |
| ATOM | 448 | C | ASN | 63 | 6.385 | 11.897 | 14.801 | 1.00 | 20.27 |
| ATOM | 449 | O | ASN | 63 | 6.037 | 12.930 | 15.363 | 1.00 | 19.93 |
| ATOM | 450 | N | HIS | 64 | 7.645 | 11.472 | 14.795 | 1.00 | 18.13 |
| ATOM | 451 | CA | HIS | 64 | 8.696 | 12.228 | 15.459 | 1.00 | 17.11 |
| ATOM | 452 | CB | HIS | 64 | 8.666 | 11.908 | 16.960 | 1.00 | 16.62 |
| ATOM | 453 | CG | HIS | 64 | 9.600 | 12.744 | 17.769 | 1.00 | 15.90 |
| ATOM | 454 | CD2 | HIS | 64 | 9.402 | 13.904 | 18.439 | 1.00 | 15.85 |
| ATOM | 455 | ND1 | HIS | 64 | 10.934 | 12.438 | 17.917 | 1.00 | 16.76 |
| ATOM | 456 | CE1 | HIS | 64 | 11.519 | 13.373 | 18.642 | 1.00 | 16.09 |
| ATOM | 457 | NE2 | HIS | 64 | 10.611 | 14.275 | 18.971 | 1.00 | 15.69 |
| ATOM | 458 | C | HIS | 64 | 10.038 | 11.910 | 14.827 | 1.00 | 17.07 |
| ATOM | 459 | O | HIS | 64 | 10.278 | 10.781 | 14.397 | 1.00 | 16.68 |
| ATOM | 460 | N | GLU | 65 | 10.918 | 12.908 | 14.771 | 1.00 | 16.86 |
| ATOM | 461 | CA | GLU | 65 | 12.227 | 12.746 | 14.142 | 1.00 | 17.23 |

FIG.11B-11

| | | | | | | | | |
|---|---|---|---|---|---|---|---|---|
| ATOM | 462 | CB | GLU | 65 | 12.977 | 14.081 | 14.097 | 1.00 19.17 |
| ATOM | 463 | CG | GLU | 65 | 13.115 | 14.589 | 15.530 | 1.00 23.09 |
| ATOM | 464 | CD | GLU | 65 | 12.010 | 15.573 | 15.921 | 1.00 24.78 |
| ATOM | 465 | OE1 | GLU | 65 | 10.804 | 15.418 | 15.625 | 1.00 26.63 |
| ATOM | 466 | OE2 | GLU | 65 | 12.412 | 16.555 | 16.575 | 1.00 29.13 |
| ATOM | 467 | C | GLU | 65 | 13.165 | 11.705 | 14.764 | 1.00 16.61 |
| ATOM | 468 | O | GLU | 65 | 14.136 | 11.290 | 14.123 | 1.00 15.95 |
| ATOM | 469 | N | ASN | 66 | 12.881 | 11.287 | 15.999 | 1.00 15.86 |
| ATOM | 470 | CA | ASN | 66 | 13.718 | 10.276 | 16.645 | 1.00 15.10 |
| ATOM | 471 | CB | ASN | 66 | 14.251 | 10.768 | 17.999 | 1.00 14.82 |
| ATOM | 472 | CG | ASN | 66 | 15.223 | 11.978 | 17.803 | 1.00 14.88 |
| ATOM | 473 | OD1 | ASN | 66 | 14.921 | 13.102 | 18.214 | 1.00 15.31 |
| ATOM | 474 | ND2 | ASN | 66 | 16.373 | 11.732 | 17.171 | 1.00 14.43 |
| ATOM | 475 | C | ASN | 66 | 12.968 | 8.975 | 16.839 | 1.00 15.46 |
| ATOM | 476 | O | ASN | 66 | 13.285 | 8.192 | 17.740 | 1.00 14.42 |
| ATOM | 477 | N | VAL | 67 | 11.976 | 8.742 | 15.980 | 1.00 15.06 |
| ATOM | 478 | CA | VAL | 67 | 11.188 | 7.519 | 16.015 | 1.00 14.66 |
| ATOM | 479 | CB | VAL | 67 | 9.752 | 7.773 | 16.576 | 1.00 14.46 |
| ATOM | 480 | CG1 | VAL | 67 | 8.896 | 6.527 | 16.418 | 1.00 14.49 |
| ATOM | 481 | CG2 | VAL | 67 | 9.817 | 8.155 | 18.064 | 1.00 14.92 |
| ATOM | 482 | C | VAL | 67 | 11.079 | 7.032 | 14.567 | 1.00 15.45 |
| ATOM | 483 | O | VAL | 67 | 10.730 | 7.812 | 13.682 | 1.00 15.32 |
| ATOM | 484 | N | VAL | 68 | 11.398 | 5.762 | 14.326 | 1.00 14.74 |
| ATOM | 485 | CA | VAL | 68 | 11.318 | 5.209 | 12.968 | 1.00 14.94 |
| ATOM | 486 | CB | VAL | 68 | 11.621 | 3.688 | 12.985 | 1.00 14.98 |
| ATOM | 487 | CG1 | VAL | 68 | 11.344 | 3.072 | 11.604 | 1.00 15.35 |
| ATOM | 488 | CG2 | VAL | 68 | 13.087 | 3.466 | 13.331 | 1.00 13.74 |
| ATOM | 489 | C | VAL | 68 | 9.953 | 5.508 | 12.374 | 1.00 16.26 |
| ATOM | 490 | O | VAL | 68 | 8.932 | 5.061 | 12.890 | 1.00 16.70 |
| ATOM | 491 | N | LYS | 69 | 9.939 | 6.255 | 11.272 | 1.00 17.50 |
| ATOM | 492 | CA | LYS | 69 | 8.688 | 6.638 | 10.629 | 1.00 20.22 |
| ATOM | 493 | CB | LYS | 69 | 8.948 | 7.640 | 9.496 | 1.00 22.64 |
| ATOM | 494 | CG | LYS | 69 | 9.172 | 9.162 | 9.649 | 1.00 26.66 |
| ATOM | 495 | CD | LYS | 69 | 10.454 | 9.843 | 10.196 | 1.00 29.16 |
| ATOM | 496 | CE | LYS | 69 | 10.263 | 11.379 | 10.284 | 1.00 29.24 |
| ATOM | 497 | NZ | LYS | 69 | 11.485 | 12.071 | 10.783 | 1.00 31.62 |
| ATOM | 498 | C | LYS | 69 | 7.927 | 5.460 | 10.056 | 1.00 20.86 |
| ATOM | 499 | O | LYS | 69 | 8.526 | 4.540 | 9.506 | 1.00 19.95 |
| ATOM | 500 | N | PHE | 70 | 6.605 | 5.497 | 10.204 | 1.00 21.61 |
| ATOM | 501 | CA | PHE | 70 | 5.708 | 4.465 | 9.696 | 1.00 22.90 |
| ATOM | 502 | CB | PHE | 70 | 4.624 | 4.154 | 10.731 | 1.00 23.86 |
| ATOM | 503 | CG | PHE | 70 | 3.610 | 3.142 | 10.275 | 1.00 25.07 |

FIG.11B-12

| | | | | | | | | |
|---|---|---|---|---|---|---|---|---|
| ATOM | 504 | CD1 | PHE | 70 | 3.984 | 1.828 | 10.020 | 1.00 25.78 |
| ATOM | 505 | CD2 | PHE | 70 | 2.272 | 3.496 | 10.149 | 1.00 25.74 |
| ATOM | 506 | CE1 | PHE | 70 | 3.038 | 0.873 | 9.652 | 1.00 27.17 |
| ATOM | 507 | CE2 | PHE | 70 | 1.310 | 2.547 | 9.780 | 1.00 26.29 |
| ATOM | 508 | CZ | PHE | 70 | 1.695 | 1.237 | 9.534 | 1.00 26.19 |
| ATOM | 509 | C | PHE | 70 | 5.020 | 5.030 | 8.425 | 1.00 23.33 |
| ATOM | 510 | O | PHE | 70 | 4.312 | 6.038 | 8.492 | 1.00 22.78 |
| ATOM | 511 | N | TYR | 71 | 5.226 | 4.372 | 7.291 | 1.00 24.38 |
| ATOM | 512 | CA | TYR | 71 | 4.639 | 4.836 | 6.037 | 1.00 26.22 |
| ATOM | 513 | CB | TYR | 71 | 5.615 | 4.622 | 4.886 | 1.00 25.69 |
| ATOM | 514 | CG | TYR | 71 | 6.947 | 5.313 | 5.058 | 1.00 25.34 |
| ATOM | 515 | CD1 | TYR | 71 | 7.023 | 6.687 | 5.293 | 1.00 25.68 |
| ATOM | 516 | CE1 | TYR | 71 | 8.263 | 7.337 | 5.366 | 1.00 25.78 |
| ATOM | 517 | CD2 | TYR | 71 | 8.139 | 4.606 | 4.910 | 1.00 25.28 |
| ATOM | 518 | CE2 | TYR | 71 | 9.372 | 5.243 | 4.982 | 1.00 25.14 |
| ATOM | 519 | CZ | TYR | 71 | 9.427 | 6.608 | 5.204 | 1.00 25.13 |
| ATOM | 520 | OH | TYR | 71 | 10.653 | 7.239 | 5.223 | 1.00 26.09 |
| ATOM | 521 | C | TYR | 71 | 3.327 | 4.161 | 5.657 | 1.00 27.64 |
| ATOM | 522 | O | TYR | 71 | 2.579 | 4.675 | 4.817 | 1.00 28.91 |
| ATOM | 523 | N | GLY | 72 | 3.044 | 3.016 | 6.269 | 1.00 28.78 |
| ATOM | 524 | CA | GLY | 72 | 1.814 | 2.306 | 5.967 | 1.00 30.86 |
| ATOM | 525 | C | GLY | 72 | 1.968 | 0.802 | 6.067 | 1.00 31.92 |
| ATOM | 526 | O | GLY | 72 | 3.057 | 0.297 | 6.326 | 1.00 31.91 |
| ATOM | 527 | N | HIS | 73 | 0.872 | 0.080 | 5.862 | 1.00 33.79 |
| ATOM | 528 | CA | HIS | 73 | 0.900 | -1.376 | 5.932 | 1.00 35.69 |
| ATOM | 529 | CB | HIS | 73 | 0.508 | -1.844 | 7.333 | 1.00 35.93 |
| ATOM | 530 | CG | HIS | 73 | -0.894 | -1.487 | 7.718 | 1.00 35.89 |
| ATOM | 531 | CD2 | HIS | 73 | -1.460 | -0.295 | 8.022 | 1.00 36.24 |
| ATOM | 532 | ND1 | HIS | 73 | -1.900 | -2.424 | 7.814 | 1.00 35.93 |
| ATOM | 533 | CE1 | HIS | 73 | -3.025 | -1.825 | 8.163 | 1.00 36.12 |
| ATOM | 534 | NE2 | HIS | 73 | -2.785 | -0.533 | 8.296 | 1.00 36.36 |
| ATOM | 535 | C | HIS | 73 | -0.058 | -1.992 | 4.924 | 1.00 37.26 |
| ATOM | 536 | O | HIS | 73 | -1.020 | -1.351 | 4.503 | 1.00 37.54 |
| ATOM | 537 | N | ARG | 74 | 0.215 | -3.236 | 4.542 | 1.00 39.37 |
| ATOM | 538 | CA | ARG | 74 | -0.617 | -3.957 | 3.582 | 1.00 41.57 |
| ATOM | 539 | CB | ARG | 74 | 0.193 | -4.335 | 2.342 | 1.00 42.35 |
| ATOM | 540 | CG | ARG | 74 | 0.662 | -3.169 | 1.465 | 1.00 43.17 |
| ATOM | 541 | CD | ARG | 74 | 1.492 | -3.729 | 0.290 | 1.00 43.98 |
| ATOM | 542 | NE | ARG | 74 | 0.755 | -4.738 | -0.469 | 1.00 44.77 |
| ATOM | 543 | CZ | ARG | 74 | 1.259 | -5.412 | -1.497 | 1.00 44.92 |
| ATOM | 544 | NH1 | ARG | 74 | 2.505 | -5.184 | -1.892 | 1.00 45.32 |
| ATOM | 545 | NH2 | ARG | 74 | 0.523 | -6.320 | -2.126 | 1.00 45.08 |

FIG.11B-13

| | | | | | | | | |
|---|---|---|---|---|---|---|---|---|
| ATOM | 546 | C | ARG | 74 | -1.194 | -5.241 | 4.175 | 1.00 42.67 |
| ATOM | 547 | O | ARG | 74 | -0.714 | -5.738 | 5.196 | 1.00 43.41 |
| ATOM | 548 | N | ARG | 75 | -2.219 | -5.773 | 3.513 | 1.00 43.71 |
| ATOM | 549 | CA | ARG | 75 | -2.904 | -6.993 | 3.945 | 1.00 44.56 |
| ATOM | 550 | CB | ARG | 75 | -4.356 | -6.992 | 3.455 | 1.00 44.64 |
| ATOM | 551 | CG | ARG | 75 | -5.231 | -5.765 | 3.791 | 1.00 45.27 |
| ATOM | 552 | CD | ARG | 75 | -5.688 | -5.646 | 5.256 | 1.00 45.40 |
| ATOM | 553 | NE | ARG | 75 | -6.632 | -6.700 | 5.620 | 1.00 45.56 |
| ATOM | 554 | CZ | ARG | 75 | -7.160 | -6.844 | 6.831 | 1.00 45.42 |
| ATOM | 555 | NH1 | ARG | 75 | -6.835 | -6.002 | 7.804 | 1.00 45.59 |
| ATOM | 556 | NH2 | ARG | 75 | -8.021 | -7.825 | 7.071 | 1.00 45.46 |
| ATOM | 557 | C | ARG | 75 | -2.253 | -8.266 | 3.377 | 1.00 44.76 |
| ATOM | 558 | O | ARG | 75 | -1.782 | -9.124 | 4.124 | 1.00 45.26 |
| ATOM | 559 | N | GLU | 76 | -2.247 | -8.370 | 2.052 | 1.00 44.88 |
| ATOM | 560 | CA | GLU | 76 | -1.680 | -9.517 | 1.346 | 1.00 44.86 |
| ATOM | 561 | CB | GLU | 76 | -0.152 | -9.439 | 1.337 | 1.00 45.21 |
| ATOM | 562 | CG | GLU | 76 | 0.450 | -10.469 | 0.334 | 1.00 45.31 |
| ATOM | 563 | CD | GLU | 76 | 0.050 | -10.137 | -1.107 | 1.00 45.52 |
| ATOM | 564 | OE1 | GLU | 76 | 0.511 | -9.104 | -1.639 | 1.00 45.49 |
| ATOM | 565 | OE2 | GLU | 76 | -0.731 | -10.912 | -1.704 | 1.00 45.23 |
| ATOM | 566 | C | GLU | 76 | -2.116 | -10.859 | 1.960 | 1.00 44.61 |
| ATOM | 567 | O | GLU | 76 | -1.297 | -11.758 | 2.171 | 1.00 44.52 |
| ATOM | 568 | N | GLY | 77 | -3.409 | -10.977 | 2.247 | 1.00 44.26 |
| ATOM | 569 | CA | GLY | 77 | -3.938 | -12.204 | 2.819 | 1.00 43.80 |
| ATOM | 570 | C | GLY | 77 | -3.414 | -12.551 | 4.202 | 1.00 43.49 |
| ATOM | 571 | O | GLY | 77 | -3.923 | -12.054 | 5.208 | 1.00 43.67 |
| ATOM | 572 | N | ASN | 78 | -2.402 | -13.415 | 4.251 | 1.00 43.27 |
| ATOM | 573 | CA | ASN | 78 | -1.809 | -13.841 | 5.517 | 1.00 43.15 |
| ATOM | 574 | CB | ASN | 78 | -1.743 | -15.371 | 5.593 | 1.00 43.84 |
| ATOM | 575 | CG | ASN | 78 | -3.146 | -15.993 | 5.490 | 1.00 44.43 |
| ATOM | 576 | OD1 | ASN | 78 | -3.797 | -15.925 | 4.444 | 1.00 44.43 |
| ATOM | 577 | ND2 | ASN | 78 | -3.608 | -16.593 | 6.583 | 1.00 44.71 |
| ATOM | 578 | C | ASN | 78 | -0.382 | -13.285 | 5.753 | 1.00 42.53 |
| ATOM | 579 | O | ASN | 78 | 0.299 | -13.684 | 6.699 | 1.00 43.03 |
| ATOM | 580 | N | ILE | 79 | 0.061 | -12.378 | 4.888 | 1.00 41.52 |
| ATOM | 581 | CA | ILE | 79 | 1.387 | -11.782 | 5.035 | 1.00 40.34 |
| ATOM | 582 | CB | ILE | 79 | 2.264 | -12.027 | 3.778 | 1.00 40.55 |
| ATOM | 583 | CG2 | ILE | 79 | 3.645 | -11.411 | 3.973 | 1.00 40.53 |
| ATOM | 584 | CG1 | ILE | 79 | 2.415 | -13.530 | 3.519 | 1.00 40.50 |
| ATOM | 585 | CD1 | ILE | 79 | 3.142 | -14.304 | 4.645 | 1.00 40.17 |
| ATOM | 586 | C | ILE | 79 | 1.243 | -10.281 | 5.242 | 1.00 39.50 |
| ATOM | 587 | O | ILE | 79 | 0.747 | -9.578 | 4.362 | 1.00 39.47 |

FIG.11B-14

| | | | | | | | | |
|---|---|---|---|---|---|---|---|---|
| ATOM | 588 | N | GLN | 80 | 1.658 | -9.794 | 6.411 | 1.00 38.59 |
| ATOM | 589 | CA | GLN | 80 | 1.584 | -8.368 | 6.729 | 1.00 37.48 |
| ATOM | 590 | CB | GLN | 80 | 1.413 | -8.135 | 8.237 | 1.00 38.53 |
| ATOM | 591 | CG | GLN | 80 | 0.116 | -8.469 | 8.997 | 1.00 39.05 |
| ATOM | 592 | CD | GLN | 80 | -1.025 | -7.622 | 8.446 | 1.00 39.69 |
| ATOM | 593 | OE1 | GLN | 80 | -0.923 | -6.397 | 8.363 | 1.00 40.14 |
| ATOM | 594 | NE2 | GLN | 80 | -2.119 | -8.277 | 8.069 | 1.00 39.68 |
| ATOM | 595 | C | GLN | 80 | 2.865 | -7.668 | 6.312 | 1.00 36.30 |
| ATOM | 596 | O | GLN | 80 | 3.963 | -8.158 | 6.570 | 1.00 36.40 |
| ATOM | 597 | N | TYR | 81 | 2.721 | -6.518 | 5.662 | 1.00 34.84 |
| ATOM | 598 | CA | TYR | 81 | 3.870 | -5.741 | 5.194 | 1.00 33.41 |
| ATOM | 599 | CB | TYR | 81 | 3.809 | -5.546 | 3.674 | 1.00 33.77 |
| ATOM | 600 | CG | TYR | 81 | 4.000 | -6.809 | 2.856 | 1.00 34.37 |
| ATOM | 601 | CD1 | TYR | 81 | 5.272 | -7.243 | 2.492 | 1.00 34.27 |
| ATOM | 602 | CE1 | TYR | 81 | 5.452 | -8.406 | 1.740 | 1.00 34.76 |
| ATOM | 603 | CD2 | TYR | 81 | 2.903 | -7.571 | 2.450 | 1.00 34.73 |
| ATOM | 604 | CE2 | TYR | 81 | 3.074 | -8.735 | 1.701 | 1.00 34.90 |
| ATOM | 605 | CZ | TYR | 81 | 4.349 | -9.145 | 1.350 | 1.00 34.65 |
| ATOM | 606 | OH | TYR | 81 | 4.517 | -10.296 | 0.614 | 1.00 35.49 |
| ATOM | 607 | C | TYR | 81 | 3.873 | -4.343 | 5.834 | 1.00 31.88 |
| ATOM | 608 | O | TYR | 81 | 2.965 | -3.548 | 5.602 | 1.00 32.17 |
| ATOM | 609 | N | LEU | 82 | 4.893 | -4.048 | 6.636 | 1.00 29.86 |
| ATOM | 610 | CA | LEU | 82 | 4.985 | -2.738 | 7.272 | 1.00 28.10 |
| ATOM | 611 | CB | LEU | 82 | 5.310 | -2.871 | 8.769 | 1.00 28.19 |
| ATOM | 612 | CG | LEU | 82 | 4.240 | -3.477 | 9.686 | 1.00 29.26 |
| ATOM | 613 | CD1 | LEU | 82 | 4.674 | -3.203 | 11.133 | 1.00 28.77 |
| ATOM | 614 | CD2 | LEU | 82 | 2.873 | -2.867 | 9.431 | 1.00 29.93 |
| ATOM | 615 | C | LEU | 82 | 6.083 | -1.916 | 6.606 | 1.00 26.82 |
| ATOM | 616 | O | LEU | 82 | 7.241 | -2.326 | 6.582 | 1.00 26.42 |
| ATOM | 617 | N | PHE | 83 | 5.711 | -0.765 | 6.054 | 1.00 25.82 |
| ATOM | 618 | CA | PHE | 83 | 6.673 | 0.106 | 5.387 | 1.00 24.50 |
| ATOM | 619 | CB | PHE | 83 | 6.008 | 0.772 | 4.180 | 1.00 25.77 |
| ATOM | 620 | CG | PHE | 83 | 5.548 | -0.209 | 3.142 | 1.00 27.12 |
| ATOM | 621 | CD1 | PHE | 83 | 4.377 | -0.942 | 3.324 | 1.00 28.41 |
| ATOM | 622 | CD2 | PHE | 83 | 6.322 | -0.447 | 2.013 | 1.00 28.63 |
| ATOM | 623 | CE1 | PHE | 83 | 3.984 | -1.908 | 2.389 | 1.00 29.75 |
| ATOM | 624 | CE2 | PHE | 83 | 5.941 | -1.408 | 1.074 | 1.00 29.85 |
| ATOM | 625 | CZ | PHE | 83 | 4.769 | -2.140 | 1.268 | 1.00 29.73 |
| ATOM | 626 | C | PHE | 83 | 7.185 | 1.100 | 6.382 | 1.00 23.00 |
| ATOM | 627 | O | PHE | 83 | 6.427 | 1.908 | 6.910 | 1.00 22.13 |
| ATOM | 628 | N | LEU | 84 | 8.492 | 1.044 | 6.628 | 1.00 21.28 |
| ATOM | 629 | CA | LEU | 84 | 9.144 | 1.901 | 7.616 | 1.00 20.54 |

FIG.11B-15

| ATOM | 630 | CB  | LEU | 84 | 9.713  | 1.040  | 8.745  | 1.00 | 19.57 |
| ATOM | 631 | CG  | LEU | 84 | 8.713  | 0.013  | 9.290  | 1.00 | 18.62 |
| ATOM | 632 | CD1 | LEU | 84 | 9.495  | -1.049 | 10.055 | 1.00 | 19.29 |
| ATOM | 633 | CD2 | LEU | 84 | 7.671  | 0.657  | 10.175 | 1.00 | 19.74 |
| ATOM | 634 | C   | LEU | 84 | 10.331 | 2.710  | 7.085  | 1.00 | 20.28 |
| ATOM | 635 | O   | LEU | 84 | 10.912 | 2.396  | 6.041  | 1.00 | 20.78 |
| ATOM | 636 | N   | GLU | 85 | 10.691 | 3.746  | 7.834  | 1.00 | 19.73 |
| ATOM | 637 | CA  | GLU | 85 | 11.828 | 4.596  | 7.502  | 1.00 | 19.25 |
| ATOM | 638 | CB  | GLU | 85 | 11.983 | 5.690  | 8.563  | 1.00 | 19.19 |
| ATOM | 639 | CG  | GLU | 85 | 13.227 | 6.565  | 8.390  | 1.00 | 19.69 |
| ATOM | 640 | CD  | GLU | 85 | 13.164 | 7.676  | 9.440  | 1.00 | 20.12 |
| ATOM | 641 | OE1 | GLU | 85 | 13.955 | 8.637  | 9.305  | 1.00 | 20.13 |
| ATOM | 642 | OE2 | GLU | 85 | 12.341 | 7.578  | 10.375 | 1.00 | 18.21 |
| ATOM | 643 | C   | GLU | 85 | 13.105 | 3.768  | 7.474  | 1.00 | 19.30 |
| ATOM | 644 | O   | GLU | 85 | 13.454 | 3.115  | 8.461  | 1.00 | 18.82 |
| ATOM | 645 | N   | TYR | 86 | 13.806 | 3.775  | 6.346  | 1.00 | 18.76 |
| ATOM | 646 | CA  | TYR | 86 | 15.037 | 3.021  | 6.249  | 1.00 | 18.51 |
| ATOM | 647 | CB  | TYR | 86 | 15.406 | 2.799  | 4.782  | 1.00 | 19.67 |
| ATOM | 648 | CG  | TYR | 86 | 16.774 | 2.195  | 4.610  | 1.00 | 20.99 |
| ATOM | 649 | CD1 | TYR | 86 | 17.106 | 0.992  | 5.233  | 1.00 | 21.68 |
| ATOM | 650 | CE1 | TYR | 86 | 18.372 | 0.434  | 5.091  | 1.00 | 22.49 |
| ATOM | 651 | CD2 | TYR | 86 | 17.747 | 2.827  | 3.829  | 1.00 | 21.14 |
| ATOM | 652 | CE2 | TYR | 86 | 19.019 | 2.272  | 3.682  | 1.00 | 22.21 |
| ATOM | 653 | CZ  | TYR | 86 | 19.321 | 1.082  | 4.318  | 1.00 | 23.27 |
| ATOM | 654 | OH  | TYR | 86 | 20.585 | 0.548  | 4.216  | 1.00 | 25.97 |
| ATOM | 655 | C   | TYR | 86 | 16.167 | 3.769  | 6.953  | 1.00 | 18.53 |
| ATOM | 656 | O   | TYR | 86 | 16.444 | 4.927  | 6.631  | 1.00 | 17.92 |
| ATOM | 657 | N   | CYS | 87 | 16.797 | 3.110  | 7.926  | 1.00 | 18.60 |
| ATOM | 658 | CA  | CYS | 87 | 17.904 | 3.705  | 8.678  | 1.00 | 19.08 |
| ATOM | 659 | CB  | CYS | 87 | 17.697 | 3.474  | 10.187 | 1.00 | 18.77 |
| ATOM | 660 | SG  | CYS | 87 | 16.171 | 4.310  | 10.710 | 1.00 | 18.39 |
| ATOM | 661 | C   | CYS | 87 | 19.193 | 3.058  | 8.186  | 1.00 | 18.78 |
| ATOM | 662 | O   | CYS | 87 | 19.571 | 1.968  | 8.626  | 1.00 | 19.02 |
| ATOM | 663 | N   | SER | 88 | 19.879 | 3.739  | 7.271  | 1.00 | 19.59 |
| ATOM | 664 | CA  | SER | 88 | 21.098 | 3.200  | 6.687  | 1.00 | 20.13 |
| ATOM | 665 | CB  | SER | 88 | 21.508 | 4.021  | 5.458  | 1.00 | 20.76 |
| ATOM | 666 | OG  | SER | 88 | 21.898 | 5.331  | 5.835  | 1.00 | 21.97 |
| ATOM | 667 | C   | SER | 88 | 22.308 | 3.098  | 7.584  | 1.00 | 20.67 |
| ATOM | 668 | O   | SER | 88 | 23.273 | 2.419  | 7.240  | 1.00 | 21.00 |
| ATOM | 669 | N   | GLY | 89 | 22.263 | 3.758  | 8.739  | 1.00 | 20.40 |
| ATOM | 670 | CA  | GLY | 89 | 23.392 | 3.718  | 9.648  | 1.00 | 20.92 |
| ATOM | 671 | C   | GLY | 89 | 23.476 | 2.498  | 10.544 | 1.00 | 20.54 |

FIG.11B-16

| | | | | | | | | | |
|---|---|---|---|---|---|---|---|---|---|
| ATOM | 672 | O | GLY | 89 | 24.443 | 2.343 | 11.285 | 1.00 | 21.32 |
| ATOM | 673 | N | GLY | 90 | 22.465 | 1.636 | 10.497 | 1.00 | 20.52 |
| ATOM | 674 | CA | GLY | 90 | 22.495 | 0.435 | 11.308 | 1.00 | 20.74 |
| ATOM | 675 | C | GLY | 90 | 22.057 | 0.669 | 12.739 | 1.00 | 19.72 |
| ATOM | 676 | O | GLY | 90 | 21.393 | 1.653 | 13.041 | 1.00 | 19.15 |
| ATOM | 677 | N | GLU | 91 | 22.454 | -0.243 | 13.618 | 1.00 | 19.25 |
| ATOM | 678 | CA | GLU | 91 | 22.095 | -0.175 | 15.032 | 1.00 | 18.39 |
| ATOM | 679 | CB | GLU | 91 | 21.985 | -1.580 | 15.616 | 1.00 | 19.43 |
| ATOM | 680 | CG | GLU | 91 | 20.935 | -2.428 | 14.909 | 1.00 | 20.97 |
| ATOM | 681 | CD | GLU | 91 | 20.884 | -3.864 | 15.432 | 1.00 | 21.99 |
| ATOM | 682 | OE1 | GLU | 91 | 20.081 | -4.642 | 14.863 | 1.00 | 23.57 |
| ATOM | 683 | OE2 | GLU | 91 | 21.624 | -4.182 | 16.387 | 1.00 | 20.79 |
| ATOM | 684 | C | GLU | 91 | 23.102 | 0.554 | 15.861 | 1.00 | 17.51 |
| ATOM | 685 | O | GLU | 91 | 24.289 | 0.558 | 15.549 | 1.00 | 18.50 |
| ATOM | 686 | N | LEU | 92 | 22.628 | 1.188 | 16.931 | 1.00 | 16.35 |
| ATOM | 687 | CA | LEU | 92 | 23.507 | 1.908 | 17.845 | 1.00 | 16.25 |
| ATOM | 688 | CB | LEU | 92 | 22.684 | 2.598 | 18.945 | 1.00 | 15.21 |
| ATOM | 689 | CG | LEU | 92 | 23.525 | 3.275 | 20.041 | 1.00 | 13.57 |
| ATOM | 690 | CD1 | LEU | 92 | 24.312 | 4.465 | 19.512 | 1.00 | 14.82 |
| ATOM | 691 | CD2 | LEU | 92 | 22.545 | 3.710 | 21.139 | 1.00 | 14.32 |
| ATOM | 692 | C | LEU | 92 | 24.417 | 0.890 | 18.448 | 1.00 | 17.07 |
| ATOM | 693 | O | LEU | 92 | 25.559 | 1.185 | 18.784 | 1.00 | 16.10 |
| ATOM | 694 | N | PHE | 93 | 23.918 | -0.342 | 18.552 | 1.00 | 17.48 |
| ATOM | 695 | CA | PHE | 93 | 24.678 | -1.438 | 19.121 | 1.00 | 20.02 |
| ATOM | 696 | CB | PHE | 93 | 23.888 | -2.751 | 18.999 | 1.00 | 21.58 |
| ATOM | 697 | CG | PHE | 93 | 24.629 | -3.956 | 19.521 | 1.00 | 23.36 |
| ATOM | 698 | CD1 | PHE | 93 | 25.553 | -4.628 | 18.721 | 1.00 | 23.91 |
| ATOM | 699 | CD2 | PHE | 93 | 24.420 | -4.402 | 20.822 | 1.00 | 24.46 |
| ATOM | 700 | CE1 | PHE | 93 | 26.261 | -5.730 | 19.212 | 1.00 | 25.32 |
| ATOM | 701 | CE2 | PHE | 93 | 25.124 | -5.506 | 21.328 | 1.00 | 25.27 |
| ATOM | 702 | CZ | PHE | 93 | 26.045 | -6.168 | 20.522 | 1.00 | 24.89 |
| ATOM | 703 | C | PHE | 93 | 26.039 | -1.606 | 18.425 | 1.00 | 21.14 |
| ATOM | 704 | O | PHE | 93 | 27.050 | -1.856 | 19.082 | 1.00 | 20.61 |
| ATOM | 705 | N | ASP | 94 | 26.051 | -1.450 | 17.104 | 1.00 | 21.54 |
| ATOM | 706 | CA | ASP | 94 | 27.277 | -1.614 | 16.318 | 1.00 | 22.83 |
| ATOM | 707 | CB | ASP | 94 | 26.908 | -1.933 | 14.857 | 1.00 | 24.16 |
| ATOM | 708 | CG | ASP | 94 | 26.277 | -3.346 | 14.811 | 1.00 | 25.84 |
| ATOM | 709 | OD1 | ASP | 94 | 25.502 | -3.688 | 13.893 | 1.00 | 29.46 |
| ATOM | 710 | OD2 | ASP | 94 | 26.543 | -4.189 | 15.686 | 1.00 | 26.49 |
| ATOM | 711 | C | ASP | 94 | 28.249 | -0.425 | 16.407 | 1.00 | 22.49 |
| ATOM | 712 | O | ASP | 94 | 29.365 | -0.497 | 15.896 | 1.00 | 23.70 |
| ATOM | 713 | N | ARG | 95 | 27.839 | 0.645 | 17.084 | 1.00 | 21.43 |

FIG.11B-17

| ATOM | 714 | CA | ARG | 95 | 28.685 | 1.826 | 17.250 | 1.00 | 20.91 |
|------|-----|-----|-----|-----|--------|--------|--------|------|-------|
| ATOM | 715 | CB | ARG | 95 | 27.837 | 3.099 | 17.129 | 1.00 | 23.48 |
| ATOM | 716 | CG | ARG | 95 | 27.411 | 3.256 | 15.674 | 1.00 | 26.51 |
| ATOM | 717 | CD | ARG | 95 | 28.661 | 3.755 | 14.919 | 1.00 | 28.94 |
| ATOM | 718 | NE | ARG | 95 | 29.128 | 5.018 | 15.492 | 1.00 | 32.20 |
| ATOM | 719 | CZ | ARG | 95 | 28.577 | 6.203 | 15.239 | 1.00 | 33.03 |
| ATOM | 720 | NH1 | ARG | 95 | 27.544 | 6.292 | 14.407 | 1.00 | 35.34 |
| ATOM | 721 | NH2 | ARG | 95 | 29.038 | 7.291 | 15.836 | 1.00 | 33.60 |
| ATOM | 722 | C | ARG | 95 | 29.378 | 1.815 | 18.636 | 1.00 | 20.22 |
| ATOM | 723 | O | ARG | 95 | 30.171 | 2.706 | 18.957 | 1.00 | 20.16 |
| ATOM | 724 | N | ILE | 96 | 29.051 | 0.802 | 19.435 | 1.00 | 19.47 |
| ATOM | 725 | CA | ILE | 96 | 29.605 | 0.640 | 20.771 | 1.00 | 18.75 |
| ATOM | 726 | CB | ILE | 96 | 28.532 | 0.091 | 21.721 | 1.00 | 18.34 |
| ATOM | 727 | CG2 | ILE | 96 | 29.123 | -0.162 | 23.104 | 1.00 | 18.88 |
| ATOM | 728 | CG1 | ILE | 96 | 27.371 | 1.085 | 21.777 | 1.00 | 17.58 |
| ATOM | 729 | CD1 | ILE | 96 | 26.167 | 0.580 | 22.596 | 1.00 | 16.35 |
| ATOM | 730 | C | ILE | 96 | 30.775 | -0.298 | 20.702 | 1.00 | 19.98 |
| ATOM | 731 | O | ILE | 96 | 30.609 | -1.486 | 20.427 | 1.00 | 19.77 |
| ATOM | 732 | N | GLU | 97 | 31.968 | 0.230 | 20.943 | 1.00 | 19.99 |
| ATOM | 733 | CA | GLU | 97 | 33.168 | -0.597 | 20.886 | 1.00 | 22.20 |
| ATOM | 734 | CB | GLU | 97 | 34.383 | 0.292 | 20.633 | 1.00 | 24.46 |
| ATOM | 735 | CG | GLU | 97 | 34.631 | 1.057 | 19.276 | 1.00 | 28.88 |
| ATOM | 736 | CD | GLU | 97 | 33.720 | 2.218 | 18.832 | 1.00 | 31.18 |
| ATOM | 737 | OE1 | GLU | 97 | 33.585 | 3.250 | 19.536 | 1.00 | 32.29 |
| ATOM | 738 | OE2 | GLU | 97 | 33.142 | 2.070 | 17.730 | 1.00 | 33.32 |
| ATOM | 739 | C | GLU | 97 | 33.307 | -1.427 | 22.185 | 1.00 | 21.17 |
| ATOM | 740 | O | GLU | 97 | 33.320 | -0.886 | 23.289 | 1.00 | 21.38 |
| ATOM | 741 | N | PRO | 98 | 33.391 | -2.757 | 22.055 | 1.00 | 21.50 |
| ATOM | 742 | CD | PRO | 98 | 33.282 | -3.558 | 20.817 | 1.00 | 21.52 |
| ATOM | 743 | CA | PRO | 98 | 33.519 | -3.622 | 23.231 | 1.00 | 21.75 |
| ATOM | 744 | CB | PRO | 98 | 33.765 | -4.998 | 22.611 | 1.00 | 21.99 |
| ATOM | 745 | CG | PRO | 98 | 32.982 | -4.935 | 21.349 | 1.00 | 22.40 |
| ATOM | 746 | C | PRO | 98 | 34.593 | -3.186 | 24.219 | 1.00 | 22.45 |
| ATOM | 747 | O | PRO | 98 | 35.722 | -2.885 | 23.827 | 1.00 | 22.61 |
| ATOM | 748 | N | ASP | 99 | 34.212 | -3.168 | 25.495 | 1.00 | 23.48 |
| ATOM | 749 | CA | ASP | 99 | 35.072 | -2.804 | 26.616 | 1.00 | 24.51 |
| ATOM | 750 | CB | ASP | 99 | 36.323 | -3.695 | 26.634 | 1.00 | 27.46 |
| ATOM | 751 | CG | ASP | 99 | 36.003 | -5.182 | 26.423 | 1.00 | 30.42 |
| ATOM | 752 | OD1 | ASP | 99 | 35.439 | -5.526 | 25.362 | 1.00 | 32.42 |
| ATOM | 753 | OD2 | ASP | 99 | 36.309 | -6.023 | 27.298 | 1.00 | 32.91 |
| ATOM | 754 | C | ASP | 99 | 35.524 | -1.341 | 26.625 | 1.00 | 23.52 |
| ATOM | 755 | O | ASP | 99 | 36.266 | -0.917 | 27.512 | 1.00 | 23.73 |

FIG.11B-18

| ATOM | 756 | N | ILE | 100 | 35.082 | -0.561 | 25.650 | 1.00 | 22.38 |
| ATOM | 757 | CA | ILE | 100 | 35.490 | 0.828 | 25.594 | 1.00 | 21.76 |
| ATOM | 758 | CB | ILE | 100 | 36.493 | 1.045 | 24.440 | 1.00 | 23.97 |
| ATOM | 759 | CG2 | ILE | 100 | 37.824 | 0.408 | 24.782 | 1.00 | 24.47 |
| ATOM | 760 | CG1 | ILE | 100 | 36.017 | 0.329 | 23.181 | 1.00 | 25.90 |
| ATOM | 761 | CD1 | ILE | 100 | 37.095 | 0.266 | 22.055 | 1.00 | 28.42 |
| ATOM | 762 | C | ILE | 100 | 34.351 | 1.797 | 25.504 | 1.00 | 20.24 |
| ATOM | 763 | O | ILE | 100 | 34.340 | 2.797 | 26.212 | 1.00 | 19.97 |
| ATOM | 764 | N | GLY | 101 | 33.389 | 1.512 | 24.637 | 1.00 | 18.48 |
| ATOM | 765 | CA | GLY | 101 | 32.249 | 2.405 | 24.481 | 1.00 | 16.99 |
| ATOM | 766 | C | GLY | 101 | 32.418 | 3.264 | 23.241 | 1.00 | 16.69 |
| ATOM | 767 | O | GLY | 101 | 32.595 | 2.739 | 22.136 | 1.00 | 17.27 |
| ATOM | 768 | N | MET | 102 | 32.324 | 4.581 | 23.419 | 1.00 | 16.05 |
| ATOM | 769 | CA | MET | 102 | 32.483 | 5.546 | 22.335 | 1.00 | 15.12 |
| ATOM | 770 | CB | MET | 102 | 31.181 | 5.702 | 21.541 | 1.00 | 15.01 |
| ATOM | 771 | CG | MET | 102 | 30.080 | 6.447 | 22.316 | 1.00 | 14.98 |
| ATOM | 772 | SD | MET | 102 | 28.559 | 6.611 | 21.344 | 1.00 | 14.69 |
| ATOM | 773 | CE | MET | 102 | 28.049 | 4.872 | 21.224 | 1.00 | 14.44 |
| ATOM | 774 | C | MET | 102 | 32.834 | 6.921 | 22.981 | 1.00 | 14.62 |
| ATOM | 775 | O | MET | 102 | 32.713 | 7.100 | 24.202 | 1.00 | 13.88 |
| ATOM | 776 | N | PRO | 103 | 33.264 | 7.894 | 22.171 | 1.00 | 15.17 |
| ATOM | 777 | CD | PRO | 103 | 33.526 | 7.844 | 20.723 | 1.00 | 14.81 |
| ATOM | 778 | CA | PRO | 103 | 33.609 | 9.213 | 22.715 | 1.00 | 14.86 |
| ATOM | 779 | CB | PRO | 103 | 33.984 | 10.003 | 21.459 | 1.00 | 15.81 |
| ATOM | 780 | CG | PRO | 103 | 34.530 | 8.944 | 20.559 | 1.00 | 16.07 |
| ATOM | 781 | C | PRO | 103 | 32.435 | 9.812 | 23.479 | 1.00 | 15.44 |
| ATOM | 782 | O | PRO | 103 | 31.308 | 9.789 | 22.994 | 1.00 | 14.56 |
| ATOM | 783 | N | GLU | 104 | 32.701 | 10.351 | 24.664 | 1.00 | 15.05 |
| ATOM | 784 | CA | GLU | 104 | 31.646 | 10.948 | 25.484 | 1.00 | 15.48 |
| ATOM | 785 | CB | GLU | 104 | 32.263 | 11.608 | 26.727 | 1.00 | 16.12 |
| ATOM | 786 | CG | GLU | 104 | 31.299 | 11.754 | 27.906 | 1.00 | 15.88 |
| ATOM | 787 | CD | GLU | 104 | 32.003 | 12.243 | 29.171 | 1.00 | 17.77 |
| ATOM | 788 | OE1 | GLU | 104 | 31.686 | 13.387 | 29.576 | 1.00 | 17.94 |
| ATOM | 789 | OE2 | GLU | 104 | 32.848 | 11.498 | 29.737 | 1.00 | 17.72 |
| ATOM | 790 | C | GLU | 104 | 30.748 | 11.959 | 24.731 | 1.00 | 16.01 |
| ATOM | 791 | O | GLU | 104 | 29.533 | 11.998 | 24.960 | 1.00 | 15.90 |
| ATOM | 792 | N | PRO | 105 | 31.324 | 12.790 | 23.840 | 1.00 | 16.31 |
| ATOM | 793 | CD | PRO | 105 | 32.740 | 13.149 | 23.642 | 1.00 | 17.39 |
| ATOM | 794 | CA | PRO | 105 | 30.442 | 13.732 | 23.140 | 1.00 | 16.34 |
| ATOM | 795 | CB | PRO | 105 | 31.427 | 14.609 | 22.360 | 1.00 | 17.22 |
| ATOM | 796 | CG | PRO | 105 | 32.645 | 14.618 | 23.260 | 1.00 | 17.15 |
| ATOM | 797 | C | PRO | 105 | 29.418 | 12.999 | 22.282 | 1.00 | 15.69 |

FIG.11B-19

| ATOM | 798 | O   | PRO | 105 | 28.262 | 13.414 | 22.179 | 1.00 | 15.94 |
| ATOM | 799 | N   | ASP | 106 | 29.846 | 11.913 | 21.651 | 1.00 | 15.00 |
| ATOM | 800 | CA  | ASP | 106 | 28.946 | 11.142 | 20.810 | 1.00 | 15.05 |
| ATOM | 801 | CB  | ASP | 106 | 29.695 | 10.033 | 20.070 | 1.00 | 17.35 |
| ATOM | 802 | CG  | ASP | 106 | 30.678 | 10.536 | 19.027 | 1.00 | 20.16 |
| ATOM | 803 | OD1 | ASP | 106 | 30.627 | 11.731 | 18.686 | 1.00 | 23.79 |
| ATOM | 804 | OD2 | ASP | 106 | 31.495 | 9.725  | 18.541 | 1.00 | 24.67 |
| ATOM | 805 | C   | ASP | 106 | 27.863 | 10.473 | 21.654 | 1.00 | 14.46 |
| ATOM | 806 | O   | ASP | 106 | 26.696 | 10.403 | 21.240 | 1.00 | 13.76 |
| ATOM | 807 | N   | ALA | 107 | 28.249 | 9.956  | 22.816 | 1.00 | 13.14 |
| ATOM | 808 | CA  | ALA | 107 | 27.284 | 9.307  | 23.692 | 1.00 | 12.29 |
| ATOM | 809 | CB  | ALA | 107 | 27.990 | 8.674  | 24.900 | 1.00 | 11.81 |
| ATOM | 810 | C   | ALA | 107 | 26.256 | 10.368 | 24.177 | 1.00 | 12.80 |
| ATOM | 811 | O   | ALA | 107 | 25.065 | 10.098 | 24.262 | 1.00 | 11.19 |
| ATOM | 812 | N   | GLN | 108 | 26.735 | 11.571 | 24.478 | 1.00 | 12.72 |
| ATOM | 813 | CA  | GLN | 108 | 25.838 | 12.620 | 24.964 | 1.00 | 13.51 |
| ATOM | 814 | CB  | GLN | 108 | 26.648 | 13.839 | 25.395 | 1.00 | 13.39 |
| ATOM | 815 | CG  | GLN | 108 | 25.730 | 14.775 | 26.208 | 1.00 | 13.91 |
| ATOM | 816 | CD  | GLN | 108 | 26.315 | 16.169 | 26.290 | 1.00 | 14.73 |
| ATOM | 817 | OE1 | GLN | 108 | 26.409 | 16.750 | 27.380 | 1.00 | 18.02 |
| ATOM | 818 | NE2 | GLN | 108 | 26.690 | 16.726 | 25.142 | 1.00 | 13.66 |
| ATOM | 819 | C   | GLN | 108 | 24.828 | 13.007 | 23.886 | 1.00 | 12.49 |
| ATOM | 820 | O   | GLN | 108 | 23.643 | 13.184 | 24.163 | 1.00 | 12.86 |
| ATOM | 821 | N   | ARG | 109 | 25.298 | 13.139 | 22.652 | 1.00 | 12.91 |
| ATOM | 822 | CA  | ARG | 109 | 24.412 | 13.495 | 21.544 | 1.00 | 12.93 |
| ATOM | 823 | CB  | ARG | 109 | 25.242 | 13.672 | 20.270 | 1.00 | 15.25 |
| ATOM | 824 | CG  | ARG | 109 | 24.424 | 13.899 | 18.967 | 1.00 | 17.36 |
| ATOM | 825 | CD  | ARG | 109 | 25.431 | 14.120 | 17.816 | 1.00 | 20.06 |
| ATOM | 826 | NE  | ARG | 109 | 26.088 | 12.870 | 17.433 | 1.00 | 25.24 |
| ATOM | 827 | CZ  | ARG | 109 | 25.498 | 11.902 | 16.732 | 1.00 | 25.26 |
| ATOM | 828 | NH1 | ARG | 109 | 24.251 | 12.039 | 16.331 | 1.00 | 24.49 |
| ATOM | 829 | NH2 | ARG | 109 | 26.157 | 10.787 | 16.442 | 1.00 | 29.46 |
| ATOM | 830 | C   | ARG | 109 | 23.334 | 12.421 | 21.342 | 1.00 | 12.86 |
| ATOM | 831 | O   | ARG | 109 | 22.153 | 12.739 | 21.192 | 1.00 | 12.23 |
| ATOM | 832 | N   | PHE | 110 | 23.742 | 11.154 | 21.345 | 1.00 | 11.06 |
| ATOM | 833 | CA  | PHE | 110 | 22.778 | 10.075 | 21.174 | 1.00 | 11.02 |
| ATOM | 834 | CB  | PHE | 110 | 23.453 | 8.706  | 21.090 | 1.00 | 11.45 |
| ATOM | 835 | CG  | PHE | 110 | 24.187 | 8.462  | 19.801 | 1.00 | 12.74 |
| ATOM | 836 | CD1 | PHE | 110 | 23.586 | 8.730  | 18.567 | 1.00 | 12.74 |
| ATOM | 837 | CD2 | PHE | 110 | 25.470 | 7.916  | 19.822 | 1.00 | 12.74 |
| ATOM | 838 | CE1 | PHE | 110 | 24.255 | 8.453  | 17.360 | 1.00 | 13.26 |
| ATOM | 839 | CE2 | PHE | 110 | 26.142 | 7.633  | 18.622 | 1.00 | 14.73 |

FIG.11B-20

| | | | | | | | | |
|---|---|---|---|---|---|---|---|---|
| ATOM | 840 | CZ | PHE | 110 | 25.539 | 7.899 | 17.401 | 1.00 13.07 |
| ATOM | 841 | C | PHE | 110 | 21.819 | 10.031 | 22.356 | 1.00 11.04 |
| ATOM | 842 | O | PHE | 110 | 20.631 | 9.735 | 22.192 | 1.00 10.10 |
| ATOM | 843 | N | PHE | 111 | 22.325 | 10.298 | 23.558 | 1.00 10.21 |
| ATOM | 844 | CA | PHE | 111 | 21.455 | 10.278 | 24.729 | 1.00 10.84 |
| ATOM | 845 | CB | PHE | 111 | 22.279 | 10.392 | 26.022 | 1.00 10.93 |
| ATOM | 846 | CG | PHE | 111 | 21.483 | 10.099 | 27.265 | 1.00 11.01 |
| ATOM | 847 | CD1 | PHE | 111 | 21.091 | 8.793 | 27.569 | 1.00 10.73 |
| ATOM | 848 | CD2 | PHE | 111 | 21.087 | 11.137 | 28.111 | 1.00 11.89 |
| ATOM | 849 | CE1 | PHE | 111 | 20.298 | 8.528 | 28.710 | 1.00 12.71 |
| ATOM | 850 | CE2 | PHE | 111 | 20.307 | 10.888 | 29.235 | 1.00 12.60 |
| ATOM | 851 | CZ | PHE | 111 | 19.907 | 9.581 | 29.536 | 1.00 12.53 |
| ATOM | 852 | C | PHE | 111 | 20.423 | 11.414 | 24.651 | 1.00 10.82 |
| ATOM | 853 | O | PHE | 111 | 19.276 | 11.251 | 25.049 | 1.00 10.73 |
| ATOM | 854 | N | HIS | 112 | 20.834 | 12.560 | 24.125 | 1.00 11.50 |
| ATOM | 855 | CA | HIS | 112 | 19.908 | 13.678 | 23.986 | 1.00 12.31 |
| ATOM | 856 | CB | HIS | 112 | 20.562 | 14.893 | 23.322 | 1.00 12.79 |
| ATOM | 857 | CG | HIS | 112 | 21.594 | 15.584 | 24.158 | 1.00 14.79 |
| ATOM | 858 | CD2 | HIS | 112 | 22.655 | 16.344 | 23.797 | 1.00 14.31 |
| ATOM | 859 | ND1 | HIS | 112 | 21.544 | 15.626 | 25.534 | 1.00 15.64 |
| ATOM | 860 | CE1 | HIS | 112 | 22.523 | 16.389 | 25.987 | 1.00 12.99 |
| ATOM | 861 | NE2 | HIS | 112 | 23.212 | 16.838 | 24.951 | 1.00 17.59 |
| ATOM | 862 | C | HIS | 112 | 18.788 | 13.282 | 23.019 | 1.00 12.56 |
| ATOM | 863 | O | HIS | 112 | 17.608 | 13.540 | 23.278 | 1.00 13.20 |
| ATOM | 864 | N | GLN | 113 | 19.179 | 12.659 | 21.906 | 1.00 12.60 |
| ATOM | 865 | CA | GLN | 113 | 18.226 | 12.236 | 20.881 | 1.00 12.31 |
| ATOM | 866 | CB | GLN | 113 | 18.967 | 11.756 | 19.622 | 1.00 12.91 |
| ATOM | 867 | CG | GLN | 113 | 19.661 | 12.997 | 18.985 | 1.00 13.65 |
| ATOM | 868 | CD | GLN | 113 | 20.372 | 12.578 | 17.695 | 1.00 17.58 |
| ATOM | 869 | OE1 | GLN | 113 | 20.322 | 11.416 | 17.302 | 1.00 20.92 |
| ATOM | 870 | NE2 | GLN | 113 | 21.037 | 13.530 | 17.037 | 1.00 17.64 |
| ATOM | 871 | C | GLN | 113 | 17.338 | 11.160 | 21.406 | 1.00 12.18 |
| ATOM | 872 | O | GLN | 113 | 16.142 | 11.132 | 21.113 | 1.00 12.09 |
| ATOM | 873 | N | LEU | 114 | 17.906 | 10.267 | 22.209 | 1.00 10.60 |
| ATOM | 874 | CA | LEU | 114 | 17.116 | 9.188 | 22.804 | 1.00 10.15 |
| ATOM | 875 | CB | LEU | 114 | 18.024 | 8.262 | 23.621 | 1.00 9.54 |
| ATOM | 876 | CG | LEU | 114 | 17.324 | 7.170 | 24.451 | 1.00 10.18 |
| ATOM | 877 | CD1 | LEU | 114 | 16.473 | 6.276 | 23.565 | 1.00 9.65 |
| ATOM | 878 | CD2 | LEU | 114 | 18.382 | 6.296 | 25.143 | 1.00 8.88 |
| ATOM | 879 | C | LEU | 114 | 16.043 | 9.818 | 23.754 | 1.00 9.97 |
| ATOM | 880 | O | LEU | 114 | 14.863 | 9.448 | 23.725 | 1.00 9.93 |
| ATOM | 881 | N | MET | 115 | 16.455 | 10.763 | 24.589 | 1.00 9.92 |

FIG.11B-21

| | | | | | | | | |
|---|---|---|---|---|---|---|---|---|
| ATOM | 882 | CA | MET | 115 | 15.485 | 11.403 | 25.489 | 1.00 11.27 |
| ATOM | 883 | CB | MET | 115 | 16.162 | 12.439 | 26.386 | 1.00 12.20 |
| ATOM | 884 | CG | MET | 115 | 17.001 | 11.884 | 27.520 | 1.00 12.71 |
| ATOM | 885 | SD | MET | 115 | 16.069 | 10.850 | 28.678 | 1.00 15.32 |
| ATOM | 886 | CE | MET | 115 | 16.509 | 9.262 | 27.927 | 1.00 10.45 |
| ATOM | 887 | C | MET | 115 | 14.379 | 12.124 | 24.719 | 1.00 11.42 |
| ATOM | 888 | O | MET | 115 | 13.218 | 12.126 | 25.129 | 1.00 12.59 |
| ATOM | 889 | N | ALA | 116 | 14.741 | 12.739 | 23.599 | 1.00 12.11 |
| ATOM | 890 | CA | ALA | 116 | 13.762 | 13.454 | 22.785 | 1.00 11.80 |
| ATOM | 891 | CB | ALA | 116 | 14.458 | 14.124 | 21.613 | 1.00 12.68 |
| ATOM | 892 | C | ALA | 116 | 12.697 | 12.456 | 22.290 | 1.00 12.52 |
| ATOM | 893 | O | ALA | 116 | 11.496 | 12.737 | 22.347 | 1.00 12.58 |
| ATOM | 894 | N | GLY | 117 | 13.153 | 11.299 | 21.818 | 1.00 10.70 |
| ATOM | 895 | CA | GLY | 117 | 12.236 | 10.276 | 21.338 | 1.00 11.42 |
| ATOM | 896 | C | GLY | 117 | 11.375 | 9.700 | 22.446 | 1.00 11.35 |
| ATOM | 897 | O | GLY | 117 | 10.176 | 9.490 | 22.267 | 1.00 11.68 |
| ATOM | 898 | N | VAL | 118 | 11.976 | 9.441 | 23.606 | 1.00 11.46 |
| ATOM | 899 | CA | VAL | 118 | 11.221 | 8.877 | 24.721 | 1.00 10.70 |
| ATOM | 900 | CB | VAL | 118 | 12.191 | 8.367 | 25.805 | 1.00 10.80 |
| ATOM | 901 | CG1 | VAL | 118 | 11.423 | 7.893 | 27.032 | 1.00 11.15 |
| ATOM | 902 | CG2 | VAL | 118 | 13.005 | 7.230 | 25.232 | 1.00 10.87 |
| ATOM | 903 | C | VAL | 118 | 10.199 | 9.886 | 25.280 | 1.00 11.94 |
| ATOM | 904 | O | VAL | 118 | 9.043 | 9.514 | 25.567 | 1.00 12.27 |
| ATOM | 905 | N | VAL | 119 | 10.619 | 11.143 | 25.428 | 1.00 11.92 |
| ATOM | 906 | CA | VAL | 119 | 9.718 | 12.200 | 25.898 | 1.00 13.60 |
| ATOM | 907 | CB | VAL | 119 | 10.376 | 13.614 | 25.844 | 1.00 14.14 |
| ATOM | 908 | CG1 | VAL | 119 | 9.310 | 14.696 | 25.990 | 1.00 14.89 |
| ATOM | 909 | CG2 | VAL | 119 | 11.385 | 13.763 | 26.972 | 1.00 14.60 |
| ATOM | 910 | C | VAL | 119 | 8.506 | 12.256 | 24.966 | 1.00 13.79 |
| ATOM | 911 | O | VAL | 119 | 7.355 | 12.380 | 25.405 | 1.00 14.60 |
| ATOM | 912 | N | TYR | 120 | 8.773 | 12.159 | 23.669 | 1.00 13.68 |
| ATOM | 913 | CA | TYR | 120 | 7.687 | 12.192 | 22.696 | 1.00 13.72 |
| ATOM | 914 | CB | TYR | 120 | 8.243 | 12.109 | 21.286 | 1.00 14.04 |
| ATOM | 915 | CG | TYR | 120 | 7.157 | 11.900 | 20.273 | 1.00 15.90 |
| ATOM | 916 | CD1 | TYR | 120 | 6.309 | 12.949 | 19.914 | 1.00 16.61 |
| ATOM | 917 | CE1 | TYR | 120 | 5.250 | 12.740 | 19.032 | 1.00 17.36 |
| ATOM | 918 | CD2 | TYR | 120 | 6.924 | 10.641 | 19.732 | 1.00 16.53 |
| ATOM | 919 | CE2 | TYR | 120 | 5.869 | 10.421 | 18.859 | 1.00 17.32 |
| ATOM | 920 | CZ | TYR | 120 | 5.038 | 11.475 | 18.509 | 1.00 18.22 |
| ATOM | 921 | OH | TYR | 120 | 3.998 | 11.244 | 17.634 | 1.00 18.59 |
| ATOM | 922 | C | TYR | 120 | 6.705 | 11.001 | 22.906 | 1.00 13.65 |
| ATOM | 923 | O | TYR | 120 | 5.481 | 11.193 | 23.015 | 1.00 13.76 |

FIG.11B-22

| | | | | | | | | |
|---|---|---|---|---|---|---|---|---|
| ATOM | 924 | N | LEU | 121 | 7.245 | 9.786 | 22.968 | 1.00 11.97 |
| ATOM | 925 | CA | LEU | 121 | 6.407 | 8.610 | 23.155 | 1.00 11.14 |
| ATOM | 926 | CB | LEU | 121 | 7.262 | 7.337 | 23.236 | 1.00 10.46 |
| ATOM | 927 | CG | LEU | 121 | 8.001 | 6.961 | 21.937 | 1.00  9.60 |
| ATOM | 928 | CD1 | LEU | 121 | 8.830 | 5.695 | 22.199 | 1.00 12.56 |
| ATOM | 929 | CD2 | LEU | 121 | 7.039 | 6.749 | 20.774 | 1.00 11.38 |
| ATOM | 930 | C | LEU | 121 | 5.576 | 8.726 | 24.452 | 1.00 11.75 |
| ATOM | 931 | O | LEU | 121 | 4.373 | 8.479 | 24.455 | 1.00 10.61 |
| ATOM | 932 | N | HIS | 122 | 6.234 | 9.089 | 25.553 | 1.00 11.66 |
| ATOM | 933 | CA | HIS | 122 | 5.524 | 9.194 | 26.820 | 1.00 11.84 |
| ATOM | 934 | CB | HIS | 122 | 6.528 | 9.447 | 27.951 | 1.00 12.54 |
| ATOM | 935 | CG | HIS | 122 | 7.381 | 8.255 | 28.262 | 1.00 11.35 |
| ATOM | 936 | CD2 | HIS | 122 | 7.382 | 7.003 | 27.747 | 1.00 12.10 |
| ATOM | 937 | ND1 | HIS | 122 | 8.348 | 8.266 | 29.248 | 1.00 11.14 |
| ATOM | 938 | CE1 | HIS | 122 | 8.905 | 7.070 | 29.328 | 1.00 11.31 |
| ATOM | 939 | NE2 | HIS | 122 | 8.335 | 6.284 | 28.431 | 1.00 10.75 |
| ATOM | 940 | C | HIS | 122 | 4.455 | 10.255 | 26.753 | 1.00 12.85 |
| ATOM | 941 | O | HIS | 122 | 3.391 | 10.127 | 27.374 | 1.00 13.14 |
| ATOM | 942 | N | GLY | 123 | 4.724 | 11.291 | 25.973 | 1.00 13.41 |
| ATOM | 943 | CA | GLY | 123 | 3.767 | 12.371 | 25.838 | 1.00 14.75 |
| ATOM | 944 | C | GLY | 123 | 2.469 | 11.927 | 25.198 | 1.00 16.34 |
| ATOM | 945 | O | GLY | 123 | 1.398 | 12.472 | 25.519 | 1.00 17.30 |
| ATOM | 946 | N | ILE | 124 | 2.555 | 10.946 | 24.305 | 1.00 15.33 |
| ATOM | 947 | CA | ILE | 124 | 1.373 | 10.429 | 23.625 | 1.00 16.62 |
| ATOM | 948 | CB | ILE | 124 | 1.660 | 10.125 | 22.128 | 1.00 19.17 |
| ATOM | 949 | CG2 | ILE | 124 | 2.685 | 9.029 | 21.991 | 1.00 20.31 |
| ATOM | 950 | CG1 | ILE | 124 | 0.365 | 9.716 | 21.423 | 1.00 21.41 |
| ATOM | 951 | CD1 | ILE | 124 | -0.700 | 10.819 | 21.404 | 1.00 24.63 |
| ATOM | 952 | C | ILE | 124 | 0.840 | 9.193 | 24.325 | 1.00 15.39 |
| ATOM | 953 | O | ILE | 124 | -0.067 | 8.535 | 23.821 | 1.00 16.38 |
| ATOM | 954 | N | GLY | 125 | 1.418 | 8.873 | 25.481 | 1.00 14.25 |
| ATOM | 955 | CA | GLY | 125 | 0.958 | 7.740 | 26.270 | 1.00 14.26 |
| ATOM | 956 | C | GLY | 125 | 1.420 | 6.364 | 25.839 | 1.00 14.37 |
| ATOM | 957 | O | GLY | 125 | 0.787 | 5.364 | 26.176 | 1.00 13.70 |
| ATOM | 958 | N | ILE | 126 | 2.512 | 6.304 | 25.087 | 1.00 14.23 |
| ATOM | 959 | CA | ILE | 126 | 3.021 | 5.012 | 24.644 | 1.00 14.92 |
| ATOM | 960 | CB | ILE | 126 | 3.259 | 4.960 | 23.088 | 1.00 17.26 |
| ATOM | 961 | CG2 | ILE | 126 | 2.042 | 5.480 | 22.346 | 1.00 18.55 |
| ATOM | 962 | CG1 | ILE | 126 | 4.559 | 5.667 | 22.723 | 1.00 21.12 |
| ATOM | 963 | CD1 | ILE | 126 | 5.816 | 4.689 | 22.744 | 1.00 23.73 |
| ATOM | 964 | C | ILE | 126 | 4.355 | 4.674 | 25.332 | 1.00 13.61 |
| ATOM | 965 | O | ILE | 126 | 5.209 | 5.554 | 25.532 | 1.00 12.38 |

FIG.11B-23

| | | | | | | | | |
|---|---|---|---|---|---|---|---|---|
| ATOM | 966 | N | THR | 127 | 4.514 | 3.416 | 25.725 | 1.00 12.02 |
| ATOM | 967 | CA | THR | 127 | 5.787 | 2.991 | 26.304 | 1.00 12.59 |
| ATOM | 968 | CB | THR | 127 | 5.630 | 2.446 | 27.729 | 1.00 13.49 |
| ATOM | 969 | OG1 | THR | 127 | 5.288 | 3.516 | 28.613 | 1.00 21.14 |
| ATOM | 970 | CG2 | THR | 127 | 6.923 | 1.830 | 28.190 | 1.00 8.53 |
| ATOM | 971 | C | THR | 127 | 6.362 | 1.951 | 25.381 | 1.00 11.65 |
| ATOM | 972 | O | THR | 127 | 5.646 | 1.065 | 24.907 | 1.00 12.97 |
| ATOM | 973 | N | HIS | 128 | 7.665 | 2.054 | 25.103 | 1.00 12.24 |
| ATOM | 974 | CA | HIS | 128 | 8.321 | 1.123 | 24.187 | 1.00 12.15 |
| ATOM | 975 | CB | HIS | 128 | 9.648 | 1.736 | 23.711 | 1.00 11.49 |
| ATOM | 976 | CG | HIS | 128 | 10.375 | 0.904 | 22.699 | 1.00 11.68 |
| ATOM | 977 | CD2 | HIS | 128 | 10.471 | 1.012 | 21.350 | 1.00 11.46 |
| ATOM | 978 | ND1 | HIS | 128 | 11.119 | -0.200 | 23.050 | 1.00 11.90 |
| ATOM | 979 | CE1 | HIS | 128 | 11.641 | -0.741 | 21.961 | 1.00 12.68 |
| ATOM | 980 | NE2 | HIS | 128 | 11.262 | -0.025 | 20.915 | 1.00 12.57 |
| ATOM | 981 | C | HIS | 128 | 8.517 | -0.242 | 24.817 | 1.00 12.15 |
| ATOM | 982 | O | HIS | 128 | 8.260 | -1.275 | 24.192 | 1.00 11.72 |
| ATOM | 983 | N | ARG | 129 | 8.968 | -0.236 | 26.070 | 1.00 11.07 |
| ATOM | 984 | CA | ARG | 129 | 9.191 | -1.462 | 26.849 | 1.00 11.47 |
| ATOM | 985 | CB | ARG | 129 | 7.931 | -2.343 | 26.858 | 1.00 12.32 |
| ATOM | 986 | CG | ARG | 129 | 6.807 | -1.547 | 27.487 | 1.00 12.84 |
| ATOM | 987 | CD | ARG | 129 | 5.709 | -2.441 | 28.097 | 1.00 12.85 |
| ATOM | 988 | NE | ARG | 129 | 4.988 | -3.179 | 27.067 | 1.00 12.16 |
| ATOM | 989 | CZ | ARG | 129 | 3.911 | -3.911 | 27.316 | 1.00 13.84 |
| ATOM | 990 | NH1 | ARG | 129 | 3.446 | -3.991 | 28.565 | 1.00 13.82 |
| ATOM | 991 | NH2 | ARG | 129 | 3.304 | -4.553 | 26.317 | 1.00 14.27 |
| ATOM | 992 | C | ARG | 129 | 10.380 | -2.359 | 26.501 | 1.00 12.13 |
| ATOM | 993 | O | ARG | 129 | 10.592 | -3.375 | 27.159 | 1.00 11.76 |
| ATOM | 994 | N | ASP | 130 | 11.162 | -1.999 | 25.488 | 1.00 10.41 |
| ATOM | 995 | CA | ASP | 130 | 12.332 | -2.823 | 25.147 | 1.00 11.17 |
| ATOM | 996 | CB | ASP | 130 | 11.914 | -3.937 | 24.157 | 1.00 11.51 |
| ATOM | 997 | CG | ASP | 130 | 12.950 | -5.082 | 24.156 | 1.00 13.34 |
| ATOM | 998 | OD1 | ASP | 130 | 12.988 | -5.895 | 23.184 | 1.00 13.30 |
| ATOM | 999 | OD2 | ASP | 130 | 13.732 | -5.178 | 25.127 | 1.00 13.23 |
| ATOM | 1000 | C | ASP | 130 | 13.442 | -1.969 | 24.584 | 1.00 10.24 |
| ATOM | 1001 | O | ASP | 130 | 14.048 | -2.300 | 23.564 | 1.00 10.99 |
| ATOM | 1002 | N | ILE | 131 | 13.735 | -0.848 | 25.245 | 1.00 9.92 |
| ATOM | 1003 | CA | ILE | 131 | 14.787 | 0.047 | 24.763 | 1.00 10.16 |
| ATOM | 1004 | CB | ILE | 131 | 14.705 | 1.408 | 25.463 | 1.00 10.21 |
| ATOM | 1005 | CG2 | ILE | 131 | 15.892 | 2.312 | 25.040 | 1.00 10.96 |
| ATOM | 1006 | CG1 | ILE | 131 | 13.350 | 2.041 | 25.136 | 1.00 10.91 |
| ATOM | 1007 | CD1 | ILE | 131 | 13.075 | 3.389 | 25.902 | 1.00 12.36 |

FIG.11B-24

| | | | | | | | | |
|---|---|---|---|---|---|---|---|---|
| ATOM | 1008 | C | ILE | 131 | 16.152 | -0.580 | 25.017 | 1.00 10.07 |
| ATOM | 1009 | O | ILE | 131 | 16.449 | -0.979 | 26.134 | 1.00 11.34 |
| ATOM | 1010 | N | LYS | 132 | 16.969 | -0.643 | 23.970 | 1.00 10.08 |
| ATOM | 1011 | CA | LYS | 132 | 18.314 | -1.214 | 24.029 | 1.00 10.81 |
| ATOM | 1012 | CB | LYS | 132 | 18.256 | -2.741 | 24.204 | 1.00 10.84 |
| ATOM | 1013 | CG | LYS | 132 | 17.367 | -3.496 | 23.156 | 1.00 11.39 |
| ATOM | 1014 | CD | LYS | 132 | 17.443 | -5.018 | 23.486 | 1.00 13.71 |
| ATOM | 1015 | CE | LYS | 132 | 16.477 | -5.789 | 22.554 | 1.00 13.34 |
| ATOM | 1016 | NZ | LYS | 132 | 16.456 | -7.271 | 22.822 | 1.00 13.78 |
| ATOM | 1017 | C | LYS | 132 | 18.974 | -0.793 | 22.721 | 1.00 11.06 |
| ATOM | 1018 | O | LYS | 132 | 18.285 | -0.412 | 21.767 | 1.00 12.07 |
| ATOM | 1019 | N | PRO | 133 | 20.307 | -0.857 | 22.651 | 1.00 12.09 |
| ATOM | 1020 | CD | PRO | 133 | 21.235 | -1.277 | 23.717 | 1.00 11.84 |
| ATOM | 1021 | CA | PRO | 133 | 21.040 | -0.455 | 21.442 | 1.00 12.30 |
| ATOM | 1022 | CB | PRO | 133 | 22.499 | -0.707 | 21.838 | 1.00 11.29 |
| ATOM | 1023 | CG | PRO | 133 | 22.486 | -0.504 | 23.347 | 1.00 11.82 |
| ATOM | 1024 | C | PRO | 133 | 20.595 | -1.090 | 20.156 | 1.00 13.29 |
| ATOM | 1025 | O | PRO | 133 | 20.667 | -0.452 | 19.089 | 1.00 12.31 |
| ATOM | 1026 | N | GLU | 134 | 20.120 | -2.335 | 20.236 | 1.00 13.34 |
| ATOM | 1027 | CA | GLU | 134 | 19.657 | -3.033 | 19.047 | 1.00 14.29 |
| ATOM | 1028 | CB | GLU | 134 | 19.393 | -4.512 | 19.354 | 1.00 15.51 |
| ATOM | 1029 | CG | GLU | 134 | 20.601 | -5.281 | 19.934 | 1.00 16.70 |
| ATOM | 1030 | CD | GLU | 134 | 20.784 | -5.274 | 21.434 | 1.00 18.54 |
| ATOM | 1031 | OE1 | GLU | 134 | 20.556 | -4.248 | 22.115 | 1.00 16.56 |
| ATOM | 1032 | OE2 | GLU | 134 | 21.194 | -6.364 | 21.905 | 1.00 19.18 |
| ATOM | 1033 | C | GLU | 134 | 18.372 | -2.412 | 18.486 | 1.00 14.42 |
| ATOM | 1034 | O | GLU | 134 | 18.064 | -2.566 | 17.293 | 1.00 14.80 |
| ATOM | 1035 | N | ASN | 135 | 17.625 | -1.715 | 19.345 | 1.00 13.51 |
| ATOM | 1036 | CA | ASN | 135 | 16.367 | -1.086 | 18.941 | 1.00 12.98 |
| ATOM | 1037 | CB | ASN | 135 | 15.252 | -1.396 | 19.955 | 1.00 12.53 |
| ATOM | 1038 | CG | ASN | 135 | 14.698 | -2.831 | 19.831 | 1.00 13.89 |
| ATOM | 1039 | OD1 | ASN | 135 | 14.234 | -3.421 | 20.815 | 1.00 15.19 |
| ATOM | 1040 | ND2 | ASN | 135 | 14.730 | -3.374 | 18.620 | 1.00 13.17 |
| ATOM | 1041 | C | ASN | 135 | 16.471 | 0.417 | 18.760 | 1.00 12.77 |
| ATOM | 1042 | O | ASN | 135 | 15.462 | 1.118 | 18.757 | 1.00 13.83 |
| ATOM | 1043 | N | LEU | 136 | 17.699 | 0.910 | 18.607 | 1.00 11.66 |
| ATOM | 1044 | CA | LEU | 136 | 17.953 | 2.330 | 18.386 | 1.00 12.25 |
| ATOM | 1045 | CB | LEU | 136 | 18.689 | 2.925 | 19.593 | 1.00 12.78 |
| ATOM | 1046 | CG | LEU | 136 | 17.899 | 2.887 | 20.912 | 1.00 12.80 |
| ATOM | 1047 | CD1 | LEU | 136 | 18.839 | 3.437 | 22.009 | 1.00 13.44 |
| ATOM | 1048 | CD2 | LEU | 136 | 16.599 | 3.711 | 20.833 | 1.00 14.59 |
| ATOM | 1049 | C | LEU | 136 | 18.779 | 2.378 | 17.091 | 1.00 13.15 |

FIG.11B-25

| | | | | | | | | |
|---|---|---|---|---|---|---|---|---|
| ATOM | 1050 | O | LEU | 136 | 19.957 | 2.043 | 17.084 | 1.00 13.18 |
| ATOM | 1051 | N | LEU | 137 | 18.124 | 2.735 | 15.991 | 1.00 13.60 |
| ATOM | 1052 | CA | LEU | 137 | 18.783 | 2.775 | 14.692 | 1.00 14.28 |
| ATOM | 1053 | CB | LEU | 137 | 17.814 | 2.291 | 13.611 | 1.00 14.14 |
| ATOM | 1054 | CG | LEU | 137 | 17.210 | 0.941 | 14.025 | 1.00 15.38 |
| ATOM | 1055 | CD1 | LEU | 137 | 16.280 | 0.448 | 12.879 | 1.00 14.24 |
| ATOM | 1056 | CD2 | LEU | 137 | 18.300 | -0.074 | 14.319 | 1.00 15.67 |
| ATOM | 1057 | C | LEU | 137 | 19.287 | 4.124 | 14.359 | 1.00 15.19 |
| ATOM | 1058 | O | LEU | 137 | 18.884 | 5.118 | 14.952 | 1.00 15.24 |
| ATOM | 1059 | N | LEU | 138 | 20.174 | 4.178 | 13.372 | 1.00 16.26 |
| ATOM | 1060 | CA | LEU | 138 | 20.779 | 5.433 | 12.952 | 1.00 16.85 |
| ATOM | 1061 | CB | LEU | 138 | 22.296 | 5.385 | 13.183 | 1.00 17.95 |
| ATOM | 1062 | CG | LEU | 138 | 22.811 | 5.144 | 14.617 | 1.00 19.40 |
| ATOM | 1063 | CD1 | LEU | 138 | 22.251 | 6.225 | 15.531 | 1.00 19.08 |
| ATOM | 1064 | CD2 | LEU | 138 | 22.399 | 3.760 | 15.102 | 1.00 22.69 |
| ATOM | 1065 | C | LEU | 138 | 20.534 | 5.671 | 11.461 | 1.00 17.74 |
| ATOM | 1066 | O | LEU | 138 | 20.604 | 4.731 | 10.676 | 1.00 17.49 |
| ATOM | 1067 | N | ASP | 139 | 20.236 | 6.913 | 11.083 | 1.00 18.21 |
| ATOM | 1068 | CA | ASP | 139 | 20.013 | 7.235 | 9.673 | 1.00 20.36 |
| ATOM | 1069 | CB | ASP | 139 | 18.989 | 8.371 | 9.527 | 1.00 20.49 |
| ATOM | 1070 | CG | ASP | 139 | 19.372 | 9.764 | 9.970 | 1.00 20.35 |
| ATOM | 1071 | OD1 | ASP | 139 | 18.491 | 10.652 | 9.888 | 1.00 23.24 |
| ATOM | 1072 | OD2 | ASP | 139 | 20.517 | 10.002 | 10.389 | 1.00 21.14 |
| ATOM | 1073 | C | ASP | 139 | 21.345 | 7.624 | 9.073 | 1.00 21.49 |
| ATOM | 1074 | O | ASP | 139 | 22.381 | 7.469 | 9.709 | 1.00 20.83 |
| ATOM | 1075 | N | GLU | 140 | 21.330 | 8.115 | 7.836 | 1.00 23.55 |
| ATOM | 1076 | CA | GLU | 140 | 22.564 | 8.511 | 7.169 | 1.00 25.49 |
| ATOM | 1077 | CB | GLU | 140 | 22.282 | 8.952 | 5.726 | 1.00 27.10 |
| ATOM | 1078 | CG | GLU | 140 | 21.287 | 10.082 | 5.469 | 1.00 30.90 |
| ATOM | 1079 | CD | GLU | 140 | 19.954 | 9.585 | 5.973 | 1.00 32.27 |
| ATOM | 1080 | OE1 | GLU | 140 | 19.575 | 8.466 | 5.572 | 1.00 34.20 |
| ATOM | 1081 | OE2 | GLU | 140 | 19.282 | 10.287 | 6.757 | 1.00 35.13 |
| ATOM | 1082 | C | GLU | 140 | 23.386 | 9.625 | 7.867 | 1.00 25.97 |
| ATOM | 1083 | O | GLU | 140 | 24.593 | 9.727 | 7.649 | 1.00 26.62 |
| ATOM | 1084 | N | ARG | 141 | 22.736 | 10.444 | 8.692 | 1.00 26.36 |
| ATOM | 1085 | CA | ARG | 141 | 23.432 | 11.515 | 9.408 | 1.00 26.34 |
| ATOM | 1086 | CB | ARG | 141 | 22.628 | 12.821 | 9.362 | 1.00 28.11 |
| ATOM | 1087 | CG | ARG | 141 | 22.492 | 13.508 | 7.970 | 1.00 30.79 |
| ATOM | 1088 | CD | ARG | 141 | 21.702 | 14.853 | 7.950 | 1.00 32.84 |
| ATOM | 1089 | NE | ARG | 141 | 22.291 | 15.861 | 8.833 | 1.00 35.77 |
| ATOM | 1090 | CZ | ARG | 141 | 21.964 | 16.036 | 10.113 | 1.00 37.04 |
| ATOM | 1091 | NH1 | ARG | 141 | 21.039 | 15.271 | 10.681 | 1.00 36.95 |

FIG.11B-26

| ATOM | 1092 | NH2 | ARG | 141 | 22.564 | 16.981 | 10.828 | 1.00 | 37.88 |
|------|------|-----|-----|-----|--------|--------|--------|------|-------|
| ATOM | 1093 | C | ARG | 141 | 23.645 | 11.156 | 10.879 | 1.00 | 25.65 |
| ATOM | 1094 | O | ARG | 141 | 23.877 | 12.026 | 11.720 | 1.00 | 25.46 |
| ATOM | 1095 | N | ASP | 142 | 23.579 | 9.868 | 11.184 | 1.00 | 23.88 |
| ATOM | 1096 | CA | ASP | 142 | 23.755 | 9.403 | 12.559 | 1.00 | 23.96 |
| ATOM | 1097 | CB | ASP | 142 | 25.128 | 9.800 | 13.107 | 1.00 | 26.22 |
| ATOM | 1098 | CG | ASP | 142 | 26.194 | 8.903 | 12.523 | 1.00 | 28.88 |
| ATOM | 1099 | OD1 | ASP | 142 | 25.919 | 7.694 | 12.418 | 1.00 | 29.81 |
| ATOM | 1100 | OD2 | ASP | 142 | 27.300 | 9.375 | 12.182 | 1.00 | 31.98 |
| ATOM | 1101 | C | ASP | 142 | 22.677 | 9.917 | 13.533 | 1.00 | 22.68 |
| ATOM | 1102 | O | ASP | 142 | 22.940 | 10.092 | 14.729 | 1.00 | 21.46 |
| ATOM | 1103 | N | ASN | 143 | 21.475 | 10.172 | 13.025 | 1.00 | 21.05 |
| ATOM | 1104 | CA | ASN | 143 | 20.387 | 10.603 | 13.909 | 1.00 | 19.86 |
| ATOM | 1105 | CB | ASN | 143 | 19.326 | 11.401 | 13.156 | 1.00 | 19.72 |
| ATOM | 1106 | CG | ASN | 143 | 19.848 | 12.766 | 12.784 | 1.00 | 20.89 |
| ATOM | 1107 | OD1 | ASN | 143 | 19.752 | 13.190 | 11.621 | 1.00 | 23.00 |
| ATOM | 1108 | ND2 | ASN | 143 | 20.404 | 13.472 | 13.762 | 1.00 | 18.41 |
| ATOM | 1109 | C | ASN | 143 | 19.749 | 9.348 | 14.453 | 1.00 | 18.33 |
| ATOM | 1110 | O | ASN | 143 | 19.447 | 8.437 | 13.698 | 1.00 | 18.35 |
| ATOM | 1111 | N | LEU | 144 | 19.536 | 9.295 | 15.766 | 1.00 | 16.77 |
| ATOM | 1112 | CA | LEU | 144 | 18.957 | 8.108 | 16.383 | 1.00 | 16.09 |
| ATOM | 1113 | CB | LEU | 144 | 19.337 | 8.075 | 17.867 | 1.00 | 15.65 |
| ATOM | 1114 | CG | LEU | 144 | 18.727 | 7.080 | 18.855 | 1.00 | 14.93 |
| ATOM | 1115 | CD1 | LEU | 144 | 19.744 | 6.887 | 19.992 | 1.00 | 14.95 |
| ATOM | 1116 | CD2 | LEU | 144 | 17.374 | 7.585 | 19.387 | 1.00 | 15.73 |
| ATOM | 1117 | C | LEU | 144 | 17.450 | 8.022 | 16.194 | 1.00 | 15.54 |
| ATOM | 1118 | O | LEU | 144 | 16.739 | 9.029 | 16.265 | 1.00 | 15.24 |
| ATOM | 1119 | N | LYS | 145 | 16.973 | 6.800 | 15.972 | 1.00 | 14.42 |
| ATOM | 1120 | CA | LYS | 145 | 15.557 | 6.557 | 15.744 | 1.00 | 15.14 |
| ATOM | 1121 | CB | LYS | 145 | 15.295 | 6.210 | 14.277 | 1.00 | 15.62 |
| ATOM | 1122 | CG | LYS | 145 | 15.953 | 7.083 | 13.201 | 1.00 | 18.61 |
| ATOM | 1123 | CD | LYS | 145 | 15.096 | 8.291 | 13.029 | 1.00 | 19.20 |
| ATOM | 1124 | CE | LYS | 145 | 15.797 | 9.269 | 12.033 | 1.00 | 19.98 |
| ATOM | 1125 | NZ | LYS | 145 | 14.861 | 10.344 | 11.574 | 1.00 | 19.93 |
| ATOM | 1126 | C | LYS | 145 | 15.126 | 5.339 | 16.535 | 1.00 | 13.97 |
| ATOM | 1127 | O | LYS | 145 | 15.655 | 4.248 | 16.329 | 1.00 | 13.07 |
| ATOM | 1128 | N | ILE | 146 | 14.166 | 5.526 | 17.436 | 1.00 | 13.48 |
| ATOM | 1129 | CA | ILE | 146 | 13.654 | 4.417 | 18.238 | 1.00 | 12.91 |
| ATOM | 1130 | CB | ILE | 146 | 12.723 | 4.928 | 19.336 | 1.00 | 12.90 |
| ATOM | 1131 | CG2 | ILE | 146 | 12.066 | 3.737 | 20.070 | 1.00 | 13.04 |
| ATOM | 1132 | CG1 | ILE | 146 | 13.538 | 5.762 | 20.324 | 1.00 | 13.51 |
| ATOM | 1133 | CD1 | ILE | 146 | 12.694 | 6.479 | 21.403 | 1.00 | 13.33 |

FIG.11B-27

```
ATOM   1134  C    ILE  146      12.901   3.476  17.301  1.00 13.05
ATOM   1135  O    ILE  146      12.012   3.904  16.559  1.00 12.88
ATOM   1136  N    SER  147      13.238   2.192  17.382  1.00 12.43
ATOM   1137  CA   SER  147      12.681   1.173  16.496  1.00 13.35
ATOM   1138  CB   SER  147      13.822   0.665  15.593  1.00 14.71
ATOM   1139  OG   SER  147      13.489  -0.508  14.855  1.00 15.66
ATOM   1140  C    SER  147      12.038  -0.011  17.174  1.00 14.00
ATOM   1141  O    SER  147      12.369  -0.344  18.318  1.00 12.67
ATOM   1142  N    ASP  148      11.110  -0.640  16.451  1.00 14.20
ATOM   1143  CA   ASP  148      10.417  -1.855  16.883  1.00 14.80
ATOM   1144  CB   ASP  148      11.453  -2.915  17.282  1.00 16.84
ATOM   1145  CG   ASP  148      10.867  -4.294  17.493  1.00 19.50
ATOM   1146  OD1  ASP  148      11.660  -5.228  17.723  1.00 23.01
ATOM   1147  OD2  ASP  148       9.636  -4.457  17.430  1.00 19.78
ATOM   1148  C    ASP  148       9.426  -1.695  17.980  1.00 15.21
ATOM   1149  O    ASP  148       9.767  -1.794  19.152  1.00 15.83
ATOM   1150  N    PHE  149       8.166  -1.494  17.610  1.00 14.13
ATOM   1151  CA   PHE  149       7.101  -1.309  18.585  1.00 14.87
ATOM   1152  CB   PHE  149       6.252  -0.114  18.143  1.00 15.09
ATOM   1153  CG   PHE  149       6.974   1.187  18.274  1.00 15.25
ATOM   1154  CD1  PHE  149       7.860   1.608  17.292  1.00 15.38
ATOM   1155  CD2  PHE  149       6.844   1.952  19.440  1.00 14.86
ATOM   1156  CE1  PHE  149       8.623   2.776  17.464  1.00 14.94
ATOM   1157  CE2  PHE  149       7.599   3.114  19.621  1.00 14.99
ATOM   1158  CZ   PHE  149       8.487   3.524  18.636  1.00 14.89
ATOM   1159  C    PHE  149       6.304  -2.544  18.811  1.00 15.24
ATOM   1160  O    PHE  149       5.145  -2.484  19.220  1.00 16.36
ATOM   1161  N    GLY  150       6.936  -3.691  18.572  1.00 16.17
ATOM   1162  CA   GLY  150       6.269  -4.970  18.746  1.00 16.47
ATOM   1163  C    GLY  150       5.947  -5.286  20.197  1.00 16.83
ATOM   1164  O    GLY  150       5.093  -6.126  20.481  1.00 17.90
ATOM   1165  N    LEU  151       6.621  -4.626  21.127  1.00 15.78
ATOM   1166  CA   LEU  151       6.326  -4.871  22.541  1.00 16.37
ATOM   1167  CB   LEU  151       7.584  -5.298  23.292  1.00 17.64
ATOM   1168  CG   LEU  151       8.078  -6.619  22.700  1.00 19.89
ATOM   1169  CD1  LEU  151       9.341  -6.989  23.457  1.00 19.60
ATOM   1170  CD2  LEU  151       7.040  -7.730  22.782  1.00 20.88
ATOM   1171  C    LEU  151       5.729  -3.663  23.222  1.00 15.93
ATOM   1172  O    LEU  151       5.392  -3.723  24.405  1.00 16.32
ATOM   1173  N    ALA  152       5.567  -2.577  22.466  1.00 14.33
ATOM   1174  CA   ALA  152       5.020  -1.329  22.994  1.00 14.78
ATOM   1175  CB   ALA  152       5.196  -0.205  21.964  1.00 14.02
```

FIG.11B-28

| | | | | | | | | |
|---|---|---|---|---|---|---|---|---|
| ATOM | 1176 | C | ALA | 152 | 3.559 | -1.412 | 23.400 | 1.00 14.74 |
| ATOM | 1177 | O | ALA | 152 | 2.820 | -2.287 | 22.946 | 1.00 16.44 |
| ATOM | 1178 | N | THR | 153 | 3.134 | -0.498 | 24.262 | 1.00 14.29 |
| ATOM | 1179 | CA | THR | 153 | 1.736 | -0.486 | 24.678 | 1.00 14.48 |
| ATOM | 1180 | CB | THR | 153 | 1.465 | -1.570 | 25.767 | 1.00 15.01 |
| ATOM | 1181 | OG1 | THR | 153 | 0.052 | -1.803 | 25.857 | 1.00 15.18 |
| ATOM | 1182 | CG2 | THR | 153 | 1.985 | -1.140 | 27.135 | 1.00 16.34 |
| ATOM | 1183 | C | THR | 153 | 1.305 | 0.866 | 25.134 | 1.00 14.74 |
| ATOM | 1184 | O | THR | 153 | 2.124 | 1.764 | 25.321 | 1.00 14.16 |
| ATOM | 1185 | N | VAL | 154 | -0.002 | 1.036 | 25.283 | 1.00 15.49 |
| ATOM | 1186 | CA | VAL | 154 | -0.574 | 2.294 | 25.744 | 1.00 16.27 |
| ATOM | 1187 | CB | VAL | 154 | -2.024 | 2.446 | 25.187 | 1.00 17.58 |
| ATOM | 1188 | CG1 | VAL | 154 | -2.721 | 3.669 | 25.796 | 1.00 18.88 |
| ATOM | 1189 | CG2 | VAL | 154 | -1.978 | 2.573 | 23.672 | 1.00 18.48 |
| ATOM | 1190 | C | VAL | 154 | -0.584 | 2.280 | 27.288 | 1.00 16.33 |
| ATOM | 1191 | O | VAL | 154 | -1.096 | 1.337 | 27.896 | 1.00 17.03 |
| ATOM | 1192 | N | PHE | 155 | 0.002 | 3.296 | 27.917 | 1.00 14.86 |
| ATOM | 1193 | CA | PHE | 155 | -0.011 | 3.348 | 29.372 | 1.00 14.65 |
| ATOM | 1194 | CB | PHE | 155 | 1.411 | 3.401 | 29.968 | 1.00 13.64 |
| ATOM | 1195 | CG | PHE | 155 | 2.088 | 4.733 | 29.830 | 1.00 12.64 |
| ATOM | 1196 | CD1 | PHE | 155 | 2.810 | 5.044 | 28.675 | 1.00 11.40 |
| ATOM | 1197 | CD2 | PHE | 155 | 1.984 | 5.696 | 30.836 | 1.00 12.17 |
| ATOM | 1198 | CE1 | PHE | 155 | 3.412 | 6.282 | 28.520 | 1.00 12.13 |
| ATOM | 1199 | CE2 | PHE | 155 | 2.592 | 6.960 | 30.691 | 1.00 13.02 |
| ATOM | 1200 | CZ | PHE | 155 | 3.311 | 7.254 | 29.522 | 1.00 12.14 |
| ATOM | 1201 | C | PHE | 155 | -0.830 | 4.566 | 29.831 | 1.00 14.29 |
| ATOM | 1202 | O | PHE | 155 | -1.041 | 4.748 | 31.027 | 1.00 14.95 |
| ATOM | 1203 | N | ARG | 156 | -1.257 | 5.406 | 28.888 | 1.00 14.44 |
| ATOM | 1204 | CA | ARG | 156 | -2.082 | 6.570 | 29.246 | 1.00 14.70 |
| ATOM | 1205 | CB | ARG | 156 | -1.241 | 7.846 | 29.410 | 1.00 15.59 |
| ATOM | 1206 | CG | ARG | 156 | -2.174 | 8.962 | 30.089 | 1.00 17.04 |
| ATOM | 1207 | CD | ARG | 156 | -1.525 | 10.389 | 29.970 | 1.00 18.38 |
| ATOM | 1208 | NE | ARG | 156 | -0.159 | 10.425 | 30.482 | 1.00 18.17 |
| ATOM | 1209 | CZ | ARG | 156 | 0.922 | 10.609 | 29.719 | 1.00 18.70 |
| ATOM | 1210 | NH1 | ARG | 156 | 0.795 | 10.779 | 28.411 | 1.00 18.30 |
| ATOM | 1211 | NH2 | ARG | 156 | 2.131 | 10.605 | 30.265 | 1.00 19.27 |
| ATOM | 1212 | C | ARG | 156 | -3.100 | 6.807 | 28.154 | 1.00 14.58 |
| ATOM | 1213 | O | ARG | 156 | -2.753 | 6.945 | 26.984 | 1.00 14.45 |
| ATOM | 1214 | N | TYR | 157 | -4.372 | 6.858 | 28.541 | 1.00 14.25 |
| ATOM | 1215 | CA | TYR | 157 | -5.441 | 7.060 | 27.574 | 1.00 14.50 |
| ATOM | 1216 | CB | TYR | 157 | -6.040 | 5.715 | 27.173 | 1.00 15.15 |
| ATOM | 1217 | CG | TYR | 157 | -6.845 | 5.770 | 25.902 | 1.00 15.19 |

FIG.11B-29

| ATOM | 1218 | CD1 | TYR | 157 | -6.219 | 5.814 | 24.653 | 1.00 | 16.14 |
| ATOM | 1219 | CE1 | TYR | 157 | -6.965 | 5.864 | 23.472 | 1.00 | 16.78 |
| ATOM | 1220 | CD2 | TYR | 157 | -8.232 | 5.780 | 25.945 | 1.00 | 15.85 |
| ATOM | 1221 | CE2 | TYR | 157 | -8.987 | 5.832 | 24.783 | 1.00 | 17.07 |
| ATOM | 1222 | CZ | TYR | 157 | -8.356 | 5.875 | 23.548 | 1.00 | 17.48 |
| ATOM | 1223 | OH | TYR | 157 | -9.129 | 5.956 | 22.403 | 1.00 | 17.82 |
| ATOM | 1224 | C | TYR | 157 | -6.507 | 7.890 | 28.231 | 1.00 | 15.01 |
| ATOM | 1225 | O | TYR | 157 | -6.867 | 7.632 | 29.379 | 1.00 | 15.42 |
| ATOM | 1226 | N | ASN | 158 | -7.013 | 8.887 | 27.505 | 1.00 | 16.30 |
| ATOM | 1227 | CA | ASN | 158 | -8.033 | 9.786 | 28.047 | 1.00 | 16.67 |
| ATOM | 1228 | CB | ASN | 158 | -9.345 | 9.023 | 28.285 | 1.00 | 16.49 |
| ATOM | 1229 | CG | ASN | 158 | -10.097 | 8.800 | 26.961 | 1.00 | 15.70 |
| ATOM | 1230 | OD1 | ASN | 158 | -10.988 | 7.954 | 26.882 | 1.00 | 16.14 |
| ATOM | 1231 | ND2 | ASN | 158 | -9.741 | 9.569 | 25.927 | 1.00 | 13.85 |
| ATOM | 1232 | C | ASN | 158 | -7.543 | 10.420 | 29.336 | 1.00 | 18.61 |
| ATOM | 1233 | O | ASN | 158 | -8.312 | 10.640 | 30.278 | 1.00 | 17.84 |
| ATOM | 1234 | N | ASN | 159 | -6.242 | 10.706 | 29.348 | 1.00 | 19.74 |
| ATOM | 1235 | CA | ASN | 159 | -5.530 | 11.321 | 30.462 | 1.00 | 22.33 |
| ATOM | 1236 | CB | ASN | 159 | -6.099 | 12.713 | 30.758 | 1.00 | 24.30 |
| ATOM | 1237 | CG | ASN | 159 | -4.976 | 13.515 | 31.438 | 1.00 | 26.68 |
| ATOM | 1238 | OD1 | ASN | 159 | -3.879 | 13.667 | 30.885 | 1.00 | 28.50 |
| ATOM | 1239 | ND2 | ASN | 159 | -5.249 | 14.021 | 32.633 | 1.00 | 29.10 |
| ATOM | 1240 | C | ASN | 159 | -5.522 | 10.478 | 31.742 | 1.00 | 22.20 |
| ATOM | 1241 | O | ASN | 159 | -5.259 | 10.992 | 32.824 | 1.00 | 24.01 |
| ATOM | 1242 | N | ARG | 160 | -5.808 | 9.185 | 31.621 | 1.00 | 21.47 |
| ATOM | 1243 | CA | ARG | 160 | -5.803 | 8.298 | 32.781 | 1.00 | 20.69 |
| ATOM | 1244 | CB | ARG | 160 | -7.141 | 7.559 | 32.907 | 1.00 | 23.48 |
| ATOM | 1245 | CG | ARG | 160 | -8.091 | 8.097 | 34.011 | 1.00 | 28.38 |
| ATOM | 1246 | CD | ARG | 160 | -7.621 | 7.848 | 35.471 | 1.00 | 30.43 |
| ATOM | 1247 | NE | ARG | 160 | -8.739 | 7.883 | 36.411 | 1.00 | 34.64 |
| ATOM | 1248 | CZ | ARG | 160 | -9.202 | 8.978 | 37.008 | 1.00 | 35.54 |
| ATOM | 1249 | NH1 | ARG | 160 | -8.640 | 10.160 | 36.779 | 1.00 | 36.58 |
| ATOM | 1250 | NH2 | ARG | 160 | -10.246 | 8.890 | 37.829 | 1.00 | 37.21 |
| ATOM | 1251 | C | ARG | 160 | -4.668 | 7.290 | 32.612 | 1.00 | 19.16 |
| ATOM | 1252 | O | ARG | 160 | -4.591 | 6.601 | 31.602 | 1.00 | 18.07 |
| ATOM | 1253 | N | GLU | 161 | -3.778 | 7.225 | 33.597 | 1.00 | 17.48 |
| ATOM | 1254 | CA | GLU | 161 | -2.654 | 6.297 | 33.530 | 1.00 | 17.30 |
| ATOM | 1255 | CB | GLU | 161 | -1.528 | 6.741 | 34.468 | 1.00 | 16.64 |
| ATOM | 1256 | CG | GLU | 161 | -0.264 | 5.834 | 34.412 | 1.00 | 16.91 |
| ATOM | 1257 | CD | GLU | 161 | 0.821 | 6.223 | 35.416 | 1.00 | 18.42 |
| ATOM | 1258 | OE1 | GLU | 161 | 1.882 | 5.569 | 35.377 | 1.00 | 16.94 |
| ATOM | 1259 | OE2 | GLU | 161 | 0.606 | 7.154 | 36.224 | 1.00 | 19.58 |

FIG.11B-30

| ATOM | 1260 | C | GLU | 161 | -3.060 | 4.909 | 33.903 | 1.00 | 17.47 |
| ATOM | 1261 | O | GLU | 161 | -3.846 | 4.696 | 34.836 | 1.00 | 17.69 |
| ATOM | 1262 | N | ARG | 162 | -2.522 | 3.941 | 33.177 | 1.00 | 18.18 |
| ATOM | 1263 | CA | ARG | 162 | -2.785 | 2.536 | 33.425 | 1.00 | 18.75 |
| ATOM | 1264 | CB | ARG | 162 | -3.133 | 1.824 | 32.121 | 1.00 | 22.41 |
| ATOM | 1265 | CG | ARG | 162 | -3.510 | 0.361 | 32.099 | 1.00 | 26.57 |
| ATOM | 1266 | CD | ARG | 162 | -4.025 | 0.042 | 30.639 | 1.00 | 29.14 |
| ATOM | 1267 | NE | ARG | 162 | -5.085 | 0.956 | 30.197 | 1.00 | 32.40 |
| ATOM | 1268 | CZ | ARG | 162 | -5.832 | 0.771 | 29.106 | 1.00 | 32.85 |
| ATOM | 1269 | NH1 | ARG | 162 | -6.771 | 1.651 | 28.776 | 1.00 | 33.54 |
| ATOM | 1270 | NH2 | ARG | 162 | -5.649 | -0.301 | 28.346 | 1.00 | 33.73 |
| ATOM | 1271 | C | ARG | 162 | -1.485 | 1.899 | 33.950 | 1.00 | 17.95 |
| ATOM | 1272 | O | ARG | 162 | -0.453 | 2.015 | 33.296 | 1.00 | 17.82 |
| ATOM | 1273 | N | LEU | 163 | -1.532 | 1.248 | 35.113 | 1.00 | 16.28 |
| ATOM | 1274 | CA | LEU | 163 | -0.330 | 0.593 | 35.641 | 1.00 | 15.46 |
| ATOM | 1275 | CB | LEU | 163 | -0.493 | 0.202 | 37.117 | 1.00 | 16.31 |
| ATOM | 1276 | CG | LEU | 163 | -0.758 | 1.459 | 37.945 | 1.00 | 16.62 |
| ATOM | 1277 | CD1 | LEU | 163 | -1.147 | 1.014 | 39.334 | 1.00 | 17.07 |
| ATOM | 1278 | CD2 | LEU | 163 | 0.467 | 2.387 | 37.975 | 1.00 | 16.61 |
| ATOM | 1279 | C | LEU | 163 | -0.113 | -0.686 | 34.842 | 1.00 | 15.82 |
| ATOM | 1280 | O | LEU | 163 | -1.077 | -1.349 | 34.424 | 1.00 | 16.39 |
| ATOM | 1281 | N | LEU | 164 | 1.147 | -1.031 | 34.611 | 1.00 | 14.65 |
| ATOM | 1282 | CA | LEU | 164 | 1.465 | -2.231 | 33.842 | 1.00 | 15.17 |
| ATOM | 1283 | CB | LEU | 164 | 2.642 | -1.950 | 32.903 | 1.00 | 15.48 |
| ATOM | 1284 | CG | LEU | 164 | 2.340 | -0.814 | 31.914 | 1.00 | 16.69 |
| ATOM | 1285 | CD1 | LEU | 164 | 3.528 | -0.691 | 30.973 | 1.00 | 17.58 |
| ATOM | 1286 | CD2 | LEU | 164 | 1.084 | -1.060 | 31.127 | 1.00 | 18.21 |
| ATOM | 1287 | C | LEU | 164 | 1.811 | -3.403 | 34.730 | 1.00 | 14.77 |
| ATOM | 1288 | O | LEU | 164 | 2.200 | -3.219 | 35.883 | 1.00 | 15.24 |
| ATOM | 1289 | N | ASN | 165 | 1.678 | -4.616 | 34.197 | 1.00 | 15.82 |
| ATOM | 1290 | CA | ASN | 165 | 2.017 | -5.809 | 34.962 | 1.00 | 17.49 |
| ATOM | 1291 | CB | ASN | 165 | 0.760 | -6.388 | 35.633 | 1.00 | 18.54 |
| ATOM | 1292 | CG | ASN | 165 | -0.289 | -6.794 | 34.623 | 1.00 | 18.94 |
| ATOM | 1293 | OD1 | ASN | 165 | -1.310 | -6.122 | 34.458 | 1.00 | 21.86 |
| ATOM | 1294 | ND2 | ASN | 165 | -0.038 | -7.887 | 33.929 | 1.00 | 18.29 |
| ATOM | 1295 | C | ASN | 165 | 2.692 | -6.894 | 34.084 | 1.00 | 18.31 |
| ATOM | 1296 | O | ASN | 165 | 3.203 | -7.887 | 34.595 | 1.00 | 19.20 |
| ATOM | 1297 | N | LYS | 166 | 2.701 | -6.687 | 32.773 | 1.00 | 18.68 |
| ATOM | 1298 | CA | LYS | 166 | 3.297 | -7.664 | 31.862 | 1.00 | 20.26 |
| ATOM | 1299 | CB | LYS | 166 | 2.916 | -7.359 | 30.408 | 1.00 | 21.66 |
| ATOM | 1300 | CG | LYS | 166 | 3.530 | -8.249 | 29.267 | 1.00 | 24.00 |
| ATOM | 1301 | CD | LYS | 166 | 3.333 | -7.673 | 27.802 | 1.00 | 26.84 |

FIG. 11B-31

| ATOM | 1302 | CE | LYS | 166 | 3.949 | -8.340 | 26.520 | 1.00 | 27.03 |
| ATOM | 1303 | NZ | LYS | 166 | 5.449 | -8.227 | 26.415 | 1.00 | 28.54 |
| ATOM | 1304 | C | LYS | 166 | 4.794 | -7.686 | 31.950 | 1.00 | 20.70 |
| ATOM | 1305 | O | LYS | 166 | 5.447 | -6.639 | 31.963 | 1.00 | 18.98 |
| ATOM | 1306 | N | MET | 167 | 5.355 | -8.886 | 32.019 | 1.00 | 21.49 |
| ATOM | 1307 | CA | MET | 167 | 6.800 | -9.013 | 32.071 | 1.00 | 23.10 |
| ATOM | 1308 | CB | MET | 167 | 7.203 | -10.281 | 32.863 | 1.00 | 26.20 |
| ATOM | 1309 | CG | MET | 167 | 7.427 | -10.090 | 34.463 | 1.00 | 29.77 |
| ATOM | 1310 | SD | MET | 167 | 7.743 | -11.672 | 35.352 | 1.00 | 36.62 |
| ATOM | 1311 | CE | MET | 167 | 6.109 | -12.412 | 35.356 | 1.00 | 34.01 |
| ATOM | 1312 | C | MET | 167 | 7.298 | -9.031 | 30.615 | 1.00 | 22.75 |
| ATOM | 1313 | O | MET | 167 | 6.861 | -9.837 | 29.789 | 1.00 | 22.16 |
| ATOM | 1314 | N | CYS | 168 | 8.169 | -8.083 | 30.292 | 1.00 | 21.44 |
| ATOM | 1315 | CA | CYS | 168 | 8.750 | -8.011 | 28.963 | 1.00 | 20.77 |
| ATOM | 1316 | CB | CYS | 168 | 7.754 | -7.523 | 27.926 | 1.00 | 22.35 |
| ATOM | 1317 | SG | CYS | 168 | 6.960 | -5.964 | 28.305 | 1.00 | 26.07 |
| ATOM | 1318 | C | CYS | 168 | 9.915 | -7.126 | 28.970 | 1.00 | 18.90 |
| ATOM | 1319 | O | CYS | 168 | 10.132 | -6.357 | 29.914 | 1.00 | 17.73 |
| ATOM | 1320 | N | GLY | 169 | 10.696 | -7.219 | 27.903 | 1.00 | 17.73 |
| ATOM | 1321 | CA | GLY | 169 | 11.908 | -6.437 | 27.812 | 1.00 | 15.14 |
| ATOM | 1322 | C | GLY | 169 | 13.074 | -7.384 | 27.579 | 1.00 | 15.05 |
| ATOM | 1323 | O | GLY | 169 | 12.889 | -8.485 | 27.043 | 1.00 | 14.39 |
| ATOM | 1324 | N | THR | 170 | 14.264 | -6.957 | 27.990 | 1.00 | 12.82 |
| ATOM | 1325 | CA | THR | 170 | 15.498 | -7.726 | 27.817 | 1.00 | 13.82 |
| ATOM | 1326 | CB | THR | 170 | 16.278 | -7.119 | 26.624 | 1.00 | 12.90 |
| ATOM | 1327 | OG1 | THR | 170 | 15.476 | -7.208 | 25.432 | 1.00 | 13.36 |
| ATOM | 1328 | CG2 | THR | 170 | 17.582 | -7.853 | 26.399 | 1.00 | 14.59 |
| ATOM | 1329 | C | THR | 170 | 16.183 | -7.607 | 29.174 | 1.00 | 13.27 |
| ATOM | 1330 | O | THR | 170 | 16.504 | -6.502 | 29.615 | 1.00 | 13.03 |
| ATOM | 1331 | N | LEU | 171 | 16.412 | -8.744 | 29.830 | 1.00 | 13.36 |
| ATOM | 1332 | CA | LEU | 171 | 16.961 | -8.761 | 31.187 | 1.00 | 14.06 |
| ATOM | 1333 | CB | LEU | 171 | 17.427 | -10.190 | 31.522 | 1.00 | 15.16 |
| ATOM | 1334 | CG | LEU | 171 | 16.873 | -10.997 | 32.714 | 1.00 | 20.32 |
| ATOM | 1335 | CD1 | LEU | 171 | 15.558 | -10.455 | 33.272 | 1.00 | 17.54 |
| ATOM | 1336 | CD2 | LEU | 171 | 16.747 | -12.464 | 32.274 | 1.00 | 18.34 |
| ATOM | 1337 | C | LEU | 171 | 18.032 | -7.726 | 31.600 | 1.00 | 13.09 |
| ATOM | 1338 | O | LEU | 171 | 17.877 | -7.043 | 32.629 | 1.00 | 12.73 |
| ATOM | 1339 | N | PRO | 172 | 19.128 | -7.608 | 30.836 | 1.00 | 12.83 |
| ATOM | 1340 | CD | PRO | 172 | 19.556 | -8.419 | 29.679 | 1.00 | 13.47 |
| ATOM | 1341 | CA | PRO | 172 | 20.161 | -6.633 | 31.212 | 1.00 | 12.48 |
| ATOM | 1342 | CB | PRO | 172 | 21.238 | -6.839 | 30.147 | 1.00 | 12.98 |
| ATOM | 1343 | CG | PRO | 172 | 21.049 | -8.280 | 29.732 | 1.00 | 13.76 |

FIG.11B-32

| | | | | | | | | |
|---|---|---|---|---|---|---|---|---|
| ATOM | 1344 | C | PRO | 172 | 19.673 | -5.187 | 31.274 | 1.00 12.70 |
| ATOM | 1345 | O | PRO | 172 | 20.249 | -4.360 | 31.993 | 1.00 12.82 |
| ATOM | 1346 | N | TYR | 173 | 18.624 | -4.894 | 30.521 | 1.00 11.48 |
| ATOM | 1347 | CA | TYR | 173 | 18.062 | -3.547 | 30.452 | 1.00 11.83 |
| ATOM | 1348 | CB | TYR | 173 | 17.718 | -3.207 | 29.009 | 1.00 12.45 |
| ATOM | 1349 | CG | TYR | 173 | 18.897 | -3.324 | 28.087 | 1.00 12.78 |
| ATOM | 1350 | CD1 | TYR | 173 | 19.693 | -2.222 | 27.820 | 1.00 13.91 |
| ATOM | 1351 | CE1 | TYR | 173 | 20.812 | -2.319 | 26.989 | 1.00 14.46 |
| ATOM | 1352 | CD2 | TYR | 173 | 19.236 | -4.546 | 27.501 | 1.00 13.62 |
| ATOM | 1353 | CE2 | TYR | 173 | 20.347 | -4.657 | 26.668 | 1.00 15.04 |
| ATOM | 1354 | CZ | TYR | 173 | 21.128 | -3.539 | 26.419 | 1.00 15.41 |
| ATOM | 1355 | OH | TYR | 173 | 22.231 | -3.623 | 25.594 | 1.00 18.27 |
| ATOM | 1356 | C | TYR | 173 | 16.771 | -3.330 | 31.236 | 1.00 12.34 |
| ATOM | 1357 | O | TYR | 173 | 16.294 | -2.199 | 31.346 | 1.00 11.61 |
| ATOM | 1358 | N | VAL | 174 | 16.205 | -4.388 | 31.800 | 1.00 12.77 |
| ATOM | 1359 | CA | VAL | 174 | 14.927 | -4.226 | 32.484 | 1.00 12.44 |
| ATOM | 1360 | CB | VAL | 174 | 14.149 | -5.562 | 32.469 | 1.00 14.29 |
| ATOM | 1361 | CG1 | VAL | 174 | 14.648 | -6.479 | 33.574 | 1.00 15.43 |
| ATOM | 1362 | CG2 | VAL | 174 | 12.646 | -5.292 | 32.580 | 1.00 14.81 |
| ATOM | 1363 | C | VAL | 174 | 15.052 | -3.659 | 33.929 | 1.00 12.17 |
| ATOM | 1364 | O | VAL | 174 | 16.020 | -3.917 | 34.619 | 1.00 12.63 |
| ATOM | 1365 | N | ALA | 175 | 14.059 | -2.869 | 34.324 | 1.00 11.21 |
| ATOM | 1366 | CA | ALA | 175 | 14.018 | -2.252 | 35.654 | 1.00 11.66 |
| ATOM | 1367 | CB | ALA | 175 | 12.929 | -1.210 | 35.686 | 1.00 13.92 |
| ATOM | 1368 | C | ALA | 175 | 13.755 | -3.319 | 36.743 | 1.00 11.10 |
| ATOM | 1369 | O | ALA | 175 | 12.995 | -4.250 | 36.529 | 1.00 12.27 |
| ATOM | 1370 | N | PRO | 176 | 14.346 | -3.148 | 37.928 | 1.00 11.44 |
| ATOM | 1371 | CD | PRO | 176 | 15.232 | -2.035 | 38.314 | 1.00 12.40 |
| ATOM | 1372 | CA | PRO | 176 | 14.174 | -4.106 | 39.026 | 1.00 12.63 |
| ATOM | 1373 | CB | PRO | 176 | 15.124 | -3.569 | 40.097 | 1.00 12.54 |
| ATOM | 1374 | CG | PRO | 176 | 15.164 | -2.081 | 39.831 | 1.00 12.85 |
| ATOM | 1375 | C | PRO | 176 | 12.734 | -4.318 | 39.479 | 1.00 13.15 |
| ATOM | 1376 | O | PRO | 176 | 12.368 | -5.422 | 39.919 | 1.00 13.29 |
| ATOM | 1377 | N | GLU | 177 | 11.906 | -3.292 | 39.346 | 1.00 12.90 |
| ATOM | 1378 | CA | GLU | 177 | 10.525 | -3.432 | 39.788 | 1.00 14.16 |
| ATOM | 1379 | CB | GLU | 177 | 9.798 | -2.087 | 39.740 | 1.00 14.13 |
| ATOM | 1380 | CG | GLU | 177 | 9.624 | -1.333 | 38.419 | 1.00 13.02 |
| ATOM | 1381 | CD | GLU | 177 | 10.815 | -0.414 | 38.186 | 1.00 13.91 |
| ATOM | 1382 | OE1 | GLU | 177 | 10.624 | 0.519 | 37.371 | 1.00 13.00 |
| ATOM | 1383 | OE2 | GLU | 177 | 11.914 | -0.606 | 38.767 | 1.00 13.08 |
| ATOM | 1384 | C | GLU | 177 | 9.746 | -4.486 | 38.978 | 1.00 15.90 |
| ATOM | 1385 | O | GLU | 177 | 8.798 | -5.064 | 39.482 | 1.00 17.12 |

FIG.11B-33

| ATOM | 1386 | N   | LEU | 178 | 10.129 | -4.729 | 37.726 | 1.00 | 16.49 |
|------|------|-----|-----|-----|--------|--------|--------|------|-------|
| ATOM | 1387 | CA  | LEU | 178 | 9.424  | -5.742 | 36.943 | 1.00 | 19.28 |
| ATOM | 1388 | CB  | LEU | 178 | 9.957  | -5.804 | 35.506 | 1.00 | 22.15 |
| ATOM | 1389 | CG  | LEU | 178 | 9.454  | -6.848 | 34.501 | 1.00 | 24.53 |
| ATOM | 1390 | CD1 | LEU | 178 | 10.036 | -8.220 | 34.827 | 1.00 | 25.14 |
| ATOM | 1391 | CD2 | LEU | 178 | 7.927  | -6.873 | 34.518 | 1.00 | 25.07 |
| ATOM | 1392 | C   | LEU | 178 | 9.622  | -7.096 | 37.565 | 1.00 | 20.37 |
| ATOM | 1393 | O   | LEU | 178 | 8.739  | -7.954 | 37.516 | 1.00 | 20.98 |
| ATOM | 1394 | N   | LEU | 179 | 10.791 | -7.302 | 38.155 | 1.00 | 20.27 |
| ATOM | 1395 | CA  | LEU | 179 | 11.101 | -8.584 | 38.766 | 1.00 | 21.63 |
| ATOM | 1396 | CB  | LEU | 179 | 12.617 | -8.838 | 38.700 | 1.00 | 21.75 |
| ATOM | 1397 | CG  | LEU | 179 | 13.233 | -8.817 | 37.294 | 1.00 | 23.23 |
| ATOM | 1398 | CD1 | LEU | 179 | 14.748 | -8.931 | 37.351 | 1.00 | 22.87 |
| ATOM | 1399 | CD2 | LEU | 179 | 12.639 | -9.954 | 36.485 | 1.00 | 22.80 |
| ATOM | 1400 | C   | LEU | 179 | 10.628 | -8.700 | 40.202 | 1.00 | 22.23 |
| ATOM | 1401 | O   | LEU | 179 | 10.591 | -9.799 | 40.767 | 1.00 | 24.11 |
| ATOM | 1402 | N   | LYS | 180 | 10.230 | -7.594 | 40.810 | 1.00 | 21.86 |
| ATOM | 1403 | CA  | LYS | 180 | 9.827  | -7.680 | 42.212 | 1.00 | 22.25 |
| ATOM | 1404 | CB  | LYS | 180 | 10.813 | -6.909 | 43.092 | 1.00 | 24.33 |
| ATOM | 1405 | CG  | LYS | 180 | 10.945 | -5.385 | 42.935 | 1.00 | 27.64 |
| ATOM | 1406 | CD  | LYS | 180 | 11.950 | -4.753 | 43.967 | 1.00 | 30.62 |
| ATOM | 1407 | CE  | LYS | 180 | 13.334 | -5.432 | 43.916 | 1.00 | 31.90 |
| ATOM | 1408 | NZ  | LYS | 180 | 14.305 | -4.830 | 44.871 | 1.00 | 34.05 |
| ATOM | 1409 | C   | LYS | 180 | 8.454  | -7.213 | 42.594 | 1.00 | 21.51 |
| ATOM | 1410 | O   | LYS | 180 | 8.007  | -7.463 | 43.718 | 1.00 | 21.61 |
| ATOM | 1411 | N   | ARG | 181 | 7.760  | -6.547 | 41.680 | 1.00 | 20.15 |
| ATOM | 1412 | CA  | ARG | 181 | 6.438  | -6.015 | 41.981 | 1.00 | 19.69 |
| ATOM | 1413 | CB  | ARG | 181 | 6.455  | -4.483 | 41.919 | 1.00 | 20.79 |
| ATOM | 1414 | CG  | ARG | 181 | 7.705  | -3.742 | 42.554 | 1.00 | 23.16 |
| ATOM | 1415 | CD  | ARG | 181 | 8.028  | -2.949 | 43.866 | 1.00 | 27.13 |
| ATOM | 1416 | NE  | ARG | 181 | 7.696  | -3.723 | 45.039 | 1.00 | 26.61 |
| ATOM | 1417 | CZ  | ARG | 181 | 8.122  | -3.493 | 46.281 | 1.00 | 27.46 |
| ATOM | 1418 | NH1 | ARG | 181 | 7.708  | -4.294 | 47.244 | 1.00 | 25.45 |
| ATOM | 1419 | NH2 | ARG | 181 | 8.959  | -2.501 | 46.570 | 1.00 | 29.25 |
| ATOM | 1420 | C   | ARG | 181 | 5.384  | -6.516 | 40.995 | 1.00 | 19.43 |
| ATOM | 1421 | O   | ARG | 181 | 5.679  | -6.774 | 39.818 | 1.00 | 18.33 |
| ATOM | 1422 | N   | ARG | 182 | 4.153  | -6.673 | 41.468 | 1.00 | 18.70 |
| ATOM | 1423 | CA  | ARG | 182 | 3.090  | -7.125 | 40.576 | 1.00 | 19.47 |
| ATOM | 1424 | CB  | ARG | 182 | 1.813  | -7.460 | 41.348 | 1.00 | 22.25 |
| ATOM | 1425 | CG  | ARG | 182 | 0.886  | -8.101 | 40.297 | 1.00 | 26.02 |
| ATOM | 1426 | CD  | ARG | 182 | -0.443 | -8.656 | 40.836 | 1.00 | 27.77 |
| ATOM | 1427 | NE  | ARG | 182 | -1.305 | -7.590 | 41.330 | 1.00 | 31.09 |

FIG.11B-34

| | | | | | | | | |
|---|---|---|---|---|---|---|---|---|
| ATOM | 1428 | CZ | ARG | 182 | -2.507 | -7.787 | 41.859 | 1.00 33.26 |
| ATOM | 1429 | NH1 | ARG | 182 | -2.995 | -9.017 | 41.970 | 1.00 34.85 |
| ATOM | 1430 | NH2 | ARG | 182 | -3.225 | -6.749 | 42.269 | 1.00 34.56 |
| ATOM | 1431 | C | ARG | 182 | 2.728 | -6.068 | 39.537 | 1.00 18.40 |
| ATOM | 1432 | O | ARG | 182 | 2.482 | -6.397 | 38.372 | 1.00 19.29 |
| ATOM | 1433 | N | GLU | 183 | 2.668 | -4.808 | 39.958 | 1.00 17.24 |
| ATOM | 1434 | CA | GLU | 183 | 2.337 | -3.715 | 39.049 | 1.00 16.19 |
| ATOM | 1435 | CB | GLU | 183 | 0.974 | -3.102 | 39.394 | 1.00 17.54 |
| ATOM | 1436 | CG | GLU | 183 | -0.225 | -4.044 | 39.253 | 1.00 19.75 |
| ATOM | 1437 | CD | GLU | 183 | -1.439 | -3.182 | 39.621 | 1.00 21.38 |
| ATOM | 1438 | OE1 | GLU | 183 | -1.593 | -2.835 | 40.813 | 1.00 23.31 |
| ATOM | 1439 | OE2 | GLU | 183 | -2.208 | -2.855 | 38.697 | 1.00 21.76 |
| ATOM | 1440 | C | GLU | 183 | 3.387 | -2.621 | 39.147 | 1.00 15.05 |
| ATOM | 1441 | O | GLU | 183 | 4.085 | -2.503 | 40.148 | 1.00 13.47 |
| ATOM | 1442 | N | PHE | 184 | 3.480 | -1.797 | 38.111 | 1.00 14.19 |
| ATOM | 1443 | CA | PHE | 184 | 4.474 | -0.738 | 38.107 | 1.00 14.24 |
| ATOM | 1444 | CB | PHE | 184 | 5.861 | -1.343 | 37.825 | 1.00 14.97 |
| ATOM | 1445 | CG | PHE | 184 | 5.849 | -2.409 | 36.762 | 1.00 13.01 |
| ATOM | 1446 | CD1 | PHE | 184 | 5.814 | -2.079 | 35.414 | 1.00 14.32 |
| ATOM | 1447 | CD2 | PHE | 184 | 5.768 | -3.752 | 37.122 | 1.00 13.96 |
| ATOM | 1448 | CE1 | PHE | 184 | 5.688 | -3.068 | 34.441 | 1.00 14.25 |
| ATOM | 1449 | CE2 | PHE | 184 | 5.637 | -4.754 | 36.154 | 1.00 13.88 |
| ATOM | 1450 | CZ | PHE | 184 | 5.595 | -4.407 | 34.814 | 1.00 14.77 |
| ATOM | 1451 | C | PHE | 184 | 4.138 | 0.318 | 37.093 | 1.00 14.04 |
| ATOM | 1452 | O | PHE | 184 | 3.427 | 0.063 | 36.120 | 1.00 12.37 |
| ATOM | 1453 | N | HIS | 185 | 4.631 | 1.524 | 37.342 | 1.00 12.36 |
| ATOM | 1454 | CA | HIS | 185 | 4.442 | 2.649 | 36.434 | 1.00 13.40 |
| ATOM | 1455 | CB | HIS | 185 | 4.892 | 3.934 | 37.121 | 1.00 13.03 |
| ATOM | 1456 | CG | HIS | 185 | 3.947 | 4.418 | 38.174 | 1.00 12.93 |
| ATOM | 1457 | CD2 | HIS | 185 | 4.013 | 4.381 | 39.527 | 1.00 12.64 |
| ATOM | 1458 | ND1 | HIS | 185 | 2.770 | 5.065 | 37.865 | 1.00 12.62 |
| ATOM | 1459 | CE1 | HIS | 185 | 2.155 | 5.412 | 38.981 | 1.00 13.67 |
| ATOM | 1460 | NE2 | HIS | 185 | 2.886 | 5.012 | 40.005 | 1.00 12.93 |
| ATOM | 1461 | C | HIS | 185 | 5.292 | 2.422 | 35.164 | 1.00 13.36 |
| ATOM | 1462 | O | HIS | 185 | 6.444 | 1.978 | 35.236 | 1.00 13.73 |
| ATOM | 1463 | N | ALA | 186 | 4.723 | 2.728 | 34.005 | 1.00 12.12 |
| ATOM | 1464 | CA | ALA | 186 | 5.444 | 2.519 | 32.754 | 1.00 11.23 |
| ATOM | 1465 | CB | ALA | 186 | 4.494 | 2.722 | 31.587 | 1.00 12.26 |
| ATOM | 1466 | C | ALA | 186 | 6.677 | 3.422 | 32.541 | 1.00 11.54 |
| ATOM | 1467 | O | ALA | 186 | 7.739 | 2.964 | 32.104 | 1.00 10.68 |
| ATOM | 1468 | N | GLU | 187 | 6.530 | 4.698 | 32.855 | 1.00 10.75 |
| ATOM | 1469 | CA | GLU | 187 | 7.602 | 5.648 | 32.564 | 1.00 10.72 |

FIG.11B-35

| | | | | | | | | | |
|---|---|---|---|---|---|---|---|---|---|
| ATOM | 1470 | CB | GLU | 187 | 7.133 | 7.070 | 32.879 | 1.00 | 11.96 |
| ATOM | 1471 | CG | GLU | 187 | 6.042 | 7.443 | 31.817 | 1.00 | 13.69 |
| ATOM | 1472 | CD | GLU | 187 | 5.429 | 8.758 | 32.247 | 1.00 | 15.11 |
| ATOM | 1473 | OE1 | GLU | 187 | 5.768 | 9.825 | 31.693 | 1.00 | 15.93 |
| ATOM | 1474 | OE2 | GLU | 187 | 4.596 | 8.703 | 33.175 | 1.00 | 16.67 |
| ATOM | 1475 | C | GLU | 187 | 8.974 | 5.371 | 33.186 | 1.00 | 10.14 |
| ATOM | 1476 | O | GLU | 187 | 9.990 | 5.441 | 32.487 | 1.00 | 10.23 |
| ATOM | 1477 | N | PRO | 188 | 9.032 | 5.065 | 34.490 | 1.00 | 10.27 |
| ATOM | 1478 | CD | PRO | 188 | 7.972 | 5.138 | 35.507 | 1.00 | 10.22 |
| ATOM | 1479 | CA | PRO | 188 | 10.346 | 4.792 | 35.105 | 1.00 | 10.11 |
| ATOM | 1480 | CB | PRO | 188 | 10.013 | 4.656 | 36.610 | 1.00 | 10.75 |
| ATOM | 1481 | CG | PRO | 188 | 8.762 | 5.516 | 36.770 | 1.00 | 9.50 |
| ATOM | 1482 | C | PRO | 188 | 11.046 | 3.548 | 34.514 | 1.00 | 10.42 |
| ATOM | 1483 | O | PRO | 188 | 12.261 | 3.450 | 34.570 | 1.00 | 10.08 |
| ATOM | 1484 | N | VAL | 189 | 10.284 | 2.601 | 33.957 | 1.00 | 11.14 |
| ATOM | 1485 | CA | VAL | 189 | 10.893 | 1.404 | 33.363 | 1.00 | 10.35 |
| ATOM | 1486 | CB | VAL | 189 | 9.798 | 0.368 | 33.002 | 1.00 | 10.10 |
| ATOM | 1487 | CG1 | VAL | 189 | 10.406 | -0.821 | 32.238 | 1.00 | 10.42 |
| ATOM | 1488 | CG2 | VAL | 189 | 9.118 | -0.113 | 34.271 | 1.00 | 11.67 |
| ATOM | 1489 | C | VAL | 189 | 11.706 | 1.826 | 32.106 | 1.00 | 10.38 |
| ATOM | 1490 | O | VAL | 189 | 12.848 | 1.387 | 31.906 | 1.00 | 10.25 |
| ATOM | 1491 | N | ASP | 190 | 11.117 | 2.692 | 31.284 | 1.00 | 10.88 |
| ATOM | 1492 | CA | ASP | 190 | 11.811 | 3.165 | 30.102 | 1.00 | 10.93 |
| ATOM | 1493 | CB | ASP | 190 | 10.873 | 3.938 | 29.160 | 1.00 | 11.48 |
| ATOM | 1494 | CG | ASP | 190 | 9.993 | 3.059 | 28.286 | 1.00 | 12.68 |
| ATOM | 1495 | OD1 | ASP | 190 | 10.297 | 1.881 | 28.008 | 1.00 | 12.41 |
| ATOM | 1496 | OD2 | ASP | 190 | 8.958 | 3.577 | 27.818 | 1.00 | 13.13 |
| ATOM | 1497 | C | ASP | 190 | 12.991 | 4.064 | 30.512 | 1.00 | 10.81 |
| ATOM | 1498 | O | ASP | 190 | 14.032 | 4.050 | 29.855 | 1.00 | 10.56 |
| ATOM | 1499 | N | VAL | 191 | 12.850 | 4.818 | 31.603 | 1.00 | 10.14 |
| ATOM | 1500 | CA | VAL | 191 | 13.963 | 5.665 | 32.039 | 1.00 | 9.64 |
| ATOM | 1501 | CB | VAL | 191 | 13.568 | 6.510 | 33.259 | 1.00 | 9.54 |
| ATOM | 1502 | CG1 | VAL | 191 | 14.815 | 7.130 | 33.895 | 1.00 | 10.40 |
| ATOM | 1503 | CG2 | VAL | 191 | 12.573 | 7.614 | 32.808 | 1.00 | 10.05 |
| ATOM | 1504 | C | VAL | 191 | 15.173 | 4.766 | 32.422 | 1.00 | 9.21 |
| ATOM | 1505 | O | VAL | 191 | 16.327 | 5.059 | 32.085 | 1.00 | 9.71 |
| ATOM | 1506 | N | TRP | 192 | 14.889 | 3.691 | 33.145 | 1.00 | 9.61 |
| ATOM | 1507 | CA | TRP | 192 | 15.935 | 2.769 | 33.572 | 1.00 | 9.80 |
| ATOM | 1508 | CB | TRP | 192 | 15.321 | 1.662 | 34.439 | 1.00 | 9.06 |
| ATOM | 1509 | CG | TRP | 192 | 16.300 | 0.619 | 34.873 | 1.00 | 10.53 |
| ATOM | 1510 | CD2 | TRP | 192 | 16.870 | 0.465 | 36.183 | 1.00 | 10.09 |
| ATOM | 1511 | CE2 | TRP | 192 | 17.739 | -0.646 | 36.129 | 1.00 | 10.53 |

FIG.11B-36

| | | | | | | | | |
|---|---|---|---|---|---|---|---|---|
| ATOM | 1512 | CE3 | TRP | 192 | 16.722 | 1.150 | 37.398 | 1.00 11.26 |
| ATOM | 1513 | CD1 | TRP | 192 | 16.834 | -0.371 | 34.105 | 1.00 10.22 |
| ATOM | 1514 | NE1 | TRP | 192 | 17.695 | -1.135 | 34.852 | 1.00 11.11 |
| ATOM | 1515 | CZ2 | TRP | 192 | 18.466 | -1.091 | 37.245 | 1.00 11.96 |
| ATOM | 1516 | CZ3 | TRP | 192 | 17.442 | 0.703 | 38.514 | 1.00 11.54 |
| ATOM | 1517 | CH2 | TRP | 192 | 18.305 | -0.409 | 38.421 | 1.00 10.99 |
| ATOM | 1518 | C | TRP | 192 | 16.684 | 2.150 | 32.394 | 1.00 9.91 |
| ATOM | 1519 | O | TRP | 192 | 17.927 | 2.133 | 32.389 | 1.00 9.89 |
| ATOM | 1520 | N | SER | 193 | 15.949 | 1.619 | 31.412 | 1.00 9.48 |
| ATOM | 1521 | CA | SER | 193 | 16.618 | 1.031 | 30.253 | 1.00 9.06 |
| ATOM | 1522 | CB | SER | 193 | 15.610 | 0.363 | 29.307 | 1.00 9.01 |
| ATOM | 1523 | OG | SER | 193 | 14.587 | 1.257 | 28.916 | 1.00 11.65 |
| ATOM | 1524 | C | SER | 193 | 17.463 | 2.104 | 29.510 | 1.00 9.89 |
| ATOM | 1525 | O | SER | 193 | 18.520 | 1.780 | 28.967 | 1.00 9.64 |
| ATOM | 1526 | N | CYS | 194 | 16.999 | 3.356 | 29.479 | 1.00 9.70 |
| ATOM | 1527 | CA | CYS | 194 | 17.796 | 4.415 | 28.847 | 1.00 9.62 |
| ATOM | 1528 | CB | CYS | 194 | 17.061 | 5.766 | 28.851 | 1.00 9.27 |
| ATOM | 1529 | SG | CYS | 194 | 15.742 | 5.746 | 27.560 | 1.00 12.52 |
| ATOM | 1530 | C | CYS | 194 | 19.151 | 4.594 | 29.654 | 1.00 9.45 |
| ATOM | 1531 | O | CYS | 194 | 20.178 | 4.902 | 29.068 | 1.00 9.86 |
| ATOM | 1532 | N | GLY | 195 | 19.104 | 4.380 | 30.965 | 1.00 9.58 |
| ATOM | 1533 | CA | GLY | 195 | 20.307 | 4.477 | 31.793 | 1.00 9.44 |
| ATOM | 1534 | C | GLY | 195 | 21.288 | 3.352 | 31.471 | 1.00 10.40 |
| ATOM | 1535 | O | GLY | 195 | 22.498 | 3.555 | 31.435 | 1.00 10.09 |
| ATOM | 1536 | N | ILE | 196 | 20.762 | 2.156 | 31.232 | 1.00 10.86 |
| ATOM | 1537 | CA | ILE | 196 | 21.631 | 1.023 | 30.897 | 1.00 12.49 |
| ATOM | 1538 | CB | ILE | 196 | 20.823 | -0.290 | 30.971 | 1.00 13.21 |
| ATOM | 1539 | CG2 | ILE | 196 | 19.584 | -0.159 | 30.189 | 1.00 18.11 |
| ATOM | 1540 | CG1 | ILE | 196 | 21.610 | -1.452 | 30.371 | 1.00 14.47 |
| ATOM | 1541 | CD1 | ILE | 196 | 22.737 | -1.828 | 31.133 | 1.00 18.68 |
| ATOM | 1542 | C | ILE | 196 | 22.249 | 1.273 | 29.493 | 1.00 11.39 |
| ATOM | 1543 | O | ILE | 196 | 23.409 | 0.928 | 29.249 | 1.00 11.50 |
| ATOM | 1544 | N | VAL | 197 | 21.476 | 1.887 | 28.592 | 1.00 10.64 |
| ATOM | 1545 | CA | VAL | 197 | 21.989 | 2.198 | 27.257 | 1.00 9.96 |
| ATOM | 1546 | CB | VAL | 197 | 20.868 | 2.778 | 26.358 | 1.00 9.29 |
| ATOM | 1547 | CG1 | VAL | 197 | 21.465 | 3.425 | 25.088 | 1.00 10.47 |
| ATOM | 1548 | CG2 | VAL | 197 | 19.911 | 1.637 | 25.963 | 1.00 10.17 |
| ATOM | 1549 | C | VAL | 197 | 23.129 | 3.209 | 27.398 | 1.00 10.49 |
| ATOM | 1550 | O | VAL | 197 | 24.161 | 3.108 | 26.726 | 1.00 10.94 |
| ATOM | 1551 | N | LEU | 198 | 22.944 | 4.178 | 28.292 | 1.00 10.69 |
| ATOM | 1552 | CA | LEU | 198 | 23.977 | 5.194 | 28.517 | 1.00 11.25 |
| ATOM | 1553 | CB | LEU | 198 | 23.537 | 6.200 | 29.571 | 1.00 12.55 |

FIG.11B-37

| ATOM | 1554 | CG | LEU | 198 | 23.879 | 7.664 | 29.261 | 1.00 | 16.51 |
| --- | --- | --- | --- | --- | --- | --- | --- | --- | --- |
| ATOM | 1555 | CD1 | LEU | 198 | 23.869 | 8.361 | 30.615 | 1.00 | 12.50 |
| ATOM | 1556 | CD2 | LEU | 198 | 25.154 | 7.918 | 28.500 | 1.00 | 13.83 |
| ATOM | 1557 | C | LEU | 198 | 25.253 | 4.511 | 29.047 | 1.00 | 11.79 |
| ATOM | 1558 | O | LEU | 198 | 26.371 | 4.801 | 28.600 | 1.00 | 11.82 |
| ATOM | 1559 | N | THR | 199 | 25.067 | 3.592 | 29.985 | 1.00 | 11.20 |
| ATOM | 1560 | CA | THR | 199 | 26.199 | 2.862 | 30.574 | 1.00 | 11.87 |
| ATOM | 1561 | CB | THR | 199 | 25.699 | 1.860 | 31.641 | 1.00 | 11.32 |
| ATOM | 1562 | OG1 | THR | 199 | 25.041 | 2.585 | 32.677 | 1.00 | 11.23 |
| ATOM | 1563 | CG2 | THR | 199 | 26.878 | 1.088 | 32.291 | 1.00 | 11.31 |
| ATOM | 1564 | C | THR | 199 | 26.947 | 2.154 | 29.486 | 1.00 | 12.08 |
| ATOM | 1565 | O | THR | 199 | 28.181 | 2.237 | 29.410 | 1.00 | 12.74 |
| ATOM | 1566 | N | ALA | 200 | 26.202 | 1.474 | 28.614 | 1.00 | 13.09 |
| ATOM | 1567 | CA | ALA | 200 | 26.805 | 0.737 | 27.506 | 1.00 | 13.17 |
| ATOM | 1568 | CB | ALA | 200 | 25.720 | 0.002 | 26.712 | 1.00 | 12.95 |
| ATOM | 1569 | C | ALA | 200 | 27.589 | 1.668 | 26.568 | 1.00 | 14.04 |
| ATOM | 1570 | O | ALA | 200 | 28.690 | 1.345 | 26.140 | 1.00 | 13.51 |
| ATOM | 1571 | N | MET | 201 | 27.023 | 2.822 | 26.241 | 1.00 | 12.86 |
| ATOM | 1572 | CA | MET | 201 | 27.725 | 3.728 | 25.335 | 1.00 | 12.63 |
| ATOM | 1573 | CB | MET | 201 | 26.849 | 4.930 | 24.954 | 1.00 | 12.56 |
| ATOM | 1574 | CG | MET | 201 | 25.592 | 4.544 | 24.110 | 1.00 | 13.61 |
| ATOM | 1575 | SD | MET | 201 | 24.831 | 6.026 | 23.390 | 1.00 | 12.69 |
| ATOM | 1576 | CE | MET | 201 | 24.080 | 6.854 | 24.850 | 1.00 | 12.19 |
| ATOM | 1577 | C | MET | 201 | 29.011 | 4.268 | 25.933 | 1.00 | 12.12 |
| ATOM | 1578 | O | MET | 201 | 29.997 | 4.484 | 25.222 | 1.00 | 12.45 |
| ATOM | 1579 | N | LEU | 202 | 29.019 | 4.458 | 27.247 | 1.00 | 11.16 |
| ATOM | 1580 | CA | LEU | 202 | 30.199 | 5.014 | 27.907 | 1.00 | 12.42 |
| ATOM | 1581 | CB | LEU | 202 | 29.782 | 5.864 | 29.110 | 1.00 | 12.19 |
| ATOM | 1582 | CG | LEU | 202 | 28.994 | 7.113 | 28.691 | 1.00 | 11.96 |
| ATOM | 1583 | CD1 | LEU | 202 | 28.551 | 7.912 | 29.931 | 1.00 | 13.07 |
| ATOM | 1584 | CD2 | LEU | 202 | 29.891 | 7.960 | 27.796 | 1.00 | 12.51 |
| ATOM | 1585 | C | LEU | 202 | 31.262 | 4.003 | 28.384 | 1.00 | 13.40 |
| ATOM | 1586 | O | LEU | 202 | 32.414 | 4.384 | 28.610 | 1.00 | 14.80 |
| ATOM | 1587 | N | ALA | 203 | 30.893 | 2.734 | 28.514 | 1.00 | 13.10 |
| ATOM | 1588 | CA | ALA | 203 | 31.839 | 1.726 | 28.988 | 1.00 | 15.17 |
| ATOM | 1589 | CB | ALA | 203 | 31.424 | 1.252 | 30.367 | 1.00 | 14.79 |
| ATOM | 1590 | C | ALA | 203 | 32.004 | 0.521 | 28.047 | 1.00 | 15.81 |
| ATOM | 1591 | O | ALA | 203 | 32.926 | -0.290 | 28.216 | 1.00 | 17.03 |
| ATOM | 1592 | N | GLY | 204 | 31.117 | 0.394 | 27.070 | 1.00 | 15.77 |
| ATOM | 1593 | CA | GLY | 204 | 31.218 | -0.728 | 26.149 | 1.00 | 17.71 |
| ATOM | 1594 | C | GLY | 204 | 30.957 | -2.072 | 26.803 | 1.00 | 18.37 |
| ATOM | 1595 | O | GLY | 204 | 31.451 | -3.112 | 26.340 | 1.00 | 19.10 |

FIG. 11B-38

| ATOM | 1596 | N | GLU | 205 | 30.199 | -2.052 | 27.888 | 1.00 | 18.22 |
| --- | --- | --- | --- | --- | --- | --- | --- | --- | --- |
| ATOM | 1597 | CA | GLU | 205 | 29.850 | -3.268 | 28.610 | 1.00 | 19.72 |
| ATOM | 1598 | CB | GLU | 205 | 30.977 | -3.692 | 29.552 | 1.00 | 22.13 |
| ATOM | 1599 | CG | GLU | 205 | 31.134 | -3.004 | 30.896 | 1.00 | 24.83 |
| ATOM | 1600 | CD | GLU | 205 | 32.225 | -3.740 | 31.729 | 1.00 | 25.92 |
| ATOM | 1601 | OE1 | GLU | 205 | 32.102 | -4.890 | 32.202 | 1.00 | 28.12 |
| ATOM | 1602 | OE2 | GLU | 205 | 33.274 | -3.121 | 31.912 | 1.00 | 26.08 |
| ATOM | 1603 | C | GLU | 205 | 28.582 | -3.039 | 29.424 | 1.00 | 18.53 |
| ATOM | 1604 | O | GLU | 205 | 28.292 | -1.915 | 29.845 | 1.00 | 18.22 |
| ATOM | 1605 | N | LEU | 206 | 27.819 | -4.107 | 29.622 | 1.00 | 17.56 |
| ATOM | 1606 | CA | LEU | 206 | 26.579 | -4.045 | 30.396 | 1.00 | 17.14 |
| ATOM | 1607 | CB | LEU | 206 | 25.563 | -5.054 | 29.847 | 1.00 | 17.00 |
| ATOM | 1608 | CG | LEU | 206 | 25.030 | -4.728 | 28.447 | 1.00 | 18.03 |
| ATOM | 1609 | CD1 | LEU | 206 | 26.152 | -4.419 | 27.471 | 1.00 | 22.13 |
| ATOM | 1610 | CD2 | LEU | 206 | 24.233 | -5.927 | 27.948 | 1.00 | 17.79 |
| ATOM | 1611 | C | LEU | 206 | 26.976 | -4.351 | 31.811 | 1.00 | 16.84 |
| ATOM | 1612 | O | LEU | 206 | 27.782 | -5.263 | 32.057 | 1.00 | 16.85 |
| ATOM | 1613 | N | PRO | 207 | 26.420 | -3.604 | 32.777 | 1.00 | 16.25 |
| ATOM | 1614 | CD | PRO | 207 | 25.415 | -2.545 | 32.548 | 1.00 | 15.91 |
| ATOM | 1615 | CA | PRO | 207 | 26.712 | -3.757 | 34.209 | 1.00 | 16.93 |
| ATOM | 1616 | CB | PRO | 207 | 26.077 | -2.503 | 34.816 | 1.00 | 16.06 |
| ATOM | 1617 | CG | PRO | 207 | 24.870 | -2.295 | 33.934 | 1.00 | 15.81 |
| ATOM | 1618 | C | PRO | 207 | 26.305 | -5.042 | 34.871 | 1.00 | 17.01 |
| ATOM | 1619 | O | PRO | 207 | 27.012 | -5.518 | 35.767 | 1.00 | 17.85 |
| ATOM | 1620 | N | TRP | 208 | 25.181 | -5.626 | 34.454 | 1.00 | 16.29 |
| ATOM | 1621 | CA | TRP | 208 | 24.726 | -6.868 | 35.074 | 1.00 | 16.75 |
| ATOM | 1622 | CB | TRP | 208 | 24.006 | -6.564 | 36.392 | 1.00 | 16.28 |
| ATOM | 1623 | CG | TRP | 208 | 23.028 | -5.406 | 36.304 | 1.00 | 15.34 |
| ATOM | 1624 | CD2 | TRP | 208 | 23.198 | -4.109 | 36.880 | 1.00 | 15.76 |
| ATOM | 1625 | CE2 | TRP | 208 | 22.085 | -3.323 | 36.492 | 1.00 | 14.77 |
| ATOM | 1626 | CE3 | TRP | 208 | 24.186 | -3.530 | 37.686 | 1.00 | 14.76 |
| ATOM | 1627 | CD1 | TRP | 208 | 21.843 | -5.365 | 35.608 | 1.00 | 15.76 |
| ATOM | 1628 | NE1 | TRP | 208 | 21.273 | -4.112 | 35.717 | 1.00 | 15.54 |
| ATOM | 1629 | CZ2 | TRP | 208 | 21.935 | -1.991 | 36.882 | 1.00 | 14.39 |
| ATOM | 1630 | CZ3 | TRP | 208 | 24.037 | -2.206 | 38.078 | 1.00 | 15.33 |
| ATOM | 1631 | CH2 | TRP | 208 | 22.915 | -1.445 | 37.674 | 1.00 | 14.72 |
| ATOM | 1632 | C | TRP | 208 | 23.801 | -7.720 | 34.202 | 1.00 | 17.33 |
| ATOM | 1633 | O | TRP | 208 | 23.167 | -7.214 | 33.270 | 1.00 | 17.29 |
| ATOM | 1634 | N | ASP | 209 | 23.739 | -9.013 | 34.514 | 1.00 | 18.37 |
| ATOM | 1635 | CA | ASP | 209 | 22.885 | -9.953 | 33.786 | 1.00 | 18.97 |
| ATOM | 1636 | CB | ASP | 209 | 23.083 | -11.397 | 34.282 | 1.00 | 22.30 |
| ATOM | 1637 | CG | ASP | 209 | 24.466 | -11.974 | 34.039 | 1.00 | 23.93 |

FIG.11B-39

| | | | | | | | | |
|---|---|---|---|---|---|---|---|---|
| ATOM | 1638 | OD1 | ASP | 209 | 25.057 | -11.638 | 32.994 | 1.00 25.16 |
| ATOM | 1639 | OD2 | ASP | 209 | 24.939 | -12.771 | 34.884 | 1.00 27.15 |
| ATOM | 1640 | C | ASP | 209 | 21.406 | -9.587 | 33.984 | 1.00 18.77 |
| ATOM | 1641 | O | ASP | 209 | 20.604 | -9.675 | 33.052 | 1.00 17.74 |
| ATOM | 1642 | N | GLN | 210 | 21.068 | -9.178 | 35.205 | 1.00 18.55 |
| ATOM | 1643 | CA | GLN | 210 | 19.712 | -8.775 | 35.559 | 1.00 19.19 |
| ATOM | 1644 | CB | GLN | 210 | 18.805 | -10.003 | 35.664 | 1.00 20.25 |
| ATOM | 1645 | CG | GLN | 210 | 19.377 | -11.006 | 36.658 | 1.00 21.64 |
| ATOM | 1646 | CD | GLN | 210 | 18.489 | -12.229 | 36.576 | 1.00 23.03 |
| ATOM | 1647 | OE1 | GLN | 210 | 18.452 | -12.918 | 35.555 | 1.00 23.31 |
| ATOM | 1648 | NE2 | GLN | 210 | 17.765 | -12.503 | 37.650 | 1.00 24.19 |
| ATOM | 1649 | C | GLN | 210 | 19.775 | -8.010 | 36.865 | 1.00 19.59 |
| ATOM | 1650 | O | GLN | 210 | 20.691 | -8.209 | 37.669 | 1.00 18.71 |
| ATOM | 1651 | N | PRO | 211 | 18.806 | -7.111 | 37.105 | 1.00 18.57 |
| ATOM | 1652 | CD | PRO | 211 | 17.799 | -6.619 | 36.150 | 1.00 18.07 |
| ATOM | 1653 | CA | PRO | 211 | 18.783 | -6.311 | 38.334 | 1.00 19.80 |
| ATOM | 1654 | CB | PRO | 211 | 17.999 | -5.071 | 37.895 | 1.00 19.10 |
| ATOM | 1655 | CG | PRO | 211 | 16.995 | -5.644 | 37.004 | 1.00 18.49 |
| ATOM | 1656 | C | PRO | 211 | 18.202 | -7.039 | 39.533 | 1.00 21.25 |
| ATOM | 1657 | O | PRO | 211 | 17.149 | -6.664 | 40.049 | 1.00 20.53 |
| ATOM | 1658 | N | SER | 212 | 18.914 | -8.068 | 39.986 | 1.00 22.92 |
| ATOM | 1659 | CA | SER | 212 | 18.476 | -8.876 | 41.122 | 1.00 25.26 |
| ATOM | 1660 | CB | SER | 212 | 18.232 | -10.322 | 40.696 | 1.00 25.71 |
| ATOM | 1661 | OG | SER | 212 | 17.269 | -10.404 | 39.656 | 1.00 27.04 |
| ATOM | 1662 | C | SER | 212 | 19.540 | -8.909 | 42.200 | 1.00 26.27 |
| ATOM | 1663 | O | SER | 212 | 20.728 | -8.823 | 41.911 | 1.00 26.27 |
| ATOM | 1664 | N | ASP | 213 | 19.112 | -9.031 | 43.449 | 1.00 28.30 |
| ATOM | 1665 | CA | ASP | 213 | 20.060 | -9.091 | 44.558 | 1.00 30.12 |
| ATOM | 1666 | CB | ASP | 213 | 19.308 | -9.155 | 45.885 | 1.00 31.41 |
| ATOM | 1667 | CG | ASP | 213 | 18.700 | -7.785 | 46.123 | 1.00 32.87 |
| ATOM | 1668 | OD1 | ASP | 213 | 17.794 | -7.695 | 46.971 | 1.00 34.35 |
| ATOM | 1669 | OD2 | ASP | 213 | 19.131 | -6.806 | 45.478 | 1.00 33.85 |
| ATOM | 1670 | C | ASP | 213 | 20.950 | -10.325 | 44.402 | 1.00 30.47 |
| ATOM | 1671 | O | ASP | 213 | 22.085 | -10.347 | 44.881 | 1.00 30.66 |
| ATOM | 1672 | N | SER | 214 | 20.431 | -11.345 | 43.722 | 1.00 30.65 |
| ATOM | 1673 | CA | SER | 214 | 21.182 | -12.577 | 43.493 | 1.00 30.71 |
| ATOM | 1674 | CB | SER | 214 | 20.266 | -13.676 | 42.955 | 1.00 31.27 |
| ATOM | 1675 | OG | SER | 214 | 19.713 | -13.315 | 41.699 | 1.00 33.24 |
| ATOM | 1676 | C | SER | 214 | 22.295 | -12.353 | 42.480 | 1.00 30.15 |
| ATOM | 1677 | O | SER | 214 | 23.180 | -13.201 | 42.301 | 1.00 30.59 |
| ATOM | 1678 | N | CYS | 215 | 22.237 | -11.212 | 41.802 | 1.00 28.37 |
| ATOM | 1679 | CA | CYS | 215 | 23.248 | -10.857 | 40.817 | 1.00 27.11 |

FIG.11B-40

| | | | | | | | | |
|---|---|---|---|---|---|---|---|---|
| ATOM | 1680 | CB | CYS | 215 | 22.615 | -10.052 | 39.679 | 1.00 27.35 |
| ATOM | 1681 | SG | CYS | 215 | 23.795 | -9.692 | 38.381 | 1.00 24.98 |
| ATOM | 1682 | C | CYS | 215 | 24.290 | -10.029 | 41.524 | 1.00 26.85 |
| ATOM | 1683 | O | CYS | 215 | 24.046 | -8.879 | 41.881 | 1.00 25.26 |
| ATOM | 1684 | N | GLN | 216 | 25.465 | -10.618 | 41.730 | 1.00 26.11 |
| ATOM | 1685 | CA | GLN | 216 | 26.547 | -9.945 | 42.432 | 1.00 25.73 |
| ATOM | 1686 | CB | GLN | 216 | 27.806 | -10.824 | 42.396 | 1.00 27.39 |
| ATOM | 1687 | CG | GLN | 216 | 28.908 | -10.267 | 43.303 | 1.00 29.33 |
| ATOM | 1688 | CD | GLN | 216 | 28.445 | -10.161 | 44.773 | 1.00 30.23 |
| ATOM | 1689 | OE1 | GLN | 216 | 28.777 | -9.201 | 45.469 | 1.00 31.39 |
| ATOM | 1690 | NE2 | GLN | 216 | 27.691 | -11.153 | 45.236 | 1.00 29.72 |
| ATOM | 1691 | C | GLN | 216 | 26.867 | -8.526 | 41.914 | 1.00 24.91 |
| ATOM | 1692 | O | GLN | 216 | 27.064 | -7.606 | 42.705 | 1.00 24.59 |
| ATOM | 1693 | N | GLU | 217 | 26.904 | -8.356 | 40.597 | 1.00 23.79 |
| ATOM | 1694 | CA | GLU | 217 | 27.214 | -7.054 | 40.015 | 1.00 22.82 |
| ATOM | 1695 | CB | GLU | 217 | 27.325 | -7.161 | 38.490 | 1.00 23.60 |
| ATOM | 1696 | CG | GLU | 217 | 28.545 | -7.945 | 37.893 | 1.00 25.50 |
| ATOM | 1697 | CD | GLU | 217 | 28.552 | -9.382 | 38.379 | 1.00 26.01 |
| ATOM | 1698 | OE1 | GLU | 217 | 27.461 | -9.984 | 38.421 | 1.00 26.36 |
| ATOM | 1699 | OE2 | GLU | 217 | 29.642 | -9.904 | 38.709 | 1.00 27.79 |
| ATOM | 1700 | C | GLU | 217 | 26.168 | -6.008 | 40.387 | 1.00 22.40 |
| ATOM | 1701 | O | GLU | 217 | 26.494 | -4.833 | 40.597 | 1.00 21.57 |
| ATOM | 1702 | N | TYR | 218 | 24.909 | -6.430 | 40.467 | 1.00 21.63 |
| ATOM | 1703 | CA | TYR | 218 | 23.854 | -5.496 | 40.834 | 1.00 21.45 |
| ATOM | 1704 | CB | TYR | 218 | 22.469 | -6.076 | 40.518 | 1.00 20.94 |
| ATOM | 1705 | CG | TYR | 218 | 21.349 | -5.103 | 40.821 | 1.00 20.26 |
| ATOM | 1706 | CD1 | TYR | 218 | 21.289 | -3.860 | 40.185 | 1.00 20.20 |
| ATOM | 1707 | CE1 | TYR | 218 | 20.290 | -2.943 | 40.488 | 1.00 19.98 |
| ATOM | 1708 | CD2 | TYR | 218 | 20.371 | -5.401 | 41.769 | 1.00 20.62 |
| ATOM | 1709 | CE2 | TYR | 218 | 19.371 | -4.492 | 42.081 | 1.00 20.13 |
| ATOM | 1710 | CZ | TYR | 218 | 19.336 | -3.263 | 41.436 | 1.00 19.91 |
| ATOM | 1711 | OH | TYR | 218 | 18.345 | -2.359 | 41.727 | 1.00 20.57 |
| ATOM | 1712 | C | TYR | 218 | 23.988 | -5.145 | 42.332 | 1.00 22.12 |
| ATOM | 1713 | O | TYR | 218 | 23.853 | -3.988 | 42.706 | 1.00 21.46 |
| ATOM | 1714 | N | SER | 219 | 24.261 | -6.139 | 43.178 | 1.00 22.64 |
| ATOM | 1715 | CA | SER | 219 | 24.423 | -5.854 | 44.605 | 1.00 23.55 |
| ATOM | 1716 | CB | SER | 219 | 24.738 | -7.128 | 45.403 | 1.00 24.17 |
| ATOM | 1717 | OG | SER | 219 | 23.642 | -8.018 | 45.381 | 1.00 26.99 |
| ATOM | 1718 | C | SER | 219 | 25.580 | -4.878 | 44.801 | 1.00 23.48 |
| ATOM | 1719 | O | SER | 219 | 25.481 | -3.930 | 45.578 | 1.00 24.10 |
| ATOM | 1720 | N | ASP | 220 | 26.673 | -5.109 | 44.082 | 1.00 23.52 |
| ATOM | 1721 | CA | ASP | 220 | 27.837 | -4.240 | 44.169 | 1.00 22.96 |

FIG. 11B-41

| | | | | | | | | |
|---|---|---|---|---|---|---|---|---|
| ATOM | 1722 | CB | ASP | 220 | 28.941 | -4.732 | 43.232 | 1.00 24.39 |
| ATOM | 1723 | CG | ASP | 220 | 29.580 | -5.983 | 43.835 | 1.00 25.92 |
| ATOM | 1724 | OD1 | ASP | 220 | 30.398 | -6.603 | 43.128 | 1.00 28.41 |
| ATOM | 1725 | OD2 | ASP | 220 | 29.278 | -6.340 | 44.992 | 1.00 27.22 |
| ATOM | 1726 | C | ASP | 220 | 27.480 | -2.786 | 43.828 | 1.00 22.40 |
| ATOM | 1727 | O | ASP | 220 | 28.005 | -1.855 | 44.428 | 1.00 22.30 |
| ATOM | 1728 | N | TRP | 221 | 26.585 | -2.594 | 42.865 | 1.00 21.17 |
| ATOM | 1729 | CA | TRP | 221 | 26.179 | -1.241 | 42.498 | 1.00 20.70 |
| ATOM | 1730 | CB | TRP | 221 | 25.391 | -1.291 | 41.176 | 1.00 19.27 |
| ATOM | 1731 | CG | TRP | 221 | 24.638 | -0.020 | 40.833 | 1.00 17.73 |
| ATOM | 1732 | CD2 | TRP | 221 | 25.191 | 1.230 | 40.395 | 1.00 16.84 |
| ATOM | 1733 | CE2 | TRP | 221 | 24.106 | 2.117 | 40.187 | 1.00 17.43 |
| ATOM | 1734 | CE3 | TRP | 221 | 26.491 | 1.688 | 40.154 | 1.00 17.01 |
| ATOM | 1735 | CD1 | TRP | 221 | 23.287 | 0.156 | 40.874 | 1.00 17.87 |
| ATOM | 1736 | NE1 | TRP | 221 | 22.959 | 1.435 | 40.491 | 1.00 17.27 |
| ATOM | 1737 | CZ2 | TRP | 221 | 24.284 | 3.438 | 39.747 | 1.00 16.90 |
| ATOM | 1738 | CZ3 | TRP | 221 | 26.668 | 3.013 | 39.715 | 1.00 16.65 |
| ATOM | 1739 | CH2 | TRP | 221 | 25.573 | 3.864 | 39.518 | 1.00 17.11 |
| ATOM | 1740 | C | TRP | 221 | 25.376 | -0.599 | 43.651 | 1.00 21.75 |
| ATOM | 1741 | O | TRP | 221 | 25.617 | 0.552 | 44.015 | 1.00 21.20 |
| ATOM | 1742 | N | LYS | 222 | 24.441 | -1.351 | 44.225 | 1.00 23.83 |
| ATOM | 1743 | CA | LYS | 222 | 23.641 | -0.828 | 45.324 | 1.00 26.15 |
| ATOM | 1744 | CB | LYS | 222 | 22.564 | -1.831 | 45.735 | 1.00 26.74 |
| ATOM | 1745 | CG | LYS | 222 | 21.471 | -1.821 | 44.636 | 1.00 27.05 |
| ATOM | 1746 | CD | LYS | 222 | 20.119 | -2.467 | 45.022 | 1.00 28.62 |
| ATOM | 1747 | CE | LYS | 222 | 20.199 | -3.943 | 45.413 | 1.00 28.17 |
| ATOM | 1748 | NZ | LYS | 222 | 18.869 | -4.443 | 45.862 | 1.00 30.18 |
| ATOM | 1749 | C | LYS | 222 | 24.524 | -0.497 | 46.528 | 1.00 27.58 |
| ATOM | 1750 | O | LYS | 222 | 24.150 | 0.320 | 47.371 | 1.00 27.87 |
| ATOM | 1751 | N | GLU | 223 | 25.694 | -1.126 | 46.586 | 1.00 29.19 |
| ATOM | 1752 | CA | GLU | 223 | 26.650 | -0.902 | 47.670 | 1.00 30.71 |
| ATOM | 1753 | CB | GLU | 223 | 27.426 | -2.187 | 47.975 | 1.00 32.35 |
| ATOM | 1754 | CG | GLU | 223 | 26.514 | -3.389 | 48.320 | 1.00 35.04 |
| ATOM | 1755 | CD | GLU | 223 | 27.341 | -4.629 | 48.610 | 1.00 36.39 |
| ATOM | 1756 | OE1 | GLU | 223 | 28.026 | -4.647 | 49.652 | 1.00 37.89 |
| ATOM | 1757 | OE2 | GLU | 223 | 27.315 | -5.583 | 47.799 | 1.00 38.16 |
| ATOM | 1758 | C | GLU | 223 | 27.641 | 0.207 | 47.299 | 1.00 31.11 |
| ATOM | 1759 | O | GLU | 223 | 28.595 | 0.476 | 48.035 | 1.00 31.11 |
| ATOM | 1760 | N | LYS | 224 | 27.414 | 0.835 | 46.147 | 1.00 31.36 |
| ATOM | 1761 | CA | LYS | 224 | 28.250 | 1.935 | 45.669 | 1.00 31.60 |
| ATOM | 1762 | CB | LYS | 224 | 28.250 | 3.084 | 46.683 | 1.00 32.70 |
| ATOM | 1763 | CG | LYS | 224 | 26.902 | 3.828 | 46.813 | 1.00 34.17 |

FIG.11B-42

| ATOM | 1764 | CD | LYS | 224 | 25.731 | 2.967 | 47.318 | 1.00 | 35.15 |
|------|------|-----|-----|-----|--------|-------|--------|------|-------|
| ATOM | 1765 | CE | LYS | 224 | 25.845 | 2.601 | 48.823 | 1.00 | 36.31 |
| ATOM | 1766 | NZ | LYS | 224 | 25.781 | 3.822 | 49.677 | 1.00 | 37.18 |
| ATOM | 1767 | C | LYS | 224 | 29.720 | 1.607 | 45.343 | 1.00 | 31.34 |
| ATOM | 1768 | O | LYS | 224 | 30.595 | 2.467 | 45.463 | 1.00 | 31.10 |
| ATOM | 1769 | N | LYS | 225 | 29.982 | 0.377 | 44.918 | 1.00 | 30.93 |
| ATOM | 1770 | CA | LYS | 225 | 31.347 | -0.028 | 44.574 | 1.00 | 31.37 |
| ATOM | 1771 | CB | LYS | 225 | 31.493 | -1.543 | 44.742 | 1.00 | 31.69 |
| ATOM | 1772 | CG | LYS | 225 | 31.227 | -1.904 | 46.232 | 1.00 | 32.87 |
| ATOM | 1773 | CD | LYS | 225 | 31.162 | -3.409 | 46.591 | 1.00 | 33.45 |
| ATOM | 1774 | CE | LYS | 225 | 32.345 | -4.339 | 46.300 | 1.00 | 35.03 |
| ATOM | 1775 | NZ | LYS | 225 | 32.064 | -5.731 | 46.759 | 1.00 | 36.16 |
| ATOM | 1776 | C | LYS | 225 | 31.641 | 0.382 | 43.114 | 1.00 | 30.98 |
| ATOM | 1777 | O | LYS | 225 | 31.751 | -0.465 | 42.230 | 1.00 | 30.71 |
| ATOM | 1778 | N | THR | 226 | 31.766 | 1.685 | 42.886 | 1.00 | 31.21 |
| ATOM | 1779 | CA | THR | 226 | 32.009 | 2.208 | 41.546 | 1.00 | 31.56 |
| ATOM | 1780 | CB | THR | 226 | 31.458 | 3.659 | 41.422 | 1.00 | 31.65 |
| ATOM | 1781 | OG1 | THR | 226 | 31.977 | 4.479 | 42.478 | 1.00 | 32.08 |
| ATOM | 1782 | CG2 | THR | 226 | 29.939 | 3.650 | 41.514 | 1.00 | 31.20 |
| ATOM | 1783 | C | THR | 226 | 33.464 | 2.137 | 41.108 | 1.00 | 31.92 |
| ATOM | 1784 | O | THR | 226 | 33.869 | 2.803 | 40.155 | 1.00 | 32.06 |
| ATOM | 1785 | N | TYR | 227 | 34.252 | 1.326 | 41.807 | 1.00 | 32.46 |
| ATOM | 1786 | CA | TYR | 227 | 35.653 | 1.151 | 41.456 | 1.00 | 32.59 |
| ATOM | 1787 | CB | TYR | 227 | 36.518 | 1.115 | 42.724 | 1.00 | 33.51 |
| ATOM | 1788 | CG | TYR | 227 | 36.011 | 0.186 | 43.801 | 1.00 | 34.46 |
| ATOM | 1789 | CD1 | TYR | 227 | 36.185 | -1.196 | 43.703 | 1.00 | 35.44 |
| ATOM | 1790 | CE1 | TYR | 227 | 35.714 | -2.052 | 44.699 | 1.00 | 35.37 |
| ATOM | 1791 | CD2 | TYR | 227 | 35.351 | 0.691 | 44.920 | 1.00 | 34.76 |
| ATOM | 1792 | CE2 | TYR | 227 | 34.874 | -0.154 | 45.917 | 1.00 | 35.15 |
| ATOM | 1793 | CZ | TYR | 227 | 35.058 | -1.521 | 45.802 | 1.00 | 35.04 |
| ATOM | 1794 | OH | TYR | 227 | 34.576 | -2.348 | 46.791 | 1.00 | 35.61 |
| ATOM | 1795 | C | TYR | 227 | 35.762 | -0.135 | 40.664 | 1.00 | 32.78 |
| ATOM | 1796 | O | TYR | 227 | 36.852 | -0.539 | 40.254 | 1.00 | 32.53 |
| ATOM | 1797 | N | LEU | 228 | 34.614 | -0.779 | 40.464 | 1.00 | 32.64 |
| ATOM | 1798 | CA | LEU | 228 | 34.517 | -2.022 | 39.709 | 1.00 | 33.70 |
| ATOM | 1799 | CB | LEU | 228 | 33.390 | -2.897 | 40.261 | 1.00 | 33.23 |
| ATOM | 1800 | CG | LEU | 228 | 33.791 | -3.328 | 41.675 | 1.00 | 33.68 |
| ATOM | 1801 | CD1 | LEU | 228 | 32.676 | -4.197 | 42.238 | 1.00 | 33.31 |
| ATOM | 1802 | CD2 | LEU | 228 | 35.116 | -4.095 | 41.668 | 1.00 | 33.11 |
| ATOM | 1803 | C | LEU | 228 | 34.264 | -1.734 | 38.222 | 1.00 | 34.23 |
| ATOM | 1804 | O | LEU | 228 | 33.627 | -0.743 | 37.874 | 1.00 | 34.83 |
| ATOM | 1805 | N | ASN | 229 | 34.762 | -2.640 | 37.387 | 1.00 | 35.26 |

FIG.11B-43

| ATOM | 1806 | CA  | ASN | 229 | 34.716 | -2.588 | 35.925 | 1.00 | 35.58 |
|------|------|-----|-----|-----|--------|--------|--------|------|-------|
| ATOM | 1807 | CB  | ASN | 229 | 34.458 | -3.987 | 35.346 | 1.00 | 36.34 |
| ATOM | 1808 | CG  | ASN | 229 | 35.512 | -4.243 | 34.249 | 1.00 | 37.55 |
| ATOM | 1809 | OD1 | ASN | 229 | 36.703 | -4.002 | 34.455 | 1.00 | 37.91 |
| ATOM | 1810 | ND2 | ASN | 229 | 35.069 | -4.742 | 33.096 | 1.00 | 37.37 |
| ATOM | 1811 | C   | ASN | 229 | 33.829 | -1.633 | 35.198 | 1.00 | 34.28 |
| ATOM | 1812 | O   | ASN | 229 | 34.300 | -0.626 | 34.665 | 1.00 | 35.89 |
| ATOM | 1813 | N   | PRO | 230 | 32.516 | -1.897 | 35.159 | 1.00 | 33.61 |
| ATOM | 1814 | CD  | PRO | 230 | 31.668 | -2.722 | 36.038 | 1.00 | 32.77 |
| ATOM | 1815 | CA  | PRO | 230 | 31.718 | -0.924 | 34.408 | 1.00 | 30.57 |
| ATOM | 1816 | CB  | PRO | 230 | 30.287 | -1.447 | 34.623 | 1.00 | 32.30 |
| ATOM | 1817 | CG  | PRO | 230 | 30.340 | -1.971 | 36.006 | 1.00 | 33.38 |
| ATOM | 1818 | C   | PRO | 230 | 31.960 | 0.575  | 34.781 | 1.00 | 27.81 |
| ATOM | 1819 | O   | PRO | 230 | 32.499 | 1.367  | 33.990 | 1.00 | 26.92 |
| ATOM | 1820 | N   | TRP | 231 | 31.578 | 0.918  | 35.999 | 1.00 | 24.76 |
| ATOM | 1821 | CA  | TRP | 231 | 31.652 | 2.276  | 36.514 | 1.00 | 22.97 |
| ATOM | 1822 | CB  | TRP | 231 | 30.995 | 2.295  | 37.899 | 1.00 | 21.67 |
| ATOM | 1823 | CG  | TRP | 231 | 29.833 | 1.331  | 37.961 | 1.00 | 19.36 |
| ATOM | 1824 | CD2 | TRP | 231 | 28.622 | 1.407  | 37.204 | 1.00 | 18.86 |
| ATOM | 1825 | CE2 | TRP | 231 | 27.878 | 0.239  | 37.485 | 1.00 | 18.66 |
| ATOM | 1826 | CE3 | TRP | 231 | 28.095 | 2.350  | 36.310 | 1.00 | 17.74 |
| ATOM | 1827 | CD1 | TRP | 231 | 29.773 | 0.155  | 38.660 | 1.00 | 19.31 |
| ATOM | 1828 | NE1 | TRP | 231 | 28.605 | -0.509 | 38.377 | 1.00 | 17.81 |
| ATOM | 1829 | CZ2 | TRP | 231 | 26.634 | -0.012 | 36.904 | 1.00 | 17.32 |
| ATOM | 1830 | CZ3 | TRP | 231 | 26.856 | 2.103  | 35.727 | 1.00 | 18.02 |
| ATOM | 1831 | CH2 | TRP | 231 | 26.139 | 0.928  | 36.031 | 1.00 | 17.78 |
| ATOM | 1832 | C   | TRP | 231 | 33.033 | 2.946  | 36.558 | 1.00 | 22.63 |
| ATOM | 1833 | O   | TRP | 231 | 33.128 | 4.159  | 36.415 | 1.00 | 22.81 |
| ATOM | 1834 | N   | LYS | 232 | 34.091 | 2.170  | 36.754 | 1.00 | 22.60 |
| ATOM | 1835 | CA  | LYS | 232 | 35.428 | 2.764  | 36.826 | 1.00 | 22.75 |
| ATOM | 1836 | CB  | LYS | 232 | 36.477 | 1.704  | 37.189 | 1.00 | 24.11 |
| ATOM | 1837 | CG  | LYS | 232 | 36.647 | 0.419  | 36.346 | 1.00 | 25.74 |
| ATOM | 1838 | CD  | LYS | 232 | 37.683 | -0.509 | 37.036 | 1.00 | 27.06 |
| ATOM | 1839 | CE  | LYS | 232 | 37.996 | -1.774 | 36.213 | 1.00 | 27.57 |
| ATOM | 1840 | NZ  | LYS | 232 | 39.033 | -2.612 | 36.876 | 1.00 | 28.69 |
| ATOM | 1841 | C   | LYS | 232 | 35.860 | 3.438  | 35.529 | 1.00 | 22.63 |
| ATOM | 1842 | O   | LYS | 232 | 36.790 | 4.258  | 35.522 | 1.00 | 22.71 |
| ATOM | 1843 | N   | LYS | 233 | 35.182 | 3.104  | 34.435 | 1.00 | 20.74 |
| ATOM | 1844 | CA  | LYS | 233 | 35.522 | 3.658  | 33.122 | 1.00 | 20.06 |
| ATOM | 1845 | CB  | LYS | 233 | 35.264 | 2.634  | 32.011 | 1.00 | 21.41 |
| ATOM | 1846 | CG  | LYS | 233 | 36.100 | 1.349  | 32.118 | 1.00 | 22.20 |
| ATOM | 1847 | CD  | LYS | 233 | 35.874 | 0.176  | 31.106 | 1.00 | 23.44 |

FIG.11B-44

| ATOM | 1848 | CE  | LYS | 233 | 34.596 | -0.617 | 31.187 | 1.00 | 24.11 |
|------|------|-----|-----|-----|--------|--------|--------|------|-------|
| ATOM | 1849 | NZ  | LYS | 233 | 34.558 | -1.720 | 30.177 | 1.00 | 24.50 |
| ATOM | 1850 | C   | LYS | 233 | 34.855 | 5.008  | 32.889 | 1.00 | 19.90 |
| ATOM | 1851 | O   | LYS | 233 | 35.272 | 5.662  | 31.949 | 1.00 | 18.76 |
| ATOM | 1852 | N   | ILE | 234 | 33.741 | 5.339  | 33.521 | 1.00 | 20.48 |
| ATOM | 1853 | CA  | ILE | 234 | 32.935 | 6.424  | 32.978 | 1.00 | 21.37 |
| ATOM | 1854 | CB  | ILE | 234 | 31.491 | 6.107  | 33.470 | 1.00 | 20.52 |
| ATOM | 1855 | CG2 | ILE | 234 | 30.511 | 7.217  | 33.130 | 1.00 | 20.33 |
| ATOM | 1856 | CG1 | ILE | 234 | 31.126 | 4.755  | 32.836 | 1.00 | 19.24 |
| ATOM | 1857 | CD1 | ILE | 234 | 29.665 | 4.267  | 33.021 | 1.00 | 18.12 |
| ATOM | 1858 | C   | ILE | 234 | 33.591 | 7.883  | 33.073 | 1.00 | 23.34 |
| ATOM | 1859 | O   | ILE | 234 | 34.414 | 8.250  | 32.223 | 1.00 | 26.22 |
| ATOM | 1860 | N   | ASP | 235 | 33.190 | 8.659  | 34.058 | 1.00 | 23.93 |
| ATOM | 1861 | CA  | ASP | 235 | 33.700 | 10.001 | 34.367 | 1.00 | 21.53 |
| ATOM | 1862 | CB  | ASP | 235 | 33.670 | 10.978 | 33.182 | 1.00 | 23.07 |
| ATOM | 1863 | CG  | ASP | 235 | 34.063 | 12.339 | 33.827 | 1.00 | 24.23 |
| ATOM | 1864 | OD1 | ASP | 235 | 33.209 | 13.262 | 33.921 | 1.00 | 23.91 |
| ATOM | 1865 | OD2 | ASP | 235 | 35.237 | 12.473 | 34.266 | 1.00 | 23.71 |
| ATOM | 1866 | C   | ASP | 235 | 32.742 | 10.372 | 35.366 | 1.00 | 21.02 |
| ATOM | 1867 | O   | ASP | 235 | 31.577 | 10.002 | 35.253 | 1.00 | 18.48 |
| ATOM | 1868 | N   | SER | 236 | 33.180 | 11.101 | 36.387 | 1.00 | 20.18 |
| ATOM | 1869 | CA  | SER | 236 | 32.301 | 11.481 | 37.480 | 1.00 | 20.49 |
| ATOM | 1870 | CB  | SER | 236 | 33.036 | 12.390 | 38.481 | 1.00 | 21.41 |
| ATOM | 1871 | OG  | SER | 236 | 33.526 | 13.563 | 37.863 | 1.00 | 23.42 |
| ATOM | 1872 | C   | SER | 236 | 30.995 | 12.139 | 37.117 | 1.00 | 18.82 |
| ATOM | 1873 | O   | SER | 236 | 29.971 | 11.832 | 37.730 | 1.00 | 18.56 |
| ATOM | 1874 | N   | ALA | 237 | 31.019 | 13.033 | 36.129 | 1.00 | 18.12 |
| ATOM | 1875 | CA  | ALA | 237 | 29.825 | 13.764 | 35.701 | 1.00 | 16.44 |
| ATOM | 1876 | CB  | ALA | 237 | 30.194 | 14.812 | 34.635 | 1.00 | 16.94 |
| ATOM | 1877 | C   | ALA | 237 | 28.709 | 12.817 | 35.170 | 1.00 | 15.31 |
| ATOM | 1878 | O   | ALA | 237 | 27.590 | 12.819 | 35.691 | 1.00 | 15.03 |
| ATOM | 1879 | N   | PRO | 238 | 28.991 | 12.040 | 34.116 | 1.00 | 14.33 |
| ATOM | 1880 | CD  | PRO | 238 | 30.153 | 11.960 | 33.207 | 1.00 | 13.45 |
| ATOM | 1881 | CA  | PRO | 238 | 27.908 | 11.156 | 33.665 | 1.00 | 13.64 |
| ATOM | 1882 | CB  | PRO | 238 | 28.424 | 10.619 | 32.335 | 1.00 | 12.66 |
| ATOM | 1883 | CG  | PRO | 238 | 29.934 | 10.623 | 32.526 | 1.00 | 13.78 |
| ATOM | 1884 | C   | PRO | 238 | 27.584 | 10.063 | 34.714 | 1.00 | 13.32 |
| ATOM | 1885 | O   | PRO | 238 | 26.461 | 9.578  | 34.799 | 1.00 | 13.46 |
| ATOM | 1886 | N   | LEU | 239 | 28.579 | 9.686  | 35.509 | 1.00 | 14.55 |
| ATOM | 1887 | CA  | LEU | 239 | 28.363 | 8.677  | 36.530 | 1.00 | 14.31 |
| ATOM | 1888 | CB  | LEU | 239 | 29.702 | 8.330  | 37.192 | 1.00 | 15.38 |
| ATOM | 1889 | CG  | LEU | 239 | 29.797 | 7.069  | 38.059 | 1.00 | 17.03 |

FIG.11B-45

```
ATOM  1890  CD1  LEU  239  29.461   7.543  39.426  1.00  19.97
ATOM  1891  CD2  LEU  239  28.941   5.890  37.632  1.00  16.99
ATOM  1892  C    LEU  239  27.350   9.209  37.548  1.00  14.32
ATOM  1893  O    LEU  239  26.521   8.451  38.053  1.00  13.88
ATOM  1894  N    ALA  240  27.410  10.513  37.836  1.00  13.60
ATOM  1895  CA   ALA  240  26.474  11.121  38.778  1.00  14.03
ATOM  1896  CB   ALA  240  26.834  12.596  39.042  1.00  14.41
ATOM  1897  C    ALA  240  25.049  11.017  38.214  1.00  13.80
ATOM  1898  O    ALA  240  24.105  10.815  38.959  1.00  15.01
ATOM  1899  N    LEU  241  24.911  11.141  36.898  1.00  13.56
ATOM  1900  CA   LEU  241  23.586  11.029  36.289  1.00  12.69
ATOM  1901  CB   LEU  241  23.612  11.492  34.824  1.00  12.29
ATOM  1902  CG   LEU  241  22.307  11.217  34.050  1.00  12.22
ATOM  1903  CD1  LEU  241  21.101  11.892  34.673  1.00  13.19
ATOM  1904  CD2  LEU  241  22.521  11.700  32.616  1.00  11.55
ATOM  1905  C    LEU  241  23.144   9.585  36.389  1.00  12.74
ATOM  1906  O    LEU  241  21.992   9.298  36.744  1.00  13.22
ATOM  1907  N    LEU  242  24.051   8.658  36.086  1.00  12.48
ATOM  1908  CA   LEU  242  23.697   7.242  36.165  1.00  13.46
ATOM  1909  CB   LEU  242  24.901   6.395  35.710  1.00  14.09
ATOM  1910  CG   LEU  242  24.951   5.527  34.437  1.00  17.22
ATOM  1911  CD1  LEU  242  23.861   5.790  33.451  1.00  13.60
ATOM  1912  CD2  LEU  242  26.335   5.691  33.831  1.00  14.06
ATOM  1913  C    LEU  242  23.256   6.879  37.622  1.00  13.59
ATOM  1914  O    LEU  242  22.369   6.034  37.834  1.00  13.32
ATOM  1915  N    HIS  243  23.861   7.526  38.615  1.00  14.11
ATOM  1916  CA   HIS  243  23.485   7.251  40.004  1.00  14.54
ATOM  1917  CB   HIS  243  24.385   8.001  40.998  1.00  16.02
ATOM  1918  CG   HIS  243  25.597   7.228  41.426  1.00  18.57
ATOM  1919  CD2  HIS  243  26.911   7.424  41.173  1.00  20.62
ATOM  1920  ND1  HIS  243  25.524   6.099  42.216  1.00  20.36
ATOM  1921  CE1  HIS  243  26.743   5.632  42.427  1.00  19.94
ATOM  1922  NE2  HIS  243  27.603   6.418  41.804  1.00  20.07
ATOM  1923  C    HIS  243  22.037   7.679  40.279  1.00  14.42
ATOM  1924  O    HIS  243  21.400   7.148  41.181  1.00  15.58
ATOM  1925  N    LYS  244  21.548   8.652  39.513  1.00  13.04
ATOM  1926  CA   LYS  244  20.181   9.138  39.662  1.00  12.66
ATOM  1927  CB   LYS  244  20.061  10.586  39.215  1.00  13.26
ATOM  1928  CG   LYS  244  20.819  11.500  40.245  1.00  13.78
ATOM  1929  CD   LYS  244  20.709  12.997  39.911  1.00  16.39
ATOM  1930  CE   LYS  244  21.462  13.451  38.618  1.00  16.70
ATOM  1931  NZ   LYS  244  21.476  14.962  38.449  1.00  17.30
```

FIG.11B-46

| | | | | | | | | | |
|---|---|---|---|---|---|---|---|---|---|
| ATOM | 1932 | C | LYS | 244 | 19.164 | 8.319 | 38.858 | 1.00 | 12.13 |
| ATOM | 1933 | O | LYS | 244 | 17.993 | 8.241 | 39.224 | 1.00 | 12.40 |
| ATOM | 1934 | N | ILE | 245 | 19.621 | 7.723 | 37.759 | 1.00 | 12.05 |
| ATOM | 1935 | CA | ILE | 245 | 18.747 | 6.906 | 36.912 | 1.00 | 10.91 |
| ATOM | 1936 | CB | ILE | 245 | 19.281 | 6.819 | 35.449 | 1.00 | 10.95 |
| ATOM | 1937 | CG2 | ILE | 245 | 18.405 | 5.864 | 34.617 | 1.00 | 10.91 |
| ATOM | 1938 | CG1 | ILE | 245 | 19.237 | 8.197 | 34.786 | 1.00 | 11.13 |
| ATOM | 1939 | CD1 | ILE | 245 | 19.900 | 8.235 | 33.354 | 1.00 | 12.03 |
| ATOM | 1940 | C | ILE | 245 | 18.606 | 5.451 | 37.419 | 1.00 | 12.05 |
| ATOM | 1941 | O | ILE | 245 | 17.502 | 4.913 | 37.489 | 1.00 | 13.24 |
| ATOM | 1942 | N | LEU | 246 | 19.726 | 4.831 | 37.777 | 1.00 | 12.15 |
| ATOM | 1943 | CA | LEU | 246 | 19.715 | 3.436 | 38.208 | 1.00 | 12.12 |
| ATOM | 1944 | CB | LEU | 246 | 21.025 | 2.757 | 37.761 | 1.00 | 11.77 |
| ATOM | 1945 | CG | LEU | 246 | 21.265 | 2.878 | 36.246 | 1.00 | 11.06 |
| ATOM | 1946 | CD1 | LEU | 246 | 22.614 | 2.285 | 35.841 | 1.00 | 10.74 |
| ATOM | 1947 | CD2 | LEU | 246 | 20.108 | 2.158 | 35.515 | 1.00 | 11.92 |
| ATOM | 1948 | C | LEU | 246 | 19.442 | 3.277 | 39.711 | 1.00 | 13.39 |
| ATOM | 1949 | O | LEU | 246 | 20.212 | 2.652 | 40.468 | 1.00 | 14.42 |
| ATOM | 1950 | N | VAL | 247 | 18.321 | 3.862 | 40.110 | 1.00 | 12.95 |
| ATOM | 1951 | CA | VAL | 247 | 17.828 | 3.838 | 41.483 | 1.00 | 14.07 |
| ATOM | 1952 | CB | VAL | 247 | 17.234 | 5.200 | 41.833 | 1.00 | 14.69 |
| ATOM | 1953 | CG1 | VAL | 247 | 16.472 | 5.110 | 43.156 | 1.00 | 16.48 |
| ATOM | 1954 | CG2 | VAL | 247 | 18.363 | 6.239 | 41.922 | 1.00 | 16.18 |
| ATOM | 1955 | C | VAL | 247 | 16.780 | 2.749 | 41.538 | 1.00 | 14.37 |
| ATOM | 1956 | O | VAL | 247 | 15.835 | 2.753 | 40.747 | 1.00 | 13.95 |
| ATOM | 1957 | N | GLU | 248 | 16.937 | 1.810 | 42.468 | 1.00 | 15.26 |
| ATOM | 1958 | CA | GLU | 248 | 16.008 | 0.685 | 42.579 | 1.00 | 15.38 |
| ATOM | 1959 | CB | GLU | 248 | 16.439 | -0.239 | 43.723 | 1.00 | 18.10 |
| ATOM | 1960 | CG | GLU | 248 | 15.585 | -1.547 | 43.749 | 1.00 | 22.05 |
| ATOM | 1961 | CD | GLU | 248 | 16.403 | -2.530 | 44.545 | 1.00 | 25.30 |
| ATOM | 1962 | OE1 | GLU | 248 | 16.574 | -2.268 | 45.755 | 1.00 | 27.75 |
| ATOM | 1963 | OE2 | GLU | 248 | 16.872 | -3.530 | 43.961 | 1.00 | 27.17 |
| ATOM | 1964 | C | GLU | 248 | 14.520 | 1.063 | 42.769 | 1.00 | 14.82 |
| ATOM | 1965 | O | GLU | 248 | 13.649 | 0.497 | 42.107 | 1.00 | 13.94 |
| ATOM | 1966 | N | ASN | 249 | 14.246 | 2.010 | 43.663 | 1.00 | 13.99 |
| ATOM | 1967 | CA | ASN | 249 | 12.878 | 2.435 | 43.925 | 1.00 | 14.73 |
| ATOM | 1968 | CB | ASN | 249 | 12.821 | 3.193 | 45.256 | 1.00 | 15.18 |
| ATOM | 1969 | CG | ASN | 249 | 11.435 | 3.822 | 45.519 | 1.00 | 16.41 |
| ATOM | 1970 | OD1 | ASN | 249 | 10.499 | 3.664 | 44.728 | 1.00 | 16.50 |
| ATOM | 1971 | ND2 | ASN | 249 | 11.312 | 4.528 | 46.643 | 1.00 | 16.98 |
| ATOM | 1972 | C | ASN | 249 | 12.447 | 3.336 | 42.759 | 1.00 | 13.11 |
| ATOM | 1973 | O | ASN | 249 | 12.961 | 4.438 | 42.611 | 1.00 | 14.63 |

FIG.11B-47

| | | | | | | | | | |
|---|---|---|---|---|---|---|---|---|---|
| ATOM | 1974 | N | PRO | 250 | 11.518 | 2.862 | 41.912 | 1.00 | 13.20 |
| ATOM | 1975 | CD | PRO | 250 | 10.763 | 1.599 | 42.012 | 1.00 | 12.72 |
| ATOM | 1976 | CA | PRO | 250 | 11.057 | 3.658 | 40.766 | 1.00 | 13.23 |
| ATOM | 1977 | CB | PRO | 250 | 10.079 | 2.706 | 40.055 | 1.00 | 13.24 |
| ATOM | 1978 | CG | PRO | 250 | 9.507 | 1.906 | 41.190 | 1.00 | 13.59 |
| ATOM | 1979 | C | PRO | 250 | 10.446 | 4.976 | 41.155 | 1.00 | 13.43 |
| ATOM | 1980 | O | PRO | 250 | 10.442 | 5.921 | 40.365 | 1.00 | 13.46 |
| ATOM | 1981 | N | SER | 251 | 9.904 | 5.050 | 42.368 | 1.00 | 14.06 |
| ATOM | 1982 | CA | SER | 251 | 9.303 | 6.302 | 42.803 | 1.00 | 15.63 |
| ATOM | 1983 | CB | SER | 251 | 8.386 | 6.059 | 44.002 | 1.00 | 15.27 |
| ATOM | 1984 | OG | SER | 251 | 7.238 | 5.337 | 43.589 | 1.00 | 15.42 |
| ATOM | 1985 | C | SER | 251 | 10.372 | 7.369 | 43.132 | 1.00 | 15.99 |
| ATOM | 1986 | O | SER | 251 | 10.099 | 8.558 | 43.044 | 1.00 | 19.15 |
| ATOM | 1987 | N | ALA | 252 | 11.577 | 6.933 | 43.480 | 1.00 | 16.36 |
| ATOM | 1988 | CA | ALA | 252 | 12.670 | 7.846 | 43.812 | 1.00 | 15.52 |
| ATOM | 1989 | CB | ALA | 252 | 13.504 | 7.261 | 44.950 | 1.00 | 15.97 |
| ATOM | 1990 | C | ALA | 252 | 13.568 | 8.099 | 42.602 | 1.00 | 14.86 |
| ATOM | 1991 | O | ALA | 252 | 14.398 | 9.002 | 42.603 | 1.00 | 16.55 |
| ATOM | 1992 | N | ARG | 253 | 13.407 | 7.279 | 41.577 | 1.00 | 14.26 |
| ATOM | 1993 | CA | ARG | 253 | 14.230 | 7.395 | 40.364 | 1.00 | 13.52 |
| ATOM | 1994 | CB | ARG | 253 | 13.892 | 6.245 | 39.416 | 1.00 | 13.08 |
| ATOM | 1995 | CG | ARG | 253 | 14.732 | 6.070 | 38.114 | 1.00 | 13.50 |
| ATOM | 1996 | CD | ARG | 253 | 14.277 | 4.765 | 37.436 | 1.00 | 12.90 |
| ATOM | 1997 | NE | ARG | 253 | 14.298 | 3.661 | 38.395 | 1.00 | 13.33 |
| ATOM | 1998 | CZ | ARG | 253 | 13.564 | 2.561 | 38.289 | 1.00 | 13.77 |
| ATOM | 1999 | NH1 | ARG | 253 | 13.638 | 1.625 | 39.238 | 1.00 | 12.46 |
| ATOM | 2000 | NH2 | ARG | 253 | 12.771 | 2.397 | 37.234 | 1.00 | 12.92 |
| ATOM | 2001 | C | ARG | 253 | 13.990 | 8.732 | 39.658 | 1.00 | 12.93 |
| ATOM | 2002 | O | ARG | 253 | 12.882 | 9.268 | 39.690 | 1.00 | 13.28 |
| ATOM | 2003 | N | ILE | 254 | 15.032 | 9.268 | 39.034 | 1.00 | 12.41 |
| ATOM | 2004 | CA | ILE | 254 | 14.927 | 10.544 | 38.329 | 1.00 | 12.24 |
| ATOM | 2005 | CB | ILE | 254 | 16.349 | 11.025 | 37.858 | 1.00 | 12.27 |
| ATOM | 2006 | CG2 | ILE | 254 | 16.870 | 10.133 | 36.704 | 1.00 | 12.14 |
| ATOM | 2007 | CG1 | ILE | 254 | 16.295 | 12.496 | 37.429 | 1.00 | 13.31 |
| ATOM | 2008 | CD1 | ILE | 254 | 17.706 | 13.120 | 37.107 | 1.00 | 12.84 |
| ATOM | 2009 | C | ILE | 254 | 13.951 | 10.432 | 37.157 | 1.00 | 13.19 |
| ATOM | 2010 | O | ILE | 254 | 13.853 | 9.384 | 36.510 | 1.00 | 12.84 |
| ATOM | 2011 | N | THR | 255 | 13.209 | 11.510 | 36.909 | 1.00 | 12.98 |
| ATOM | 2012 | CA | THR | 255 | 12.264 | 11.570 | 35.804 | 1.00 | 14.49 |
| ATOM | 2013 | CB | THR | 255 | 11.020 | 12.385 | 36.186 | 1.00 | 15.98 |
| ATOM | 2014 | OG1 | THR | 255 | 11.419 | 13.721 | 36.526 | 1.00 | 16.76 |
| ATOM | 2015 | CG2 | THR | 255 | 10.342 | 11.754 | 37.390 | 1.00 | 16.72 |

FIG.11B-48

| ATOM | 2016 | C | THR | 255 | 12.962 | 12.266 | 34.662 | 1.00 | 14.89 |
| ATOM | 2017 | O | THR | 255 | 14.002 | 12.908 | 34.850 | 1.00 | 14.36 |
| ATOM | 2018 | N | ILE | 256 | 12.387 | 12.180 | 33.473 | 1.00 | 14.96 |
| ATOM | 2019 | CA | ILE | 256 | 13.022 | 12.822 | 32.338 | 1.00 | 15.85 |
| ATOM | 2020 | CB | ILE | 256 | 12.323 | 12.446 | 31.031 | 1.00 | 15.90 |
| ATOM | 2021 | CG2 | ILE | 256 | 12.969 | 13.227 | 29.886 | 1.00 | 16.70 |
| ATOM | 2022 | CG1 | ILE | 256 | 12.416 | 10.929 | 30.824 | 1.00 | 16.68 |
| ATOM | 2023 | CD1 | ILE | 256 | 11.763 | 10.410 | 29.490 | 1.00 | 17.39 |
| ATOM | 2024 | C | ILE | 256 | 13.121 | 14.347 | 32.495 | 1.00 | 15.76 |
| ATOM | 2025 | O | ILE | 256 | 14.146 | 14.936 | 32.162 | 1.00 | 15.74 |
| ATOM | 2026 | N | PRO | 257 | 12.058 | 15.008 | 32.988 | 1.00 | 16.02 |
| ATOM | 2027 | CD | PRO | 257 | 10.663 | 14.579 | 33.216 | 1.00 | 16.52 |
| ATOM | 2028 | CA | PRO | 257 | 12.196 | 16.461 | 33.137 | 1.00 | 16.77 |
| ATOM | 2029 | CB | PRO | 257 | 10.845 | 16.869 | 33.730 | 1.00 | 16.80 |
| ATOM | 2030 | CG | PRO | 257 | 9.886 | 15.903 | 33.072 | 1.00 | 16.27 |
| ATOM | 2031 | C | PRO | 257 | 13.448 | 16.832 | 34.008 | 1.00 | 17.42 |
| ATOM | 2032 | O | PRO | 257 | 14.093 | 17.848 | 33.765 | 1.00 | 18.68 |
| ATOM | 2033 | N | ASP | 258 | 13.776 | 15.999 | 34.996 | 1.00 | 17.57 |
| ATOM | 2034 | CA | ASP | 258 | 14.934 | 16.252 | 35.857 | 1.00 | 17.40 |
| ATOM | 2035 | CB | ASP | 258 | 14.727 | 15.585 | 37.229 | 1.00 | 18.84 |
| ATOM | 2036 | CG | ASP | 258 | 13.770 | 16.499 | 38.040 | 1.00 | 20.18 |
| ATOM | 2037 | OD1 | ASP | 258 | 13.098 | 16.010 | 38.969 | 1.00 | 19.96 |
| ATOM | 2038 | OD2 | ASP | 258 | 13.710 | 17.711 | 37.743 | 1.00 | 22.03 |
| ATOM | 2039 | C | ASP | 258 | 16.254 | 15.810 | 35.165 | 1.00 | 16.71 |
| ATOM | 2040 | O | ASP | 258 | 17.313 | 16.400 | 35.402 | 1.00 | 17.53 |
| ATOM | 2041 | N | ILE | 259 | 16.180 | 14.792 | 34.312 | 1.00 | 16.00 |
| ATOM | 2042 | CA | ILE | 259 | 17.361 | 14.357 | 33.567 | 1.00 | 14.73 |
| ATOM | 2043 | CB | ILE | 259 | 17.061 | 13.134 | 32.658 | 1.00 | 13.25 |
| ATOM | 2044 | CG2 | ILE | 259 | 18.186 | 12.932 | 31.636 | 1.00 | 11.56 |
| ATOM | 2045 | CG1 | ILE | 259 | 16.926 | 11.870 | 33.512 | 1.00 | 13.50 |
| ATOM | 2046 | CD1 | ILE | 259 | 16.359 | 10.635 | 32.718 | 1.00 | 14.05 |
| ATOM | 2047 | C | ILE | 259 | 17.777 | 15.511 | 32.650 | 1.00 | 15.65 |
| ATOM | 2048 | O | ILE | 259 | 18.956 | 15.768 | 32.455 | 1.00 | 15.76 |
| ATOM | 2049 | N | LYS | 260 | 16.801 | 16.225 | 32.097 | 1.00 | 17.80 |
| ATOM | 2050 | CA | LYS | 260 | 17.134 | 17.318 | 31.195 | 1.00 | 19.60 |
| ATOM | 2051 | CB | LYS | 260 | 15.882 | 17.772 | 30.437 | 1.00 | 21.62 |
| ATOM | 2052 | CG | LYS | 260 | 14.787 | 18.292 | 31.278 | 1.00 | 25.24 |
| ATOM | 2053 | CD | LYS | 260 | 13.557 | 18.718 | 30.460 | 1.00 | 27.14 |
| ATOM | 2054 | CE | LYS | 260 | 12.448 | 19.266 | 31.394 | 1.00 | 28.28 |
| ATOM | 2055 | NZ | LYS | 260 | 13.018 | 20.136 | 32.457 | 1.00 | 28.09 |
| ATOM | 2056 | C | LYS | 260 | 17.787 | 18.495 | 31.910 | 1.00 | 19.77 |
| ATOM | 2057 | O | LYS | 260 | 18.302 | 19.412 | 31.258 | 1.00 | 19.52 |

FIG.11B-49

| | | | | | | | | |
|---|---|---|---|---|---|---|---|---|
| ATOM | 2058 | N | LYS | 261 | 17.769 | 18.465 | 33.244 | 1.00 19.58 |
| ATOM | 2059 | CA | LYS | 261 | 18.377 | 19.513 | 34.063 | 1.00 20.76 |
| ATOM | 2060 | CB | LYS | 261 | 17.441 | 19.911 | 35.207 | 1.00 22.07 |
| ATOM | 2061 | CG | LYS | 261 | 16.225 | 20.617 | 34.640 | 1.00 24.13 |
| ATOM | 2062 | CD | LYS | 261 | 15.304 | 20.904 | 35.853 | 1.00 25.66 |
| ATOM | 2063 | CE | LYS | 261 | 13.996 | 21.718 | 35.627 | 1.00 27.76 |
| ATOM | 2064 | NZ | LYS | 261 | 14.253 | 23.180 | 35.441 | 1.00 29.98 |
| ATOM | 2065 | C | LYS | 261 | 19.708 | 19.078 | 34.677 | 1.00 19.39 |
| ATOM | 2066 | O | LYS | 261 | 20.398 | 19.877 | 35.320 | 1.00 20.44 |
| ATOM | 2067 | N | ASP | 262 | 20.075 | 17.817 | 34.461 | 1.00 17.11 |
| ATOM | 2068 | CA | ASP | 262 | 21.307 | 17.258 | 35.002 | 1.00 16.68 |
| ATOM | 2069 | CB | ASP | 262 | 21.348 | 15.747 | 34.725 | 1.00 15.81 |
| ATOM | 2070 | CG | ASP | 262 | 22.727 | 15.133 | 34.962 | 1.00 15.09 |
| ATOM | 2071 | OD1 | ASP | 262 | 23.534 | 15.000 | 34.021 | 1.00 15.37 |
| ATOM | 2072 | OD2 | ASP | 262 | 23.049 | 14.765 | 36.105 | 1.00 15.37 |
| ATOM | 2073 | C | ASP | 262 | 22.539 | 17.953 | 34.484 | 1.00 16.67 |
| ATOM | 2074 | O | ASP | 262 | 22.595 | 18.357 | 33.322 | 1.00 15.94 |
| ATOM | 2075 | N | ARG | 263 | 23.535 | 18.094 | 35.353 | 1.00 16.49 |
| ATOM | 2076 | CA | ARG | 263 | 24.781 | 18.773 | 34.997 | 1.00 17.66 |
| ATOM | 2077 | CB | ARG | 263 | 25.751 | 18.741 | 36.179 | 1.00 19.91 |
| ATOM | 2078 | CG | ARG | 263 | 27.046 | 19.552 | 35.881 | 1.00 23.77 |
| ATOM | 2079 | CD | ARG | 263 | 27.952 | 19.734 | 37.161 | 1.00 26.98 |
| ATOM | 2080 | NE | ARG | 263 | 28.878 | 18.625 | 37.404 | 1.00 30.04 |
| ATOM | 2081 | CZ | ARG | 263 | 28.535 | 17.410 | 37.833 | 1.00 31.76 |
| ATOM | 2082 | NH1 | ARG | 263 | 27.264 | 17.108 | 38.076 | 1.00 32.73 |
| ATOM | 2083 | NH2 | ARG | 263 | 29.476 | 16.495 | 38.044 | 1.00 32.79 |
| ATOM | 2084 | C | ARG | 263 | 25.481 | 18.182 | 33.763 | 1.00 16.93 |
| ATOM | 2085 | O | ARG | 263 | 25.873 | 18.915 | 32.858 | 1.00 17.03 |
| ATOM | 2086 | N | TRP | 264 | 25.643 | 16.864 | 33.725 | 1.00 15.70 |
| ATOM | 2087 | CA | TRP | 264 | 26.297 | 16.256 | 32.577 | 1.00 14.73 |
| ATOM | 2088 | CB | TRP | 264 | 26.576 | 14.770 | 32.818 | 1.00 14.69 |
| ATOM | 2089 | CG | TRP | 264 | 27.266 | 14.159 | 31.637 | 1.00 13.54 |
| ATOM | 2090 | CD2 | TRP | 264 | 26.677 | 13.327 | 30.637 | 1.00 13.29 |
| ATOM | 2091 | CE2 | TRP | 264 | 27.683 | 13.043 | 29.683 | 1.00 13.31 |
| ATOM | 2092 | CE3 | TRP | 264 | 25.390 | 12.789 | 30.448 | 1.00 13.02 |
| ATOM | 2093 | CD1 | TRP | 264 | 28.568 | 14.345 | 31.264 | 1.00 13.98 |
| ATOM | 2094 | NE1 | TRP | 264 | 28.823 | 13.679 | 30.092 | 1.00 12.82 |
| ATOM | 2095 | CZ2 | TRP | 264 | 27.448 | 12.244 | 28.556 | 1.00 13.12 |
| ATOM | 2096 | CZ3 | TRP | 264 | 25.157 | 11.997 | 29.329 | 1.00 11.93 |
| ATOM | 2097 | CH2 | TRP | 264 | 26.178 | 11.731 | 28.397 | 1.00 11.95 |
| ATOM | 2098 | C | TRP | 264 | 25.437 | 16.398 | 31.287 | 1.00 14.29 |
| ATOM | 2099 | O | TRP | 264 | 25.954 | 16.683 | 30.199 | 1.00 13.06 |

FIG.11B-50

| ATOM | 2100 | N | TYR | 265 | 24.132 | 16.217 | 31.427 | 1.00 | 14.18 |
|------|------|------|------|------|--------|--------|--------|------|-------|
| ATOM | 2101 | CA | TYR | 265 | 23.228 | 16.327 | 30.287 | 1.00 | 14.24 |
| ATOM | 2102 | CB | TYR | 265 | 21.779 | 16.158 | 30.753 | 1.00 | 14.67 |
| ATOM | 2103 | CG | TYR | 265 | 20.786 | 16.027 | 29.623 | 1.00 | 14.92 |
| ATOM | 2104 | CD1 | TYR | 265 | 20.225 | 17.150 | 29.014 | 1.00 | 15.83 |
| ATOM | 2105 | CE1 | TYR | 265 | 19.303 | 17.016 | 27.971 | 1.00 | 16.00 |
| ATOM | 2106 | CD2 | TYR | 265 | 20.404 | 14.768 | 29.161 | 1.00 | 15.34 |
| ATOM | 2107 | CE2 | TYR | 265 | 19.492 | 14.627 | 28.124 | 1.00 | 15.43 |
| ATOM | 2108 | CZ | TYR | 265 | 18.948 | 15.747 | 27.540 | 1.00 | 16.30 |
| ATOM | 2109 | OH | TYR | 265 | 18.056 | 15.596 | 26.517 | 1.00 | 17.21 |
| ATOM | 2110 | C | TYR | 265 | 23.420 | 17.698 | 29.574 | 1.00 | 14.08 |
| ATOM | 2111 | O | TYR | 265 | 23.402 | 17.782 | 28.340 | 1.00 | 13.66 |
| ATOM | 2112 | N | ASN | 266 | 23.638 | 18.743 | 30.367 | 1.00 | 14.50 |
| ATOM | 2113 | CA | ASN | 266 | 23.816 | 20.093 | 29.832 | 1.00 | 15.04 |
| ATOM | 2114 | CB | ASN | 266 | 23.127 | 21.112 | 30.744 | 1.00 | 16.27 |
| ATOM | 2115 | CG | ASN | 266 | 21.623 | 20.873 | 30.628 | 1.00 | 17.50 |
| ATOM | 2116 | OD1 | ASN | 266 | 21.019 | 21.164 | 29.595 | 1.00 | 18.67 |
| ATOM | 2117 | ND2 | ASN | 266 | 21.017 | 20.324 | 31.689 | 1.00 | 17.20 |
| ATOM | 2118 | C | ASN | 266 | 25.283 | 20.545 | 29.665 | 1.00 | 15.81 |
| ATOM | 2119 | O | ASN | 266 | 25.551 | 21.696 | 29.333 | 1.00 | 15.28 |
| ATOM | 2120 | N | LYS | 267 | 26.229 | 19.639 | 29.867 | 1.00 | 15.30 |
| ATOM | 2121 | CA | LYS | 267 | 27.626 | 20.022 | 29.739 | 1.00 | 16.63 |
| ATOM | 2122 | CB | LYS | 267 | 28.510 | 19.009 | 30.468 | 1.00 | 18.26 |
| ATOM | 2123 | CG | LYS | 267 | 29.969 | 19.316 | 30.381 | 1.00 | 18.95 |
| ATOM | 2124 | CD | LYS | 267 | 30.607 | 18.191 | 31.212 | 1.00 | 20.54 |
| ATOM | 2125 | CE | LYS | 267 | 32.097 | 18.519 | 31.285 | 1.00 | 21.22 |
| ATOM | 2126 | NZ | LYS | 267 | 32.271 | 19.896 | 31.837 | 1.00 | 25.63 |
| ATOM | 2127 | C | LYS | 267 | 28.096 | 20.128 | 28.280 | 1.00 | 17.13 |
| ATOM | 2128 | O | LYS | 267 | 27.925 | 19.200 | 27.491 | 1.00 | 17.02 |
| ATOM | 2129 | N | PRO | 268 | 28.668 | 21.285 | 27.899 | 1.00 | 17.19 |
| ATOM | 2130 | CD | PRO | 268 | 28.680 | 22.567 | 28.624 | 1.00 | 18.04 |
| ATOM | 2131 | CA | PRO | 268 | 29.151 | 21.449 | 26.525 | 1.00 | 18.03 |
| ATOM | 2132 | CB | PRO | 268 | 29.594 | 22.914 | 26.489 | 1.00 | 18.73 |
| ATOM | 2133 | CG | PRO | 268 | 28.717 | 23.576 | 27.485 | 1.00 | 18.08 |
| ATOM | 2134 | C | PRO | 268 | 30.291 | 20.455 | 26.275 | 1.00 | 19.66 |
| ATOM | 2135 | O | PRO | 268 | 31.263 | 20.407 | 27.041 | 1.00 | 18.33 |
| ATOM | 2136 | N | LEU | 269 | 30.183 | 19.688 | 25.196 | 1.00 | 20.60 |
| ATOM | 2137 | CA | LEU | 269 | 31.191 | 18.680 | 24.884 | 1.00 | 23.11 |
| ATOM | 2138 | CB | LEU | 269 | 30.735 | 17.287 | 25.326 | 1.00 | 21.93 |
| ATOM | 2139 | CG | LEU | 269 | 30.429 | 16.951 | 26.782 | 1.00 | 21.11 |
| ATOM | 2140 | CD1 | LEU | 269 | 29.824 | 15.559 | 26.864 | 1.00 | 20.44 |
| ATOM | 2141 | CD2 | LEU | 269 | 31.709 | 17.029 | 27.611 | 1.00 | 21.85 |

FIG.11B-51

```
ATOM   2142  C   LEU  269      31.519  18.481  23.398  1.00 25.42
ATOM   2143  O   LEU  269      32.694  18.357  23.024  1.00 25.84
ATOM   2144  N   LYS  270      30.478  18.456  22.572  1.00 28.13
ATOM   2145  CA  LYS  270      30.638  18.172  21.148  1.00 31.59
ATOM   2146  CB  LYS  270      29.792  16.951  20.777  1.00 32.48
ATOM   2147  CG  LYS  270      29.974  16.336  19.385  1.00 34.36
ATOM   2148  CD  LYS  270      29.245  14.976  19.311  1.00 34.97
ATOM   2149  CE  LYS  270      29.342  14.378  17.904  1.00 36.24
ATOM   2150  NZ  LYS  270      28.578  13.107  17.794  1.00 37.61
ATOM   2151  C   LYS  270      30.326  19.247  20.152  1.00 32.71
ATOM   2152  O   LYS  270      29.331  19.965  20.267  1.00 33.61
ATOM   2153  N   LYS  271      31.182  19.353  19.143  1.00 34.01
ATOM   2154  CA  LYS  271      30.984  20.338  18.093  1.00 34.65
ATOM   2155  CB  LYS  271      32.296  20.639  17.364  1.00 34.43
ATOM   2156  CG  LYS  271      33.612  21.016  18.114  1.00 34.00
ATOM   2157  CD  LYS  271      33.425  21.680  19.493  1.00 32.78
ATOM   2158  CE  LYS  271      34.683  22.342  20.087  1.00 32.43
ATOM   2159  NZ  LYS  271      34.911  23.689  19.493  1.00 29.16
ATOM   2160  C   LYS  271      30.002  19.770  17.100  1.00 35.51
ATOM   2161  O   LYS  271      29.873  18.545  16.970  1.00 35.67
ATOM   2162  N   GLY  272      29.304  20.653  16.392  1.00 36.22
ATOM   2163  CA  GLY  272      28.334  20.207  15.412  1.00 37.58
ATOM   2164  C   GLY  272      28.974  19.331  14.357  1.00 38.77
ATOM   2165  O   GLY  272      30.181  19.085  14.392  1.00 39.05
ATOM   2166  N   ALA  273      28.165  18.859  13.415  1.00 39.07
ATOM   2167  CA  ALA  273      28.663  18.004  12.347  1.00 39.69
ATOM   2168  CB  ALA  273      27.559  17.736  11.334  1.00 39.13
ATOM   2169  C   ALA  273      29.834  18.652  11.667  1.00 40.12
ATOM   2170  O   ALA  273      30.138  19.821  11.907  1.00 40.27
ATOM   2171  N   ALA  274      30.506  17.889  10.811  1.00 40.80
ATOM   2172  CA  ALA  274      31.650  18.406  10.075  1.00 41.43
ATOM   2173  CB  ALA  274      32.667  17.297   9.834  1.00 41.17
ATOM   2174  C   ALA  274      31.149  18.955   8.761  1.00 41.68
ATOM   2175  O   ALA  274      30.049  18.613   8.317  1.00 42.49
ATOM   2176  N   ALA  275      31.947  19.820   8.143  1.00 41.82
ATOM   2177  CA  ALA  275      31.600  20.428   6.860  1.00 41.71
ATOM   2178  CB  ALA  275      31.811  19.414   5.741  1.00 41.41
ATOM   2179  C   ALA  275      30.158  20.973   6.807  1.00 41.89
ATOM   2180  O   ALA  275      29.423  20.708   5.850  1.00 42.04
ATOM   2181  N   ALA  276      29.767  21.733   7.829  1.00 41.67
ATOM   2182  CA  ALA  276      28.425  22.310   7.881  1.00 41.71
ATOM   2183  CB  ALA  276      27.377  21.201   7.836  1.00 40.99
```

FIG.11B-52

| ATOM | 2184 | C | ALA | 276 | 28.226 | 23.157 | 9.127 | 1.00 | 41.84 |
|---|---|---|---|---|---|---|---|---|---|
| ATOM | 2185 | O | ALA | 276 | 28.106 | 24.394 | 9.001 | 1.00 | 42.24 |
| ATOM | 2186 | OT | ALA | 276 | 28.190 | 22.590 | 10.239 | 1.00 | 42.70 |
| ATOM | 2187 | OH2 | WAT | 500 | 7.427 | -2.493 | 31.016 | 1.00 | 12.44 |
| ATOM | 2188 | OH2 | WAT | 501 | 7.228 | 0.472 | 30.486 | 1.00 | 11.40 |
| ATOM | 2189 | OH2 | WAT | 502 | 8.194 | 1.752 | 37.455 | 1.00 | 11.41 |
| ATOM | 2190 | OH2 | WAT | 503 | 12.286 | -2.112 | 29.696 | 1.00 | 12.42 |
| ATOM | 2191 | OH2 | WAT | 504 | 12.428 | -0.037 | 27.883 | 1.00 | 11.16 |
| ATOM | 2192 | OH2 | WAT | 505 | 8.356 | 10.402 | 31.031 | 1.00 | 13.84 |
| ATOM | 2193 | OH2 | WAT | 507 | 15.558 | -3.663 | 26.632 | 1.00 | 12.28 |
| ATOM | 2194 | OH2 | WAT | 508 | 6.988 | 4.420 | 40.772 | 1.00 | 14.28 |
| ATOM | 2195 | OH2 | WAT | 509 | 11.678 | 7.753 | 36.355 | 1.00 | 15.05 |
| ATOM | 2196 | OH2 | WAT | 510 | 9.743 | 10.806 | 33.175 | 1.00 | 13.52 |
| ATOM | 2197 | OH2 | WAT | 511 | 14.137 | -4.264 | 28.939 | 1.00 | 11.96 |
| ATOM | 2198 | OH2 | WAT | 512 | 12.161 | -1.918 | 42.464 | 1.00 | 17.92 |
| ATOM | 2199 | OH2 | WAT | 513 | 23.034 | -4.599 | 32.333 | 1.00 | 14.48 |
| ATOM | 2200 | OH2 | WAT | 514 | 13.701 | -1.328 | 31.829 | 1.00 | 13.65 |
| ATOM | 2201 | OH2 | WAT | 515 | 7.725 | 2.793 | 44.539 | 1.00 | 13.92 |
| ATOM | 2202 | OH2 | WAT | 516 | 10.498 | 8.123 | 38.870 | 1.00 | 18.75 |
| ATOM | 2203 | OH2 | WAT | 517 | 8.458 | -2.193 | 21.559 | 1.00 | 15.87 |
| ATOM | 2204 | OH2 | WAT | 518 | 3.854 | -8.500 | 37.109 | 1.00 | 21.28 |
| ATOM | 2205 | OH2 | WAT | 519 | 6.585 | 13.179 | 28.016 | 1.00 | 15.92 |
| ATOM | 2206 | OH2 | WAT | 520 | 4.308 | 6.179 | 34.254 | 1.00 | 14.46 |
| ATOM | 2207 | OH2 | WAT | 521 | -2.497 | 7.216 | 24.331 | 1.00 | 20.93 |
| ATOM | 2208 | OH2 | WAT | 522 | 25.696 | 14.974 | 36.359 | 1.00 | 15.50 |
| ATOM | 2209 | OH2 | WAT | 523 | 10.006 | -1.183 | 44.079 | 1.00 | 17.12 |
| ATOM | 2210 | OH2 | WAT | 524 | 18.801 | -3.771 | 34.262 | 1.00 | 12.85 |
| ATOM | 2211 | OH2 | WAT | 525 | 9.859 | -3.573 | 29.813 | 1.00 | 12.22 |
| ATOM | 2212 | OH2 | WAT | 526 | 23.813 | -2.488 | 12.469 | 1.00 | 24.20 |
| ATOM | 2213 | OH2 | WAT | 527 | 33.619 | 6.620 | 29.594 | 1.00 | 13.33 |
| ATOM | 2214 | OH2 | WAT | 528 | 12.025 | -0.860 | 12.686 | 1.00 | 16.92 |
| ATOM | 2215 | OH2 | WAT | 529 | 5.067 | -3.939 | 31.031 | 1.00 | 15.55 |
| ATOM | 2216 | OH2 | WAT | 530 | 16.206 | 2.905 | 45.578 | 1.00 | 21.26 |
| ATOM | 2217 | OH2 | WAT | 531 | 6.508 | 1.842 | 39.468 | 1.00 | 13.83 |
| ATOM | 2218 | OH2 | WAT | 532 | 9.848 | -0.013 | 13.922 | 1.00 | 16.77 |
| ATOM | 2219 | OH2 | WAT | 533 | 8.482 | 13.036 | 29.893 | 1.00 | 21.35 |
| ATOM | 2220 | OH2 | WAT | 534 | 1.955 | 3.242 | 33.881 | 1.00 | 14.23 |
| ATOM | 2221 | OH2 | WAT | 535 | 8.004 | 9.104 | 38.937 | 1.00 | 20.33 |
| ATOM | 2222 | OH2 | WAT | 536 | 9.589 | 8.422 | 34.802 | 1.00 | 13.64 |
| ATOM | 2223 | OH2 | WAT | 538 | 13.208 | 13.372 | 39.318 | 1.00 | 17.18 |
| ATOM | 2224 | OH2 | WAT | 539 | 12.245 | -5.696 | 20.845 | 1.00 | 19.96 |
| ATOM | 2225 | OH2 | WAT | 540 | 11.065 | -3.376 | 13.747 | 1.00 | 23.19 |

FIG.11B-53

```
ATOM   2226  OH2  WAT   542    10.329   -0.437  -17.113  1.00  15.49
ATOM   2227  OH2  WAT   543    34.999   12.972   30.493  1.00  20.46
ATOM   2228  OH2  WAT   544     6.038   -4.021  -15.260  1.00  18.16
ATOM   2229  OH2  WAT   545     2.722   -3.465   20.201  1.00  22.45
ATOM   2230  OH2  WAT   546    23.120   17.680   38.118  1.00  21.95
ATOM   2231  OH2  WAT   547     4.224   12.544   29.399  1.00  22.88
ATOM   2232  OH2  WAT   548    27.520   19.070   23.817  1.00  18.56
ATOM   2233  OH2  WAT   549    11.453    0.217  -14.778  1.00  18.21
ATOM   2234  OH2  WAT   550     8.159    8.888   13.504  1.00  22.71
ATOM   2235  OH2  WAT   551     7.518   -1.202   14.804  1.00  19.40
ATOM   2236  OH2  WAT   552    25.729    0.976   13.336  1.00  25.24
ATOM   2237  OH2  WAT   553     8.421    2.347   13.686  1.00  18.49
ATOM   2238  OH2  WAT   554    32.146   14.746   31.790  1.00  16.58
ATOM   2239  OH2  WAT   555    10.588   15.422   22.583  1.00  20.42
ATOM   2240  OH2  WAT   556    -7.789    5.192   30.091  1.00  21.72
ATOM   2241  OH2  WAT   557    24.235   11.751   41.632  1.00  23.21
ATOM   2242  OH2  WAT   558    13.097    5.532    4.167  1.00  22.65
ATOM   2243  OH2  WAT   561     7.327    8.904   36.362  1.00  19.07
ATOM   2244  OH2  WAT   562     5.298    7.204   36.854  1.00  19.10
ATOM   2245  OH2  WAT   563    17.888   14.061   15.698  1.00  28.05
ATOM   2246  OH2  WAT   564     5.803   10.952   34.891  1.00  25.56
ATOM   2247  OH2  WAT   565    19.385   -8.096   22.747  1.00  27.33
ATOM   2248  OH2  WAT   567    -5.961    9.687   24.986  1.00  28.68
ATOM   2249  OH2  WAT   568    12.502   16.572   24.587  1.00  24.90
ATOM   2250  OH2  WAT   569     4.420   13.953   22.823  1.00  19.89
ATOM   2251  OH2  WAT   570     6.037   16.089   27.263  1.00  27.33
ATOM   2252  OH2  WAT   571     0.295   -4.830   31.670  1.00  22.95
ATOM   2253  OH2  WAT   572     5.126    7.073   43.112  1.00  26.68
ATOM   2254  OH2  WAT   573     7.925   12.617   34.293  1.00  19.25
ATOM   2255  OH2  WAT   574     2.838    8.548   37.282  1.00  22.58
ATOM   2256  OH2  WAT   575     6.541    6.869   39.585  1.00  20.25
ATOM   2257  OH2  WAT   577    16.348   13.014   13.638  1.00  21.44
ATOM   2258  OH2  WAT   578    20.689  -11.863   31.456  1.00  22.24
ATOM   2259  OH2  WAT   579    28.216   -3.073   39.433  1.00  23.94
ATOM   2260  OH2  WAT   580     4.817   12.316   31.998  1.00  24.78
ATOM   2261  OH2  WAT   582     2.495   10.173   33.047  1.00  25.54
ATOM   2262  OH2  WAT   584     9.873   -9.843   26.499  1.00  22.35
ATOM   2263  OH2  WAT   585    18.849    6.343    6.565  1.00  23.80
ATOM   2264  OH2  WAT   586     5.936   15.554   24.398  1.00  32.00
ATOM   2265  OH2  WAT   587     7.942   15.782   22.364  1.00  28.34
ATOM   2266  OH2  WAT   588     6.895   14.265   32.126  1.00  25.39
ATOM   2267  OH2  WAT   589    -0.295   -3.712   42.925  1.00  25.73
```

FIG.11B-54

```
ATOM   2268  OH2  WAT   590    -3.936    9.005   35.847  1.00 24.10
ATOM   2269  OH2  WAT   591    18.913    2.038   44.494  1.00 26.21
ATOM   2270  OH2  WAT   592    28.625   -6.540   28.424  1.00 26.01
ATOM   2271  OH2  WAT   593    26.141   -9.992   35.885  1.00 25.72
ATOM   2272  OH2  WAT   594    -4.117    0.747   36.348  1.00 21.02
ATOM   2273  OH2  WAT   595     4.898   -5.492   46.334  1.00 25.89
ATOM   2274  OH2  WAT   596    -1.825   -3.880   35.982  1.00 26.80
ATOM   2275  OH2  WAT   597    17.281  -10.153   23.419  1.00 29.07
ATOM   2276  OH2  WAT   598     6.074    7.250   12.492  1.00 26.52
ATOM   2277  OH2  WAT   599    14.343    0.413  -12.155  1.00 26.20
ATOM   2278  OH2  WAT   600     5.724  -15.362   35.592  1.00 31.55
ATOM   2279  OH2  WAT   601    31.405   -5.699   25.906  1.00 31.89
ATOM   2280  OH2  WAT   602    19.144   16.433   37.632  1.00 27.84
ATOM   2281  OH2  WAT   604    -1.682   10.834   26.579  1.00 25.33
ATOM   2282  OH2  WAT   605     7.446   14.038   36.610  1.00 31.51
ATOM   2283  OH2  WAT   606     8.931  -11.385   28.785  1.00 31.07
ATOM   2284  OH2  WAT   607     2.276   13.259   17.394  1.00 29.99
ATOM   2285  OH2  WAT   608    10.037   -6.636   -8.218  1.00 29.41
ATOM   2286  OH2  WAT   609    25.470   -3.163   24.453  1.00 36.33
ATOM   2287  OH2  WAT   610     5.918   -3.633   -5.105  1.00 29.98
ATOM   2288  OH2  WAT   611    22.980  -14.777   33.710  1.00 37.86
ATOM   2289  OH2  WAT   612    29.084   -4.501   37.176  1.00 26.11
ATOM   2290  OH2  WAT   613    34.969   -5.345   38.036  1.00 36.77
ATOM   2291  OH2  WAT   614    22.538   -5.866   24.355  1.00 25.61
ATOM   2292  OH2  WAT   615     2.677    5.500   42.779  1.00 22.04
ATOM   2293  OH2  WAT   616    -1.262   -0.266    1.007  1.00 41.96
ATOM   2294  OH2  WAT   617    14.838   -2.729   15.686  1.00 26.97
ATOM   2295  OH2  WAT   618     7.254   -5.958   -4.621  1.00 32.47
ATOM   2296  OH2  WAT   619    14.437   -0.485   -7.588  1.00 24.67
ATOM   2297  OH2  WAT   620    13.993   16.537   27.899  1.00 37.44
ATOM   2298  OH2  WAT   621    35.859    6.788   17.703  1.00 36.41
ATOM   2299  OH2  WAT   622     1.225    3.363  -11.071  1.00 34.68
ATOM   2300  OH2  WAT   623    17.438   12.289   41.236  1.00 24.21
ATOM   2301  OH2  WAT   624    21.271   -0.227    7.878  1.00 33.25
ATOM   2302  OH2  WAT   625     6.639   15.315   16.521  1.00 33.67
ATOM   2303  OH2  WAT   626     6.373    4.916   13.973  1.00 25.91
ATOM   2304  OH2  WAT   627     3.444   -2.333   -2.127  1.00 34.16
ATOM   2305  OH2  WAT   628     8.270   -6.751   16.481  1.00 27.56
ATOM   2306  OH2  WAT   629    15.541   13.948   41.048  1.00 29.49
ATOM   2307  OH2  WAT   630    23.084   16.734   21.168  1.00 26.00
ATOM   2308  OH2  WAT   631    19.690    5.426  -11.485  1.00 25.65
ATOM   2309  OH2  WAT   632     2.999    1.453  -10.337  1.00 32.88
```

FIG.11B-55

| | | | | | | | | |
|---|---|---|---|---|---|---|---|---|
| ATOM | 2310 | OH2 | WAT | 633 | -10.039 | 6.144 | 37.785 | 1.00 32.06 |
| ATOM | 2311 | OH2 | WAT | 634 | 25.680 | 21.534 | 32.761 | 1.00 30.38 |
| ATOM | 2312 | OH2 | WAT | 636 | 1.101 | 14.667 | 27.285 | 1.00 33.90 |
| ATOM | 2313 | OH2 | WAT | 637 | 4.677 | -7.995 | 15.521 | 1.00 39.69 |
| ATOM | 2314 | OH2 | WAT | 638 | -4.199 | 10.629 | 27.487 | 1.00 25.74 |
| ATOM | 2315 | OH2 | WAT | 639 | 16.727 | 16.185 | 23.380 | 1.00 24.68 |
| ATOM | 2316 | OH2 | WAT | 641 | 4.762 | 8.324 | 41.074 | 1.00 32.42 |
| ATOM | 2317 | OH2 | WAT | 642 | 1.346 | -0.850 | -3.508 | 1.00 37.14 |
| ATOM | 2318 | OH2 | WAT | 643 | 6.494 | -5.448 | -2.382 | 1.00 29.92 |
| ATOM | 2319 | OH2 | WAT | 644 | -0.637 | 10.395 | 17.913 | 1.00 32.31 |
| ATOM | 2320 | OH2 | WAT | 645 | 28.896 | -3.506 | 20.216 | 1.00 28.05 |
| ATOM | 2321 | OH2 | WAT | 646 | 13.649 | -8.354 | 22.832 | 1.00 36.52 |
| ATOM | 2322 | OH2 | WAT | 647 | -4.016 | -2.000 | 41.527 | 1.00 41.51 |
| ATOM | 2323 | OH2 | WAT | 648 | -3.699 | 4.194 | 15.863 | 1.00 34.38 |
| ATOM | 2324 | OH2 | WAT | 649 | 18.236 | 9.536 | 44.036 | 1.00 40.10 |
| ATOM | 2325 | OH2 | WAT | 650 | -2.251 | -2.420 | 29.819 | 1.00 37.50 |
| ATOM | 2326 | OH2 | WAT | 651 | 28.245 | 9.734 | 16.414 | 1.00 31.59 |
| ATOM | 2327 | OH2 | WAT | 652 | 25.887 | 14.410 | 11.861 | 1.00 39.37 |
| ATOM | 2328 | OH2 | WAT | 653 | -4.668 | -3.492 | 21.738 | 1.00 38.13 |
| ATOM | 2329 | OH2 | WAT | 654 | 15.932 | 8.831 | -4.665 | 1.00 42.38 |
| ATOM | 2330 | OH2 | WAT | 655 | 39.349 | -0.041 | 40.457 | 1.00 36.11 |
| ATOM | 2331 | OH2 | WAT | 656 | 16.291 | 15.362 | 18.684 | 1.00 28.74 |
| ATOM | 2332 | OH2 | WAT | 657 | 20.650 | 8.704 | 43.546 | 1.00 26.18 |
| ATOM | 2333 | OH2 | WAT | 658 | 21.731 | 4.870 | -9.446 | 1.00 41.19 |
| ATOM | 2334 | OH2 | WAT | 659 | 27.579 | -8.698 | 29.528 | 1.00 36.99 |
| ATOM | 2335 | OH2 | WAT | 660 | 15.065 | 1.058 | -9.945 | 1.00 34.45 |
| ATOM | 2336 | C1 | ADPN | 800 | 15.589 | -7.036 | 12.366 | 1.00 29.43 |
| ATOM | 2337 | C2 | ADPN | 800 | 16.795 | -6.562 | 11.567 | 1.00 27.99 |
| ATOM | 2338 | O1 | ADPN | 800 | 16.276 | -5.540 | 10.684 | 1.00 26.79 |
| ATOM | 2339 | C3 | ADPN | 800 | 17.832 | -5.869 | 12.464 | 1.00 28.23 |
| ATOM | 2340 | O2 | ADPN | 800 | 19.138 | -6.070 | 11.920 | 1.00 29.48 |
| ATOM | 2341 | C4 | ADPN | 800 | 17.379 | -4.406 | 12.439 | 1.00 27.06 |
| ATOM | 2342 | O3 | ADPN | 800 | 18.452 | -3.550 | 12.841 | 1.00 29.12 |
| ATOM | 2343 | C5 | ADPN | 800 | 16.915 | -4.275 | 10.979 | 1.00 25.84 |
| ATOM | 2344 | N1 | ADPN | 800 | 15.939 | -3.162 | 10.843 | 1.00 23.38 |
| ATOM | 2345 | C6 | ADPN | 800 | 14.655 | -3.121 | 11.351 | 1.00 23.14 |
| ATOM | 2346 | N2 | ADPN | 800 | 14.038 | -1.962 | 10.976 | 1.00 22.86 |
| ATOM | 2347 | C7 | ADPN | 800 | 14.938 | -1.266 | 10.236 | 1.00 22.16 |
| ATOM | 2348 | C8 | ADPN | 800 | 14.895 | -0.025 | 9.594 | 1.00 22.13 |
| ATOM | 2349 | N3 | ADPN | 800 | 13.812 | 0.764 | 9.707 | 1.00 21.32 |
| ATOM | 2350 | N4 | ADPN | 800 | 16.025 | 0.390 | 8.889 | 1.00 21.64 |
| ATOM | 2351 | C9 | ADPN | 800 | 17.152 | -0.341 | 8.819 | 1.00 21.90 |

FIG.11B-56

| | | | | | | | | | |
|---|---|---|---|---|---|---|---|---|---|
| ATOM | 2352 | N5  | ADPN | 800 | 17.271 | -1.548 | 9.430  | 1.00 | 21.98 |
| ATOM | 2353 | C10 | ADPN | 800 | 16.144 | -2.011 | 10.140 | 1.00 | 22.86 |
| ATOM | 2354 | S   | SO4  | 901 | -0.220 | -4.850 | 27.961 | 1.00 | 26.12 |
| ATOM | 2355 | O1  | SO4  | 901 | 0.507  | -5.374 | 26.794 | 1.00 | 26.13 |
| ATOM | 2356 | O2  | SO4  | 901 | 0.700  | -4.720 | 29.109 | 1.00 | 28.87 |
| ATOM | 2357 | O3  | SO4  | 901 | -1.308 | -5.781 | 28.341 | 1.00 | 24.66 |
| ATOM | 2358 | O4  | SO4  | 901 | -0.818 | -3.538 | 27.657 | 1.00 | 29.71 |
| END  |      |     |      |     |        |        |        |      |       |

FIG.11B-57

SEQUENCE LISTING

<160> NUMBER OF SEQ ID NOS: 24

<210> SEQ ID NO 1
<211> LENGTH: 1821
<212> TYPE: DNA
<213> ORGANISM: Homo sapiens

<400> SEQUENCE: 1

| | | | | | | |
|---|---|---|---|---|---|---|
| ggccggacag | tccgccgagg | tgctcggtgg | agtcatggca | gtgcccttttg | tggaagactg | 60 |
| ggacttggtg | caaaccctgg | gagaaggtgc | ctatggagaa | gttcaacttg | ctgtgaatag | 120 |
| agtaactgaa | gaagcagtcg | cagtgaagat | tgtagatatg | aagcgtgccg | tagactgtcc | 180 |
| agaaaatatt | aagaaagaga | tctgtatcaa | taaaatgcta | aatcatgaaa | atgtagtaaa | 240 |
| attctatggt | cacaggagag | aaggcaatat | ccaatattta | tttctggagt | actgtagtgg | 300 |
| aggagagctt | tttgacagaa | tagagccaga | cataggcatg | cctgaaccag | atgctcagag | 360 |
| attcttccat | caactcatgg | cagggtggt | ttatctgcat | ggtattggaa | taactcacag | 420 |
| ggatattaaa | ccagaaaatc | ttctgttgga | tgaaagggat | aacctcaaaa | tctcagactt | 480 |
| tggcttggca | acagtatttc | ggtataataa | tcgtgagcgt | ttgttgaaca | agatgtgtgg | 540 |
| tactttacca | tatgttgctc | cagaacttct | gaagagaaga | gaatttcatg | cagaaccagt | 600 |
| tgatgtttgg | tcctgtggaa | tagtacttac | tgcaatgctc | gctggagaat | tgccatggga | 660 |
| ccaacccagt | gacagctgtc | aggagtattc | tgactggaaa | gaaaaaaaaa | catacctcaa | 720 |
| cccttggaaa | aaaatcgatt | ctgctcctct | agctctgctg | cataaaatct | tagttgagaa | 780 |
| tccatcagca | agaattacca | ttccagacat | caaaaaagat | agatggtaca | acaaaccct | 840 |
| caagaaaggg | gcaaaaggc | cccgagtcac | ttcaggtggt | gtgtcagagt | ctcccagtgg | 900 |
| attttctaag | cacattcaat | ccaatttgga | cttctctcca | gtaaacagtg | cttcagtga | 960 |
| agaaaatgtg | aagtactcca | gttctcagcc | agaaccccgc | acaggtctttt | ccttatggga | 1020 |
| taccagcccc | tcatacattg | ataaattggt | acaagggatc | agcttttccc | agcccacatg | 1080 |
| tcctgatcat | atgcttttga | atagtcagtt | acttggcacc | ccaggatcct | cacagaaccc | 1140 |
| ctggcagcgg | ttggtcaaaa | gaatgacacg | attcttacc | aaattggatg | cagacaaatc | 1200 |
| ttatcaatgc | ctgaaagaga | cttgtgagaa | gttgggctat | caatggaaga | aagttgtat | 1260 |
| gaatcaggtt | actatatcaa | caactgatag | gagaaacaat | aaactcattt | tcaaagtgaa | 1320 |
| tttgttagaa | atggatgata | aaatattggt | tgacttccgg | ctttctaagg | gtgatggatt | 1380 |
| ggagttcaag | agacacttcc | tgaagattaa | agggaagctg | attgatattg | tgagcagcca | 1440 |
| gaaggtttgg | cttcctgcca | catgatcgga | ccatcggctc | tggggaatcc | tggtgaatat | 1500 |
| agtgctgcta | tgttgacatt | attcttccta | gagaagatta | tcctgtcctg | caactgcaa | 1560 |
| atagtagttc | ctgaagtgtt | cacttccctg | tttatccaaa | catcttccaa | tttattttgt | 1620 |
| ttgttcggca | tacaaataat | acctatatct | taattgtaag | caaaactttg | gggaaaggat | 1680 |
| gaatagaatt | catttgatta | tttcttcatg | tgtgtttagt | atctgaattt | gaaactcatc | 1740 |
| tggtggaaac | caagtttcag | gggacatgag | ttttccagct | tttatacaca | cgtatctcat | 1800 |
| ttttatcaaa | acattttgtt | t | | | | 1821 |

<210> SEQ ID NO 2
<211> LENGTH: 476
<212> TYPE: PRT
<213> ORGANISM: Homo sapiens

```
<400> SEQUENCE: 2

Met Ala Val Pro Phe Val Glu Asp Trp Asp Leu Val Gly Thr Leu Gly
 1               5                  10                  15

Glu Gly Ala Tyr Gly Glu Val Gln Leu Ala Val Asn Arg Val Thr Glu
            20                  25                  30

Glu Ala Val Ala Val Lys Ile Val Asp Met Lys Arg Ala Val Asp Cys
        35                  40                  45

Pro Glu Asn Ile Lys Lys Glu Ile Cys Ile Asn Lys Met Leu Asn His
    50                  55                  60

Glu Asn Val Val Lys Phe Tyr Gly His Arg Arg Gly Asn Ile Gln
65                  70                  75                  80

Tyr Leu Phe Leu Glu Tyr Cys Ser Gly Gly Glu Leu Phe Asp Arg Ile
                85                  90                  95

Glu Pro Asp Ile Gly Met Pro Glu Pro Asp Ala Gln Arg Phe Phe His
            100                 105                 110

Gln Leu Met Ala Gly Val Val Tyr Leu His Gly Ile Gly Ile Thr His
        115                 120                 125

Arg Asp Ile Lys Pro Glu Asn Leu Leu Leu Asp Glu Arg Asp Asn Leu
    130                 135                 140

Lys Ile Ser Asp Phe Gly Leu Ala Thr Val Phe Arg Tyr Asn Asn Arg
145                 150                 155                 160

Glu Arg Leu Leu Asn Lys Met Cys Gly Thr Leu Pro Tyr Val Ala Pro
                165                 170                 175

Glu Leu Leu Lys Arg Arg Glu Phe His Ala Glu Pro Val Asp Val Trp
            180                 185                 190

Ser Cys Gly Ile Val Leu Thr Ala Met Leu Ala Gly Glu Leu Pro Trp
        195                 200                 205

Asp Gln Pro Ser Asp Ser Cys Gln Glu Tyr Ser Asp Trp Lys Glu Lys
    210                 215                 220

Lys Thr Tyr Leu Asn Pro Trp Lys Lys Ile Asp Ser Ala Pro Leu Ala
225                 230                 235                 240

Leu Leu His Lys Ile Leu Val Glu Asn Pro Ser Ala Arg Ile Thr Ile
                245                 250                 255

Pro Asp Ile Lys Lys Asp Arg Trp Tyr Asn Lys Pro Leu Lys Lys Gly
            260                 265                 270

Ala Lys Arg Pro Arg Val Thr Ser Gly Gly Val Ser Glu Ser Pro Ser
        275                 280                 285

Gly Phe Ser Lys His Ile Gln Ser Asn Leu Asp Phe Ser Pro Val Asn
    290                 295                 300

Ser Ala Ser Ser Glu Glu Asn Val Lys Tyr Ser Ser Ser Gln Pro Glu
305                 310                 315                 320

Pro Arg Thr Gly Leu Ser Leu Trp Asp Thr Ser Pro Ser Tyr Ile Asp
                325                 330                 335

Lys Leu Val Gln Gly Ile Ser Phe Ser Gln Pro Thr Cys Pro Asp His
            340                 345                 350

Met Leu Leu Asn Ser Gly Leu Leu Gly Thr Pro Gly Ser Ser Gln Asn
        355                 360                 365

Pro Trp Gln Arg Leu Val Lys Arg Met Thr Arg Phe Phe Thr Lys Leu
    370                 375                 380

Asp Ala Asp Lys Ser Tyr Gln Cys Leu Lys Glu Thr Cys Glu Lys Leu
385                 390                 395                 400

Gln Tyr Gln Trp Lys Lys Ser Cys Met Asn Gln Val Thr Ile Ser Thr
```

```
                    405                 410                 415
Thr Asp Arg Arg Asn Asn Lys Leu Ile Phe Lys Val Asn Leu Leu Glu
                420                 425                 430

Met Asp Asp Lys Ile Leu Val Asp Phe Arg Leu Ser Lys Gly Asp Gly
            435                 440                 445

Leu Glu Phe Lys Arg His Phe Leu Lys Ile Lys Gly Lys Leu Ile Asp
    450                 455                 460

Ile Val Ser Ser Gln Lys Val Trp Leu Pro Ala Thr
465                 470                 475

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: PCR primer

<400> SEQUENCE: 3
gagctcagta ccatctatct tttttgatgt ctgg                              34

<210> SEQ ID NO 4
<211> LENGTH: 47
<212> TYPE: DNA
<213> ORGANISM: Artificial Sequence
<220> FEATURE:
<223> OTHER INFORMATION: Description of Artificial Sequence: PCR primer

<400> SEQUENCE: 4
gagctcagtt ggtggtggtg gtggtgtcca ctgggagact ctgacac                47

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 5
gagctcatcc actgggagac tctgacac                                     28

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: PCR primer

<400> SEQUENCE: 6
ccatggagct caagaaaggg gcaaaaagg                                    29

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 7
gagctcattg gtcccatggc aattctcc                                     28

<210> SEQ ID NO 8
<211> LENGTH: 46
<212> TYPE: DNA
<213> ORGANISM: Artificial Sequence
```

<220> FEATURE:
<223> OTHER INFORMATION: Description of Artificial Sequence: PCR primer

<400> SEQUENCE: 8
gagctcagtg gtggtggtgg tggtggtggt cccatggcaa ttctcc          46

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: PCR primer

<400> SEQUENCE: 9
gagctcactc aactaagatt ttatgcagca g          31

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: PCR primer

<400> SEQUENCE: 10
gagctcagtg gtggtggtgg tggtgctcaa ctaagatttt atgcagcag          49

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 11

Pro Leu Ala Arg Thr Leu Ser Val Ala Gly Leu Pro Gly Lys Lys
 1               5                  10                  15

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: synthetic
      peptide
<223> OTHER INFORMATION: Biotinylated

<400> SEQUENCE: 12

Lys Ala Gly Ala Gly Pro Leu Ala Arg Thr Leu Ser Val Ala Gly Leu
 1               5                  10                  15

Pro Gly Lys

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 13

Pro Leu Ala Arg Thr Leu Ser Val Ala Gly Leu Pro Gly Ala Gly Ala
 1               5                  10                  15

Gly Ala Gly Ala Lys
            20

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 14
tgaataatcc ggcatatgta taggtttttt                               30

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: synthetic peptide
<221> NAME/KEY: MOD_RES
<222> LOCATION: (7)
<223> OTHER INFORMATION: phosphorylated serine

<400> SEQUENCE: 15

Pro Leu Ala Arg Thr Leu Ser Val Ala Gly Leu Pro Gly Lys Lys
 1               5                  10                  15

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: synthetic peptide
<221> NAME/KEY: MOD_RES
<222> LOCATION: (7)
<223> OTHER INFORMATION: phosphorylated serine
<223> OTHER INFORMATION: Biotinylated

<400> SEQUENCE: 16

Pro Leu Ala Arg Thr Leu Ser Val Gly Ala Leu Pro Gly Lys
 1               5                  10

<210> SEQ ID NO 17
<211> LENGTH: 473
<212> TYPE: PRT
<213> ORGANISM: Homo sapiens

<400> SEQUENCE: 17

Met Ser Thr Glu Leu Phe Ser Ser Thr Arg Glu Gly Ser Ser Gly
 1               5                  10                  15

Ser Gly Pro Ser Phe Arg Ser Asn Gln Arg Lys Met Leu Asn Leu Leu
                20                  25                  30

Leu Glu Arg Asp Thr Ser Phe Thr Val Cys Pro Asp Val Pro Arg Thr
            35                  40                  45

Pro Val Gly Lys Phe Leu Gly Asp Ser Ala Asn Leu Ser Ile Leu Ser
        50                  55                  60

Gly Gly Thr Pro Lys Cys Cys Leu Asp Leu Ser Asn Leu Ser Ser Gly
 65                  70                  75                  80

Glu Ile Thr Ala Thr Gln Leu Thr Thr Ser Ala Asp Leu Asp Glu Thr
                85                  90                  95

Gly His Leu Asp Ser Ser Gly Leu Gln Glu Val His Leu Ala Gly Met
            100                 105                 110

Asn His Asp Gln His Leu Met Lys Cys Ser Pro Ala Gln Leu Leu Cys
        115                 120                 125

Ser Thr Pro Asn Gly Leu Asp Arg Gly His Arg Lys Arg Asp Ala Met
    130                 135                 140

Cys Ser Ser Ala Asn Lys Glu Asn Asp Asn Gly Asn Leu Val Asp
145                 150                 155                 160

Ser Glu Met Lys Tyr Leu Gly Ser Pro Ile Thr Thr Val Pro Lys Leu
                165                 170                 175

Asp Lys Asn Pro Asn Leu Gly Glu Asp Gln Ala Glu Ile Ser Asp
            180                 185                 190

Glu Leu Met Glu Phe Ser Leu Lys Asp Gln Glu Ala Lys Val Ser Arg
        195                 200                 205

Ser Gly Leu Tyr Arg Ser Pro Ser Met Pro Glu Asn Leu Asn Arg Pro
    210                 215                 220

Arg Leu Lys Gln Val Glu Lys Phe Lys Asp Asn Thr Ile Pro Asp Lys
225                 230                 235                 240

Val Lys Lys Lys Tyr Phe Ser Gly Gln Gly Lys Leu Arg Lys Gly Leu
                245                 250                 255

Cys Leu Lys Lys Thr Val Ser Leu Cys Asp Ile Thr Ile Thr Gln Met
            260                 265                 270

Leu Glu Glu Asp Ser Asn Gln Gly His Leu Ile Gly Asp Phe Ser Lys
        275                 280                 285

Val Cys Ala Leu Pro Thr Val Ser Gly Lys His Gln Asp Leu Lys Tyr
    290                 295                 300

Val Asn Pro Glu Thr Val Ala Ala Leu Leu Ser Gly Lys Phe Gln Gly
305                 310                 315                 320

Leu Ile Glu Lys Phe Tyr Val Ile Asp Cys Arg Tyr Pro Tyr Glu Tyr
                325                 330                 335

Leu Gly Gly His Ile Gln Gly Ala Leu Asn Leu Tyr Ser Gln Glu Glu
            340                 345                 350

Leu Phe Asn Phe Phe Leu Lys Lys Pro Ile Val Pro Leu Asp Thr Gln
        355                 360                 365

Lys Arg Ile Ile Ile Val Phe His Cys Glu Phe Ser Ser Glu Arg Gly
    370                 375                 380

Pro Arg Met Cys Arg Cys Leu Arg Glu Glu Asp Arg Ser Leu Asn Gln
385                 390                 395                 400

Tyr Pro Ala Leu Tyr Tyr Pro Glu Leu Tyr Ile Leu Lys Gly Gly Tyr
                405                 410                 415

Arg Asp Phe Phe Pro Glu Tyr Met Glu Leu Cys Glu Pro Gln Ser Tyr
            420                 425                 430

Cys Pro Met His His Gln Asp His Lys Thr Glu Leu Leu Arg Cys Arg
        435                 440                 445

Ser Gln Ser Lys Val Gln Glu Gly Glu Arg Gln Leu Arg Glu Gln Ile
    450                 455                 460

Ala Leu Leu Val Lys Asp Met Ser Pro
465                 470

<210> SEQ ID NO 18
<211> LENGTH: 289
<212> TYPE: PRT
<213> ORGANISM: Murine sp.

<400> SEQUENCE: 18

Met Ala Val Pro Phe Val Glu Asp Trp Asp Leu Val Gln Thr Leu Gly
  1               5                  10                  15

Glu Gly Ala Tyr Gly Glu Val Gln Leu Ala Val Asn Arg Ile Thr Glu

```
            20                  25                  30
Gln Ala Val Ala Val Lys Ile Val Asp Met Lys Arg Ala Ile Asp Cys
        35                  40                  45

Pro Gln Asn Ile Lys Lys Glu Ile Cys Ile Asn Lys Met Leu Ser His
    50                  55                  60

Glu Asn Val Val Lys Phe Tyr Gly His Arg Arg Glu Gly His Ile Gln
65                  70                  75                  80

Tyr Leu Phe Leu Glu Tyr Cys Ser Gly Gly Glu Leu Phe Asp Arg Ile
                85                  90                  95

Glu Pro Asp Ile Gly Met Pro Glu Gln Asp Ala Gln Arg Phe Phe His
            100                 105                 110

Gln Leu Met Ala Gly Val Val Tyr Leu His Gly Ile Gly Ile Thr His
            115                 120                 125

Arg Asp Ile Lys Pro Glu Asn Leu Leu Leu Asp Glu Arg Asp Asn Leu
130                 135                 140

Lys Ile Ser Asp Phe Gly Leu Ala Thr Val Phe Arg His Asn Asn Arg
145                 150                 155                 160

Glu Arg Leu Leu Asn Lys Met Cys Gly Thr Leu Pro Tyr Val Ala Pro
                165                 170                 175

Glu Leu Leu Lys Arg Lys Glu Phe His Ala Glu Pro Val Asp Val Trp
            180                 185                 190

Ser Cys Gly Ile Val Leu Thr Ala Met Leu Ala Gly Glu Leu Pro Trp
            195                 200                 205

Asp Gln Pro Ser Asp Ser Cys Gln Glu Tyr Ser Asp Trp Lys Glu Lys
        210                 215                 220

Lys Thr Tyr Leu Asn Pro Trp Lys Lys Ile Asp Ser Ala Pro Leu Ala
225                 230                 235                 240

Leu Leu His Lys Ile Leu Val Glu Thr Pro Ser Ala Arg Ile Thr Ile
                245                 250                 255

Pro Asp Ile Lys Lys Asp Arg Trp Tyr Asn Lys Pro Leu Asn Arg Gly
            260                 265                 270

Ala Lys Arg Pro Arg Ala Thr Ser Gly Gly Met Ser Glu Ser Ser Ser
        275                 280                 285

Gly

<210> SEQ ID NO 19
<211> LENGTH: 288
<212> TYPE: PRT
<213> ORGANISM: Xenopus sp.

<400> SEQUENCE: 19

Met Ala Val Pro Phe Val Glu Asp Trp Asp Leu Val Gln Thr Leu Gly
1               5                   10                  15

Glu Gly Ala Tyr Gly Glu Val Gln Leu Ala Val Asn Arg Lys Thr Glu
            20                  25                  30

Glu Ala Val Ala Val Lys Ile Val Asp Met Thr Arg Ala Ala Asp Cys
        35                  40                  45

Pro Glu Asn Ile Lys Lys Glu Ile Cys Ile Asn Arg Met Leu Ser His
    50                  55                  60

Thr Asn Ile Val Arg Phe Tyr Gly His Arg Arg Glu Gly Asn Ile Gln
65                  70                  75                  80

Tyr Leu Phe Leu Glu Tyr Cys Arg Gly Gly Glu Leu Phe Asp Arg Ile
                85                  90                  95

Glu Pro Asp Val Gly Met Pro Glu Gln Asp Ala Gln Lys Phe Phe Gln
```

-continued

```
            100                 105                 110
Gln Leu Ile Ala Gly Val Glu Tyr Leu His Ser Ile Gly Ile Thr His
        115                 120                 125

Arg Asp Ile Lys Pro Glu Asn Leu Leu Leu Asp Glu Arg Asp Gln Leu
130                 135                 140

Lys Ile Ser Asp Phe Gly Leu Ala Thr Val Phe Arg His Asn Gly Lys
145                 150                 155                 160

Glu Arg Leu Leu Ser Lys Met Cys Gly Thr Leu Pro Tyr Val Ala Pro
                165                 170                 175

Glu Leu Ile Lys Ser Arg Ala Phe His Ala Asp Pro Val Asp Val Trp
                180                 185                 190

Ser Cys Gly Ile Val Leu Thr Ala Met Leu Ala Gly Glu Leu Pro Trp
                195                 200                 205

Asp Gln Pro Asn Glu Val Cys Gln Glu Tyr Cys Asp Trp Lys Glu Lys
        210                 215                 220

Asn His Tyr Leu Thr Pro Trp Lys Lys Ile Ser Ala Thr Pro Leu Ala
225                 230                 235                 240

Leu Leu Gly Lys Met Leu Thr Glu Asn Pro Gln Ser Arg Ile Thr Ile
                245                 250                 255

Pro Asp Ile Lys Lys Asp Arg Trp Phe Thr Glu Ile Ile Lys Lys Gly
                260                 265                 270

Leu Lys Arg Ser Arg Val Ile Ser Gly Gly Ser Ser Asp Ser Ser Val
            275                 280                 285

<210> SEQ ID NO 20
<211> LENGTH: 305
<212> TYPE: PRT
<213> ORGANISM: Drosophila sp.

<400> SEQUENCE: 20

Met Ala Ala Thr Leu Thr Glu Ala Gly Thr Gly Pro Ala Ala Thr Arg
  1               5                  10                  15

Glu Phe Val Glu Gly Trp Thr Leu Ala Gln Thr Leu Gly Glu Gly Ala
                 20                  25                  30

Tyr Gly Glu Val Lys Leu Leu Ile Asn Arg Gln Thr Gly Gly Gly Cys
             35                  40                  45

Gly Met Lys Met Val Asp Leu Lys Lys His Pro Asp Ala Ala Asn Ser
     50                  55                  60

Val Arg Lys Glu Val Cys Ile Gln Lys Met Leu Gln Asp Lys His Ile
 65                  70                  75                  80

Leu Arg Phe Phe Gly Lys Arg Ser Gln Gly Ser Val Glu Tyr Ile Phe
                 85                  90                  95

Leu Glu Tyr Ala Ala Gly Gly Glu Leu Phe Asp Arg Ile Glu Pro Asp
                100                 105                 110

Val Gly Met Pro Gln His Glu Ala Gln Arg Tyr Phe Thr Gln Leu Leu
            115                 120                 125

Ser Gly Leu Asn Tyr Leu His Gln Arg Gly Ile Ala His Arg Asp Leu
        130                 135                 140

Lys Pro Glu Asn Leu Leu Leu Asp Glu His Asp Asn Val Lys Ile Ser
145                 150                 155                 160

Asp Phe Gly Met Ala Thr Met Phe Arg Cys Lys Gly Lys Glu Arg Leu
                165                 170                 175

Leu Asp Lys Arg Cys Gly Thr Leu Pro Tyr Val Ala Pro Glu Val Leu
                180                 185                 190
```

```
Gln Lys Ala Tyr Gln Pro Gln Pro Ala Asp Leu Trp Ser Cys Gly Val
            195                 200                 205

Ile Leu Val Thr Met Leu Ala Gly Glu Leu Pro Trp Asp Gln Pro Ser
        210                 215                 220

Thr Asn Cys Thr Glu Phe Thr Asn Trp Arg Asp Asn Asp His Trp Gln
225                 230                 235                 240

Leu Gln Thr Pro Trp Ser Lys Leu Asp Thr Leu Ala Ile Ser Leu Leu
            245                 250                 255

Arg Lys Leu Leu Leu Ala Thr Ser Pro Gly Thr Arg Leu Thr Leu Glu
            260                 265                 270

Lys Thr Leu Asp His Lys Trp Cys Asn Met Gln Phe Ala Asp Asn Glu
            275                 280                 285

Arg Ser Tyr Asp Leu Val Asp Ser Ala Ala Ala Leu Glu Ile Cys Ser
            290                 295                 300

Pro
305

<210> SEQ ID NO 21
<211> LENGTH: 299
<212> TYPE: PRT
<213> ORGANISM: C. elegans

<400> SEQUENCE: 21

Met Ser Ala Ala Ser Thr Thr Ser Thr Pro Ala Ala Ala Val Ala
 1               5                  10                  15

Pro Gln Gln Pro Glu Ser Leu Tyr Arg Val Val Gln Thr Leu Gly Glu
                20                  25                  30

Gly Ala Phe Gly Glu Val Leu Leu Ile Val Asn Thr Lys Asn Pro Glu
            35                  40                  45

Val Ala Ala Ala Met Lys Lys Ile Asn Ile Ala Asn Lys Ser Lys Asp
 50                  55                  60

Phe Ile Asp Asn Ile Arg Lys Glu Tyr Leu Leu Gln Lys Arg Val Ser
 65                  70                  75                  80

Ala Val Gly His Asp Asn Val Ile Arg Met Ile Gly Met Arg Asn Asp
                85                  90                  95

Pro Gln Phe Tyr Tyr Leu Phe Leu Glu Tyr Ala Asp Gly Gly Glu Leu
                100                 105                 110

Phe Asp Lys Ile Glu Pro Asp Cys Gly Met Ser Pro Val Phe Ala Gln
            115                 120                 125

Phe Tyr Phe Lys Gln Leu Ile Cys Gly Leu Lys Phe Ile His Asp Asn
130                 135                 140

Asp Val Val His Arg Asp Ile Lys Pro Glu Asn Leu Leu Leu Thr Gly
145                 150                 155                 160

Thr His Val Leu Lys Ile Ser Asp Phe Gly Met Ala Thr Leu Tyr Arg
                165                 170                 175

Asn Lys Gly Glu Glu Arg Leu Leu Asp Leu Ser Cys Gly Thr Ile Pro
            180                 185                 190

Tyr Ala Ala Pro Glu Leu Cys Ala Gly Lys Lys Tyr Arg Gly Pro Pro
            195                 200                 205

Val Asp Val Trp Ser Ser Gly Ile Val Leu Ile Ala Met Leu Thr Gly
            210                 215                 220

Glu Leu Pro Trp Asp Arg Ala Ser Asp Ala Ser Gln Ser Tyr Met Gly
225                 230                 235                 240

Trp Ile Ser Asn Thr Ser Leu Asp Glu Arg Pro Trp Lys Lys Ile Asp
            245                 250                 255
```

```
Val Arg Ala Leu Cys Met Leu Arg Lys Ile Val Thr Asp Lys Thr Asp
            260                 265                 270

Lys Arg Ala Thr Ile Glu Gln Ile Gln Ala Asp Pro Trp Tyr Gln His
        275                 280                 285

Asn Phe Gly Gln Val Glu Thr Pro Asn Gly Arg
    290                 295

<210> SEQ ID NO 22
<211> LENGTH: 306
<212> TYPE: PRT
<213> ORGANISM: S. cerevisiae

<400> SEQUENCE: 22

Met Ser Leu Ser Gln Val Ser Pro Leu Pro His Ile Lys Asp Val Val
1               5                   10                  15

Leu Gly Asp Thr Val Gly Gln Gly Ala Phe Ala Cys Val Lys Asn Ala
            20                  25                  30

His Leu Gln Met Asp Pro Ser Ile Ile Leu Ala Val Lys Phe Ile His
        35                  40                  45

Val Pro Thr Cys Lys Lys Met Gly Leu Ser Asp Lys Asp Ile Thr Lys
    50                  55                  60

Glu Val Val Leu Gln Ser Lys Cys Ser Lys His Pro Asn Val Leu Arg
65                  70                  75                  80

Leu Ile Asp Cys Asn Val Ser Lys Glu Tyr Met Trp Ile Ile Leu Glu
                85                  90                  95

Met Ala Asp Gly Gly Asp Leu Phe Asp Lys Ile Glu Pro Asp Val Gly
            100                 105                 110

Val Asp Ser Asp Val Ala Gln Phe Tyr Phe Gln Gln Leu Val Ser Ala
        115                 120                 125

Ile Asn Tyr Leu His Val Glu Cys Gly Val Ala His Arg Asp Ile Lys
    130                 135                 140

Pro Glu Asn Ile Leu Leu Asp Lys Asn Gly Asn Leu Lys Leu Ala Asp
145                 150                 155                 160

Phe Gly Leu Ala Ser Gln Phe Arg Arg Lys Asp Gly Thr Leu Arg Val
                165                 170                 175

Ser Met Asp Gln Arg Gly Ser Pro Pro Tyr Met Ala Pro Glu Val Leu
            180                 185                 190

Tyr Ser Glu Glu Gly Tyr Tyr Ala Asp Arg Thr Asp Ile Trp Ser Ile
        195                 200                 205

Gly Ile Leu Leu Phe Val Leu Leu Thr Gly Gln Thr Pro Trp Glu Leu
    210                 215                 220

Pro Ser Leu Glu Asn Glu Asp Phe Val Phe Ile Glu Asn Asp Gly
225                 230                 235                 240

Asn Leu Asn Trp Gly Pro Trp Ser Lys Ile Glu Phe Thr His Leu Asn
                245                 250                 255

Leu Leu Arg Lys Ile Leu Gln Pro Asp Pro Asn Lys Arg Val Thr Leu
            260                 265                 270

Lys Ala Leu Lys Leu His Pro Trp Val Leu Arg Arg Ala Ser Phe Ser
        275                 280                 285

Gly Asp Asp Gly Leu Cys Asn Asp Pro Glu Leu Leu Ala Lys Lys Leu
    290                 295                 300

Phe Ser
305
```

<210> SEQ ID NO 23
<211> LENGTH: 295
<212> TYPE: PRT
<213> ORGANISM: S. pombe

<400> SEQUENCE: 23

```
Met Ala Gln Lys Leu Asp Asn Phe Pro Tyr His Ile Gly Arg Glu Ile
  1               5                  10                  15
Gly Thr Gly Ala Phe Ala Ser Val Arg Leu Cys Tyr Asp Asp Asn Ala
             20                  25                  30
Lys Ile Tyr Ala Val Lys Phe Val Asn Lys Lys His Ala Thr Ser Cys
         35                  40                  45
Met Asn Ala Gly Val Trp Ala Arg Arg Met Ala Ser Glu Ile Gln Leu
     50                  55                  60
His Lys Leu Cys Asn Gly His Lys Asn Ile Ile His Phe Tyr Asn Thr
 65                  70                  75                  80
Ala Glu Asn Pro Gln Trp Arg Trp Val Val Leu Glu Phe Ala Gln Gly
                 85                  90                  95
Gly Asp Leu Phe Asp Lys Ile Glu Pro Asp Val Gly Ile Asp Glu Asp
            100                 105                 110
Val Ala Gln Phe Tyr Phe Ala Gln Leu Met Glu Gly Ile Ser Phe Met
        115                 120                 125
His Ser Lys Gly Val Ala His Arg Asp Leu Lys Pro Glu Asn Ile Leu
    130                 135                 140
Leu Asp Tyr Asn Gly Asn Leu Lys Ile Ser Asp Phe Gly Phe Ala Ser
145                 150                 155                 160
Leu Phe Ser Tyr Lys Gly Lys Ser Arg Leu Leu Asn Ser Pro Val Gly
                165                 170                 175
Ser Pro Pro Tyr Ala Ala Pro Glu Ile Thr Gln Gln Tyr Asp Gly Ser
            180                 185                 190
Lys Val Asp Val Trp Ser Cys Gly Ile Ile Leu Phe Ala Leu Leu Leu
        195                 200                 205
Gly Asn Thr Pro Trp Asp Glu Ala Ile Ser Asn Thr Gly Asp Tyr Leu
    210                 215                 220
Leu Tyr Lys Lys Gln Cys Glu Arg Pro Ser Tyr His Pro Trp Asn Leu
225                 230                 235                 240
Leu Ser Pro Gly Ala Tyr Ser Ile Ile Thr Gly Met Leu Arg Ser Asp
                245                 250                 255
Pro Phe Lys Arg Tyr Ser Val Lys His Val Val Gln His Pro Trp Leu
            260                 265                 270
Thr Ser Ser Thr Pro Phe Arg Thr Lys Asn Gly Asn Cys Ala Asp Pro
        275                 280                 285
Val Ala Leu Ala Ser Arg Leu
    290                 295
```

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: conserved motif
<221> NAME/KEY: MOD_RES
<222> LOCATION: (3)
<223> OTHER INFORMATION: variable residue
<221> NAME/KEY: MOD_RES
<222> LOCATION: (6)
<223> OTHER INFORMATION: variable residue

```
-continued

<400> SEQUENCE: 24

Ala Gln Xaa Phe Phe Xaa Gln Leu
 1               5
```

CATALYTIC DOMAIN OF THE HUMAN EFFECTOR CELL CYCLE CHECKPOINT PROTEIN KINASE MATERIALS AND METHODS FOR IDENTIFICATION OF INHIBITORS THEREOF

This application claims benefit of U.S. provisional application No. 60/162,887, filed Nov. 1, 1999.

FIELD OF THE INVENTION

The present invention generally relates to cell cycle checkpoint kinases which are essential to cellular DNA damage responses and coordinating cell cycle arrest. The checkpoint kinases play a role in the surveillance and response to DNA damage. The damage may result from external or internal forces. Such forces include but are not limited to errors in replication, DNA base damage, DNA strand breaks, or exposure to radiation or cytotoxic chemicals. These checkpoint kinases are integral in the regulatory pathways leading to cell cycle arrest and apoptosis following DNA damage, giving the cell notice and time to correct lesions prior to the initiation of replication and chromosome separation. The present invention more specifically relates to the isolation and purification of the catalytic domain of the human effector checkpoint protein kinase (hChk1) and its use in the discovery, identification and characterization of inhibitors of same.

BACKGROUND

Cell growth, division and death is essential to the life cycle of multi-celled organisms. These processes and their regulation are strikingly similar across all eukaryotic species. Somatic cell division consists of two sequential processes: DNA replication followed by chromosomal separation. The cell spends most of its time preparing for these events in a growth cycle (interphase) which in turn consists of three subphases: initial gap ($G_1$), synthesis (S), and secondary gap ($G_2$). In $G_1$, the cell, whose biosynthetic pathways were slowed during mitosis, resumes a high rate of biosynthesis. The S phase begins when DNA synthesis starts and ends when the DNA content of the nucleus has doubled. The cell then enters $G_2$, which lasts until the cell enters the final phase of division, mitotic (M). The M phase begins with nuclear envelope breakdown, chromosome condensation and formation of two identical sets of chromosomes which are separated into two new nuclei. This is followed by cell division (cytokinesis) in which each nuclei is separated into two daughter cells, which terminates the M phase and marks the beginning of interphase for the new cells.

The sequence in which the cell cycle events proceed is tightly regulated such that the initiation of one cell cycle event is dependent upon the successful completion of the prior cell cycle event. The process of monitoring genome integrity and preventing cell cycle progress in the event of DNA damage has been described as a 'cell cycle checkpoint' (Hartwell, L H et al., *Science*, 246:629–634 (1989); Weinert et al., *Genes and Dev.*, 8:652 (1994)]. Cell cycle checkpoints consist of signal transduction cascades which couple DNA damage detection to cell cycle progression. Checkpoints are control systems that coordinate cell cycle progression by influencing the formation, activation and subsequent inactivation of the cyclin-dependent kinases. Checkpoint enzymes are responsible for maintaining the order and fidelity of events of the cell cycle by blocking mitosis in response to unreplicated or damaged DNA. These enzymes prevent cell cycle progression at inappropriate times, maintain the metabolic balance of cells while the cell is arrested and in some instances can induce apoptosis (programmed cell death) when the requirements of the checkpoint have not been met (O'Connor, P M, *Cancer Surveys*, 29, 151–182 (1997); Nurse, P, *Cell*, 91, 865–867 (1997); Hartwell, L H et al, *Science*, 266, 1821–1828 (1994); Hartwell, L H et al., *Science*, 246, (1989), supra).

One series of checkpoints monitors the integrity of the genome. Upon sensing DNA damage, these "DNA damage checkpoints" block cell cycle progression in $G_1$ & $G_2$ phases, and slow progression through S phase (O'Connor, P M, *Cancer Surveys*, 29 (1997), supra; Hartwell, L H et al, *Science*, 266, (1994), supra). This action enables DNA repair to be completed before replication of the genome and subsequent separation of this genetic material into new daughter cell takes place.

Various mutations associated with malignancy affect the cancer cells ability to regulate checkpoints, allowing cells with DNA damage the increased likelihood to continue replicating and to escape damage-mediated apoptosis These factors contribute to the genomic instability which drives the genetic evolution of human cancers and contributes to the resistance of cancer cells to most current chemotherapy and radiotherapy intervention.

Due to abnormalities in the p53 tumor suppressor pathway, most cancer cells lack a functional $G_1$ checkpoint control system. This makes them particularly vulnerable to abrogation of the last remaining barrier protecting them from the cancer killing effects of DNA damaging agents: the $G_2$ checkpoint. The $G_2$ DNA damage checkpoint ensures maintenance of cell viability by delaying progression into mitosis in cells that have suffered genomic damage. The $G_2$ checkpoint is controlled by cell cycle checkpoint pathways which inhibit mitosis if previous events are incomplete or if the DNA is damaged. This regulation control system has been conserved from yeast to humans. Important in this conserved system is a kinase, Chk1 (or p56Chk1), which transduces signals from the DNA damage sensory complex to inhibit activation of the cyclin B/Cdc2 kinase which promotes mitotic entry (Peng, C Y et al, *Science*, 277, 1501–1505 (1997); Sanchez Y, et al., *Science*, 277, 1497–1501 (1997); Walworth, N et al., *Nature*, 363(6427), 368–71 (May 27, 1993); al-Khodairy et al., *Mol Biol Cell*, 5(2):147–60 (Febuary 1994); Carr et al., *Curr Biol.*, 5(10): 1179–90 (Oct. 1, 1995)). The repair checkpoint kinase, Chk1, regulates Cdc25, a phosphatase that activates Cdc2. Thus, Chk1 serves as the direct link between the $G_2$ checkpoint and the negative regulation of Cdc2.

Inactivation of Chk1 has been shown to both abrogate $G_2$ arrest induced by DNA damage inflicted by either anticancer agents or endogenous DNA damage, as well as, result in preferential killing of the resulting checkpoint defective cells (Nurse, P, *Cell*, 91, (1997), supra; Weinert, T, *Science*, 277, 1450–1451 (1997); Walworth, N et al., *Nature*, 363, (1993) supra; al-Khodairy et al., *Molec. Biol. Cell*, 5, (1994), supra; Wan, S et al., *Yeast*, 15(10A), 821–8 (July 1999)).

The fact that cancer cells have also been shown to be more vulnerable to $G_2$ checkpoint abrogation has encouraged the pursuit of $G_2$ checkpoint abrogating drugs (Wang, Q et al., *PNAS* 96: 3706–3711 (1999); Fan, S et al., *Cancer Res.*, 55, 1649–1654 (1995); Powell, S N et al., *Cancer Res.*, 55, 1643–1648 (1995); Russell, K J et al., *Cancer Res.*, 55, 1639–1642 (1995); Wang, Q et al., *J Natl Cancer Inst.*, 88, 956–967 (1996)). Such checkpoint abrogating drugs could improve the killing of tumors exposed to DNA damaging events including that inflicted by therapeutic agents, hypoxic-stress induced because of a limited blood supply (anti-angiogenic agents), or endogenous DNA damage arising as a consequence of a cancer cell's inherent genomic instability. Selective manipulation of checkpoint control in cancer cells can afford broad utilization in cancer chemotherapeutic and radiotherapy regimens and may in addition, offer a common hallmark of human cancer "genomic instability" to be exploited as the selective basis for the destruction cancer cells.

A number of lines of evidence place Chk1 as a pivotal target in DNA damage checkpoint control. However, Chk1 is a difficult enzyme to study because the full length protein is not the most active form of Chk1. While others have examined the nucleotide and amino acid sequence of the full-length checkpoint kinase and estimated the location of the kinase domain, there is a need for the isolation and purification of the kinase domain of Chk1and the maintenance of its catalytically active conformation.

SUMMARY OF THE INVENTION

The generation, kinetic characterization, and structure determination of the kinase domain of the human Chk1 protein is disclosed herein. The domain begins between residues 1 and 16 and terminates between residues 265 and 291 of the full length protein [SEQ ID NO. 2] which comprises 476 amino acids. The domain preferably extends from residues 1–265, more preferably from residues 1–289.

The invention relates to an isolated, purified polynucleotide which encodes the active conformation of the human Chk1 kinase or an active kinase analog thereof. The polynucleotide may be natural or recombinant.

The invention also relates to an isolated, soluble catalytically active polypeptide comprising the active conformation of the human Chk1 kinase or an active kinase analog thereof.

The invention encompasses both the polypeptide per se as well as salts thereof. As discussed in detail below, a high salt concentration (about 500 mM) in the buffer is used herein to prevent aggregation of peptide during purification and storage.

The invention also relates to a crystal structure of the human Chk1 kinase in the active conformation resolved to at least 2.5 Å, preferably 2.0 Å, more preferably 1.7 Å. This structure provides a three-dimensional description of the target (human Chk1) for structure-based design of small molecule inhibitors thereof as therapeutic agents.

The invention further relates to an expression vector for producing catalytically active human Chk1 kinase in a host cell.

The invention further relates to a host cell stably transformed and transfected with a polynucleotide encoding of the human Chk1 kinase, or fragment thereof, or an active kinase analog thereof, in a manner allowing the expression of the human Chk1 kinase in the active configuration.

The present invention further discloses methods for screening candidate compounds using the molecular structure of the x-ray crystallography data to model the binding of candidate compounds.

The invention further provides a method for designing and screening potentially therapeutic compounds for the treatment of hyper-proliferative or diseases related to proliferation, including but not limited to cancer and HIV infection. The putative therapeutics can be screened for activities such as (1) potentiation of the cytotoxicity of DNA damaging agents such as synthetic or natural chemotherapeutic agents and ionizing or neutron radiation; (2) enhancement of the cytotoxicity of DNA synthesis inhibitors including antimetabolites, DNA chain terminators, or other mechanisms that would lead to the inhibition of DNA synthesis; (3) enhancement of the cytotoxicity of hypoxia as would occur within tumors due to a limited blood supply; and (4) inhibition of the ability of HIV to arrest cell cycle progression such as that induced by the VPR protein. Compounds that inhibit human Chk1 kinase activity or abrogate the $G_2$ checkpoint can be used to treat or prevent the hyperproliferation associated with cancer and HIV.

The present invention provides methods for identifying potential inhibitors of the human Chk1 protein kinase by de novo design of novel drug candidate molecules that bind to and inhibit human Chk1 protein kinase activity, or that improve their potency. The x-ray crystallographic coordinates disclosed herein, allow generation of 3-dimensional models of the catalytic site and the drug binding site of the human Chk1 protein. De novo design comprises of the generation of molecules via the use of computer programs which build and link fragments or atoms into a site based upon steric and electrostatic complementarily, without reference to substrate analog structures. The drug design process begins after the structure of the target (human Chk1 kinase) is solved to at least a resolution of 2.5 Å. Refinement of the structure to a resolution of 2.0 Å or better with fixed water molecules in place provides more optimal conditions to undertake drug design.

The invention further provides a method for computational modeling of the kinase domain of human Chk1, such a model being useful in the design of compounds that interact with this domain. The method involves crystallizing the Chk1 kinase in the catalytically active configuration; resolving the x-ray structure of said active kinase, particularly the kinase domain and binding site of active Chk1; and applying the data generated from resolving the x-ray structure to a computer algorithm capable of generating a three dimensional model of the kinase domain and binding site suitable for use in designing molecules that will act as agonists or antagonists to the polypeptide. An iterative process can then be applied to various molecular structures using the computer-generated model to identify potential agonists or antagonists of the Chk1 kinase. Inhibitors of the kinase can serve as lead compounds for the design of potentially therapeutic compounds for the treatment of diseases or disorders associated with hyperproliferation or related to proliferation, such as cancer and HIV.

The invention further provides a process where the human Chk1 protein kinase is modified by deletion of the C-terminal portion of the protein so as to impart favorable physical characteristics of the resulting polypeptide. The kinase domain is suitable for analysis by nuclear magnetic resonance, high throughput screening, biochemical characterizations, x-ray crystallography, colorimetry and other diagnostic means. The most preferred deletion fragment extends from residue 1 to residue 289.

The invention further provides screening methods for use in the drug design process of potential agents to the human Chk1 protein kinase by de novo design of novel drug candidate molecules with potentially nanomolar potencies. The x-ray crystallographic coordinates disclosed based on the kinase domain of the human Chk1 protein will allow the generation of 3-dimensional models of the active binding sites of the human Chk1 protein.

The invention further provides a method for rapidly screening compounds to identify those compounds that inhibit Chk1 kinase or core structure for further Chk1 inhibitor design. The high throughput-screening assay is capable of being fully automated on robotic workstations. The assay may be radioactive. However, in a preferred embodiment the assay is a non-radioactive ELISA. In a more preferred embodiment, the assay is an ELISA that utilizes a novel antibody, rabbit anti-phosphosyntide, to specifically detect the product of the Chk1 kinase reaction in which biotin-syntide is the substrate. However, the basis of the assay includes the ability to use other substrates detectable by anti-phospho-peptide/protein antibodies. The assay may be used to screen large collections of compound libraries to discover Chk1 kinase inhibitors and potential lead compounds for the development of Chk1 kinase selective anti-cancer compounds. The assay finds utility in the screening of other syntide substrate kinase reactions involving kinases of analogous activity to Chk1.

BRIEF DESCRIPTION OF THE DRAWINGS

FIG. 8A shows a stereoview of a representative portion of the experimental density at 1.5 Å calculated to 3.0 Å with the use of phases after solvent flattening. Superimposed on the density is the final refined model. FIG. 8B shows a difference Fourier map calculated with native model-derived phases and coefficients |OF(AMP-PNP)|-|OF(native/apoenzyme)| to the diffraction of 1.7 Å and contoured at 2.5 Å. The triphosphate moiety of AMP-PNP is disordered and is omitted from the model. No $Mg^{2+}$ ions are observed.

FIGS. 11A1–11B57. The Chk1 crystal coordinates for the apoenzyme (isolated active Chk1—FIG. 11A) and the binary complex (Chk1 complexed with AMP-PNP, an ATP analog—FIG. 11B) including the coordinates of the fixed water molecules.

DETAILED DESCRIPTION OF THE INVENTION

Figure 1:
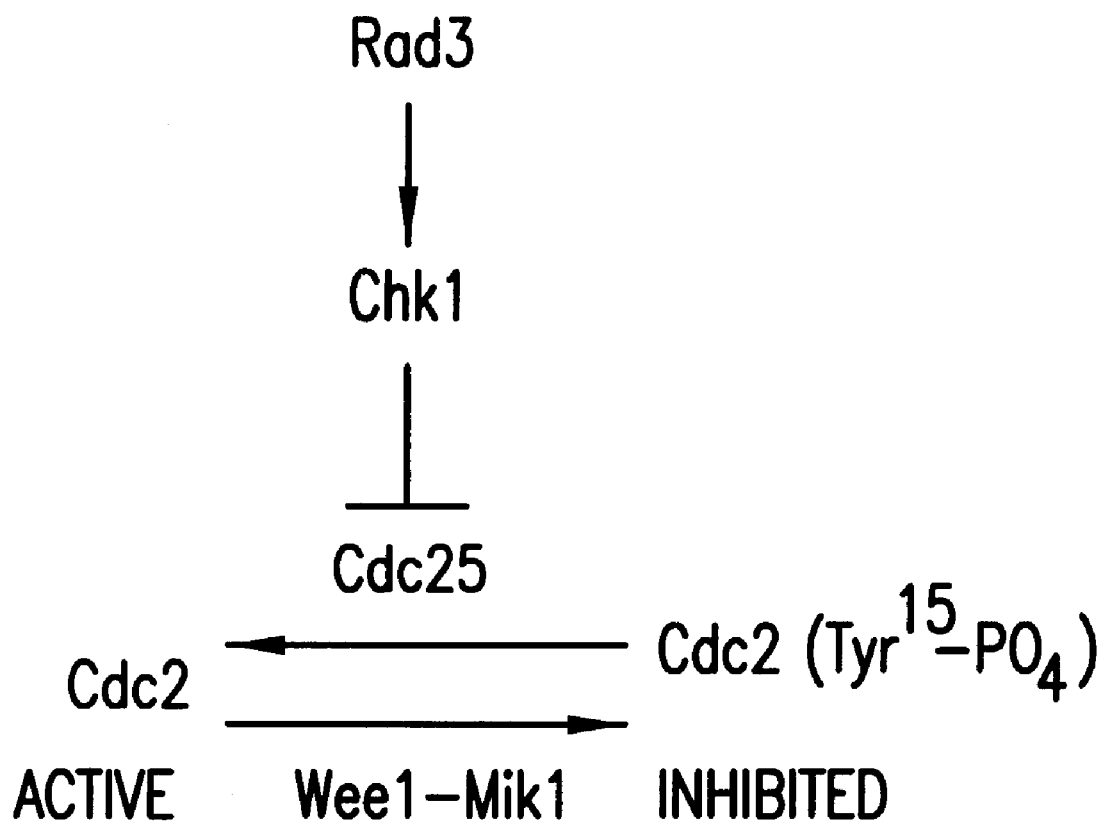
FIG. 1. The $G_2$ DNA damage checkpoint mechanism in fission yeast (Fumari et al., Science, 277: 1495–1497 (Sep. 5, 1997).

DNA damage induces the arrest of the cell cycle at the $G_2$ checkpoint. The $G_2$ DNA damage checkpoint ensures maintenance of cell viability by delaying progression into mitosis in cells which have suffered genomic damage. The $G_2$ checkpoint is controlled by cell cycle checkpoint pathways which have been extensively studied (Hartwell, L H et al., Science, 246 (1989), supra; Nurse, P et al., Nat Med, 4 (10): 1103–6 (October 1998); Peng et al., Science, 277, (1997), supra; Funari et al., Science, 277: 1495–1497 (Sep. 5, 1997); Zeng et al., Nature 395 (6701):507–510 (Oct. 1, 1998); Martinho et al., EMBO J, 17(24):7239–49 (Dec. 15, 1998); Nakajo et al., Dev. Biol. 207(2):432–44 (Mar. 15, 1999); Carr et al., Curr Biol., 5 (1995), supra). The model of the checkpoint mechanism in fission yeast is shown in FIG. 1, Furnari, et al., Science, (1997), supra. As mentioned above, the regulation control system is highly conserved from yeast to humans.

DNA damage activates the checkpoint pathway by inhibiting the dephosphorylation of the mitotic kinase Cdc2 at the tyrosine-15 residue [Cdc2 ($Y^{15}$-$PO_4$)], thereby inhibiting its mitotic initiating activity and arresting the cell cycle. This process is referred to as inhibitory phosphorylation. In order for mitosis to proceed, Cdc2 must be dephosphorylated, returning it to its active form. Phosphorylated Cdc2 is the substrate of Cdc25. Cdc25 is a dual specificity protein phosphatase that controls entry into mitosis by dephosphorylating the protein kinase Cdc2. In fission yeast, DNA damage also results in the activation of Rad3, a kinase related to the ATM/ATR proteins. Rad3 initiates the Chk1 response; the phosphorylation of Chk1 is a Rad3 dependent process (Martinho et al., EMBO J, 17 (1998), supra; Furnari et al., Science, 277 (1997), supra). Phosphorylated (active) Chk1 phosphorylates the mitotic inducer Cdc25 at the serine-216 residue of human Cdc25 [Cdc25 ($S^{216}$-$PO_4$)]. Phosphorylation of Cdc25 inhibits the function of the phosphatase in the dephosphorylation of Cdc2, an event required for mitosis to proceed. Throughout interphase but not in mitosis, Cdc25 is phosphorylated at the serine-216 residue and bound to members of the highly conserved and ubiquitously expressed family of 14-3-3 proteins. Prevention of serine-216 phosphorylation prevents 14-3-3 binding, perturbing mitotic timing and allowing cells to escape the $G_2$ checkpoint arrest induced by either unreplicated DNA or radiation induced damage.

A majority of currently accepted cancer treatments involve the induction of DNA damage including the administration of anticancer agents, chemotherapeutic agents, and radiation therapy. Cancer cells frequently become resistant to such therapies. It is suspected that such resistance is related to the innate ability of the cancer cells to arrest and repair the damage induced. If the cancer cell was unable to arrest and repair, mitosis would proceed with the DNA damage intact. The downstream result would presumably be cell death as a result of the DNA damage.

Treatments that include a mechanism for abrogating the endogenous checkpoint pathway and repair process would presumably be more effective in killing cancer cells. As many cancer cells already lack a $G_1$ checkpoint control system, a therapy that involved the inhibition of the $G_2$ checkpoint would presumably force the cancer cells to proceed through mitosis without any feedback arrest and repair process. Hence, there is a clear utility for the inhibition of the activity of Chk1, a pivotal kinase in the $G_2$ checkpoint pathway. As many of the same events that regulate the $G_2$ arrest subsequent to DNA damage also regulate the S phase delay following DNA damage, the inhibition of Chk1 finds utility in the regulation of S phase as well.

The human Chk1 sequence of amino acids 1 to 476 is available through GenBank. Full length or segments of human Chk1 cDNA corresponding to codon 1-427, 1-265, and 1-289 were separately amplified by PCR. Each was tagged at its 3'-end with six histidine codons and cloned into an expression plasmid for protein production using a Baculovirus/insect cell expression system. The protein was expressed in insect Hi-5 cells and purified by a combination of ion-exchange and affinity column chromatography. It was found that a high concentration of salt (~500 mM levels) was required for keeping the purified Chk1 kinase domain from forming a precipitate.

The kinase activity of the hChk1 was determined by monitoring the ADP production through enzymatic actions of pyruvate kinase and lactate dehydrogenase. The Chk1 kinase domain containing amino acids 1–289 showed higher enzymatic activity than the full length protein. Unlike the other forms of Chk1 which have proven difficult to work with (isolate, purify, crystallize, etc), the 1–289 kinase domain form of the human Chk1 enzyme facilitated crystallography, enzyme characterization, and high throughput screening of inhibitors. In particular, the Chk1 kinase domain was used to determine its 3-dimensional structure, which provides unique structural information for inhibitor design for therapeutic development.

As used herein, the abbreviation 'hChk1' refers to the polynucleotide encoding the human effector checkpoint kinase serving as a DNA damage/replication checkpoint kinase. The nucleic acid sequence of the polynucleotide encoding the full length protein of human Chk1 was published in Science by Sanchez et al. (*Science*, 277 (5331): 1497–1501 (1997)) and published in GenBank on Sep. 9, 1997 (AF016582). The nucleic acid sequence described therein is provided herein, shown in SEQ ID NO. 1. The corresponding peptide sequence of the full length protein is provided herein, shown in SEQ ID NO. 2. This peptide sequence was submitted to GenBank by Flaggs et al. on Nov. 3, 1997 and released on Dec. 13, 1997 (AF032874). The protein kinase was further described by Flaggs et al. in Current Biology (*Curr. Biol.*, 7(12):977–986, (1997)).

Using homology tools to examine the nucleotide and peptide sequence of Chk1, scientists have attempted to estimate the location of the kinase domain. However, the exact location of the catalytically active kinase domain has been difficult to experimentally determine, primarily as no one has ever reported isolating the kinase domain in its active configuration. Previous publications have indicated that the kinase domain extends from AA 16 to AA 264 (WO99/111795, published Mar. 11, 1999, at page 7, line 3) of SEQ ID NO. 2.

We have found that the catalytic kinase domain begins between AA1 and 16 and terminates between AA265 and AA291 of SEQ ID NO. 2. We further discovered that vector-driven protein yield is dramatically increased when a fragment extending from AA1 to AA289 (dubbed KH289) is used.

There are 22 known amino acids but 64 possible permutations of nucleic acid triplets, called "codons". Many amino acids are specified by more than one codon, a phenomenon called degeneracy. Due to the degeneracy of the genetic code, there are many functionally equivalent nucleic acid sequences that can encode the same protein. The active human Chk1 kinase set forth in SEQ ID NO. 2 can clearly be encoded by multiple nucleotide sequences and is not limited to the cDNA sequence set forth in SEQ ID NO. 1. For example, both UUU and UUC code for a phenylalanine while serine is encoded by UCU, UCC, UCA, UCG, AGU, and AGC [*Molecular Biology of the Gene*, $4^{th}$ edition, Watson, J. D. et al., editors (1987) at pages 437–438]. Functionally equivalent sequences can readily be prepared using known methods such as modified primer PCR, site-directed mutagenesis, and chemical synthesis. Such functional equivalents are within the scope of this invention.

In the examples of the present invention, the full length form of human Chk1 protein kinase (AA 1–476) is referred to as KH476. Fragments thereof are identified by the amino acid sequence. For example, the human Chk1 kinase domain (AA 1–289) is referred to as KH289 Other kinase domain sequences are referred to by amino acid numbering in a similar manner.

A. Peptides, Proteins and Antibodies

As used herein, the terms "kinase" and "protein kinase" refer to enzymes that catalyze the transfer of a phosphate residue from a nucleoside triphosphate to an amino acid side chain in selected targets. The covalent phosphorylation in turn regulates the activity of the target protein. In addition, phosphorylation frequently acts as the signal that triggers a particular process or reaction, playing an integral part in cellular regulation and control mechanisms. Clearly, inappropriate or unregulated phosphorylation can result in errors in cell signaling and the associated cell cycle and regulation processes. Most protein kinases are highly substrate specific.

As used herein, a peptide is said to be "isolated" or "purified" when it is substantially free of homologous cellular material or chemical precursors or other chemicals. The peptides of the present invention can be purified to homogeneity or other degrees of purity. The level of purification will be based on the intended use.

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, preferably less than about 20% chemical precursors or other chemicals, more preferably less than about 10% chemical precursors or other chemicals, or most preferably less than about 5% chemical precursors or other chemicals.

The isolated kinase described herein can be purified from cells that naturally express it, purified from cells that have been altered to express it (recombination), or synthesized using known protein synthesis methods. For example, a nucleic acid molecule encoding the protein kinase is cloned into an expression vector, the expression vector introduced into a host cell and the protein expressed in the host cell. The protein can then be isolated from the cells by an appropriate purification scheme using standard protein purification techniques. Many of these techniques are described in detail below.

The present invention also provides catalytically active variants of the peptides of the present invention, such as allelic/sequence variants of the peptides, non-naturally occurring recombinantly derived variants of the peptides, and orthologs and paralogs of the peptides. Such variants can be generated using techniques that are known by those skilled in the fields of recombinant nucleic acid technology and protein biochemistry.

Such variants can readily be identified/made using molecular techniques and the sequence information disclosed herein. Further, such variants can readily be distinguished from other peptides based on sequence and/or structural homology to the peptides of the present invention. The degree of homology/identity present will be based primarily on whether the peptide is a functional (active) variant or non-functional (inactive) variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, 40%, 50%, 60%, 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid 'identity' is equivalent to amino acid or nucleic acid 'homology'). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into commercially available computer programs, such as GAP in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences can be determined using the commercially available computer programs including the GAP program in the GCG software package (Devereux, J., et al., *Nucleic Acids Res.* 12(1):387 (1984)), the NWS gap DNA CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into commercially available computer programs, such as ALIGN (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using commercially available search engines, such as the NBLAST and XBLAST programs (version 2.0) of Altschul, et al. (*J. Mol. Biol.* 215:403–10 (1990)). Nucleotide searches can be performed with such programs to obtain nucleotide sequences homologous to the nucleic acid molecules of the invention. Protein searches can be performed with such programs to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)).

Full-length clones comprising one of the peptides of the present invention can readily be identified as having complete sequence identity to one of the kinases of the present invention as well as being encoded by the same genetic locus as the kinase provided herein.

Allelic variants of a peptide can readily be identified as having a high degree (significant) of sequence homology/identity to at least a portion of the peptide as well as being encoded by the same genetic locus as the kinase peptide provided herein. As used herein, two proteins (or a region of the proteins) have significant homology when the amino acid sequences are typically at least about 70–75%, 80–85%, and more typically at least about 90–95% or more homologous. A significantly homologous amino acid sequence, according to the present invention, will be encoded by a nucleic acid sequence that will hybridize to a peptide encoding nucleic acid molecule under stringent conditions as more fully described below.

Paralogs of a peptide can readily be identified as having some degree of significant sequence homology/identity to at least a portion of the kinase peptide, as being encoded by a gene from Drosophila, and as having similar activity or function. Two proteins will typically be considered paralogs when the amino acid sequences are typically at least about 70–75%, 80–85%, and more typically at least about 90–95% or more homologous through a given region or domain. Such paralogs will be encoded by a nucleic acid sequence that will hybridize to a kinase peptide encoding nucleic acid molecule under stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably human, for the development of human therapeutic targets and agents, or other invertebrates, particularly insects of economical/agriculture importance, e.g. members of the Lepidopteran and Coleopteran orders, for the development of insecticides and insecticidal targets. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinases of the present invention can readily be generated using recombinant techniques. Such variants include, but are not limited to deletions, additions and substitutions in the amino acid sequence of the kinase. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe, Tyr. Guidance concerning which amino acid changes are likely to be phenotypically silent are found in Bowie et al., *Science* 247:1306–1310 (1990).

Variant kinases can be fully functional or can lack function in one or more activities. Fully functional variants typically contain only conservative variation or variation in non-critical residues or in non-critical regions. Functional variants can also contain substitution of similar amino acids, which result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for binding can also be determined by structural analysis such as x-ray crystallography, nuclear magnetic resonance or photoaffinity labeling (Smith et al., *J. Mol. Biol.* 224:899–904 (1992); de Vos et al. *Science* 255:306–312 (1992)). Accordingly, the protein kinases of the present invention also encompass derivatives or analogs in which a substituted amino acid residue is not one encoded by the genetic code; in which a substituent group is included; in which the mature polypeptide is fused with another compound, such as a compound to increase the half-life of the polypeptide (for example, polyethylene glycol); or in which the additional amino acids are fused to the mature polypeptide, such as a leader or secretory sequence or a sequence for purification of the mature polypeptide or a pro-protein sequence.

The present invention further provides for functional, active fragments of the Chk1 kinase domain. As used herein, a fragment comprises at least 8 or more contiguous amino acid residues from the protein kinase. Such fragments can be chosen based on the ability to retain one or more of the biological activities of the kinase or could be chosen for the ability to perform a function, e.g. act as an immunogen. Particularly important fragments are catalytically activate fragments, peptides which are, for example about 8 or more amino acids in length. Such fragments will typically comprise a domain or motif of the kinase, e.g., active site or binding site. Further fragments contemplated by the present invention include, but are not limited to, domain or motif containing fragments, soluble peptide fragments, and fragments containing immunogenic structures. Predicted domains and functional sites available to those of skill in the art (e.g., by PROSITE analysis).

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques known in the art. Common modifications that occur naturally in polypeptides are described in basic texts, detailed monographs, and the research literature, and they are known to those of skill in the art.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, phenylation, racemization, selenoylation, sulfation, transfer-RNA mediated addition of amino acids to proteins such as arginylation, and ubiquitination. Such modifications are known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

The peptides of the present invention can be attached to heterologous sequences to form chimeric or fusion proteins. Such chimeric and fusion proteins comprise a peptide operatively linked to a heterologous protein having an amino acid sequence not substantially homologous to the kinase peptide. "Operatively linked" indicates that the peptide and the heterologous protein are fused in-frame. The heterologous protein can be fused to the N-terminus or C-terminus of the kinase peptide. The two peptides linked in a fusion peptide are typically derived from two independent sources, and therefore a fusion peptide comprises two linked peptides not normally found linked in nature. The two peptides may be from the same or different genome.

In some uses, the fusion protein does not affect the activity of the peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

Herein, the term 'antibody' refers to a polypeptide or group of polypeptides which are comprised of at least one antibody combining site or binding domain, said binding domain or combining site formed from the folding of variable domains of an antibody molecule to form three dimensional binding spaces with an internal surface shape and charge distribution complementary to the features of an antigen epitope. The term encompasses immunoglobulin molecules and immunologically active portions of immunoglobulin molecules, such as molecules that contain an antibody combining site or paratope. Exemplary antibody molecules are intact immunoglobulin molecules, substantially intact immunoglobulin molecules and portions of an immunoglobulin molecule, including those known in the art as Fab, FabB, F(abB)$_2$ and F(v).

B. Nucleic Acids and Polynucleotides

The present invention provides isolated nucleic acid molecules that encode the functional, active kinases of the present invention. Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA or cDNA of the organism from which the nucleic acid is derived. However, there can be some flanking nucleotide sequences, for example up to about 5 KB, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

The preferred classes of nucleic acid molecules that are comprised of the nucleotide sequences of the present are the full-length cDNA molecules and genes and genomic clones since some of the nucleic acid molecules provided in SEQ ID NO. 1 are fragments of the complete gene that exists in nature. A brief description of how various types of these nucleic acid molecules can be readily made/isolated is provided herein.

Full-length genes may be cloned from known sequence using any one of a number of methods known in the art. For example, a method which employs XL-PCR (Perkin-Elmer, Foster City, Calif.) to amplify long pieces of DNA may be used. Other methods for obtaining full-length sequences are known in the art.

The isolated nucleic acid molecules can encode the functional, active kinase plus additional amino or carboxyl-terminal amino acids, such as those that facilitate protein trafficking, prolong or shorten protein half-life or facilitate manipulation of a protein for assay or production, among other things. The isolated nucleic acid molecules include, but are not limited to, the sequence encoding the active kinase alone or in combination with coding sequences, such as a leader or secretory sequence (e.g., a pre-pro or pro-protein sequence), the sequence encoding the active kinase, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as MRNA, or in the form DNA, including cDNA and genomic DNA, obtained by cloning or produced by chemical synthetic techniques or by a combination thereof. The nucleic acid, especially DNA, can be double-stranded or single-stranded. Single-stranded nucleic acid can be the coding strand (sense strand) or the noncoding strand (antisense strand).

The invention further provides nucleic acid molecules that encode functional fragments or variants of the active kinases of the present invention. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

A fragment comprises a contiguous nucleotide sequence greater than 12 or more nucleotides. Further, a fragment could be at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods known in the art. As described above, these variants comprise a nucleotide sequence encoding a peptide that is typically 60–65%, 70–75%, 80–85%, and more typically at least about 90–95% or more homologous to the nucleotide sequence provided in SEQ ID NO. 1 or a fragment of this sequence. Such nucleic acid molecules can readily be identified as being able to hybridize under moderate to stringent conditions, to the nucleotide sequence shown in SEQ ID NO. 1 or a fragment of the sequence.

As used herein, the term "hybridizes under stringent conditions" is intended to describe conditions for hybridization and washing under which nucleotide sequences encoding a peptide at least 50–55% homologous to each other typically remain hybridized to each other. The conditions can be such that sequences at least about 65%, at least about 70%, or at least about 75% or more homologous to each other typically remains hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C, followed by one or more washes in 0.2×SSC, 0.1% SDS at 50–65 C.

The nucleic acid molecules of the present invention are useful for probes, primers, chemical intermediates, and in biological assays. The nucleic acid molecules are useful as a hybridization probe for cDNA and genomic DNA to isolate full-length cDNA and genomic clones encoding the peptide described herein and to isolate cDNA and genomic clones that correspond to variants (alleles, orthologs, etc.) producing the same or related peptides described herein.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods.

The nucleic acid molecules are also useful for designing ribozymes corresponding to all, or a part, of the mRNA produced from the nucleic acid molecules described herein.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful for making vectors that express part, or all, of the peptides.

The nucleic acid molecules are also useful as hybridization probes for determining the presence, level, form and distribution of nucleic acid expression. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of MRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a receptor-encoding nucleic acid in a sample of cells from a subject e.g., MRNA or genomic DNA, or determining if a receptor gene has been mutated.

C. Vectors and Host Cells

The invention also provides vectors containing the nucleic acid molecules described herein. The term "vector" refers to a vehicle, preferably a nucleic acid molecule, that can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC. Various expression vectors can be used to express polynucleotide encoding the active hChk1 kinase.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing MRNA transcription. These include, but are not limited to, the left promoter from bacteriophage λ, the lac, TRP, and TAC promoters from E. coli, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., (*Molecular Cloning: A Laboratory Manual. 2nd. ed.*, Cold Spring Harbor Laboratory Press, Cold Spring Harbor, N.Y., (1989)).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, eg. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express a peptide of the present invention as a fusion protein. Accordingly, the invention provides fusion vectors that allow for the production of such peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. Preferred vectors include the pET28a (Novagen, Madison, Wis.), pAcSG2 (Pharmingen, San Diego, Calif.), and pFastBac (Life Technologies, Gaithersburg, Md.). The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells. Preferred host cells of the instant invention include *E. coli* and Sf9.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced orjoined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the active protein kinases can be produced in bacteria, yeast, mammalian cells, and other cells under the control of the appropriate regulatory sequences, cell- free transcription and translation systems can also be used to produce these proteins using RNA derived from the DNA constructs described herein.

Where secretion of the peptide is desired, appropriate secretion signals are incorporated into the vector. The signal sequence can be endogenous to the peptides or heterologous to these peptides.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

The following examples are provided for illustration purposes.

III: EXAMPLES

1. Identification of the Catalytic Domain Sequence

Figure 3:
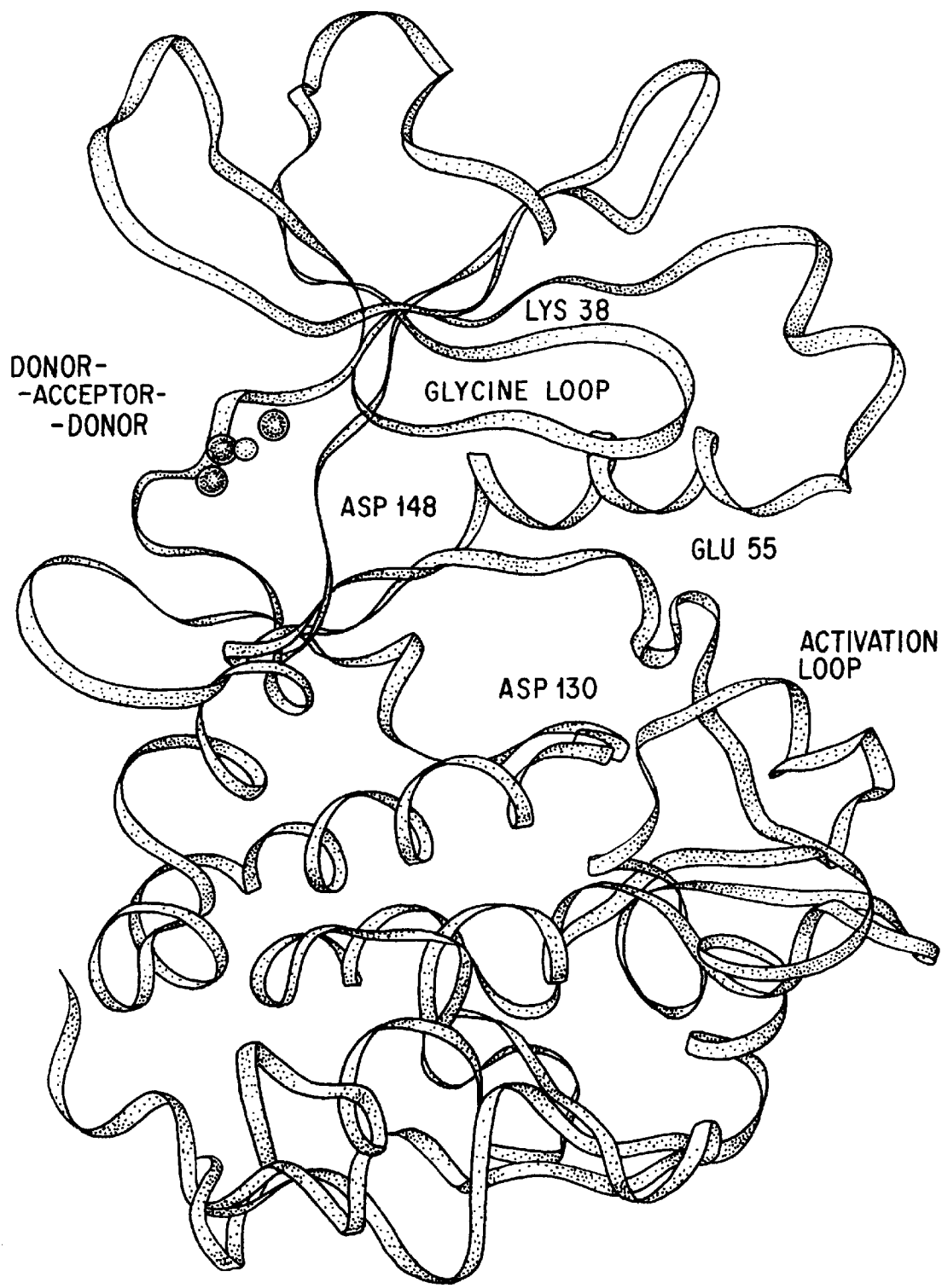
FIG. 3. The homology model of Chk1 kinase depicting the activation loop and its relationship to the catalytic loop and C helix. The Chk1 N and C-terminal lobes are shown. The fragments corresponding to the Chk1 C-helix are residues 50–58; the Chk1 catalytic loop are residues 129–132; and the Chk1 activation loop are residues 148–170.

From the complete protein sequence for the human checkpoint effector kinase (Chk1, 476 residues) available through GenBank, using sequence alignment and structures for other kinases, a homology model was devised for the kinase domain of the Chk1 protein (See FIG. 3).

Figure 9:
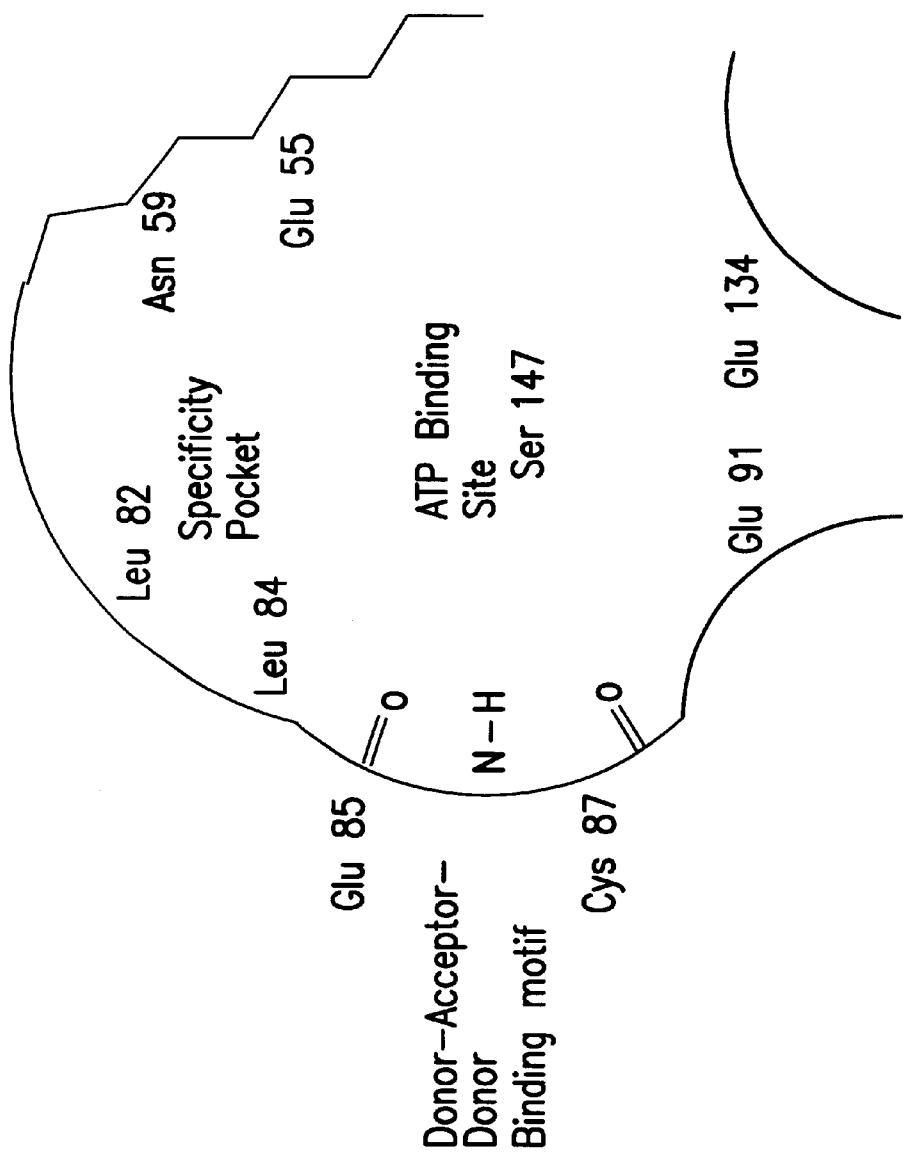
FIG. 9. Representation of the Chk1 binding sites, showing specifically the specificity pocket, the ATP binding site, and the Donor-Acceptor-Donor binding motif.

All protein kinases utilize ATP to phosphorylate their substrates, involving the transfer of a gamma phosphate to a substrate hydroxyl group. Each kinase binds ATP with its own strength, a property that is correlated by measuring $K_i$/IC50. The ATP molecule consists of adenine, ribose and tri-phosphate moieties. Each of these moieties bind to the protein in the ATP binding site (or ATP pocket). The adenine moiety always binds to the protein backbone by formation of two or three hydrogen bonds. The ribose moiety forms one to two hydrogen bonds with the protein side chains of amino acids that lay outside of the ATP pocket. The tri-phosphate moiety interacts with those catalytic amino acids of the kinase that are generally consistent across the whole protein kinase family. There is a limited specificity for each kinase within ATP binding groove. This region is referred to as the specificity pocket. Using the homology model, a schematic of the Chk1 binding site was developed, identifying the ATP binding site, the donor-acceptor-donor binding motif and the specificity pocket (See FIG. 9). This binding site is the target for inhibitor development, e.g. the development of compounds or molecules that bind to this site to the extent that the kinase activity of the Chk1 protein is blocked or inhibited. The black and red color in FIG. 9 represents the ATP binding groove; note, Ser 147 can contribute to the binding of inhibitor. The area designated by the blue color represents the region outside of the ATP pocket that can be used for enhancement of the specificity of binding. Finally, the area in pink represents the 'specificity pocket', that region that is very different from one protein to another. This site does not contribute to the ATP binding but can be used for the design of specific inhibitors. In other words, by utilizing that region of the Chk 1 binding site that is unique to Chk1 (the specificity pocket), one may design compounds that specifically inhibit Chk1 without also inhibiting the various other kinase molecules that may not be targets of the inhibition therapy.

Analysis of the C-termini of the kinase suggested that amino acids beyond residue 265 would enhance high level expression and/or maintain the appropriate crystal structure. The homology model showed this region to be flexible, such that ending the kinase domain construct within this region can prevent the disruption of potential secondary structures. Specifically, cleaving the Chk1 protein anywhere between amino acid residues 263 and 265 would result in the destruction of helical interactions at the distal end. The homology model further predicted that the kinase segment should extend to at least residue 272 to 275 and may be further extended to residue 289–291.

In addition, including the extended region in the construct prevents the C-terminal histidine tag from interacting with the kinase domain, making it accessible for affinity chromatography. Based on these analyses, construct KH289 was designed for the expression of Chk1 kinase domain of residue 1–289 with 6xHis-tag at its C-terminus. A corresponding construct without the 6xHis-tag was also made. Two other constructs were designed based on the homology model: (1) kinase domain of residues 1–210 (KH210) and (2) kinase domain of residues 1–248 (KH248).

2. Cloning

Human Chk1 cDNA was cloned by PCR using Vent polymerase (New England Biolabs, Beverly, Mass.) from human thymus and testis Marathon-Ready cDNA (Clontech, Palo Alto, Calif.) with primers synthesized (Genset, LaJolla, Calif.) based on the published sequence [SEQ ID NO. 1] (GenBank Accession number AF1016582) [Sanchez, *Science* (1997), supra.], following the instruction from the venders. Two overlapping sequences were amplified independently, one contained the sequence of nucleotides 35–830 of SEQ ID NO.1, and the other contained the sequence of nucleotides 678–1480 of SEQ ID NO.1. These overlapping sequences cover the whole coding sequence of Chk1 plus 16 basepairs (bps) of 3'-untranslational region. The cDNA of 35–830 encodes the kinase domain of residues 1–265.

The PCR oligonucleotide primer sequences are listed in Table 1. Restriction sites for cloning, codons for 6xHis-tag, and the stop codon were engineered in the PCR primers. Restriction site StuI preceded NcoI site which overlapped the initiation codon. SacI site followed the stop codon. When included, codons for 6xHis-tag preceded the stop codon, so that an expressed protein would have a 6xHis-tag at its C-terminus.

The amplified cDNA was cloned into expression cassette pCR-TOPO (plasmid from Invitrogen, Carlsbad, Calif.) following the vender's instruction and the sequences were verified by sequencing of both strands (Retrogen, San Diego, Calif.). The amplified cDNA sequence was identical to the sequence deposited in GenBank referenced above. The full-length Chk1 cDNA was constructed from these two overlapping cDNAs, ligating through the ClaI restriction site at 734–739. This full-length cDNA was used as PCR template to generate cDNA fragments for expression or directly to generate the full-length Chk1 expression vector. All the PCR products were cloned into pCR-TOPO for sequencing. Constructs were made for the expression of full-length Chk1 and various lengths of kinase domain with or without 6xHis-tag.

TABLE 1

PCR Primers*

| Primer | Sequence | SEQ ID NO. |
|---|---|---|
| chk6w | GAG CTC AGT ACC ATC TAT CTT TTT TGA TGT CTG G | 3 |
| KH289 | GAG CTC AGT TGG TGG TGG TGG TGG TGT CCA CTG GGA GAC TCT GAC AC | 4 |
| K289 | GAG CTC ATC CAC TGG GAG ACT CTG ACA C | 5 |
| Chk11 | CCA TGGAGC TCA AGA AAG GGG CAA AAA GG | 6 |
| K210 | GAG CTC ATT GGT CCC ATG GCA ATT CTC C | 7 |
| KH210 | GAG CTC AGT GGT GGT GGT GGT GGT GGT CCC ATG GCA ATT CTC C | 8 |
| K248 | GAG CTC ACT CAA CTA AGA TTr TAT GCA GCA G | 9 |
| KH248 | GAG CTC AGT GGT GGT GGT GGT GGT GCT CAA CTA AGA TTT TAT GCA GCAG | 10 |

3. Chk1 Antibodies

Peptide NRVTEEAVAVKIVDMKRAVD (residues 28–47 of SEQ ID NO. 2) was selected for generating antibody against N-terminus of human Chk1. Peptide DDKILVD-FRLSKGDGLE (residues 434–450 of SEQ ID NO. 2) was selected for generating antibody against C-terminus of human Chk1. Rabbit polyclonal antibodies were ordered through the Custom Antibody Production Services from Research Genetics, Inc. (Huntsville, Ala.). Both antibodies detected recombinant or endogenous human Chk1 as expected.

4. Fermentation

The overall scheme was follows. The 3' PCR primers were engineered to encode both untagged and tagged (with 6-histidine tag) proteins. The segment of cDNA for 1–289 was cloned into a pFastBac plasmid (obtained from Life Technologies) and an NdeI site was introduced. A recombinant baculovirus was generated using the Bacmid system (obtained from Life Technologies). The protein (KH289) was expressed in Hi-5 insect cells and purified by a combination of ion-exchange and affinity chromatography. The segments of cDNA for the full-length Chk1 (1–476AA) and the Chk1 kinase domain (1–265AA) were cloned into pAcSG2 plasmid and recombinant baculovirus was generated using BaculoGold viral DNA (obtained from Invitrogen) and a modified CellFectin transfection (obtained from Life Technologies) and plaque selection (obtained from Novagen) protocol. The expressed protein was purified using the chromatography scheme described below. High salt concentration in buffers was found to be required to prevent precipitation of the purified proteins. The details of the protocol are discussed below.

Generation of Expression Plasmids

Plasmid pFastBac-Nde was modified from the pFastBac1 vector (Life Technologies, Gaithersburg, Md.) by in vitro site-directed mutagenesis using the Muta-Gene in vitro Mutagenesis Kit (Bio-Rad, Hercules, Calif.) following the supplier's instruction. Two nucleotides were substituted in pFastBac1 using the following oligonucleotide:

TGA ATA ATC CGG CAT ATG TAT AGG TTT TTT [SEQ ID NO. 14]

This created a unique NdeI site at the original translation start site for the polyhedrin protein.

The amplified cDNA fragments were digested with the restriction enzyme StuI and SacI and cloned to plasmids pET28a (Novagen, Madison, Wis.), pAcSG2 (Pharmingen, San Diego, Calif.), or pFastBac-Nde. The pET28a vector was used for protein expression in *E. coli* and pAcSG2 and pFastBac-Nde were used for protein expression in insect cells. To clone the cDNA fragments encoding Chk1 kinase domain with amino acids 1–289 (construct KH289) into the pFastBac-Nde, the cDNA fragment was excised from the pCR-TOPO plasmid with restriction enzymes StuI and SacI, ligated between the blunt-ended NdeI site and SacI site. Plasmids with correct insertion were analyzed by restriction enzyme digestion. The full-length Chk1 and the kinase domain of residues 1–265 (KH265) with or without C-terminal 6xHis-tag were cloned into pAcSG2 using the restriction sites of StuI and SacI. Expression vectors for kinase domain of residues 1–210 (KH210) and kinase domain of residues of 1–248 (KH248) were made in pFastBac-Nde.

Expression in *E. coli* was done following the instructions supplied with the pET28a vector. Proteins expressed in the form of full-length Chk1 or kinase domain of residues 1–265 or kinase domain of residues 1–289 were in the insoluble fraction when analyzed by ReadyPreps Protein Preparation Kit (Epicentre Technologies, Madison, Wis.).

Generation of Recombinant Viruses

The Bac-to-Bac system (Life Technologies) was used to generate recombinant baculovirus for expression of the C-terminally 6xHis-tagged Chk1 kinase domain (amino acids 1–289, KH289) as instructed. Recombinant viruses were confirmed by PCR for the presence of Chk1 cDNA insertion. Protein expression was confirmed by SDS-PAGE or Western blot with the Chk1 polyclonal antibodies. The expression of KH289 appeared to be the highest among all the constructs. High titer stocks of recombinant viruses were generated by 2 to 3 rounds of amplification using Sf21 insect cells.

Recombinant viruses for expression of the full-length Chk1 and kinase domain of residues 1–265 were generated by co-transfection of Sf21 cells with pAcSG2 vector and BaculoGold (PharMingen, San Diego, Calif.).

Expression in Insect Cells

The yield of active soluble protein obtained in the *E. coli* fermentation described above was impractical for large-scale experimentation. Therefore, an alternate fermentation system was developed. Insect cells Sf9 for viral amplification, and Hi-5 cells for protein production (both from Invitrogen, Carlsbad, Calif., USA) were adapted to grow in insect medium contained 1% Fetal Bovine Serum (Life Technologies, Grand Island, N.Y., USA). Cells were propagated and maintained in suspension culture at 27° C. in either Erlenmeyer shake flask (Corning #430183) or in an upright roller bottle (Corning Inc., Corning, N.Y., USA #25290-17000) with a loosened cap for aeration. The flasks were placed in a reciprocal refrigerated shaker (Innova 4343, New Brunswick Scientific, Edison, N.J., USA) at 120 rpm. The cell density was maintained at between $5 \times 10^5$ to $2 \times 10^6$ cells/ml by diluting the cultured cell suspension with a fresh pre-warmed (27° C.) medium. The viability of insect cells was maintained at 98%. The viability of insect cells were determined by microscopic count of total stained cells by trypan blue versus the total cell number in a hemocytometer.

Sf9 insect cells were used for amplification for recombinant virus stock. The recombinant baculovirus from a single plaque was pick up by a pipette tip and added to Sf9 cells monolayer in T-25 flask (Becton Dickinson Labware, Franklin Lakes, N.J., USA) with 10 ml medium SF900II and 1% of Fetal bovine Serum (Life Technologies, Grand Island, N.Y., USA) and incubated at 27° C. After 6 days, the culture supernatant was used as first generation of virus stock (P1) for further amplification of P2 and P3 virus stocks to 2–3 L. For large scale amplification of the P2 and P3 virus stock, P1 or P2 virus stock was added to Sf9 cells at a cell density of $1 \times 10^6$ cells/ml, the infection was carried out with Multiplicity Of Infection (MOI) of 0.1, cells were grown in suspension in 500 ml of SF900II in 2 L roller bottle (Corning Inc., Corning, N.Y., USA) standing up right in a shaker incubator at 120 rpm at 27° C. for 6 days. This process was repeated until 2–3 L viral stock (P3) were obtained. The titer of this virus stock was 1 to $5 \times 10^8$ p.f.u/mL. The viral titration was determined by the plaque assay method, with serial 10-fold dilution up to $10^8$ fold. The viral stock was stored at 10° C., and used for large scale protein production within 2 months to avoid viral instability. The Hi-5 insect cells (derived from *Trichoplusia.ni* cells) which have been adapted to grow in medium Ex-cell 401 (JRH Biosciences, Lenexa, Kans., USA) with 1% Fetal Bovine Serium were used for protein production. The cells were grown in the upright roller bottle up to cell density at $2 \times 10^6$ cells/ml; and were used as seed cells for bioreactor culture. The cells were grown in a 20 L stirred bioreactor with working volume at 18L (Applikon Inc., Foster City, Calif., USA). Air flow rate was operated at about 10 ml per min per liter culture fluid. The air was fortified by pure oxygen in order to maintain the Dissolve Oxygen ($DO_2$) at 50% of air saturation. The agitation was maintained at 200 rpm throughout the cultivation. Cell density was started at about $5 \times 10^5$ cells/ml and cells were infected when the density reached $2 \times 10^6$ cells/ml. The MOI was 3 and the infection was carried out for 48 Hrs. After 48 hrs. of infection, the infected cells were harvested by centrifugation at 3,000 rpm for 10 min, at 4° C. by a refrigerated centrifuge (model PR-7000M, IEC, Needham Heights, Mass., USA). The cell pellets were collected and stored at −80° C.

5. Purification
6x-His Tagged KH289

Figure 4:
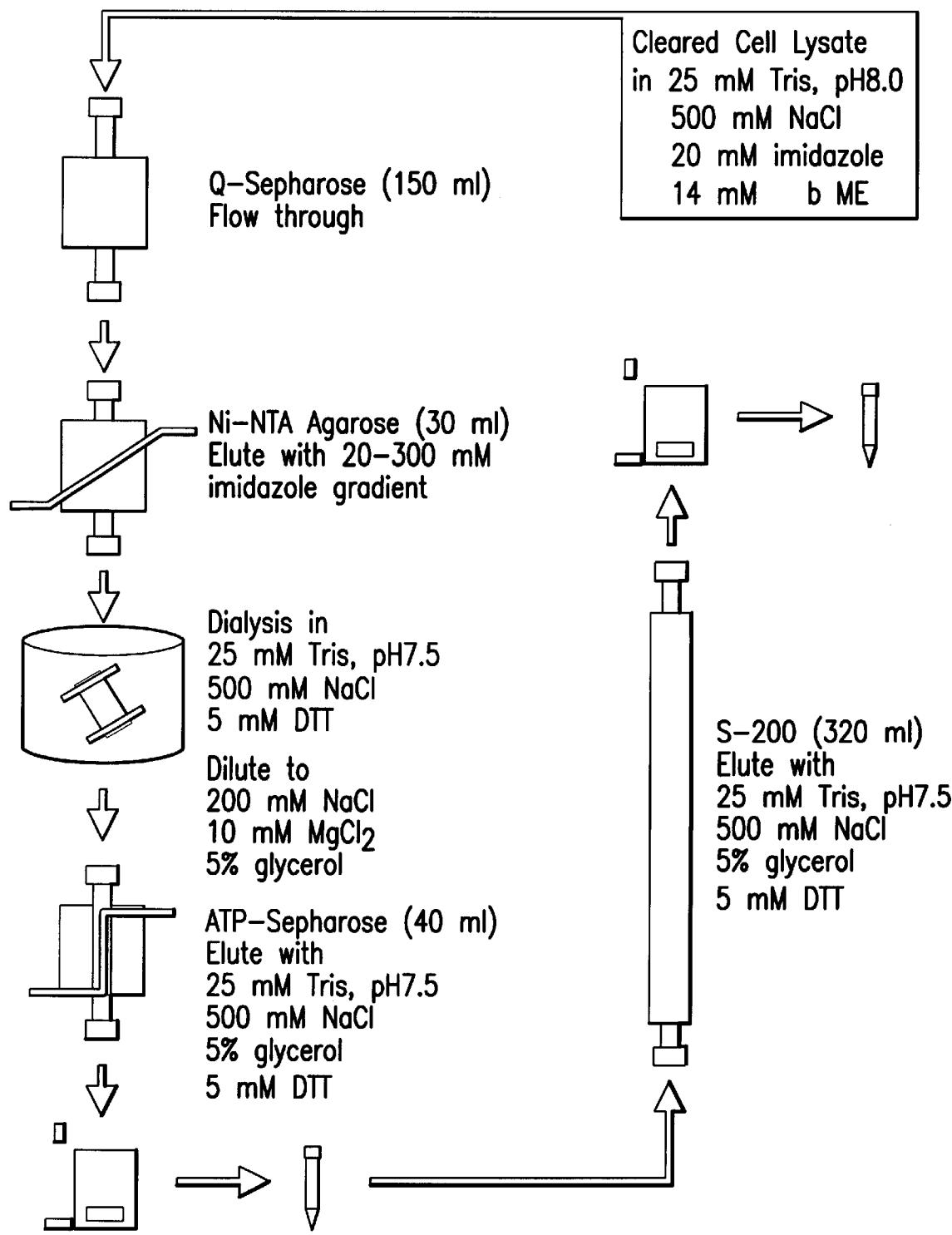
FIG. 4. The purification scheme for Chk1 kinase domain 1–289.

The basic purification scheme is depicted in FIG. 4. Frozen cell pellets were thawed, suspended in ice-cold lysis buffer, and lyzed by microfluidizer (Microfluidics Corporation, Newton, Mass.). The lysis buffer contained 25 mM Tris-HCl, pH 8.0, 500 mM NaCl, 20 mM imidazole, and 14 mM β-mercaptoethanol. The lysate was centrifuged for 40 minutes at 40,000 rpm in a Ti45 rotor in Beckman L8–70M ultracentrifuge. The soluble fraction was flowed through a 150 mL Q-Sepharose FastFlow anion exchange column (Pharmacia, Piscataway, N.J.), then loaded onto a 40 ml Ni-NTA agarose column (Qiagen, Santa Clarita, Calif.). After extensive washes with the lysis buffer, the column was eluted with 240 ml of 20 mM to 300 mM imidazole gradient in the lysis buffer. Fractions containing the Chk1 kinase domain (KH289) were identified by SDS-PAGE and pooled. The pooled fractions were dialyzed in 25 mM Tris-HCl, pH 7.5, 500 mM NaCl, 0.5 mM EDTA, and 5 mM DTT overnight. The dialyzed pool was diluted with 1.5 volumes of 25 mM Tris-HCl, pH 7.5, 20 mM $MgCl_2$, 8% glycerol, 5 mM DTT and loaded immediately onto a 40 ml ATP-Sepharose column. The column was eluted with 200 ml of 25 mM Tris-HCl, pH 7.5, 500 mM NaCl, 5 mM DTT, and 5% glycerol. Fractions containing KH289 were pooled and concentrated in a Millipore Stirred Cell under 60 psi $N_2$ and loaded onto a 320 ml HiPrep Sephacryl gel-filtration column and eluted with the same buffer. Pooled fractions were concentrated to 7–7.5 mg/ml for crystallography or ~3 mg/ml for HTS. Protein was flash-frozen in liquid $N_2$ and stored at −80° C.

Maintaining salt concentration around 500 mM NaCl including 5% glycerol was found to be crucial for preventing aggregation of Chk1 proteins during purification and storage without affecting the intended use.

6x-His Tagged KH265 and KH476 Chk1

Essentially the same methods were used to purify the full-length Chk1 and the kinase domain of residues 1–265 expressed in insect cells. The expression protein levels as measured after the Ni-NTA chromatography or the final yields were much lower than that of the KH289 (full length sequence).

Gel-filtration HPLC has been used as a means of quality control. No significant difference was observed for samples stored at room temperature, 4° C., or −80° C. for 4 days. The material eluted at a void volume that was less than 0.1%.

6. Crystallization, Crystallography and Three-dimensional Analysis

The full length Chk1 protein (1–476 AA) had proven to be difficult to crystallize until the active kinase domain (1–289 AA) was identified. This active kinase was able to be expressed at the high concentration required for use in HTS and crystallography. The Chk1 data set was collected on MarIP345 under cryotemperature with stream freeze. The HB2–092 kinase domain preparation (1–289 AA) was first used. The initial data set at 2.35 Å was obtained with overall Rsym of 4.6% and overall mosaicity for the data set is 1.2. Subsequent experiments with the HB2–101 (also a 1–289 clone) reached a 1.7 Å resolution with mosaicity of 0.38 for the kinase domain using a crystal grown in refined conditions. Both the original and subsequent crystals have a space group P21 with one molecule per asymmetric unit. The results from the crystallographic analysis are shown in Table 2 below.

TABLE 2

Statistics for the crystallographic analysis

| Crystal | Nat1 | Nat2 | AMP-PNP | Hg | Au |
|---|---|---|---|---|---|
| Internal merging and scaling | | | | | |
| Resolution (Å) | 1.7 | 2.1 | 1.7 | 2.4 | 2.0 |
| Reflections measured | 162418 | 46947 | 107449 | 64881 | 125728 |
| Unique reflection | 35032 | 19145 | 35285 | 12821 | 22086 |
| Completeness (%) | 93.6 (88.3) | 95.4 (94.6) | 94.1 (91.1) | 95.4 (96.4) | 97.5 (84.8) |
| Average I/σ | 29.9 (9.0) | 15.47 (4.38) | 26.4 (12.5) | 27.1 (11.6) | 33.5 (14.8) |
| $R_{sym}^1$ | 3.2 (18.1) | 5.0 (23.3) | 3.0 (10.0) | 6.0 (13.2) | 4.2 (11.8) |
| SIRSAS analysis | | | | | |
| Resolution (Å) | | | | 15–3.0 | 15–3.0 |
| Rcullis[2] | | | | 0.49 | 0.55 |
| Phasing power[3] (SIR/SAS) | | | | 2.27/1.98 | 2.39/1.48 |
| Figure of merit (combined) | | | | | 0.764 |
| Refinement statistics | | | | | |
| Resolution range (Å) | 7–1.7 | 7–2.1 | 7–1.7 | | |
| Reflections used[4] (F > 1 σF) | 30132 | 15804 | 31794 | | |
| Total nonhydrogen atoms | 2372 | 2354 | 2460 | | |
| Rcryst[5] (%) | 21.6 | 20.8 | 22.6 | | |
| Rfree[6] (%) | 23.5 | 25.0 | 24.9 | | |
| rmsd from ideal bond length (Å) | 0.005 | 0.006 | 0.010 | | |
| rmsd from ideal bond angle (°) | 1.30 | 1.27 | 1.58 | | |
| Average B (Å$^2$; all atoms) | 28.9 | 29.7 | 23.22 | | |

Data for the outermost resolution shell are given in parentheses.

$$^1 R_{sym} = \sum_{h}\sum_{i=1}^{N} |\bar{I}(h) - I(h)_i| \Big/ \sum_{h}\sum_{i=1}^{N} I(h)_i * 100,$$

TABLE 2-continued

Statistics for the crystallographic analysis

| Crystal | Nat1 | Nat2 | AMP-PNP | Hg | Au |
|---------|------|------|---------|----|----| where $I(h)_i$ is the ith measurement of reflection h and $I(h)$ is the mean value of the N equivalent reflections.
[2]Rcullis = $\Sigma||FPH +/- FP| - FH(calc)|/\Sigma|FPH +/- FP|$ for all centric reflections.
[3]Phasing power = r.m.s. $(|FH|/E)$, where $|FH|$ is the heavy-atom structure factor amplitude and E is the residual lack of closure.
[4]Number of reflections used in working set.
[5]Rcryst = $\Sigma||Fobs| - ||Fcalc/\Sigma|Fobs|$, where summation is over data used in the refinement.
[6]Rfree is the same calculation including the 10% of data excluded from all refinements.

Crystals were grown at 13° C. using a hanging-drop vapor-diffusion method. Two crystallization conditions produced the exact same form of crystals. The Nat1 crystal was obtained by mixing equal volume of protein solution (7- to 7.5 mg/ml protein) and reservoir solution of 13% PEG 8000 (w/v), 0.115 M $(NH_4)_2SO_4$ 0.1 M NaCacodylate (pH 6.8), 2% glycerol. The Nat2 crystal was crystallized using reservoir solution of 12% PEG8000 (w/v), 15% isopropanol, 0.1 M Hepes (pH 7.5). The crystals belong to the space group $P2_1$, and have unit cell dimensions a=45.2 Å, b=65.7 Å, c=58.1 Å, d=93.9°. The crystals contained one molecule per asymmetric unit and are 53% solvent by volume. The crystals of binary complex with AMP-PNP were obtained by co-crystallization first under the same crystallization condition as Nat1 crystal in the presence of 1.25 mM AMP-PNP and 2.5 mM $MgCl_2$, then the resulting crystals were soaked in mother liquor containing 5 mM $MgCl_2$ and 20 mM AMP-PNP for two days. The co-crystals had the identical space group ($P2_1$) and cell dimensions as the native crystals. All diffraction data were collected at −170° C. Crystals were introduced into cryoprotectant solution containing its reservoir solution and 20% glycerol. For AMP-PNP co-crystal, additional 10 mM $MgCl_2$ and AMP-PNP were included in cryoprotectant solution. Crystals were then flash frozen in a stream of nitrogen gas −170° C. All data collection was carried out with home source using CuK γ-radiation produced by a Rigalu rotation anode FR5 X-ray generator equipped with focusing mirrors and measured with a Mar 345 image-plate detector. All data were processed with the Denzo/HKL package (Otwinowski, Z., "Oscillation Data Reduction Program", *Proceedings of the CCP4 Study Weekend: Data Collection and Processing*, pp. 56–62, compiled by: L. Sawyer, et al., SERC Daresbury Laboratory, England (Jan. 29–30, 1993)).

Initial apoenzyme structure determination using Nat1 crystal data was carried out by molecular replacement (MR) using modified Cdk2 structure (omitted loop regions) (Russo, AA et al., *Nature* 382(6589):325–31 (Jul. 25, 1996)) as a search model. Rotation and translation functions using the AMoRe software (Navaza J, *Acta Crystallographic*, 50(2): Section A (March, 1994)) revealed a solution using Nat1 data from 10 to 4 Å. The MR model was refined by simulated annealing (X-plor). However, after successive rounds of rebuilding and refinement, 2Fo-Fc and Fo-Fc electron density maps were poorly defined at the loop regions which were omitted from the initial model. To obtain additional phase information, multiple isomorphous replacement was carried out with two heavy metal derivatives: 0.5 mM $HgCl_2$ (soaked for 15 hrs) and 5 mM Kau $(CN)_2$ (soaked for 17 hrs). Five Hg sites and five Au sites were identified by difference Fourier synthesis using phases generated from the MR partial model and were consistent with both isomorphous and anomalous difference Patterson maps. The positional and thermal parameters and relative occupancies for the heavy atom sites were refined using SIR data at 3 Å and anomalous data at 3.5 Å by program PHASES (Furey, W et al. "Phases: a Package of Computer Programs Designed to Compute Phase Angles for Diffraction Data from Macromolecular Crystals", *American Crystallographic Association*, Series 2, 18:73 (1990)). Sixteen cycles of solvent flattening were then carried out using phases calculated from refined Hg and Au positions. The resultant electron density maps showed a good backbone density and well-defined side chains for most part of the protein. Model building utilized the program FRODO (Jones, T. A., *J Appl Cryst*, 11: 268–272 (1978)). The missing loop regions were incorporated into the model using both MIR maps and model phased 2Fo-Fc maps. Further refinement in XPLOR (Brünger, A. T. et al., X-PLOR Version 3.1: A System for X-ray Crystallography and NMR", Yale University Press, (1992)) and then CNS (Brünger, A. T. et al., Crystallography & NMR System, *Acta Cryst.*, D54: 905–921 (1998)) were continued with both conjugate gradient minimization and simulated annealing, then followed by manually rebuilding.

Refinement of Nat2 structure was carried out by using refined Nat1 model but omitting residues 153–170 as well as $SO_4$. Fo-Fc maps showed well defined densities for the omitting region and its conformation is exactly same as that in Nat1.

Refinement of the binary complex with AMP-PNP was proceeded with refining the position of the refined apo-enzyme model (Nat1) as rigid body against the complex data using CNS program. Fo-Fc maps with σA (Read, R. J., *Acta Cryst.*, A42: 140–149 (1986)) weighting showed clear density for the adenine and ribose components of AMP-PNP. The conformation of residues forming the binding pocket was checked in simulated annealing omit maps before including the adenine and ribose components of AMP-PNP.

The apo-enzyme model (Nat1) included all atoms for residues 2 to 44 and 48 to 276, 183 ordered solvent molecules and one $SO_4$ molecule. The refined Nat2 structure contained the same number of residues and solvent molecules but the $SO_4$ molecule was not present. The refined AMP-PNP complex contained the same number of residues as apo-structures, with 150 ordered solvent molecules and one $SO_4$ molecule. The triphosphate moiety of AMP-PNP was disordered and no $Mg^{2+}$ ions were visible. The final model had all residues in "most favored" or "additional allowed" regions of the Ramachandran plot according to PROCHECK (Laskowski R A et al., *J. Appl. Cryst.*, 26: 283–291 (1993)), with no residues in "generously allowed" or "disallowed" REGIONS, indicating the well refined nature of the identified crystal structure. The terms "generously allowed" and "disallowed" are descriptions of the configuration of Phi and Psi angles of the protein structure. A well refined protein structure should not place these angles in the unpreferred or non-naturally occurring configurations.

7. The Overall Kinase Structure

The crystal structures of the kinase domain of human Chk1 and its binary complex with an ATP analog, AMP-PNP, have been determined to 1.7 Å resolution. Both structures contain the kinase core domain (residues 2–267) and residues in the linker region that connects the N-terminal kinase domain with the C-terminal region of Chk1. The crystallographic analysis is summarized in Table 2. The Chk1 crystal coordinates for the apoenzyme (isolated active Chk1) and the binary complex (Chk1 complexed with AMP-PNP, an ATP analog) are shown in FIGS. 11A and 11B, respectively. The coordinates of the fixed water molecules are also included therein.

Figure 5:
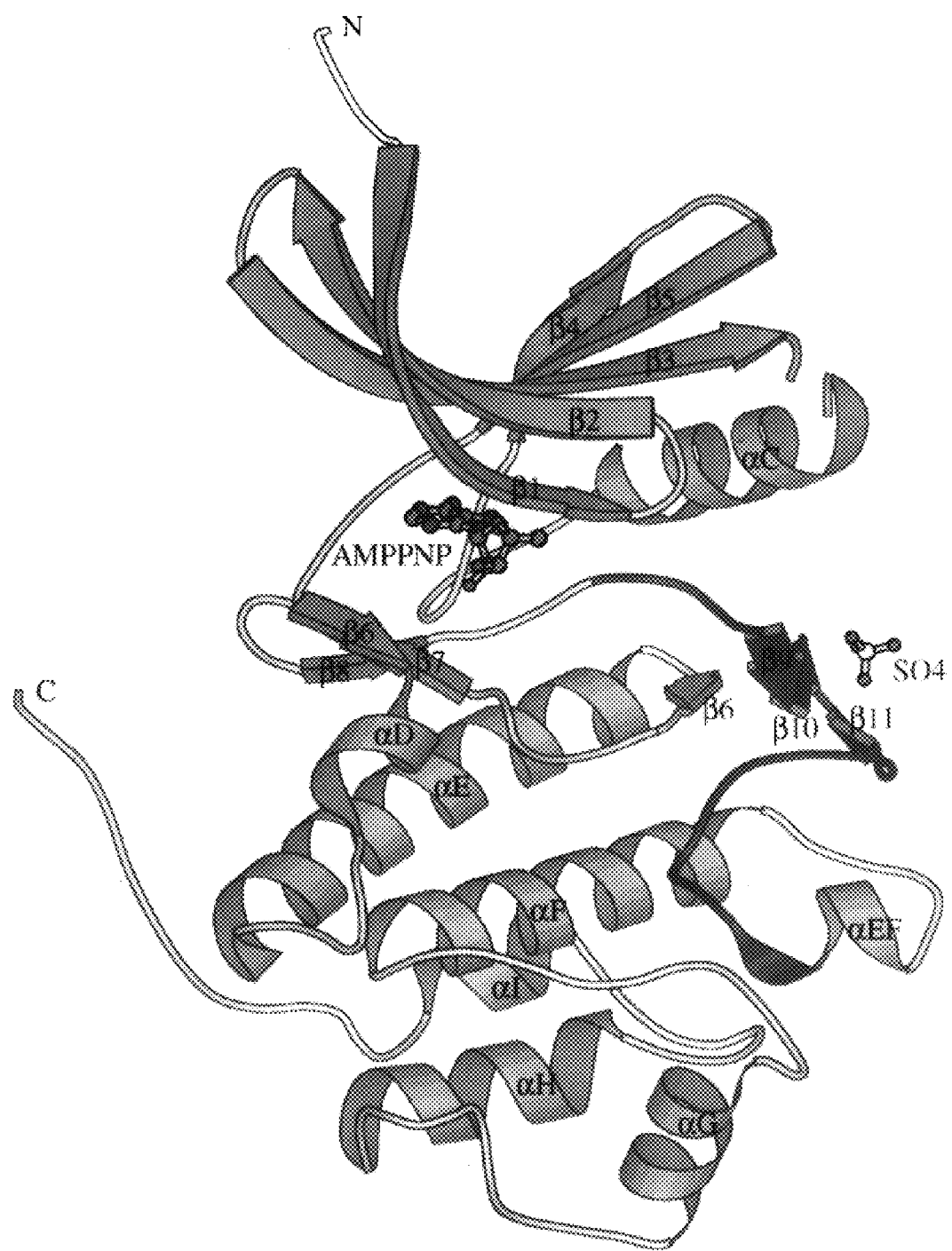
FIG. 5. The structure of human Chk1 kinase domain identified using the crystal resolved to 1.7 Å. A ribbon diagram of the binary complex structure of Chk1 with AMP-PNP showing the secondary structural elements and the loops discussed in the text. The α-helices are shown in blue, the β-strands in cyan, the catalytic loop in orange, the activation loop in red. AMP-PNP and sulfate ion are shown as ball and stick models. The termini are denoted by N and C.

The kinase domain of human Chk1 has a canonical kinase two-lobe fold, with the ATP binding cleft between the two lobes (FIG. 5, structure model). The smaller N-terminal lobe contains one helix ($\alpha$C) and 5 $\beta$-strands ($\beta$1 to $\beta$5) that form a curved anti-parallel $\beta$-sheet. The larger C-terminal lobe contains a cluster of 7 helices ($\alpha$D to $\alpha$I), packed against 6 $\beta$ strands ($\beta$6 to $\beta$11) which border the cleft. One $\beta$ strand ($\beta$6') comprises the hinge region connecting the two lobes. In both apoenzyme and binary structures, the ATP binding site, catalytic residues, and the activation loop are well ordered. Comparison with crystal structures of other kinases indicates that the Chk1 kinase domain is closely related to PhK (Lowe, E D et al., *EMBO J*, 16(22):6646–58 (Nov. 17, 1997)) (See FIG. 1A, 1B). The N-terminal lobe (Residues 2–90) superimposes with an r.m.s. derivation for C$\alpha$ atoms of 1.1 Å, while the C-terminal lobe (Residues 91–276) superimposes with an r.m.s. derivation for C$\alpha$ atoms of 0.9 Å. In the C-terminal lobe, major differences are found in helix $\alpha$G, and the connecting loop between $\alpha$G and $\alpha$H. These are not included in the superposition. The Chk1 apoenzyme adopts a more open conformation compared to PhK. The N-terminal lobe of Chk1 is rotated ~15° relative to the ternary complex of PhK with its substrates. Comparison of the AMP-PNP bound Chk1 binary complex with the apoenzyme structure shows no conformational change. A high degree of sequence homology for Chk1 kinase domains of different species (FIG. 2) suggests that there is an overall structural conservation of the kinase domain. Residues that are not modeled in the current structures are not conserved in Chk1. For example, there is a six-residue insertion in the loop connecting $\beta$3 and $\alpha$C in *S. pombe* Chk1.

The two lobes are held together by an extensive hydrogen-bond network at the lobe interface which involves the loop linking $\alpha$C and $\beta$4 of the N-terminal lobe, $\beta$6' of the hinge region, and $\beta$7 and $\beta$8 of the C-terminal lobe. This network extends from the back of the protein to the front opening of the ATP binding cleft. Residues involved in this network also form part of the pocket that interacts with the adenine moiety of AMP-PNP. Strand $\beta$8 immediately precedes the kinase conserved DFG motif, in which Asp148 is important for the alignment of the phosphate groups of ATP. The only reported mutation in the Chk1 kinase domain is at the lobe interface. Replacement of the conserved Glu85 by Asp leads to a temperature-sensitive phenotype in fission yeast in which the mutant maintains cell cycle arrest after UV irradiation but impairs the DNA replication checkpoint at nonpermissive temperature (Francesconi, S et al., *EMBO J*, 16(6):1332–41 (Mar. 17, 1997)). The side chain of Glu85 at the end of strand $\beta$5 forms hydrogen bonds with the side chain of conserved Lys145 from strand $\beta$8 as well as with the main chain amide of conserved Lys69 that precedes strand $\beta$4. These interactions, together with the extensive hydrogen-bond network at the lobe interface, appear to play an important role in maintaining the correct disposition of the N-terminal lobe and the DFG loop during lobe movement. The Glu to Asp mutation, while maintaining similar charge, would not be long enough to form those hydrogen bonds provided by Glu85, thereby weakening lobe interactions and rendering the mutant protein less stable at higher temperature.

Most of the invariant residues of Chk1 proteins are located in the C-terminal lobe. Many of them are also conserved among Ser/Thr kinases and are involved in stabilizing the catalytically active kinase conformation and in binding ATP. The positions of several invariant motifs of Chk1 proteins are noteworthy. Compared with other Ser/Thr kinases, the IEPDIG motif (residues 96–101) shortens $\alpha$D to a one-turn helix, since Pro98 initiates a tight turn between $\alpha$D and $\alpha$E. This turn interacts with the C-terminus of helix $\alpha$F through a backbone hydrogen bond between Asp99 and the invariant Gly204. In this turn, Glu97 forms backbone hydrogen bonds with Ile100 and Gly101. The unique conformation of this motif appears to be important for peptide substrate interaction, since the side chains of Ile96 and Pro98 form part of a hydrophobic pocket that interact with the peptide substrate as discussed below. Helix $\alpha$E contains a conserved motif of AQXFFXQL (residues 107–114), with the hydrophobic residues buried inside the C-terminal lobe. The side chain of Gln108 projects towards the linker region that follows the kinases core domain and forms hydrogen bonds directly or through a water molecule to backbone atoms of Lys267, Leu269 and Lys270. Although Chk1 sequences diverge in this linker region, these backbone interactions with Gln108 could still be conserved, holding the linker against the N-terminus of $\alpha$E. Helix $\alpha$G is positioned differently compared with $\alpha$G of PhK. Two sets of invariant PW residues (207 and 208, 230 and 231) flanking $\alpha$G, although separated by 21 residues, are in van der Waals contact and connected to the hydrophobic core of the C-terminal lobe. This stabilizes the surface for peptide substrate interaction.

Activation and Catalytic Loops

Interesting features of the Chk1 kinase domain include interactions that stabilize the activation loop. The structure of the activation loop determines the alignment of residues contacting ATP and performing catalysis in protein kinases. Interacting with the catalytic loop, the activation loop orients the catalytic Asp; interacting with the N-terminal lobe, the activation loop closes the N and C terminal lobes and aligns residues that interact with the phosphates of ATP. The activation loop is defined as the region between the conserved motifs of DFG and APE corresponding to residues 148 to 177 of Chk1. Conformational changes in the activation loop serve as a major regulatory mechanism for kinase activity. In the human Chk1 structures, the activation loop is folded in a conformation similar to those found in structures of active kinases, consistent with the observation that the Chk1 kinase domain is constitutively active. This active conformation is stabilized by special features of Chk1 secondary structures and their side chain interactions (FIGS. 3 and 5, homology model and crystal structure).

The N-terminus of the activation loop interacts with the catalytic loop through the interaction of $\beta$6 and $\beta$9. Immediately following $\beta$9, $\beta$10 interacts with $\beta$11 to form a two-stranded $\beta$-loop with a turn at Asn159. This $\beta$-loop is packed against the N-terminus of the catalytic loop and positions the highly conserved Arg156 and Glu161. The side chain of Arg156 interacts with the carbonyl of the invariant His122 at the end of $\alpha$E. Through the invariant Asp190, the side chain of His122 is connected to the amide of Arg129, adjacent to the catalytic residue Asp130. The carboxyl of Glu161forms a hydrogen bond with the imidazole of His185 that precedes αF. These interactions anchor this end of the activation loop to the core of the C-terminal lobe. The center of the activation loop interacts with the rest of C-terminal lobe through two backbone hydrogen bonds between Leu164 and Phe184. The activation loop ends at its C-terminus with a turn which is supported by αEF. In human Chk1, αEF is anchored at two positions to the core of the C-terminal lobe through two ion-pairs, one is the invariant kinase ion-pair between Glu177 and Arg253, another is between Lys180and Glu248 which is unique to Chk1. This extra ion-pair constrains the movement of αEF, and in turn the movement of the C-terminal end of the activation loop. The pair of Lys180 and Glu248 is only conserved in vertebrate Chk1, suggesting potential flexibility of αEF and the activation loop of Chk1 in lower organisms such as *S. pombe*.

Crystal structures of kinases indicate that the conformation of the activation loop is influenced by its negative charge which neutralizes a cluster of positively charged residues, although the ionic interaction may not be absolutely required as in the case of mammalian casein kinase I. The negative charge is provided by phosphate through phosphorylation, carboxyl group of Glu, or solvent ions. In Chk1, the positively charged cluster of Arg129, Arg162, Lys166, and Lys54 is present, but no phosphorylation is observed. In both the apoenzyme and binary complex structures determined to 1.7 Å, a sulfate ion was close to the phosphate position of the phosphothreonine (Thr197) in PKA. This sulfate ion interacts with Arg129, Arg162, and Thr153. Sulfate is present in the crystallization solution and could contribute to the stability of the positively charged cluster and the activation loop. To clarify the role of this sulfate ion and to better understand the interactions that stabilize the activation loop, crystals were produced under sulfate-free condition and determined the structure to 2.1 Å (Table 2). This 2.1 Å structure is referred as Nat2 structure, whereas the 1.7 Å apoenzyme structure is referred as Nat1 structure. In Nat2 structure, no sulfate ion is present.

Superimposition of Nat1 and Nat2 structures revealed similar conformations for the corresponding activation loops except for the side chain of Arg162 which turns toward the solvent in Nat2 structure. The side chain of Arg162 is flexible in both structures as indicated by its high temperature factors. Arg162 is an invariant residue of Chk1 and its function is not readily apparent from the structure. In both the Nat1 and Nat2 structures, the side chain of Arg129 forms hydrogen bonds to three main chain carbonyl oxygens (Leu151, Ala152, and Lys166) directly or via water molecules. The positive charge of Arg129 could be neutralized by the thiol group of Cys168 which is in the vicinity of side chains of Lys166 and Arg129. In this basic environment, this thiol could become a thiolate ion. Cys168 is invariant in Chk1 and is conserved in many kinases such as PKA and PhK. Our results rule out the role of sulfate ion in stabilization of the activation loop of Chk1. Instead, the activation loop and the catalytic loop are stabilized by its unique secondary structures and their extensive side chain interactions.

Figure 2A:
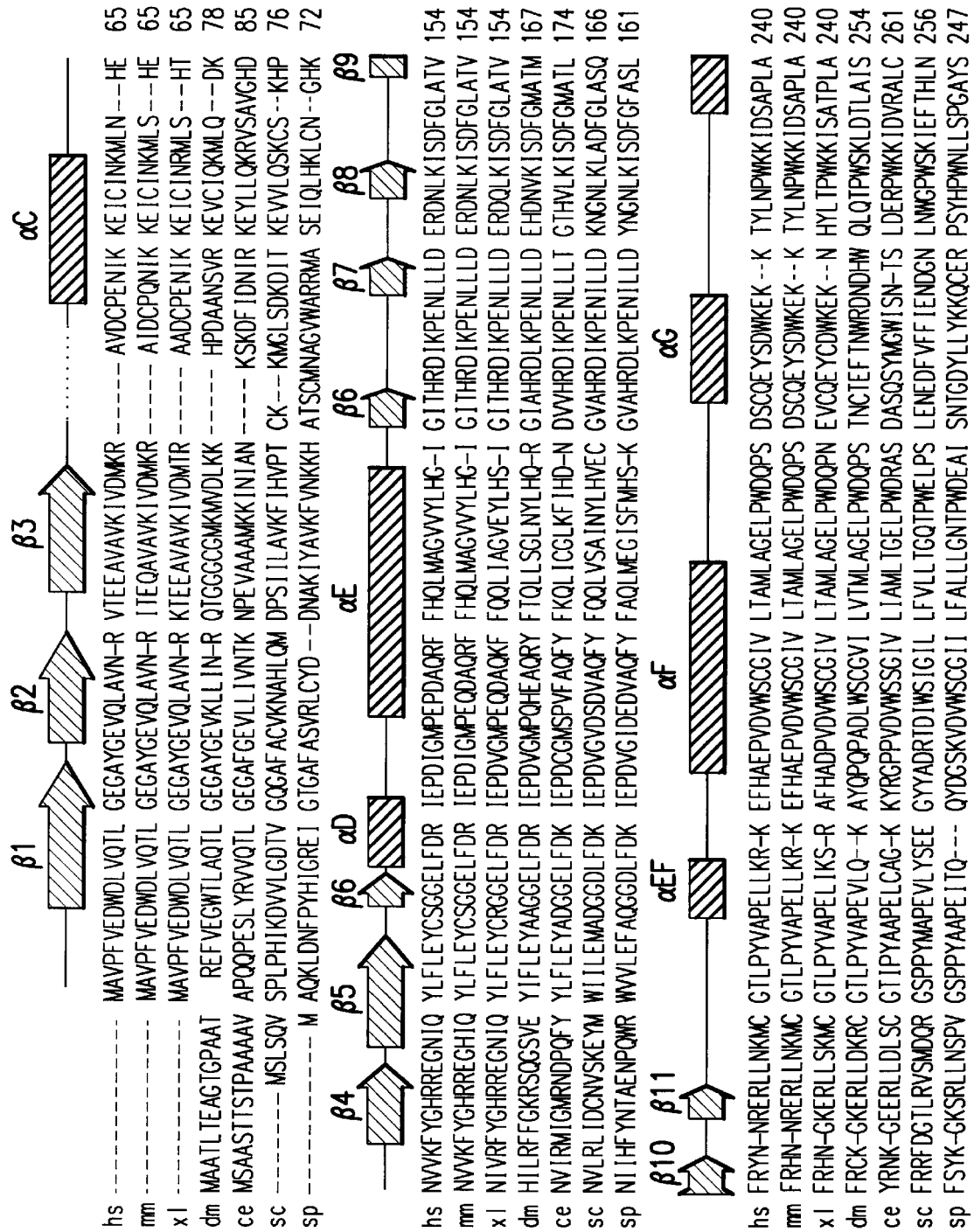
FIGS. 2A–2B. Sequence alignment of Chk1 kinase domains of human (hs)(SEQ ID NO:2), mouse (mm)(SEQ ID NO:18), Xenopus (xl)(SEQ ID NO:19), fruit fly (dm) (SEQ ID NO:20), C. elegans (ce)(SEQ ID NO:21), S. cerevisiae (sc)(SEQ ID NO:22), and S. pombe (sp)(SEQ ID NO:23), Secondary structural elements of human Chk1 are shown above the alignment. The numbers of amino acids are shown on the right. Invariant residues among these species are in red and human Chk1 residues that also conserved in other species are in cyan.
Figure 2B:
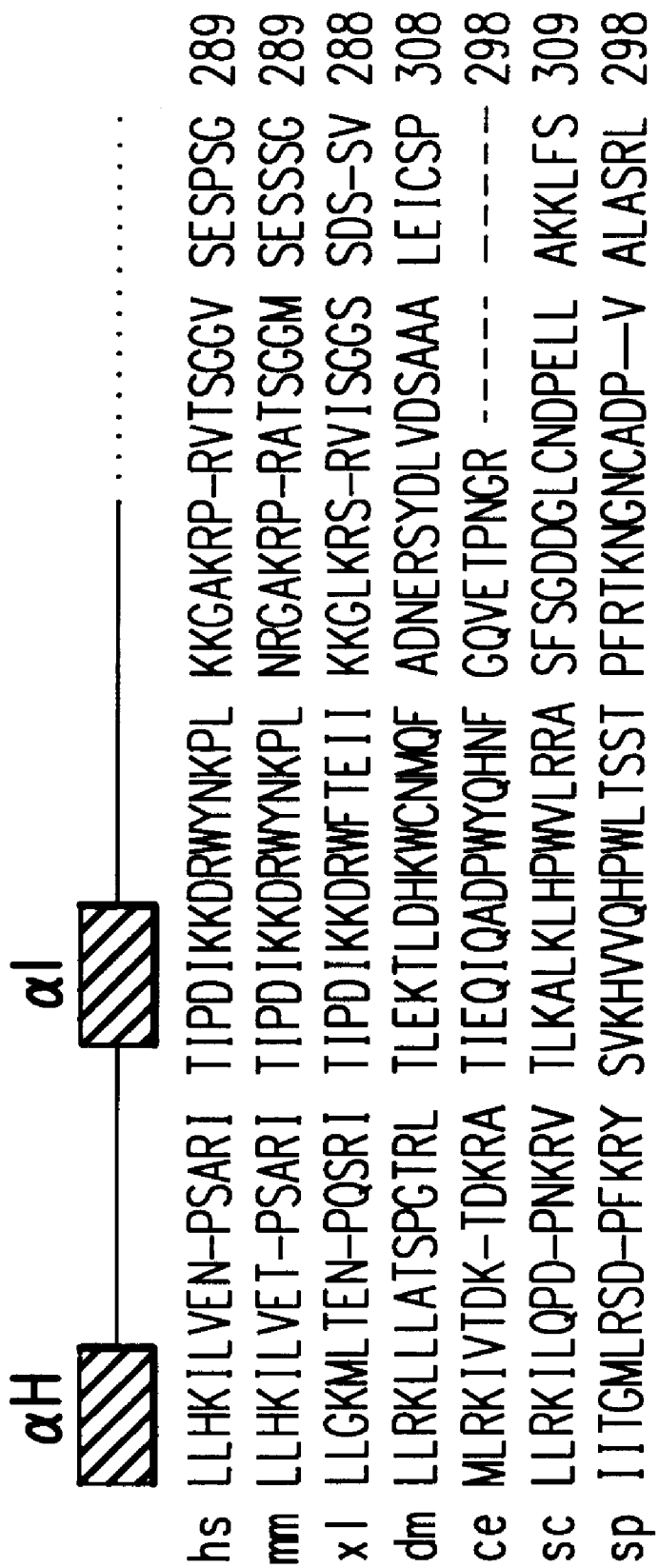

A difference between Chk1 and other kinases is the permuted positions of Lys166 and Thr153 (FIG. 2). Lys166 occupies the equivalent position as Glu182 of PhK and the phosphorylated Thr197 of PKA, whereas Thr153 is equivalent to Lys189 of PKA. The side chain of Thr153 forms a hydrogen bond with the side chain of Lys54 located in helix αC. Thr153 is conserved in Chk1 (Thr or Ser) and is a candidate for phosphorylation in the activation loop. The permuted position, however, makes phosphorylation of Thr153 unlikely. The activation loop is already in an active conformation in Chk1 and phosphorylation would be unnecessary. Lys54 is conserved in all but *S. pombe* Chk1 and adjacent to Glu55 which forms the invariant ion-pair with Lys38 in active kinases. The interaction between Thr153 and Lys54, therefore, appears to play a similar role to the interaction between His87 and the phosphate of Thr197 of PKA. The side chain of Lys166 points to Cys168 and its position appears to play a role in determining the substrate specificity as discussed below. In *S. pombe* Chk1, the residue that corresponds with Lys166 is Ser, suggesting potential regulation of the activity of *S. pombe* Chk1 through phosphorylation. Concomitantly, the activation loop of *S. pombe* Chk1 appears to be more flexible since its substitutions would disrupt some of the interactions that stabilize the activation loop.

Catalytic Residues and AMP-PNP Binding

The glycine-rich loop that anchors the phosphate groups of ATP in kinases is poorly ordered in Chk1, as evidenced by the high B factors in this region for both apoenzyme structures and AMP-PNP bound binary complex structure. Residues 18–21 at the apex of the loop between β1 and β2 are flexible with poor electron density. These residues are highly conserved in kinases and anchor the β-phosphate of ATP in ATP-bound kinase structures. The flexibility of this loop could play a role in regulating Chk1 kinase activity, indeed, Tyr20 present in higher organisms corresponds structurally to Tyr15 of Cdc2 which following phosphorylation inhibits Cdc2 activity (Coleman T R, et al., *Curr Opin Cell Bio*, 6(6):877–82 (December 1994); Russo, A A et al., *Nature*, (1996), supra).

Figure 6:
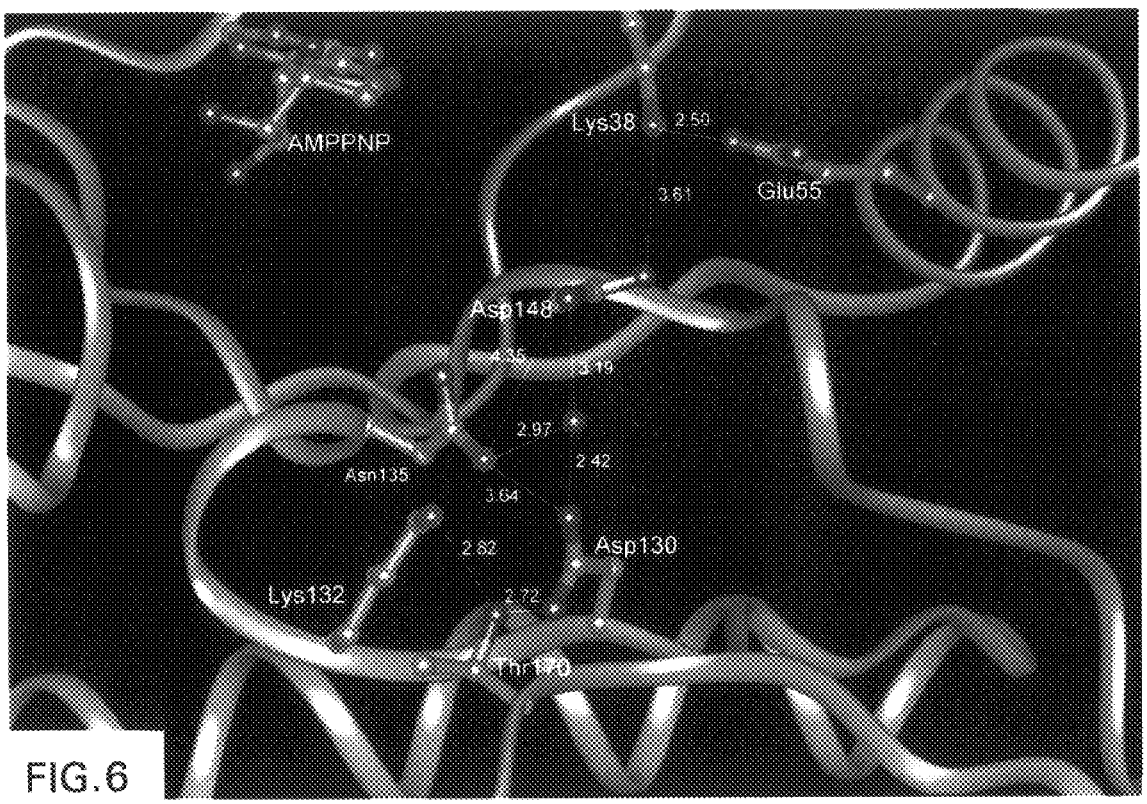
FIG. 6. Catalytic site of Chk1. Cross section of the catalytic site of human Chk1 with AMP-PNP. Protein C α-ribbon representations are shown in purple for Chk1. The side chains of the catalytic site residues are shown as ball and stick models and are color-coded by atom type: carbon, green; nitrogen, blue; oxygen, red. The distances (Å) along the dotted lines between the catalytic site residues are shown.

One striking feature among the active ternary complexes such as PKA and PhK is the close similarity of the active site residue conformation, their interactions with the ATP and coordination of the metal ions. The binary complexes that have been solved show no such conservation (Knighton D R, et al., *J Mol Biol*, 220(2):217–20 (Jul. 20, 1991); Bossemeyer, D et al., *EMBO J*, 12(3): 849–59 (March 1993); Zheng J, et al., *Protein Sci*, 2(10):1559–73 (October 1993); Owen D J, et al., *Structure*, 3(5):467–82 (May 15, 1995); Lowe, et al., *EMBO J*, (Nov. 17, 1997), supra.). Many of the active site residues in the Chk1 structure have interactions quite similar to those in ternary complexes of Phk and PKA (FIG. 4A, 4B). In the N-terminal lobe, the invariant ion pair of active kinases is present between Lys38 and Glu55; the corresponding Lys in PhK and PKA interacts with α and β phosphates of ATP. Helix αC is firmly attached to the rest of N-terminal lobe through hydrophobic interactions and is in an active position relative to the rest of the N-terminal lobe. It also interacts with the DFG loop in the C-terminal lobe, the side chain of Glu55 from αC rests above Gly150. The relative side chain positions of Lys38, Glu55, and Asp148 are similar to those for the corresponding residues in the ternary complexes of PKA and PhK. These residues in PKA and PhK, together with the glycine-rich loop, coordinate a $Mg^{2+}$ and anchor the α and β phosphates of ATP. In the C-terminal lobe, the conformation of the catalytic loop (residues 130–135) of Chk1 is nearly identical to that in PhK with the side chains of Asp 130, Lys132, and Asn135 in Chk1 nearly superimposable to the corresponding residues Asp149, Lys51, and Asn154 in PhK in which Lys151 binds to the γ-phosphate of AMP-PNP and Asn154 chelates another $Mg^{2+}$ that binds to the β and γ phosphates of AMP-PNP. Thr170 is conserved in all serine/threonine protein kinases and appears to determine the specificity of Ser/Thr verses Tyr as phospho-acceptor. Thr170forms hydrogen bonds with Asp130and Lys132 analogous to Thr186 in PhK and these interactions are needed for the positioning the carbonyl of the catalytic residue Asp130. The residues of Chk1, however, are far apart from those in the N-terminal lobe and the DFG loop due to the somewhat open lobe conformation (FIG. 6). The DFG loop is positioned higher than its counter parts in PKA and PhK. Lys38Nε is 10 Å away from Asp130Oδ2, compared with 8.2 Å in Phk and 7.8 Å in PKA. Asp148Oδ1 is 6 Å away from Asp130Oδ2, compared with 3.8 Å in PhK and 4.8 Å in PKA. In Chk1, one water molecule is located between Asp148 and Asp130and is hydrogen bonded to Asp130Oδ2 as well as Asn135Oδ1. The side chain of Asn135 is over 1 Å farther away from Asp148 relative to the active conformation in PhK. The residues that are necessary for ATP phosphate binding and catalysis are clustered in two separate parts, although they maintain their local interactions. The lack of electron density of the triphosphate moiety of AMP-PNP in the binary complex of Chk1 probably results from misalignment of these residues as well as flexibility in the glycine-rich loop.

The adenine and ribose moieties are clearly defined in our current model. As in all the structures of kinases with ATP, the adenine base is almost completely buried in a hydrophobic pocket between the two lobes, and hydrogen bonds are formed between N6 of adenine and the main chain carbonyl of Glu85, and between N1 and amide of Cys87. As in PhK, Chk1 N7 interacts with the side chain of Ser147 via a water molecule in Chk1. However, the ribose ring adopts a C2'-endo conformation similar to that in the inactive form of Cdk2 (PDB ID code 1HCK, (De Bondt H L, et al., *Nature*, 363(6430):595–602 (Jun. 17 1993); Schulze-Gahmen U et al., *J Med Chem*, 39(23):4540–6 (Nov. 8, 1996)), with the O2' hydrogen-bonding to Glu91, and O3' hydrogen bonding to the carbonyl of Leu15 in the glycine-rich loop. In comparison, the ribose rings have C3'-endo puckering in the active ternary complexes of PKA and PhK.

Substrate Specificity and Interactions that Stabilize the Closed Conformation

The structured activation loop of Chk1 provided an opportunity to explore the basis of peptide substrate specificity. The close resemblance of Chk1 with PhK and the available structures of PhK with and without peptide substrate enable us to model the interactions of peptide substrate with Chk1. The interaction of kinases with their peptide substrates has been analyzed for three kinases, PKA with an inhibitor peptide of PKI (PDB code 1ATP, (Knighton D R, *J Mol Biol*, (Jul. 20, 1991), supra.), PhK with MC-peptide (PDB code 2PHK, (Lowe, et al., *EMBO J*. (Nov. 17, 1997), supra.), and insulin receptor tyrosine kinase with a peptide substrate (PDB code 1IR3, (Hubbard S R, *EMBO J*, 16(18):5572–81(Sep. 15, 1997)). In all three tertiary complex structures, the backbones of peptide substrates around the phosphate acceptor residues adopt extended conformation and interact mainly with the C-terminal lobes.

The known Chk1 kinase substrate is the Cdc25C protein phosphatase. Several phosphate acceptor Ser residues have been identified in the Cdc25C protein sequence (SEQ ID NO. 17). Consensus features can be derived from sequences surrounding the phosphate acceptor Ser (position P): The N-terminal P–3 position is a conserved Arg, P–5 positions prefers bulky hydrophobic residues, and P–2 is Ser or Thr. Phosphorylation of Ser216 of human Cdc25C is required for DNA damage induced G2 arrest and Ser216 is phosphorylated by Chk1 in vitro (Peng et al., *Science* (1997), supra.; Sanchez et al., *Science* (1997), supra). Therefore, the peptide LYRSPSMPE spanning residues 211–219 of human Cdc25C was used to model the interaction of peptide substrate with Chk1, based on the ternary complex of PhK with MC-peptide.

Figure 7:
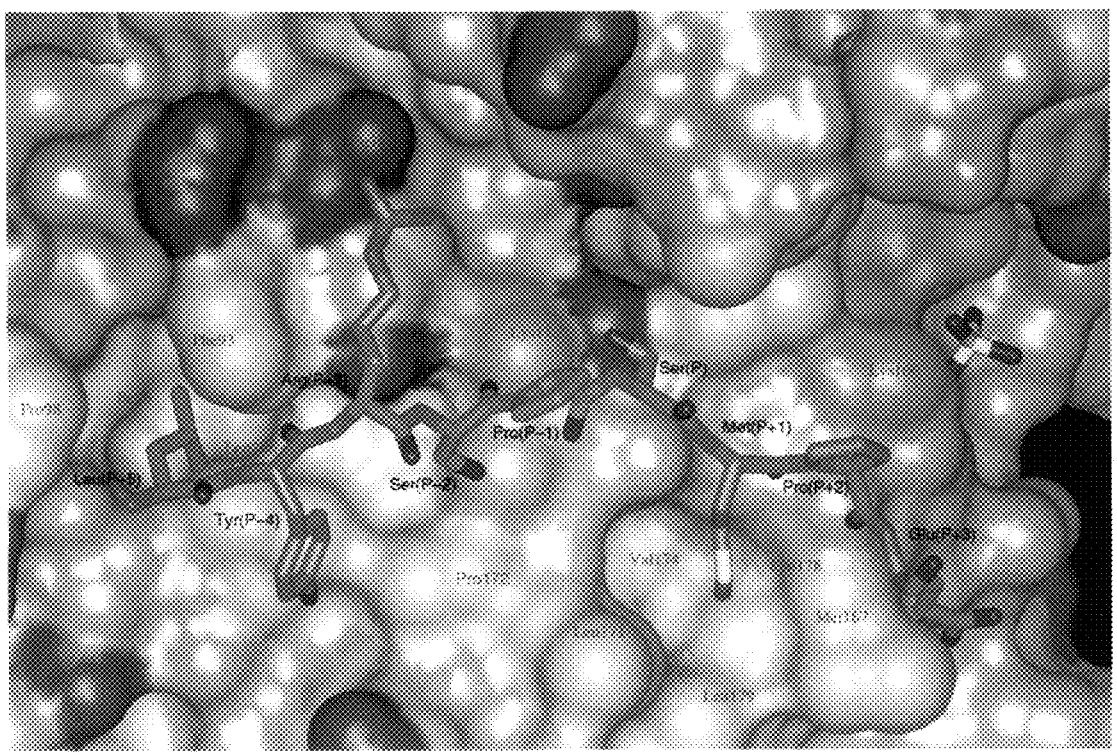
FIG. 7. Molecular surface of the Chk1 with modeled CDC25C peptide. The molecular surface of Chk1 is colored as follows: basic side chains are shown in blue, acidic side chains in red, and non-polar side chains in violate. CDC25C peptide (residues 211–219) is shown as tick model and color-coded by atom type: carbon, green; nitrogen, blue; oxygen, red; sulfur, yellow.
Figure 8A:
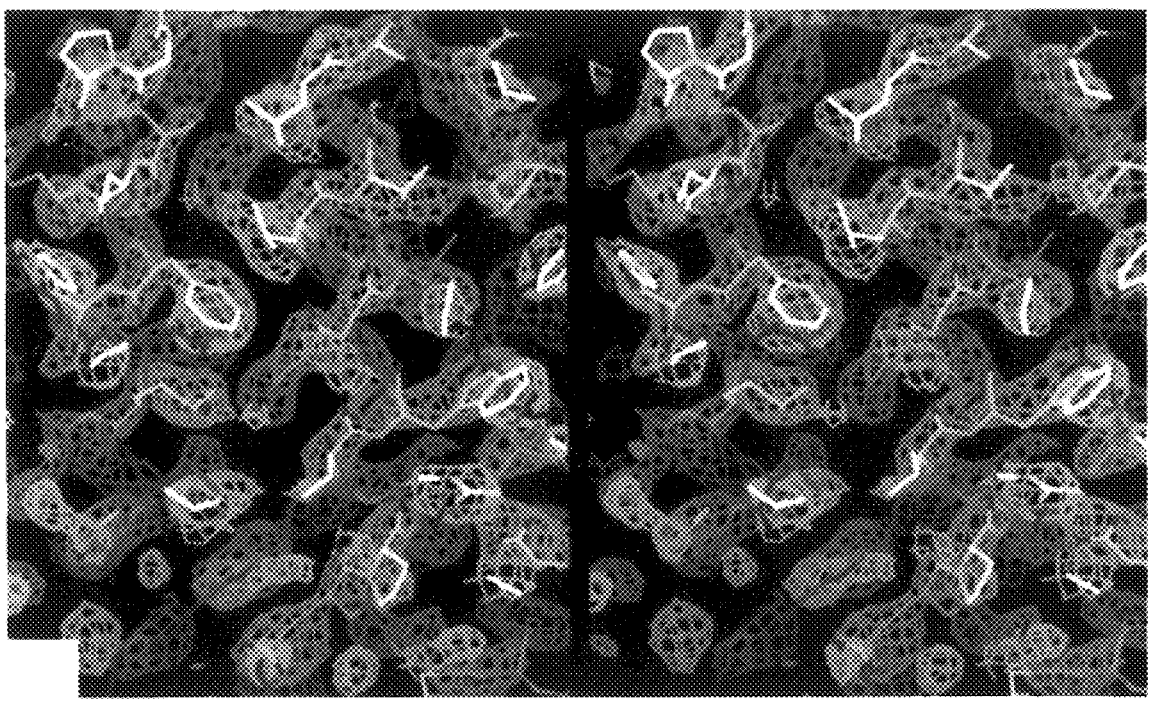
FIGS. 8A–8B. Stereoview of representative electron density map.
Figure 8B:
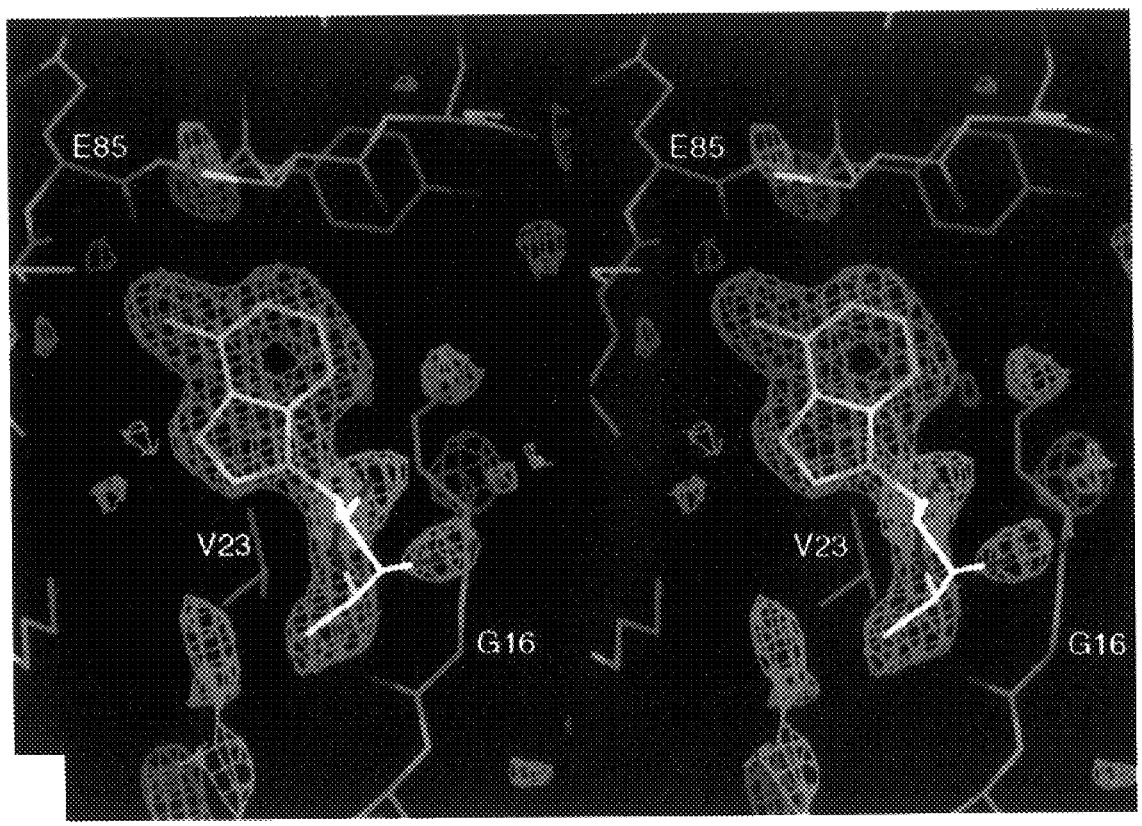

The modeled Cdc25C peptide easily fits into a groove on the C-terminal lobe of Chk1, following a path very similar to that of the MC-peptide bound to PhK (FIG. 7). The Oγ atom of Ser(P), the presumed nucleophile in the phosphate transfer reaction, is very close to an ordered water molecule in Chk1 structures. This water molecule hydrogen bonds to both the Asp130Oδ2 and Lys132Nε. Superposition. of Chk1 and PhK shows that this water molecule would be 3.4 Å from the γ-phosphorus atom of the AMP-PNP in PhK. The position of this water molecule probably indicates the approximate location of the seryl hydroxyl during catalysis.

The hydrophobic side chain of Leu(P–5) fits into the hydrophobic pocket formed by Phe93, Ile96, Pro98, and Leu206. All of these residues except Leu206 are invariant in Chk1 proteins. The side chain of Arg(P–3) points towards Glu91of Chk1. However, in its extended conformation, the guanidinium group of this Arg can only make a hydrogen bond (3 Å) with the carboxyl of Glu91. In both PKA and PhK, the guanidinium of Arg(P–3) forms a salt bridge (2.5 Å) with the carboxyl of the corresponding Glu residues. As discussed below, ionic interaction of Arg and Glu91 could be established after lobe closure.

The side chain of Ser(P–2) could make a hydrogen bond to the backbone carbonyl oxygen of Pro(P–1). In PhK, Gln(P–2) of the MC-peptide interacts with Ser188. This interaction is not available to Chk1 since it has an invariant Pro172 in the corresponding position of Ser188 in PhK. Pro172, then, may contribute to the specificity of Chk1 for Ser or Thr at P–2 position and the internal hydrogen bond provided by Ser or Thr at P–2 position may play a role in maintaining the conformation of the substrate backbone at its N-terminus.

The hydrophobic side chain of Met(P+1) projects into a hydrophobic pocket formed by residues of Leu171, Val174, Leu178, Leu179, and Met167. The P+2 position can only accommodate a small side chain or a turn due to the unique position of Lys166. Lys166 is conserved among vertebrate Chk1 proteins. Correspondingly, Pro is found at the P+2 position of the Cdc25 substrates. Pro(P+2) creates a consensus 14-3-3 binding site once the Ser(P) is phosphorylated. The Lys166 of human Chk1 is a Ser residue in *S. pombe* Chk1. The side chain of *S. pombe* Chk1 could be phosphorylated and point to the position corresponding to the sulfate ion in human Chk1 structure. Correspondingly, bulky side chains are present at the P+2 position of the substrates of *S. pombe* Chk1.

Phosphorylation of Cdc25C by Chk1 is very specific such that the Ser(P–2) is not phosphorylated. This is important for Cdc25C regulation since phosphorylation at the P–2 position would destroy the 14-3-3 binding site. Our model clearly indicates determinants for Chk1 substrate specificity: hydrophobic interaction through the P–5 and P+1, ionic interaction through P–3, Ser/Thr at P–2, and small amino acid side chains at the P+2 position.

Although the recombinant Chk1 kinase domain is active when assayed in solution, the structure reveals that it is not in a closed catalytically active conformation in either the apoenzyme or the binary crystal structure. This result suggests that the apoenzyme and the ATP bound binary complex favor the open conformation. Lobe movement is common in kinase domains and catalysis requires a closed conformation (Cox S, et al., *Curr Opin Struct Biol*, 4(6):893–901 (December 1994); Gangal M, et al., *Biochemistry*, 37(39)

:13728–35 (Sep. 29, 1998)). Interactions that stabilize the closed active conformation have not been addressed in detail in previous reports. Our model suggests that a key interaction in Chk1 is the ion-pair between Glu91 with Arg(P–3) of peptide substrate.

Superposition of Chk1 and PhK structures indicates that lobe closure of Chk1 can be achieved by a simple rotation of the N-terminal lobe by ~15 degree around residue Glu91. This rotation would place Glu91 closer to Arg(P–3) and establish an ion-pair between the carboxylate group of Glu91 and the guanidinium group of the Arg(P–3). Lobe closure could also change the ribose conformation of AMP-PNP to a C3'-endo conformation from the C2'-endo conformation in the binary complex. The catalytically active kinase ternary complex structures reported to date have their respective ribose rings puckered in a C3'-endo conformation. For Chk1, when the ribose is modeled in a C3'-endo conformation, two hydrogen bonds can form between the carboxyl group of Glu91 and the O2' and O3' of the ribose. In comparison, the binary complex of Chk1 with AMP-PNP has only one hydrogen bond between Glu91 and the ribose. The Chk1 kinase domain in solution likely shifts dynamically ("breathes") between the open and closed conformation. The current Chk1 structures have open conformations and have revealed that the ATP binding cleft is accessible to solution. In the closed conformation, residues for phosphate binding and catalysis come together and align the phosphate for transfer. The additional interaction of Glu91 with Arg (P–3) of peptide substrate and with the ribose of ATP would shift the equilibrium to the closed active conformation. Therefore, peptide substrates gain specificity partly through their ability to stabilize the closed catalytically active conformation of Chk1.

8. Regulation of Chk1 Kinase Activity

Phosphorylation of the Chk1 substrate, Cdc25, and the resulting cell cycle arrest has been correlated with the activation of Chk1 after DNA damage. Whether phosphorylation of Chk1 regulates its kinase activity is unclear. The structure of human Chk1 suggests that its activity is not regulated through phosphorylation of the activation loop. Instead, the activation loop of Chk1 appears to be anchored by extensive interactions through rigid secondary structures and their side chains. Interestingly, phosphorylation of the activation loop could occur in S. pombe Chk1 which has a Ser substitution at the position of Lys166. Whether Chk1 is regulated differently in S. pombe and mammals requires the identification of residues that are phosphorylated after DNA damage.

The structure of the Chk1 kinase domain and its binary complex with AMP-PNP provide insight into its activation mechanism. First, the structures reveal an unique arrangement of the residues for phosphate binding and catalysis. Specifically; the residues for α and β phosphate binding are separated from those for γ phosphate binding and catalysis. Alignment of these residues is achieved in a closed conformation which is stabilized by peptide substrate. Our model predicts low ATPase activity of Chk1 and favors an ordered kinetic mechanism in which ATP binding precedes the peptide substrate binding. Secondly, the structures exclude a role for the activation loop of human Chk1 in regulating the kinase domain conformation. The activation loop is most likely maintained by rigid secondary structures and the extensive interactions of their side chains. However, a possibility of different regulatory mechanism exists for S. pombe Chk1, which may reflect their different cell cycle processes and different DNA damage repair mechanisms. In addition, the interactions that stabilize the active kinase conformation have been identified. The presence of Glu in many kinase hinge regions and Arg at P–3 position of their substrates suggests a general role for this interaction in maintaining the closed conformation for Ser/Thr kinases. Interactions that determine the peptide substrate specificity suggest a consensus sequence that is useful to identify potential Chk1 substrate. Finally, Chk1 kinase domain structure provides a guide for its future characterization as well as design of specific inhibitors that could abrogate checkpoint control for cancer therapy.

9. Enzymatic Activity of Chk1

The enzymatic activity of a kinase is measured by its ability to catalyze the transfer of a phosphate residue from a nucleoside triphosphate to an amino acid side chain in a selected protein target. The conversion of ATP to ADP generally accompanies the catalytic reaction. Herein, a synthetic substrate peptide, Syntide-2, having amino acid sequence PLARTLSVAGLPGKK (SEQ ID NO. 11) was utilized. The production of ADP from ATP that accompanies phosphoryl transfer to the substrate was coupled to oxidation of NADH using phosphoenolpyruvate (PEP) through the actions of pyruvate kinase (PK) and lactic dehydrogenase (LDH). The oxidation of NADH was monitored by following the decrease of absorbance at 340 nm (e340=6.22 cm−1 mM−1) using a HP8452 spectrophotometer. Typical reaction solutions contained: 4 mM PEP, 0.15 mM NADH, 28 units of LDH/mL, 16 units of PK/mL, 3 mM DTT, 0.125 mM Syntide-2, 0.15 mM ATP and 25 mM $MgCl_2$ in 50 mM TRIS pH 7.5; 400 mM NaCl. Assays were initiated with 10 nM of kinase domain of Chk1, KH289. $K_i$ values were determined by measuring initial enzyme activity in the presence of varying concentrations of inhibitors. The data were analyzed using Enzyme Kinetic and Kaleidagraph software.

The table below (Table 3) compares three different preparations of Chk1. The first preparation is the full length form, which comprises amino acids 1–476 of SEQ ID NO. 2. The next preparation contains proteolytically cleaved fragments, a mixture of Chk1 protein fragments obtained from the full-length protein during fermentation. The exact enzymes involved and cleavage site generated for these fragments is unknown. However, analysis of the fragments indicated that one of them is similar in size to the 1–289. The third preparation is the kinase domain of amino acids 1–289 of SEQ ID NO. 2 (KH289) As mentioned above, the assay used detects the ADP product by coupling through the enzymatic actions of pyruvate kinase and lactate dehydrogenase.

TABLE 3

| Prep No. | Prep | Concentration | Rate/min | Activity | Ki |
| --- | --- | --- | --- | --- | --- |
| HA2-013 | Full Length Chk1 | 75 nM | 0.0190 | 1 (control) | 48 ± 1 nM |
| HA2-022 | Proteolytically cleaved Chk1 | 2 nM | 0.0208 | +38 fold | 37 ± 5 nM |
| HB2-061 | Kinase Domain Chk1 (1–289) | 7.3 nM | 0.0200 | +10 fold | 68 ± 12 nM |

Additional activity comparison experiments were performed using new preparations of full length Chk1, proteolitically cleaved Chk1, and kinase domain Chk1. The preparation conditions were as described above. Once again, the cleaved preparation was 38 fold more active than the non-cleaved preparation.

10. High Throughput Screens

The following substrates were tested for peptide content and activity:

TABLE 4

Peptide Substrates

| | | Activity | Peptide |
|---|---|---|---|
| Syntide 2 | PLARTLSVAGLPGKK (SEQ ID NO. 11) | 100% | 75% |
| Syntide 3 | KAGAG-PLARTLSVAGLPG-Biotin-K (SEQ ID NO. 12) | 67% | 50% |
| Syntide 4 | Ac-PLARTLSVAGLPG-AGAGAGAK (SEQ ID NO. 13) | 72% | 45% |
| Syntide 5 | PLARTLS (PO$_3$) VAGLPGKK (SEQ ID NO. 15) | NT | 42% |
| Syntide 6 | PLARTLS (PO$_3$) VGALPGK (Biotin) (SEQ ID NO. 16) | NT | 77% |

As described in detail below, an aspect of the invention involves a nonradioactive ELISA based assay suitable for high throughput screening (HTS). The development of the ELISA based CHK1 kinase HTS assay was first initiated with a monoclonal anti-phosphoserine antibody called Clone PSR-45, supplied by Sigma. New Chk peptide substrates, analogues of Syntide2, were synthesized to validate this assay. These peptides are listed in Table 4. Biotin-Syntide-2 (SEQ ID NO. 12), and N-terminus acetylated Syntide-2 (SEQ ID NO. 13) and the expected peptide products after CHK phosphorylation, serine phosphorylated Syntide 2 (SEQ ID NO. 15), and serine phosphorylated biotin-Syntide 2 (SEQ ID NO. 16) were synthesized for assay development. Although the assay worked well in solution with these peptides, it did not work when the peptide (serine phosphorylated Syntide 2—SEQ ID NO. 15) was immobilized on DNA BIND (Costar) 96 well plates. This antibody also did not work well when the biotin-labeled peptide was immobilized using Neutravidin coated 96 well plates (Pierce). To circumvent these issues, a polyclonal antibody specifically directed against phosphorylated Syntide-2 (SEQ ID NO. 15) was raised in rabbits. The rabbit polyclonal anti-phosphosyntide antibody was found to quantitatively and specifically recognize phosphoserine on both Syntide 2-Ser-PO$_3$ (assay on DNA BIND plates) or on biotin-Syntide 2-Ser-PO$_3$ (assayed on Neutravidin coated 96 well plates) when compared with the unphosphorylated peptide counterparts. A modified Chk1 HTS assay ELISA was developed using His-tagged KH289 Chk1 kinase, biotin-syntide substrate assayed on Neutravidin coated 96 well plates, and the rabbit anti-phosphosyntide antibody to detect the phosphorylated product.

This Chk1 kinase ELISA HTS allowed for the robotic screening of compound libraries. Herein, the Beckman robotics station was used. First, the Chk1 kinase was assayed in Neutravidin coated 96-well plates in 100 μL/well of reaction mixture. The reaction mixture comprised 50 mM Tris-HCl (pH 7.5), 10 mM MgCl$_2$, 3 mM DTT, 400 mM NaCl, 50 μM ATP, 10 μM biotin-Syntide 2 peptide substrate and 10 nM Chk1 kinase (KH289). The assay was performed both with and without 20 μM test compound. Herein, the biotin Syntide 2 substrate had the following sequence: PLARTLSVAGLPGK-biotin-K (SEQ ID NO. 12).

Figure 10:
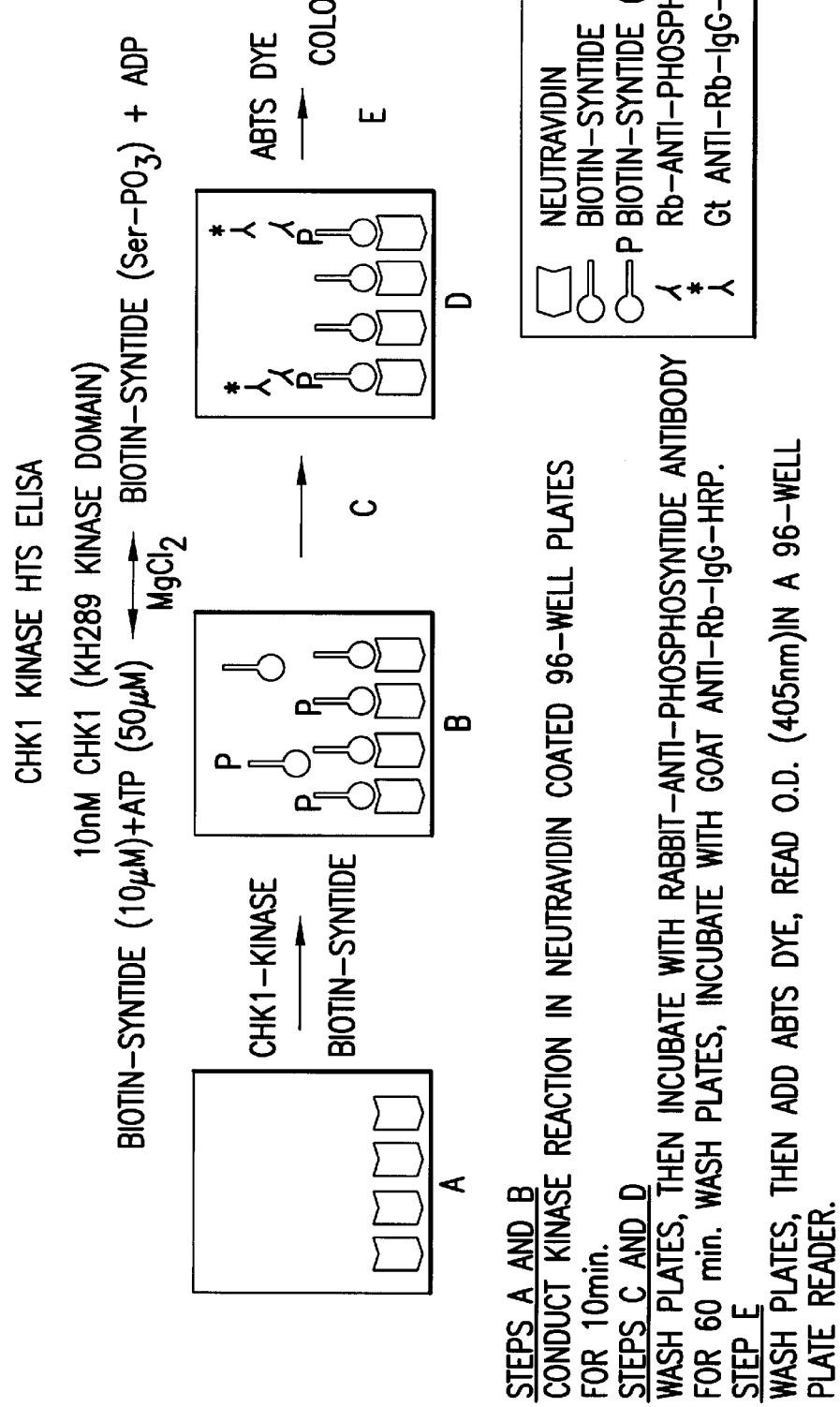
FIG. 10. The high throughput ELISA protocol.

The assay is depicted in FIG. 10. In step A, 93 μL of reaction mixture (less both the Chk1 kinase and the biotin-syntide) is added, followed by the addition of 2 μL of test compound (20 μM final). The kinase reaction is initiated by the addition of 5 μL of enzyme-substrate stock (200 nM Chk1 kinase and 200 μM biotin-syntide). The kinase reaction is allowed to proceed for 10 min at room temperature (≅22° C.) as shown in Step B. Following 10 minutes of kinase reaction, both phosphorylated and unphosphorylated biotin-Syntide 2 are bound to the Neutravidin coated plate. In step C, the plates are washed with PBS/Tween-20 to terminate the kinase reaction and to remove the unbound phosphorylated or non-phosphorylated biotin-Syntide 2. In step D, the plates are incubated at room temperature for 60 minutes with rabbit anti-phosphosyntide antibody (1:40,000 dilution; 100 μL/well). The anti-phosphosyntide antibody binds specifically to the serine-phosphorylated biotin-Syntide 2. The unbound antibody is removed with washes of PBS/Tween-20. The plates are then incubated at room temperature for 60 minutes with goat-anti-rabbit-IgG(Fc)-HRP (horseradish peroxidase) antibody. In step E, the plates are washed with PBS/Tween to remove the unbound secondary antibody. Then, 100 μL/well chromogenic dye ABTS (HRP substrate) is added. The color development, resulting from the HRP reaction, is allowed to take place for 18 minutes. This is followed by absorbance measurement at 405 nm in a 96-well plate reader. The Chk1 kinase activity is directly proportional to the optical density of the color formed.

All references cited herein are incorporated by reference in their entirety.

While the invention has been described in conjunction with examples thereof, it is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

SEQUENCE LISTINGS

SEQ ID NO. 1—full length human Chk1 (nucleotide sequence—1821 base pairs)
SEQ ID NO. 2—full length human Chk 1 (peptide sequence—476 AA)
SEQ ID NO. 3—PCR primer (chk6w)
SEQ ID NO. 4—PCR primer (KH289)
SEQ ID NO. 5—PCR primer (K289)
SEQ ID NO. 6—PCR primer (Chk11)
SEQ ID NO. 7—PCR primer (K210)
SEQ ID NO. 8—PCR primer (KH210)
SEQ ID NO. 9—PCR primer (K248)
SEQ ID NO. 10—PCR primer (KH248)
SEQ ID NO. 11—synthetic substrate peptide, Syntide-2
SEQ ID NO. 12—synthetic substrate peptide, Syntide-3
SEQ ID NO. 13—synthetic substrate peptide, Syntide-4
SEQ ID NO. 14—oligonucleotide primer
SEQ ID NO. 15—serine phosphorylated Syntide-2
SEQ ID NO. 16—serine phosphorylated biotin Syntide-2
SEQ ID NO. 17—peptide sequence for Cdc25 protein phosphatase

What is claimed:

1. A composition comprising an isolated, purified polynucleotide, which encodes a catalytically active human ChkI kinase domain as represented by the polypeptide consisting of amino acids 1–291 of SEQ ID NO:2.

2. An expression vector comprising a polynucleotide encoding a catalytically active human ChkI kinase domain as represented by the polypeptide consisting of amino acids of amino acids 1–291 of SEQ ID NO:2 and a selectable marker.

3. The vector of claim 2 wherein said vector is selected from the group consisting of pET28a, pAcSG2, and pFastBac.

4. The vector of claim 2 wherein said vector is pFastBac-Nde.

5. The vector of claim 2 wherein said selectable marker is selected from the group consisting of beta galactosidase, green fluorescent protein, and luciferase.

6. A host cell stably transformed or transfected with a polynucleotide encoding a catalytically active human ChkI domain as represented by the polypeptide consisting of amino acids 1–291 of SEQ ID NO:2 in a manner allowing the expression in said host cell of the human ChkI kinase domain.

7. The host cell of claim 6 wherein said host is *E. coli*.

8. The host cell of claim 6 wherein said host is a recombinant baculovirus.

9. The host cell of claim 6 wherein said host is an insect cell.

10. The host cell of claim 9 wherein said insect cell is Sf9.

11. The host cell of claim 6 wherein said host cell is transformed or transfected with said polynucleotide via an expression vector comprising said polynucleotide; transcriptional and translational regulatory sequences functional in said host cell operably linked to said human ChkI kinase domain-encoding polynucleotide; and a selectable marker.

12. The host cell of claim 11 wherein said expression vector is selected from the group consisting of pET28a, pAcSG2, and pFastBac.

13. The host cell of claim 11 wherein said expression vector is pFastBac-Nde.

14. The host cell of claim 11 wherein said selectable marker is selected from the group consisting of beta galactosidase, green fluorescent protein, and luciferase.

15. A composition comprising an isolated, purified polynucleotide, which encodes a catalytically active human ChkI kinase domain as represented by the polypeptide consisting of amino acids 16–289 of SEQ ID NO:2.

16. A composition comprising an isolated, purified polynucleotide, which encodes a catalytically active human ChkI kinase domain as represented by the polypeptide consisting of amino acids 16–291 of SEQ ID NO:2.

17. A composition comprising an isolated, purified polynucleotide, which encodes a catalytically active human ChkI kinase domain as represented by the polypeptide consisting of amino acids 1–289 of SEQ ID NO:2.

* * * * *